US008068991B2

(12) United States Patent
Jung et al.

(10) Patent No.: US 8,068,991 B2
(45) Date of Patent: *Nov. 29, 2011

(54) SYSTEMS AND METHODS FOR TRANSMITTING PATHOGEN RELATED INFORMATION AND RESPONDING

(75) Inventors: Edward K. Y. Jung, Bellevue, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 659 days.

This patent is subject to a terminal disclaimer.

(21) Appl. No.: 11/900,660

(22) Filed: Sep. 11, 2007

(65) Prior Publication Data

US 2008/0183396 A1 Jul. 31, 2008

Related U.S. Application Data

(63) Continuation-in-part of application No. 11/900,649, filed on Sep. 11, 2007, and a continuation-in-part of application No. 11/900,637, filed on Sep. 11, 2007, and a continuation-in-part of application No. 11/893,608, filed on Aug. 15, 2007, and a continuation-in-part of application No. 11/893,606, filed on Aug. 15, 2007, and a continuation-in-part of application No. 11/893,605, filed on Aug. 15, 2007, and a continuation-in-part of application No. 11/888,627, filed on Jul. 31, 2007, and a continuation-in-part of application No. 11/888,614, filed on Jul. 31, 2007, and a continuation-in-part of application No. 11/888,613, filed on Jul. 31, 2007, now Pat. No. 7,827,042, and a continuation-in-part of application No. 11/824,604, filed on Jun. 28, 2007, and a continuation-in-part of application No. 11/824,529, filed on Jun. 28, 2007, and a continuation-in-part of application No. 11/799,465, filed on Apr. 30, 2007, and a continuation-in-part of application No. 11/799,462, filed on Apr. 30, 2007, and a continuation-in-part of application No. 11/729,301, filed on Mar. 27, 2007, and a continuation-in-part of application No. 11/729,276, filed on Mar. 27, 2007, and a continuation-in-part of application No. 11/729,275, filed on Mar. 27, 2007, and a continuation-in-part of application No. 11/729,274, filed on Mar. 27, 2007, and a continuation-in-part of application No. 11/637,638, filed on Dec. 11, 2006, now Pat. No. 7,927,787, and a continuation-in-part of application No. 11/637,616, filed on Dec. 11, 2006, and a continuation-in-part of application No. 11/523,809, filed on Sep. 18, 2006, and a continuation-in-part of application No. 11/523,766, filed on Sep. 18, 2006, and a continuation-in-part of application No. 11/518,540, filed on Sep. 8, 2006, and a continuation-in-part of application No. 11/515,357, filed on Sep. 1, 2006, and a continuation-in-part of application No. 11/486,998, filed on Jul. 14, 2006, and a continuation-in-part of application No. 11/486,973, filed on Jul. 14, 2006, and a continuation-in-part of application No. 11/478,341, filed on Jun. 28, 2006, and a continuation-in-part of application No. 11/478,296, filed on Jun. 28, 2006, and a continuation-in-part of application No. 11/474,109, filed on Jun. 23, 2006, and a continuation-in-part of application No. 11/453,571, filed on Jun. 14, 2006, and a continuation-in-part of application No. 11/314,945, filed on Dec. 20, 2005, and a continuation-in-part of application No. 11/291,482, filed on Nov. 30, 2005.

(51) Int. Cl.
*G06F 7/00* (2006.01)
(52) U.S. Cl. ............ 702/19; 702/20; 703/11; 703/12; 707/700; 424/184.1
(58) Field of Classification Search .................. None
See application file for complete search history.

(56) References Cited

U.S. PATENT DOCUMENTS

| | | | |
|---|---|---|---|
| 3,971,065 | A | 7/1976 | Bayer |
| 4,009,078 | A | 2/1977 | Wilkins et al. |
| 4,081,356 | A | 3/1978 | Zierdt |
| 4,257,041 | A | 3/1981 | Masucci |

(Continued)

FOREIGN PATENT DOCUMENTS

DE 10 2004 040785 A1 3/2006

(Continued)

OTHER PUBLICATIONS

"AIC At-Home Test Kit-Introductory Offer (1 per customer, first time buyers Only)"; Amazon.com; Bearing dates of 1996-2006; pp. 1-4; Amazon.com, Inc.; located at: http://www.amazon.com/gp/product/B0006JMPRG/ref=sr_11_1/103-2429377-9250203?ie=UTF8; printed on Jul. 10, 2006.
Abrams, Bernard; "Standing Rx packaging on its head"; Packagingdigest.com; Bearing a date of Jun. 2005; pp. 1-3; located at http://www.packagingdigest.com/articles/200506/38.php; printed on Jun. 21, 2006.
Actis-Goretta, Lucas; Ottaviani, Javier I.; Fraga, Cesar G.; "Inhibition of Angiotensin Converting Enzyme Activity by Flavanol-Rich Foods"; Journal of Agricultural and Food Chemistry; Bearing a date of 2006; pp. 229-234; vol. 54; American Chemical Society.
Aihara, K; Kajimoto, O; Hirata, H; Takahashi, R; Nakamura, Y; "Effect of powdered fermented milk with *Lactobacillus helveticus* on subjects with high-normal blood pressure or mild hypertension"; J. Am. Coll. Nutr.; Bearing a date of Aug. 2005; pp. 257-265 (pp. 1-2); vol. 24, No. 4; PubMed; located at: http://www.ncbi.nlm.nih.gov/sites/entrez?db=pubmed&list_uids=16093403&cmd=Retrieve&indexed=google; printed on Jun. 25, 2007.

(Continued)

*Primary Examiner* — Mary Zeman

(57) ABSTRACT

The present disclosure relates to methods and systems that may be used for detection of one or more pathogens and determining one or more agents in response to pathogen detection.

30 Claims, 61 Drawing Sheets

U.S. PATENT DOCUMENTS

| | | |
|---|---|---|
| 4,436,378 A | 3/1984 | Kirkman |
| 4,567,185 A | 1/1986 | Sackner |
| 4,729,636 A | 3/1988 | Te Velde et al. |
| 4,807,967 A | 2/1989 | Veenvliet et al. |
| 4,847,764 A | 7/1989 | Halvorson |
| 4,857,716 A | 8/1989 | Gombrich et al. |
| 5,006,343 A | 4/1991 | Benson et al. |
| 5,054,493 A | 10/1991 | Cohn et al. |
| 5,093,268 A | 3/1992 | Leventis et al. |
| 5,284,656 A | 2/1994 | Platz et al. |
| 5,300,302 A | 4/1994 | Tachon et al. |
| 5,307,263 A | 4/1994 | Brown |
| 5,354,934 A | 10/1994 | Pitt et al. |
| 5,412,560 A | 5/1995 | Dennison |
| 5,490,962 A | 2/1996 | Cima et al. |
| 5,654,011 A | 8/1997 | Jackson et al. |
| 5,672,154 A | 9/1997 | Sillén et al. |
| 5,686,429 A | 11/1997 | Lin et al. |
| 5,692,502 A | 12/1997 | Alpert |
| 5,700,998 A | 12/1997 | Palti |
| 5,704,350 A | 1/1998 | Williams, III |
| 5,716,852 A | 2/1998 | Yager et al. |
| 5,719,123 A | 2/1998 | Morley et al. |
| 5,726,404 A | 3/1998 | Brody |
| 5,737,539 A | 4/1998 | Edelson et al. |
| 5,747,349 A | 5/1998 | van den Engh et al. |
| 5,758,095 A | 5/1998 | Albaum et al. |
| 5,758,096 A | 5/1998 | Barsky et al. |
| 5,765,606 A | 6/1998 | Takemasa et al. |
| 5,770,226 A | 6/1998 | Hughes, Jr. et al. |
| 5,780,014 A | 7/1998 | Eljamal et al. |
| 5,807,579 A | 9/1998 | Vilkov et al. |
| 5,820,876 A | 10/1998 | Hoffmann |
| 5,824,494 A | 10/1998 | Feldberg |
| 5,837,196 A | 11/1998 | Pinkel et al. |
| 5,839,438 A | 11/1998 | Graettinger et al. |
| 5,873,369 A | 2/1999 | Laniado et al. |
| 5,882,931 A | 3/1999 | Petersen |
| 5,907,291 A | 5/1999 | Chen et al. |
| 5,922,210 A | 7/1999 | Brody et al. |
| 5,932,100 A | 8/1999 | Yager et al. |
| 5,940,801 A | 8/1999 | Brown |
| 5,945,115 A | 8/1999 | Dunn et al. |
| 5,948,684 A | 9/1999 | Weigl et al. |
| 5,954,640 A | 9/1999 | Szabo |
| 5,955,269 A | 9/1999 | Ghai et al. |
| 5,958,458 A | 9/1999 | Norling et al. |
| 5,971,158 A | 10/1999 | Yager et al. |
| 5,972,710 A | 10/1999 | Weigl et al. |
| 5,974,867 A | 11/1999 | Forster et al. |
| 5,993,783 A | 11/1999 | Eljamal et al. |
| 5,995,938 A | 11/1999 | Whaley |
| 6,007,775 A | 12/1999 | Yager |
| 6,021,202 A | 2/2000 | Anderson et al. |
| 6,023,916 A | 2/2000 | Bouthiette |
| 6,024,699 A | 2/2000 | Surwit et al. |
| 6,035,230 A | 3/2000 | Kang et al. |
| 6,037,167 A | 3/2000 | Adelman et al. |
| 6,087,090 A | 7/2000 | Mascarenhas |
| 6,090,545 A | 7/2000 | Wohlstadter et al. |
| 6,117,073 A | 9/2000 | Jones et al. |
| 6,128,534 A | 10/2000 | Park et al. |
| 6,139,494 A | 10/2000 | Cairnes |
| 6,161,095 A | 12/2000 | Brown |
| 6,169,068 B1 | 1/2001 | Levin et al. |
| 6,188,988 B1 | 2/2001 | Barry et al. |
| 6,194,900 B1 | 2/2001 | Freeman et al. |
| 6,221,677 B1 | 4/2001 | Wu et al. |
| 6,227,371 B1 | 5/2001 | Song |
| 6,280,771 B1 | 8/2001 | Monkhouse et al. |
| 6,287,595 B1 | 9/2001 | Loewy et al. |
| 6,295,506 B1 | 9/2001 | Heinonen et al. |
| 6,317,719 B1 | 11/2001 | Schrier et al. |
| 6,318,970 B1 | 11/2001 | Backhouse |
| 6,325,904 B1 | 12/2001 | Peeters |
| 6,330,946 B1 | 12/2001 | Allen |
| 6,335,021 B1 | 1/2002 | Cavazza |
| 6,379,929 B1 | 4/2002 | Burns et al. |
| 6,383,136 B1 | 5/2002 | Jordan |
| 6,397,190 B1 | 5/2002 | Goetz |
| 6,408,884 B1 | 6/2002 | Kamholz et al. |
| 6,409,832 B2 | 6/2002 | Weigl et al. |
| 6,421,650 B1 | 7/2002 | Goetz et al. |
| 6,451,286 B1 | 9/2002 | Modi |
| 6,454,945 B1 | 9/2002 | Weigl et al. |
| 6,468,805 B1 | 10/2002 | Smith |
| 6,482,306 B1 | 11/2002 | Yager et al. |
| 6,510,430 B1 | 1/2003 | Oberwager et al. |
| 6,523,392 B2 | 2/2003 | Porter et al. |
| 6,529,446 B1 | 3/2003 | de la Huerga |
| 6,541,213 B1 | 4/2003 | Weigl et al. |
| 6,541,478 B1 | 4/2003 | O'Malley et al. |
| 6,565,841 B1 | 5/2003 | Niven et al. |
| 6,565,874 B1 | 5/2003 | Dunn et al. |
| 6,569,630 B1 | 5/2003 | Vivekananda et al. |
| 6,576,267 B2 | 6/2003 | Gelber et al. |
| 6,582,987 B2 | 6/2003 | Jun et al. |
| 6,589,169 B1 | 7/2003 | Surwit et al. |
| 6,605,454 B2 | 8/2003 | Barenburg et al. |
| 6,616,606 B1 | 9/2003 | Petersen et al. |
| 6,630,155 B1 | 10/2003 | Chandrashekar et al. |
| 6,656,507 B2 | 12/2003 | Petereit et al. |
| 6,660,159 B1 | 12/2003 | Terstappen et al. |
| 6,664,104 B2 | 12/2003 | Pourahmadi et al. |
| 6,671,818 B1 | 12/2003 | Mikurak |
| 6,695,147 B1 | 2/2004 | Yager et al. |
| 6,699,193 B2 | 3/2004 | Crutchfield et al. |
| 6,709,676 B2 | 3/2004 | Cho |
| 6,709,869 B2 | 3/2004 | Mian et al. |
| 6,716,642 B1 | 4/2004 | Wu et al. |
| 6,730,516 B2 | 5/2004 | Jedrzejewski et al. |
| 6,742,661 B1 | 6/2004 | Schulte et al. |
| 6,759,062 B2 | 7/2004 | Gelber et al. |
| 6,763,705 B1 | 7/2004 | Thundat et al. |
| 6,764,831 B2 | 7/2004 | Cameron, Sr. et al. |
| 6,773,714 B2 | 8/2004 | Dunn et al. |
| 6,773,721 B1 | 8/2004 | Wong et al. |
| 6,780,582 B1 | 8/2004 | Wagner et al. |
| 6,787,164 B2 | 9/2004 | Gelber et al. |
| 6,790,198 B1 | 9/2004 | White et al. |
| 6,793,942 B2 | 9/2004 | Gelber et al. |
| 6,794,196 B2 | 9/2004 | Fonash et al. |
| 6,812,458 B2 | 11/2004 | Gregori et al. |
| 6,818,435 B2 | 11/2004 | Carvalho et al. |
| 6,821,730 B2 | 11/2004 | Hannah |
| 6,838,076 B2 | 1/2005 | Patton et al. |
| 6,841,544 B2 | 1/2005 | Gelber et al. |
| 6,849,396 B2 | 2/2005 | Schneider |
| 6,852,206 B2 | 2/2005 | Pawliszyn et al. |
| 6,877,892 B2 | 4/2005 | Karp |
| 6,878,755 B2 | 4/2005 | Singh et al. |
| 6,881,425 B2 | 4/2005 | Pushpangadan et al. |
| 6,888,095 B2 | 5/2005 | Khan |
| 6,921,527 B2 | 7/2005 | Platz et al. |
| 6,923,907 B2 | 8/2005 | Hobbs et al. |
| 6,926,864 B2 | 8/2005 | Peeters et al. |
| 6,935,165 B2 | 8/2005 | Bashir et al. |
| 6,946,144 B1 | 9/2005 | Jordan |
| 6,951,545 B2 | 10/2005 | Smith et al. |
| 6,955,873 B1 | 10/2005 | Blum |
| 6,958,216 B2 | 10/2005 | Kelley et al. |
| 6,960,437 B2 | 11/2005 | Enzelberger et al. |
| 6,962,720 B2 | 11/2005 | Haridas et al. |
| 6,979,463 B2 | 12/2005 | Kou |
| 6,979,471 B1 | 12/2005 | Khanuja et al. |
| 6,979,679 B2 | 12/2005 | Marcum |
| 6,980,958 B1 | 12/2005 | Surwit et al. |
| 7,005,447 B2 | 2/2006 | Ahotupa et al. |
| 7,016,752 B1 | 3/2006 | Ruben et al. |
| 7,022,288 B1 | 4/2006 | Boss |
| 7,029,441 B2 | 4/2006 | Dodds |
| 7,030,989 B2 | 4/2006 | Yager et al. |
| 7,041,317 B2 | 5/2006 | Sekiya et al. |
| 7,041,670 B2 | 5/2006 | Boojamra et al. |
| 7,041,840 B2 | 5/2006 | Gandhi |
| 7,045,145 B1 | 5/2006 | Chien |
| 7,045,159 B1 | 5/2006 | Ilic et al. |

| Patent No. | Date | Inventor |
|---|---|---|
| 7,046,357 B2 | 5/2006 | Weinberger et al. |
| 7,048,945 B2 | 5/2006 | Percel et al. |
| 7,049,312 B1 | 5/2006 | Rafferty et al. |
| 7,049,433 B2 | 5/2006 | Fan et al. |
| 7,053,107 B2 | 5/2006 | Borchardt et al. |
| 7,056,951 B2 | 6/2006 | Spireas |
| 7,070,682 B2 | 7/2006 | Lee et al. |
| 7,074,311 B1 | 7/2006 | Cunningham |
| 7,074,583 B2 | 7/2006 | Yoshizato et al. |
| 7,081,192 B1 | 7/2006 | Wang et al. |
| 7,110,646 B2 | 9/2006 | Eggleton et al. |
| 7,112,444 B2 | 9/2006 | Beebe et al. |
| 7,118,910 B2 | 10/2006 | Unger et al. |
| 7,135,616 B2 | 11/2006 | Heard et al. |
| 7,136,820 B1 | 11/2006 | Petrus |
| 7,141,385 B2 | 11/2006 | Bottomley et al. |
| 7,150,813 B2 | 12/2006 | Lean et al. |
| 7,151,982 B2 | 12/2006 | Liff et al. |
| 7,169,432 B2 | 1/2007 | Tanaka et al. |
| 7,172,897 B2 | 2/2007 | Blackburn et al. |
| 7,193,128 B2 | 3/2007 | Copenhaver et al. |
| 7,197,492 B2 | 3/2007 | Sullivan |
| 7,206,605 B2 | 4/2007 | Hattori |
| 7,215,887 B2 | 5/2007 | Ternullo et al. |
| 7,216,343 B2 | 5/2007 | Das et al. |
| 7,218,900 B2 | 5/2007 | Suzuki |
| 7,227,956 B1 | 6/2007 | Onishi |
| 7,236,595 B1 | 6/2007 | Bean et al. |
| 7,245,894 B2 | 7/2007 | Sekiguchi et al. |
| RE39,785 E | 8/2007 | Fuse |
| 7,254,160 B2 | 8/2007 | Kawamoto et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,280,975 B1 | 10/2007 | Donner |
| 7,351,739 B2 | 4/2008 | Ho et al. |
| 7,376,585 B2 | 5/2008 | Haller |
| 7,379,167 B2 | 5/2008 | Mawhirt et al. |
| 7,490,085 B2 | 2/2009 | Walker et al. |
| 7,502,666 B2 | 3/2009 | Siegel et al. |
| 7,635,594 B2 | 12/2009 | Holmes et al. |
| 2001/0003177 A1 | 6/2001 | Schena et al. |
| 2001/0022758 A1 | 9/2001 | Howard |
| 2001/0037220 A1 | 11/2001 | Merry et al. |
| 2002/0004749 A1 | 1/2002 | Froseth et al. |
| 2002/0016719 A1 | 2/2002 | Nemeth et al. |
| 2002/0019784 A1 | 2/2002 | Ritz |
| 2002/0027164 A1 | 3/2002 | Mault et al. |
| 2002/0032580 A1 | 3/2002 | Hopkins |
| 2002/0032582 A1 | 3/2002 | Feeney, Jr. et al. |
| 2002/0032620 A1 | 3/2002 | Benz et al. |
| 2002/0046948 A1 | 4/2002 | Chow et al. |
| 2002/0052763 A1 | 5/2002 | Jung Richardson |
| 2002/0055856 A1 | 5/2002 | Adams |
| 2002/0059030 A1 | 5/2002 | Otworth et al. |
| 2002/0063060 A1 | 5/2002 | Gascoyne et al. |
| 2002/0065682 A1 | 5/2002 | Goldenberg |
| 2002/0070226 A1 | 6/2002 | Liff et al. |
| 2002/0077850 A1 | 6/2002 | McMenimen et al. |
| 2002/0091991 A1 | 7/2002 | Castro |
| 2002/0095238 A1 | 7/2002 | Ahlin et al. |
| 2002/0100762 A1 | 8/2002 | Liff et al. |
| 2002/0106429 A1 | 8/2002 | Mudar et al. |
| 2002/0128259 A1 | 9/2002 | Ghazzi et al. |
| 2002/0143434 A1 | 10/2002 | Greeven et al. |
| 2002/0147317 A1 | 10/2002 | Bentsen et al. |
| 2002/0156651 A1 | 10/2002 | Florio et al. |
| 2002/0156683 A1 | 10/2002 | Stoutenburg et al. |
| 2002/0173875 A1 | 11/2002 | Wallace et al. |
| 2002/0177763 A1 | 11/2002 | Burns et al. |
| 2002/0192310 A1 | 12/2002 | Bland et al. |
| 2002/0194226 A1 | 12/2002 | Sheth et al. |
| 2002/0194502 A1 | 12/2002 | Sheth et al. |
| 2003/0005445 A1 | 1/2003 | Schein et al. |
| 2003/0019165 A1 | 1/2003 | Gallant et al. |
| 2003/0028399 A1 | 2/2003 | Davis et al. |
| 2003/0032868 A1 | 2/2003 | Graskov et al. |
| 2003/0036683 A1 | 2/2003 | Kehr et al. |
| 2003/0044832 A1 | 3/2003 | Blankenstein |
| 2003/0055531 A1 | 3/2003 | Liff et al. |
| 2003/0061123 A1 | 3/2003 | McMenimen et al. |
| 2003/0065537 A1 | 4/2003 | Evans |
| 2003/0069757 A1 | 4/2003 | Greenberg |
| 2003/0073931 A1 | 4/2003 | Boecker et al. |
| 2003/0074218 A1 | 4/2003 | Liff et al. |
| 2003/0083685 A1 | 5/2003 | Freeman et al. |
| 2003/0088333 A1 | 5/2003 | Liff et al. |
| 2003/0092039 A1 | 5/2003 | Olson-Munoz et al. |
| 2003/0105552 A1 | 6/2003 | Lunak et al. |
| 2003/0119057 A1 | 6/2003 | Gascoyne et al. |
| 2003/0121929 A1 | 7/2003 | Liff et al. |
| 2003/0125837 A1 | 7/2003 | Walace et al. |
| 2003/0135388 A1 | 7/2003 | Martucci et al. |
| 2003/0139655 A1 | 7/2003 | Dodds |
| 2003/0156724 A1 | 8/2003 | Mariano et al. |
| 2003/0158756 A1 | 8/2003 | Abramson |
| 2003/0159999 A1 | 8/2003 | Oakey et al. |
| 2003/0171950 A1 | 9/2003 | Kilgannon et al. |
| 2003/0189058 A1 | 10/2003 | Liff et al. |
| 2003/0191670 A1 | 10/2003 | Hatcher et al. |
| 2003/0193185 A1 | 10/2003 | Valley et al. |
| 2003/0204412 A1 | 10/2003 | Brier |
| 2003/0207270 A1 | 11/2003 | Kung et al. |
| 2003/0214129 A1 | 11/2003 | Adler |
| 2003/0216831 A1 | 11/2003 | Hart et al. |
| 2003/0219812 A1 | 11/2003 | Quay et al. |
| 2003/0220848 A1 | 11/2003 | Behrendt |
| 2003/0229455 A1 | 12/2003 | Bevilacqua et al. |
| 2003/0233250 A1 | 12/2003 | Joffe et al. |
| 2004/0004523 A1 | 1/2004 | Humphries et al. |
| 2004/0032330 A1 | 2/2004 | Hoffman |
| 2004/0033553 A1 | 2/2004 | Littarru et al. |
| 2004/0053290 A1 | 3/2004 | Terbrueggen et al. |
| 2004/0064342 A1 | 4/2004 | Browne et al. |
| 2004/0075272 A1 | 4/2004 | Kaufman |
| 2004/0078236 A1 | 4/2004 | Stoodley et al. |
| 2004/0081023 A1 | 4/2004 | Ho |
| 2004/0086872 A1 | 5/2004 | Childers et al. |
| 2004/0107022 A1 | 6/2004 | Gomez |
| 2004/0111298 A1 | 6/2004 | Schoenberg |
| 2004/0118757 A1 | 6/2004 | Terstappen et al. |
| 2004/0121767 A1 | 6/2004 | Simpson et al. |
| 2004/0122707 A1 | 6/2004 | Sabol et al. |
| 2004/0122790 A1 | 6/2004 | Walker et al. |
| 2004/0133705 A1 | 7/2004 | Broussard et al. |
| 2004/0138921 A1 | 7/2004 | Broussard et al. |
| 2004/0138926 A1 | 7/2004 | Ishikawa et al. |
| 2004/0143403 A1 | 7/2004 | Brandon et al. |
| 2004/0151629 A1 | 8/2004 | Pease et al. |
| 2004/0154688 A1 | 8/2004 | Geltser et al. |
| 2004/0158507 A1 | 8/2004 | Meek, Jr. et al. |
| 2004/0176984 A1 | 9/2004 | White et al. |
| 2004/0188523 A1 | 9/2004 | Lunak et al. |
| 2004/0188524 A1 | 9/2004 | Lunak et al. |
| 2004/0193316 A1 | 9/2004 | Lunak et al. |
| 2004/0210341 A1 | 10/2004 | Wallace et al. |
| 2004/0215486 A1 | 10/2004 | Braverman |
| 2004/0220498 A1 | 11/2004 | Li et al. |
| 2004/0224916 A1 | 11/2004 | Dahl et al. |
| 2004/0225203 A1 | 11/2004 | Jemison et al. |
| 2004/0243441 A1 | 12/2004 | Bocionek et al. |
| 2004/0248167 A1 | 12/2004 | Quake et al. |
| 2005/0010416 A1 | 1/2005 | Anderson et al. |
| 2005/0013863 A1 | 1/2005 | Lim et al. |
| 2005/0021413 A1 | 1/2005 | Berry et al. |
| 2005/0033606 A1 | 2/2005 | Miller |
| 2005/0038558 A1 | 2/2005 | Keene |
| 2005/0053650 A1 | 3/2005 | Chalmers |
| 2005/0060188 A1 | 3/2005 | Valley |
| 2005/0062238 A1 | 3/2005 | Broadfield et al. |
| 2005/0065645 A1 | 3/2005 | Liff et al. |
| 2005/0101841 A9 | 5/2005 | Kaylor et al. |
| 2005/0102159 A1 | 5/2005 | Mondshine |
| 2005/0110268 A1 | 5/2005 | Schone |
| 2005/0118202 A1 | 6/2005 | Yamashita et al. |
| 2005/0147667 A1 | 7/2005 | Rines |

| | | |
|---|---|---|
| 2005/0158401 A1 | 7/2005 | Morris |
| 2005/0192487 A1 | 9/2005 | Cosentino et al. |
| 2005/0216313 A1 | 9/2005 | Claud et al. |
| 2005/0216390 A1 | 9/2005 | Snider et al. |
| 2005/0218152 A1 | 10/2005 | Simon |
| 2005/0240305 A1 | 10/2005 | Bogash et al. |
| 2005/0260679 A1 | 11/2005 | Kellerman et al. |
| 2005/0261255 A1 | 11/2005 | Serhan et al. |
| 2005/0271596 A1 | 12/2005 | Friedman et al. |
| 2005/0285746 A1 | 12/2005 | Sengupta et al. |
| 2006/0015016 A1 | 1/2006 | Thornton |
| 2006/0028727 A1 | 2/2006 | Moon et al. |
| 2006/0047538 A1 | 3/2006 | Condurso et al. |
| 2006/0064250 A1 | 3/2006 | Goldstein |
| 2006/0073484 A1 | 4/2006 | Mathies et al. |
| 2006/0097516 A1 | 5/2006 | Kozlowski et al. |
| 2006/0099310 A1 | 5/2006 | Koekkoek |
| 2006/0111944 A1 | 5/2006 | Sirmans, Jr. et al. |
| 2006/0129324 A1 | 6/2006 | Rabinoff et al. |
| 2006/0169642 A1 | 8/2006 | Oakey et al. |
| 2006/0177637 A1 | 8/2006 | Kimura |
| 2006/0223178 A1 | 10/2006 | Barber et al. |
| 2006/0240150 A1 | 10/2006 | Delaney et al. |
| 2006/0254580 A1 | 11/2006 | Chalmers et al. |
| 2006/0257852 A1 | 11/2006 | Rappuoli et al. |
| 2006/0260679 A1 | 11/2006 | Aratani et al. |
| 2006/0264780 A1 | 11/2006 | Holmes et al. |
| 2006/0280307 A1 | 12/2006 | Ikushima et al. |
| 2007/0011919 A1 | 1/2007 | Case, Jr. |
| 2007/0087048 A1 | 4/2007 | Abrams et al. |
| 2007/0136092 A1 | 6/2007 | Jung et al. |
| 2008/0097784 A1 | 4/2008 | Miller et al. |
| 2009/0047297 A1 | 2/2009 | Kim et al. |

FOREIGN PATENT DOCUMENTS

| | | |
|---|---|---|
| JP | 61002060 A | 1/1986 |
| WO | WO 97/47390 | 12/1997 |
| WO | WO 98/38293 | 9/1998 |
| WO | WO 99/17119 | 4/1999 |
| WO | WO 99/45354 | 9/1999 |
| WO | WO 99/45354 A2 | 9/1999 |
| WO | WO 99/45354 A3 | 9/1999 |
| WO | WO 00/60362 | 10/2000 |
| WO | WO 00/60362 A1 | 10/2000 |
| WO | WO 01/79529 A1 | 10/2001 |
| WO | WO 03/066191 A1 | 8/2003 |
| WO | WO 03/084395 A1 | 10/2003 |
| WO | WO 2004/061085 A3 | 7/2004 |
| WO | WO 2005/041105 A1 | 5/2005 |
| WO | WO 2005/062849 A2 | 7/2005 |
| WO | WO 2006/021410 A1 | 3/2006 |
| WO | WO 2006/032044 A3 | 3/2006 |
| WO | WO 2007/061838 A2 | 5/2007 |

OTHER PUBLICATIONS

"Anemia Tests"; Home Health Testing; Bearing dates of Dec. 1, 2005 and 2000; pp. 1-3; AbDiagnostics, Inc.; located at: http://www.homehealthtesting.com/anemia-tests.htm; printed on Jul. 24, 2006.

"Antioxidant Tests"; Home Health Testing; Bearing dates of Dec. 1, 2005 and 2000; pp. 1-2; AbDiagnostics, Inc.; located at: http://www.homehealthtesting.com/antioxidant-tests.htm; printed on Jul. 24, 2006.

Appleton, David; Lockwood, Brian; "Building Bones with Nutraceuticals"; The Pharmaceutical Journal; Bearing a date of Jul. 15, 2006; pp. 78-83; vol. 277; located at: http://www.pjonline.com/pdf/articles/pj_20060715_bones.pdf; printed on Aug. 22, 2006.

Baines, I.C.; Colas, P.; "Peptide aptamers as guides for small-molecule drug discovery"; Drug Discovery Today; Apr. 2006; pp. 334-341 (p. 1); vol. 11, Issues 7-8; PubMed; located at: http://www.ncbi.nlm.nih.gov/entrez/query.fcgi?db=pubmed&cmd=Retrieve&dopt=AbstractPlus&list_uids=16580975&quely_hl=10&itool=pubmed_docsum; printed on Jan. 10, 2007.

"Basic Microfluidic Concepts"; Bearing a date of Sep. 7, 2001; pp. 1-8; located at: http://faculty.washington.edu/yagerp/microfluidicstutorial/basicconcepts/basicconcepts.htm; printed on Jan. 17, 2007.

Bassaganya-Riera, J.; Hontecillas, R.; Wannemuehler, M.; "Nutrition impact of conjugated linoleic acid: A model functional food ingredient"; In Vitro Cellular and Development Biology-Plant; May 2002; pp. 241-246 (pp. 1-2); vol. 38, No. 3; Online ISSN 1475-2689; Springer; located at: http://www.ingentaconnect.com/content/klu/ivp/2002/00000038/00000003/02002295?crawler=true; printed on Jun. 25, 2007.

Belgrader, P.; Okuzumi, M.; Pourahmadi, F.; Borkholder, D.A.; Northrup, M.A.; "A microfluidic cartridge to prepare spores for PCR analysis"; Biosensors and Bioelectronics; Jan. 2000; pp. 849-852 (p. 1); vol. 14, Issues 10-11; PubMed; located at: http://www.ncbi.nlm.nih.gov/entrez/query.fcgi?cmd=Retrieve&db=PubMed&list_uids=10945459&dopt=Abstract; printed on Jan. 9, 2007.

"Blood Testing and Sampling Kits"; BloodBook.com; Bearing dates of Nov. 19, 2005 and 2000-2005; pp. 1-2; located at: http://www.bloodbook.com/test-kits.html; printed on Jul. 10, 2006.

Blum, K; Meshkin, B; Downs, BW; "DNA based customized Nutraceutical 'gene therapy' utilizing a genoscore: a hypothesized paradigm shift of a novel approach to the diagnosis, stratification, prognosis and treatment of inflammatory processes in the human"; Med. Hypotheses; Bearing dates of 2006 and Jan. 5, 2006; pp. 1008-1018 (pp. 1-2); vol. 66, No. 5; PubMed; located at: http://www.ncbi.nlm.nih.gov/sites/entrez?db=pubmed; printed on Jun. 11, 2007.

"Body Balance: AntiOxidant Check"; Health HomeTest.com; Bearing dates of 2003-2005; pp. 1-4; B Scientific, Inc.; located at: http://www.healthhometest.com/product_info.php?products_id=39; printed on Jul. 24, 2006.

"Body Balance: FemaleCheck / Estradiol, Progesterone & Testosterone"; Health HomeTest.com; Bearing dates of 2003-2005; pp. 1-5; B Scientific, Inc.; located at: http://www.healthhometest.com/product_info.php?products_id=36; printed on Jul. 24, 2006.

"Body Balance: MaleCheck / Testosterone & DHEA"; Health HomeTest.com; Bearing dates of 2003-2005; pp. 1-4; B Scientific, Inc.; located at: http://www.healthhometest.com/product_info.php?manufacturers_id=10&products_id=40; printed on Jul. 24, 2006.

"Body Balance: Mineral Check"; Health HomeTest.com; Bearing dates of 2003-2005; pp. 1-8; B Scientific, Inc.; located at: http://www.healthhometest.com/product_info.php?products_id=35; printed on Jul. 24, 2006.

"Body Balance: Performance Check"; Health HomeTest.com; Bearing dates of 2003-2005; pp. 1-7; B Scientific, Inc.; located at: http://www.healthhometest.com/product_info.php?products_id=82; printed on Jul. 24, 2006.

"Body Balance: Sleep Check / Melatonin"; Health HomeTest.com; Bearing dates of 2003-2005; pp. 1-4; B Scientific, Inc.; located at: http://www.healthhometest.com/product_info.php?products_id=46; printed on Jul. 24, 2006.

"Body Balance: Stress Check / DHEA & Cortisol"; Health HomeTest.com; Bearing dates of 2003-2005; pp. 1-6; B Scientific, Inc.; located at: http://www.healthhometest.com/product_info.php?products_id=43; printed on Jul. 24, 2006.

"Body Building Hormone Tests"; Home Health Testing; Bearing dates of Dec. 1, 2005 and 2000; pp. 1-3; AbDiagnostics, Inc.; located at: http://www.homehealthtesting.com/performance-hormone-tests.htm; printed on Jul. 24, 2006.

Bridges, Andrew; "HIV/AIDS patients get 1$^{st}$ once-daily pill"; Associated Press; Bearing a date of 2006; pp. 1-3; Yahoo! Inc.; located at http://news.yahoo.com/s/ap/20060712/ap_on_he_me/hiv_one_pill; printed on Jul. 12, 2006.

"Browse by: Product Category"; Hach.com; Bearing a date of 2006; pp. 1-2; Hach Company; located at: http://www.hach.com/hc/browse.exploded.product.category/PREVIOUS_BREADCRUMB_ID=/SESSIONID|BzFOVFUz TnpZME1URTBOQlpuZFdWemRFMUNTZz09QTFOVUlURQ==|; printed on Jul. 14, 2006.

Brüssow, Harald; "Phage Therapy: the *Escherichia coli* experience"; Microbiology; 2005; pp. 2133-2140; vol. 151.

Buchholz, B.A.; Doherty, E.A.; Albarghouthi, M.N.; Bogdan, F.M.; Zahn, J.M.; Barron, A.E.; "Microchannel DNA Sequencing Matrices with a Thermally Controlled 'Viscosity Switch'"; Anal. Chem.; Jan. 15, 2001; pp. 157-164 (p. 1-2); vol. 73, Issue 2; PubMed; located at: http://www.ncbi.nlm.nih.gov/entrez/query.fcgi?cmd=Retrieve&db=PubMed&list_uids=11199960&dopt=Abstract; printed on Jan. 9, 2007.

Chen, ZP; Schell, JB; Ho, CT; Chen, KY; "Green tea epigallocatechin gallate shows a pronounced growth inhibitory effect on cancerous cells but not on their normal counterparts"; Cancer Lett.; Jul. 17, 1998; pp. 173-179 (pp. 1-2); vol. 129, No. 2; PubMed; located at: http://www.ncbi.nlm.nih.gov/sites/entrez?db=pubmed; printed on Jun. 22, 2007.

Chen, Haibin; Sholl, David S.; "Predictions of Selectivity and Flux for $CH_4/H_2$ Separations Using Single Walled Carbon Nanotubes as Membranes"; Journal of Membrane Science; Bearing dates of 2005 and 2006; pp. 152-160; vol. 269; Elsevier B.V.; located at: www.sciencedirect.com and www.elsevier.com/locate/memsci.

Cheng, S.B.; Skinner, C.D.; Taylor, J.; Attiya, S.; Lee, W.E.; Picelli, G.; Harrison, D.J.; "Development of a Multichannel Microfluidic Analysis System Employing Affinity Capillary Electrophoresis for Immunoassay"; Anal. Chem.; Apr. 1, 2001; pp. 1472-1479 (p. 1); vol. 73, Issue 7; PubMed; located at: http://www.ncbi.nlm.nih.gov/entrez/query.fcgi?cmd=Retrieve&db=PubMed&list_uids=11321296&dopt=Abstract; printed on Jan. 16, 2007.

Cherif, B.; Roget, A.; Villiers, C.L.; Calemczuk, R.; Leroy, V.; Marche, P.N.; Livache, T.; Villiers, M.B.; "Application 104—Clinically Related Protein—Peptide Interactions Monitored in Real Time on Novel Peptide Chips by Surface Plasmon Resonance Imaging"; Clinical Chemistry; 2006; pp. 255-262 (pp. 1-4); vol. 52; GenOptics; located at: www.genoptics-spr.com; printed on Jan. 10, 2007.

Ching, Shanfun; Lee, Helen; Hook III, Edward W.; Jacobs, Michael R.; Zenilman, Jonathan; "Ligase Chain Reaction for Detection of *Neisseria gonorrhoeae* in Urogenital Swabs"; Journal of Clinical Microbiology; Dec. 1995; pp. 3111-3114; vol. 33, No. 12; American Society for Microbiology.

Chiu, KM; Keller, ET; Crenshaw, TD; Gravenstein, S.; "Carnitine and dehydroepiandrosterone sulfate induce protein synthesis in porcine primary osteoblast-like cells"; Calcified Tissue International; Bearing a date of Jun. 1999; pp. 527-533 (pp. 1-2); vol. 64, Issue 6; PubMed; located at: http://www.ncbi.nlm.nih.gov/entrez/query.fcgi?cmd=Retrieve&db=PubMed&list_uids=10341026&dopt=Abstract; printed on Aug. 22, 2006.

Chiu, Daniel T.; Jeon, Noo Li; Huang, Sui; Kane, Ravi S.; Wargo, Christopher J.; Choi, Insung S.; Ingber, Donald E.; Whitesides, George M.; "Patterned deposition of cells and proteins onto surfaces by using three-dimensional microfluidic systems"; PNAS; Mar. 14, 2000; pp. 2408-2413; vol. 97, No. 6; located at: http://www.pnas.org/cgi/content/abstract/97/6/2408; printed on Jan. 10, 2007.

Cho, Yoon-Kyoung; Lee, Jeong-Gun; Park, Jong-Myeon; Lee, Beom-Seok; Lee, Youngsun; Ko, Christopher; "One-Step Pathogen Specific DNA Extraction From Whole Blood On A Centrifugal Microfluidic Device"; Lab on a Chip; 2007; 6 total pages; DOI 10.1039/b616115d; located at: http://www.rsc.org/publishing/journals/LC/article.asp?doi=b616115d; printed on Feb. 26, 2007.

"Clearrx System: Body"; pp. 1-4; located at http://www.index2005.dk/Members/tenamikesy/bodyObject; printed on Jun. 21, 2006.

"Clinical Laboratory: Beckman Coulter clinical systems help to simplify and automate laboratory processes"; Beckman Coulter.com; Bearing dates of 1998-2006; p. 1; Beckman Coulter, Inc.; located at: http://www.beckmancoulter.com/productshr/pr_clinical_lab.asp; printed on Jul. 14, 2006.

Collett, J.R.; Cho, E.J.; Lee, J.F.; Levy, M.; Hood, A.J.; Wan, C.; Ellington, A.D.; "Functional RNA microarrays for high-throughput screening of antiprotein aptamers"; Anal Biochem.; Mar. 1, 2005; pp. 113-123 (p. 1); vol. 338, Issue 1; PubMed; located at: http://www.ncbi.nlm.nih.gov/entrez/query.fcgi?cmd=Retrieve&db=PubMed&dopt=Citation&list_uids=15707941; printed on Jan. 10, 2007.

Collett, J.R.; Cho, E.J.; Ellington, A.D.; "Production and processing of aptamer microarrays"; Methods; Sep. 2005; pp. 4-15 (p. 1); vol. 37, Issue 1; PubMed; located at: http://www.pubmed.com; printed on Jan. 10, 2007.

Colucci, S; Mori, G; Vaira, S; Brunetti, G; Greco, G; Mancini, L; Simone, GM; Sardelli, F; Koverech, A; Zallone, A; Grano, M; "L-carnitine and isovaleryl L-carnitine fumarate positively affect human osteoblast proliferation and differentiation in vitro"; Calcified Tissue International; Bearing a date of Jun. 2005; pp. 458-465 (pp. 1-2); vol. 76, Issue 6; PubMed; located at: http://www.ncbi.nlm.nih.gov/entrez/query.fcgi?cmd=Retrieve&db=PubMed&list_uids=15906015&dopt=Abstract; printed on Aug. 22, 2006.

"Confidential Home DNA Infidelity Testing, Infidelity Test Kit"; Gtldna.com; Bearing dates of Jul. 10, 2006 and 2002-2005; pp. 1-3; The Genetic Testing Laboratories, Inc.; located at: http://www.gtldna.com/infidelity.html; printed on Jul. 10, 2006.

Cox, J. Colin; Hayhurst, Andrew; Hesselberth, Jay; Bayer, Travis S.; Georgiou, George; Ellington, Andrew D.; "Automated selection of aptamers against protein targets translated in vitro: from gene to aptamer"; Nucleic Acids Research; 2002; pp. 1-14; vol. 30, No. 20; e108; Oxford University Press; located at: http://nar.oxfordjournals.org/cgi/reprint/30/20/e108.

Davidow, Julie; "Surge in home diagnostic kits provides doctor in a box"; Seattlepi.com; Bearing dates of Mar. 29, 2006 and 1996-2006; pp. 1-4; Seattle Post-Intelligencer; located at: http://seattlepi.nwsource.com/health/264716_hometesting29.html; printed on Jul. 10, 2006.

Davis, M.T.; Stahl, D.C.; Swiderek, K.M.; Lee, T.D.; "Capillary Liquid Chromatography/Mass Spectrometry for Peptide and Protein Characterization"; Methods: A Companion to Methods in Enzymology; Shively J.E., ed.; Sep. 1994; vol. 6, Issue 3; pp. 304-314 (pp. 1-2); ScienceDirect; located at: http://www.sciencedirect.com/science?_ob=ArticleURL&_udi=B6WN5-45NJDKF-V&_coverDate=09%2F30%2F1994&_alid=525661391&_rdoc=1&_fmt=&_orig=search&_qd=1&_cdi=6953&_sort=d&view=c&_acct=C000050221&_version=1&_urlVersion=0&_userid=10&md5=1b757b816dddb9a67c083bb90ce8b592; printed on Jan. 16, 2007.

Demello, Andrew J.; "Microfluidics: DNA Amplification Moves On"; Nature; Bearing dates of Mar. 6, 2003 and 2003; pp. 28-29; vol. 422; Nature Publishing Group; located at: www.nature.com/nature.

Dertinger, Stephan K.W.; Chiu, Daniel T.; Jeon, Noo Li; Whitesides, George M.; "Generation of Gradients Having Complex Shapes Using Microfluidic Networks"; Anal. Chem.; Mar. 15, 2001; pp. 1240-1246; vol. 73, No. 6; American Chemical Society; located at: http://nljgroup.eng.uci.edu/Articles/03%20-%20pdf%20-%20ac001132d.pdf.

"Diffusion Immunoassay (DIA)"; Basic Microfluidic Concepts; Bearing a date of Sep. 7, 2001; pp. 1-13; located at: http://faculty.washington.edu/yagerp/microfluidicstutorial/dia/diffusionimmunoassayhome.htm; printed on Jan. 17, 2007.

"Direct to Consumer Blood Test Index"; PreventiveLabs.com; Bearing a date of 2004; pp. 1-6; Preventive Services, LLC; located at: http://www.preventivelabs.com/lab_test/blood_test.cfm; printed on Jul. 10, 2006.

"DR / 2400 Portable Spectrophotometer, 115 Vac"; Hach.com; Bearing at date of 2006; p. 1; Hach Company; located at: http://www.hach.com/hc/search.product.details.invoker/PackagingCode=5940000/NewLinkLabel=DR%26frasl%3B2400+Portable+Spectrophotometer%2C+115+Vac/PREVIOUS_BREADCRUMB_ID=HC_SEARCH_KEYWORD/SESSIONID|BzFOVFUzTnpFMk56WXINUIpuZFdWemRFTk9Vdz09QTFsTklURQ==|; printed on Jul. 14, 2006.

"DR 5000 UV-VIS Spectrophotometer (115 Vac)"; Hach.com; Bearing a date of 2006; p. 1; Hach Company; located at: http://www.hach.com/hc/search.product.details.invoker/PackagingCode=DR5000-01/NewLinkLabel=DR+5000+UV-Vis+Spectrophotometer%2C+115+Vac/PREVIOUS_BREADCRUMB_ID=HC_SEARCH_BROWSE_PRODUCTSpectrophotometersColorimeters/SESSIONID|B3hOVFUx TnpjeE5qYzJNakVtWjNWbGMzUkRUZz09QWxOWIRURQ==|; printed on Jul. 14, 2006.

"Drugstore.com-online pharmacy & drugstore, prescriptions filled"; drugstore.com; Bearing dates of 1999-2006; pp. 1 (Sheets 1-3), pp. 2 (Sheets 1-4), pp. 3 (Sheets 1-2) (pp. total 1-9); drugstore.com, inc.; located at: http://www.drugstore.com/search/search.asp?searchtype=1&trx=28198&trxp1=60&ipp=20&srchtree=1&search=home+test+kit&Go.x=17&Go.y=16; printed on Jul. 10, 2006.

Duffy, SJ; Vita, JA; "Effects of phenolics on vascular endothelial function"; Current Opinion in Lipidology; Bearing a date of Feb. 2003; pp. 21-27 (p. 1); vol. 14, Issue 1; PubMed; located at: http://www.ncbi.nlm.nih.gov/entrez/query.fcgi?cmd=Retrieve&db=PubMed&list_uids=12544657&dopt=Abstract; printed on Aug. 22, 2006.

Dumont, Yannick; D'Amours, Martin; Lebel, Marcel; Larivière, Richard; "Original Article: Supplementation with a low dose of L-arginine reduces blood pressure and endothelin-1 production in hypertensive uraemic rats"; Nephrol Dial Transplant; Bearing a date of 2001; pp. 746-754; vol. 16; European Renal Association-European Dialysis and Transplant Association.

Eskin, N.A. Michael; Dictionary of Nutraceuticals and Functional Foods (Functional Foods and Nutraceuticals); Bearing a date of Dec. 19, 2005; 520 pages; ISBN No. 0849315727; CRC Press (not provided).

Eteshola, E.; Leckband, D.; "Development and characterization of an ELISA assay in PDMS microfluidic channels"; Sensors and Actuators B: Chemical; Jan. 25, 2001; vol. 72, Issue 2; pp. 129-133 (pp. 1-2); Elsevier Science B.V.-ScienceDirect; located at: http://www.sciencedirect.com/science?_ob=ArticleURL&_udi=B6THH-423HKF4-5&_user=10&_coverDate=01%2F25%2F2001&_alid=522654785&_rdoc=1&_fmt=summary&_orig=search&_cdi=5283&_sort=d&_docanchor=&view=c&_acct=C000050221&_version=1&_urlVersion=0&_userid=10&md5=41f626b13a6896a2b9bd1dca5395ade9; printed on Jan. 10, 2007.

"Family Age Groups"; testsymptomsathome.com; pp. 1-4; located at: http://www.testsymptomsathome.com/family_age_groups.asp; printed on Jul. 10, 2006.

Fan, Chunhai; Plaxco, Kevin W.; Heeger, Alan J.; "Electrochemical interrogation of conformational changes as a reagentless method for the sequence-specific detection of DNA"; PNAS; Bearing a date of Aug. 5, 2003; pp. 9134-9137; vol. 100, No. 16; located at: www.pnas.org/cgi/doi/10.1073/pnas.1633515100.

Fan, Z.H.; Mangru, S.; Granzow, R.; Heaney, P.; Ho, W.; Dong, Q.; Kumar, R.; "Dynamic DNA Hybridization on a Chip Using Paramagnetic Beads"; Anal. Chem.; Nov. 1, 1999; pp. 4851-4859 (p. 1); vol. 71, Issue 21; PubMed; located at: http://www.ncbi.nlm.nih.gov/entrez/query.fcgi?cmd=Retrieve&db=PubMed&list_uids=10565276&dopt=Abstract; printed on Jan. 9, 2007.

"FDA OKs 3-Drug Combo Pill to Treat HIV"; Bearing a date of Jun. 30, 2006; pp. 1-2; FoxNews.com; located at http://www.foxnews.com/wires/2006Jun30/0,4670,AIDSRelief,00.html; printed on Jun. 30, 2006.

Felkey, Bill G.; Berger, Bruce A.; Krueger, Kem P.; "The Pharmacist's Role in Treatment Adherence—Part 5: The Impact of Pharmacy-Specific Technology"; U.S. Pharmacist; Bearing dates of 2005, 2000- 2005; and a posted date of Aug. 18, 2005; pp. 36-39 (pp. 1-6); vol. 30:08; Jobson Publishing, L.L.C.; located at: http://www.uspharmacist.com/index.asp?show=article&page=8_1547.htm; printed on Nov. 13, 2005.

"Female Hormone Tests"; Home Health Testing; Bearing dates of Dec. 1, 2005 and 2000; pp. 1-3; AbDiagnostics, Inc.; located at: http://www.homehealthtesting.com/female-hormone-tests.htm; printed on Jul. 24, 2006.

Fitzgerald, Katherine A.; O'Neill, Luke A.J.; Gearing, Andy J.H.; Callard, Robin E.; "The Cytokine Factsbook"; Bearing a date of Sep. 2001; 515 pages; 2nd Edition; ISBN No. 0121551423; Academic Press; San Francisco, CA (not provided).

Folch, A.; JO, B.H.; Hurtado, O.; Beebe, D.J.; Toner, M.; "Microfabricated elastomeric stencils for micropatterning cell cultures"; J. Biomed Mater Res.; Nov. 2000; pp. 346-353 (p. 1); vol. 52, Issue 2; PubMed; located at: http://www.ncbi.nlm.nih.gov/entrez/query.fcgi?cmd=Retrieve&db=PubMed&list_uids=10951374&dopt=Abstract; printed on Jan. 10, 2007.

Fratamico, Pina M.; Bhunia, Arun K.; Smith, James L. (Ed.); Foodborne Pathogens: Microbiology and Molecular Biology; Sep. 1, 2005; 454 pages; ISBN 1-904455-00-X; Caister Academic Press (not provided).

Gao, Huajian; Kong, Yong; "Simulation of DNA-Nanotube Interactions"; Annual Review of Materials Research.; Bearing a date of 2004; pp. 123-150 (33 total pages); vol. 34; Annual Reviews.

Gennaro, Alfonso R. (Ed); Remington: The Science and Practice of Pharmacy; Bearing a date of Dec. 15, 2000; 2077 pages; 20th Edition; ISBN No. 0683306472; Lippincott Williams and Wilkins; Philadelphia, PA (not provided).

Geyer, C.R.; Brent, R.; "Selection of Genetic Agents From Random Peptide Aptamer Expression Libraries"; Methods in Enzymology; 2000; pp. 171-208; vol. 328, Chapter 13 (not provided).

Glasgow, I.K.; Zeringue, H.C.; Beebe, D.J.; Choi, S.J.; Lyman, J.T.; Chan, N.G.; Wheeler, M.B.; "Handling individual mammalian embryos using microfluidics"; IEEE Trans Biomed Eng.; May 2001; pp. 570-578 (p. 1); vol. 48, Issue 5; PubMed; located at: http://www.ncbi.nlm.nih.gov/entrez/query.fcgi?cmd=Retrieve&db=PubMed&list_uids=11341531&dopt=Abstract; printed on Jan. 10, 2007.

Gosslau, A; Chen, M; Ho, Ci-T; Chen, KY; "Translational Therapeutics: A methoxy derivative of resveratrol analogue selectively induced activation of the mitochondrial apoptotic pathway in transformed fibroblasts"; British Journal of Cancer; Bearing dates of 2005 and Jan. 25, 2005; pp. 513-521 (pp. 1-2); vol. 92; Online ISSN: 1532-1827; Cancer Research UK; located at: http://www.nature.com/bjc/journal/v92/n3/abs/6602300a.html; printed on Jun. 22, 2007.

Gruenewald, Tara L.; Seeman, Teresa E.; Ryff, Carol D.; Karlamangla, Arun S.; Singer, Burton H.; "Combinations of biomarkers predictive of later life mortality"; PNAS; Bearing dates of Sep. 19, 2006 and 2006; pp. 14158-14163; vol. 103, No. 38; The National Academy of Sciences of the USA; located at http://www.pnas.org/cgi/doi/10.1073/pnas.0606215103.

Guthrie, J.W.; Hamula, C.L.; Zhang, H.; Le, X.C.; "Assays for cytokines using aptamers"; Methods; Apr. 2006; pp. 324-330 (p. 1); vol. 38, Issue 4; PubMed; located at: http://www.ncbi.nlm.nih.gov/entrez/query.fcgi?cmd=Retrieve&db=PubMed&list_uids=16495077&dopt=Abstract; printed on Jan. 10, 2007.

Harlow, ED; Lane, David; Antibodies: A Laboratory Manual; Dec. 1, 1988; 726 pages; ISBN: 0879693142; Cold Spring Harbor Laboratory Press (not provided).

Hatch, A.; Kamholz, A.E.; Hawkins, K.R.; Munson, M.S.; Schilling, E.A.; Weigl, B.H.; Yager, P.; "A rapid diffusion immunoassay in a T-sensor"; "Nature biotechnology"; May 2001; pp. 461-465 (p. 1); vol. 19, Issue 5; PubMed; located at: http://www.ncbi.nlm.nih.gov/entrez/query.fcgi?cmd=Retrieve&db=PubMed&list_uids=11329017&dopt=Abstract; printed on Jan. 9, 2007.

"Heart-Help's Handbook . . . Living with CM & CHF (Cardiomyopathy & Congestive Heart Failure)"; Bearing a date of Sep. 23, 2001; pp. 1-5; located at: http://www.heart-help.net/handbook.html; printed on Nov. 13, 2005.

Heller, Daniel A.; Jeng, Esther S.; Yeung, Tsun-Kwan; Martinez, Brittany M.; Moll, Anthonie E.; Gastala, Joseph B.; Strano, Michael S.; "Optical Detection of DNA Conformational Polymorphism on Single-Walled Carbon Nanotubes"; Science; Bearing a date of Jan. 27, 2006; pp. 508-511; vol. 311; located at: www.sciencemag.org.

Herr, Amy E.; Molho, Joshua I.; Santiago, Juan G.; Kenny, Thomas W.; Borkholder, David A.; Kintz, Gregory J.; Belgrader, Phillip; Northrup, M. Allen; "Investigation of a Miniaturized Capillary Isoelectric Focusing (cIEF) System Using a Full-Field Detection Approach"; pp. 1-5; Mechanical Engineering Department, Stanford University.

"The H-Filter"; H-Filter Basics; Bearing a date of Sep. 7, 2001; pp. 1-7; located at: http://faculty.washington.edu/yagerp/microfluidicstutorial/hfilter/hfilterhome.htm; printed on Jan. 17, 2007.

Hobbs, Charlotte, A.; Sherman, Stephanie, L.; Yi, Ping; Hopkins, Sarah E.; Torfs, Claudine P.; Hine, R. Jean; Pogribna, Marta; Rozen, Rima; James, S. Jill; "Polymorphisms in Genes Involved in Folate Metabolism as Maternal Risk Factors for Down Syndrome"; Am. J. Hum. Genet.; Bearing a date of 2000; pp. 623-630; vol. 67; The American Society of Human Genetics.

Hodgson, JM; Watts, GF; Playford, DA; Burke, V; Croft, KD; "Original Communication-Coenzyme Q improves blood pressure and glycaemic control: a controlled trial in subjects with type 2 diabetes"; European Journal of Clinical Nutrition; Bearing a date of 2002; pp. 1137-1142; vol. 56; Nature Publishing Group; located at: www.nature.com/ejcn.

Holt, Jason K.; Park, Hyung Gyu; Wang, Yinmin; Stadermann, Michael; Artyukhin, Alexander B.; Grigoropoulos, Costas P.; Noy, Aleksandr; Bakajin, Olgica; "Fast Mass Transport Through Sub-2-Nanometer Carbon Nanotubes"; Science; Bearing a date of May 19, 2006; pp. 1034-1037; vol. 312; located at: www.sciencemag.org.

"Home Allergy Tests"; Home Health Testing; Bearing dates of Dec. 1, 2005 and 2000 pp. 1-3; AbDiagnostics, Inc.; located at: http://www.homehealthtesting.com/allergy-tests.htm; printed on Jul. 24, 2006.

"Home DNA Maternity Testing, Test Kit, Blood Paternity Testing"; Gtldna.com; Bearing dates of 2002-2005; pp. 2-5; The Genetic Testing Laboratories, Inc.; located at: http://www.gtldna.com/maternitytest.html; printed on Jul. 10, 2006.

"Home DNA Prenatal Paternity, Maternity, Siblingship Test, Twin Zygosity, Kinship, Immigration DNA Testing"; Gtldna.com; Bearing dates of Jul. 10, 2006 and 2002-2005; pp. 1-5; The Genetic Testing Laboratories, Inc.; located at: http://www.gtldna.com/dnatests.html; printed on Jul. 10, 2006.

"Home Test Kits, Blood Groups, Diabetes, Menopause, Prostate, Osteoporosis"; WorldWideShoppingMall.co.uk; pp. 1-2; World Wide Shopping Mall (WWSM); located at: http://www.worldwideshoppingmall.co.uk/Body-Soul/shelves/home . . . ; printed on Jul. 10, 2006.

"Home Test Kits, Hepatitis Test, HIV Test, Blood Type Test"; Quick Medical: Professional and Home Health Products; Bearing a date of 2006; pp. 1-2; located at: http://www.quickmedical.com/monitors/blood_testing/; printed on Jul. 10, 2006.

"Home Test Kits"; PriceGrabber.com; pp. 1 (Sheets 1-5), pp. 2 (Sheets 1-4), pp. 3 (1-5), pp. 4 (Sheets 1-3) (pp. total 1-17); PriceGrabber.com, Inc.; located at: http://www.pricegrabber.com/search_attrib.php/page_id=1970; printed on Jul. 10, 2006.

"Hormone Tests"; Home Health Testing; Bearing dates of Dec. 1, 2005 and 2000; pp. 1-2; AbDiagnostics, Inc.; located at: http://www.homehealthtesting.com/hormone-tests.htm?gcnd-civ; printed on Jul. 24, 2006.

"Hormone Test Kit-Blood"; The Official Web Site of John R. Lee, MD: Your Information Source for Natural Hormone Balance and Natural HRT; pp. 1-3; Hormones Etc.; located at: http://www.johnleemd.com/store/prod_btest.html; printed on Jul. 10, 2006.

"Instant Anemia Test"; Health HomeTest.com; Bearing dates of 2003-2005; pp. 1-9; B Scientific, Inc.; located at: http://www.healthhometest.com/product_info.php?products_id=81; printed on Jul. 24, 2006.

"Introducing Integrated Instrument + Reagent Analysis: Hach DR 5000™ UV-VIS Spectrophotometer and DR 2800™ Portable Spectrophotometer + new Hach TNTplus™ Vial Reagents"; Hach.com; Bearing a date of 2006; pp. 1-3; Hach Company; located at: http://www.hach.com/photometry; printed on Jul. 14, 2006.

Jain, KK; "Conference Scene: Lab-on-a-Chip and Microarrays: Discovery and Development"; Pharmacogenomics; Bearing a date of 2003; pp. 123-125; vol. 4, No. 2; Ashley Publications Ltd; located at: www.pharmaco-genomics.com.

James, S. Jill; Pogribna, Marta; Pogribny, Igor P.; Melnyk, Stepan; Hine, R. Jean; Gibson, James B.; Yi, Ping; Tafoya, Dixie L.; Swenson, David H.; Wilson, Vincent L.; Gaylor, David W.; "Abnormal folate metabolism and mutation in the methylenetetrahydrofolate reductase gene may be maternal risk factors for Down syndrome"; The American Journal of Clinical Nutrition; Bearing a date of 1999; pp. 495-501; vol. 70; American Society for Clinical Nutrition; located at: www.ajcn.org; printed on Jun. 11, 2007.

Jarvius, Jonas; DNA Tools and Microfluidic Systems for Molecular Analysis; Digital Comprehensive Summaries of Uppsala Dissertations from the Faculty of Medicine 161; Bearing a date of 2006; pp. 1-66; ISBN 91-554-6616-8; Acta Universitatis Upsaliensis Uppsala.

Jeon, Noo Li; Dertinger, Stephan K.W.; Chiu, Daniel T.; Choi, Insung S.; Stroock, Abraham D.; Whitesides, George M.; "Generation of Solution and Surface Gradients Using Microfluidic Systems"; Langmuir; 2000; pp. 8311-8316; vol. 16, No. 22; American Chemical Society; located at: http://pubs.acs.org/cgi-bin/abstract.cgi/langd5/2000/16/i22/abs/la000600b.html.

Kameoka, Jun; Craighead, Harold G.; Zhang, Hongwei; Henion, Jack; "A Polymeric Microfluidic Chip for CE/MS Determination of Small Molecules"; Anal. Chem.; 2001; pp. 1935-1941 (p. 1); vol. 73, Issue 9; American Chemical Society; located at: http://pubs.acs.org/cgi-bin/abstract.cgi/ancham/2001/73/i09/abs/ac001533t.html; printed on Jan. 10, 2007.

Kamholz, Andrew E.; Schilling, Eric A.; Yager, Paul; "Optical Measurement of Transverse Molecular Diffusion in a Microchannel"; Biophysical Journal; Apr. 2001; pp. 1967-1972; vol. 80, Issue 4; located at: http://www.biophysi.org/cgi/reprint/80/4/1967.pdf; printed on Jan. 10, 2007.

Kanauchi, O; Igarashi, K; Ogata, R; Mitsuyama, K; Andoh, A; "A yeast extract high in bioactive peptides has a blood-pressure lowering effect in hypertensive model"; Curr. Med. Chem.; Bearing a date of 2005; pp. 3085-3090 (p. 1); vol. 12, No. 26; PubMed; located at: http://www.ncbi.nlm.nih.gov/sites/entrez?db=pubmed; printed on May 17, 2007.

Katan, Martijn B.; "Editorial: Health Claims for functional foods"; BMJ; Bearing a date of Jan. 24, 2004; pp. 180-181 (pp. 1-3); vol. 328; BMJ Publishing Group Ltd.; located at: http://www.bmj.com/cgi/content/full/328/7433/180; printed on Jun. 11, 2007.

Keung, WM; "Anti-dipsotropic isoflavones: the potential therapeutic agents for alcohol dependence"; Medicinal Research Reviews; Bearing a date of Nov. 2003; pp. 669-696 (pp. 1-2); vol. 23, Issue 6; PubMed; located at: http://www.ncbi.nlm.nih.gov/entrez/query.fcgi?cmd=Retrieve&db=PubMed&list_uids=12939789&dopt=Abstract; printed on Aug. 22, 2006.

Khandurina, Julia; Mcknight, Timothy E.; Jacobson, Stephen C.; Waters, Larry C.; Foote, Robert S.; Ramsey, J. Michael; "Integrated System for Rapid PCR-Based DNA Analysis in Microfluidic Devices"; Anal. Chem.; Jul. 1, 2000; pp. 2995-3000; vol. 72, No. 13, American Chemical Society.

Khosh, Farhang; Khosh, Mehdi; "Natural Approach to Hypertension"; Alternative Medicine Review; Bearing a date of 2001; pp. 590-600; vol. 6, No. 6; Thorne Research, Inc.

Kilar, F.; Hjerten, S.; "Fast and high resolution analysis of human serum transferrin by high performance isoelectric focusing in capillaries"; Electrophoresis; Jan. 1989; pp. 23-29 (p. 1); vol. 10, Issue 1; PubMed; located at: http://www.ncbi.nlm.nih.gov/entrez/querv.fcgi?cmd=Retrieve&db=PubMed&list_uids=2714234&dopt=Abstract; printed on Jan. 10, 2007.

Kirby, Romy; Cho, Eun Jeong; Gehrke, Brian; Bayer, Travis; Park, Yoon Sok; Neikirk, Dean P.; McDevitt, John T.; Ellington, Andrew D.; "Aptamer-Based Sensor Arrays for the Detection and Quantitation of Proteins"; Anal. Chem.; 2004; pp. 4066-4075 (p. 1); vol. 76, Issue 14; located at: http://pubs.acs.org/cgi-bin/abstract.cgi/ancham/2004/76/i14/abs/ac049858n.html; printed on Jan. 10, 2007.

Kitajka, Klara; Sinclair, Andrew J.; Weisinger, Richard S.; Weisinger, Harrison S.; Mathai, Michael; Jayasooriya, Anura P.; Halver, John E.; Puskás, László G.; "Biochemistry: Effects of dietary omega-3 polyunsaturated fatty acids on brain gene expression"; PNAS; Bearing a date of Jul. 27, 2004; pp. 10931-10936; vol. 101, No. 30; The National Academy of Sciences of the USA; located at: www pnas.org/cgi/doi/10.1073/pnas.0402342101.

Klinge, CM; Blankenship, KA; Risinger, KE; Bhatnagar, S; Noisin, EL; Sumanasekera, WK; Zhao, L; Brey, DM; Keynton, RS; "Resveratrol and estradiol rapidly activate MAPK signaling through estrogen receptors alpha and beta in endothelial cells"; The Journal of Biological Chemistry; Bearing a date of Mar. 4, 2005; pp. 7460-7468 (pp. 1-2); vol. 280, Issue 9; PubMed; located at: http://www.ncbi.nlm.nih.gov/entrez/query.fcgi?cmd=Retrieve&db=PubMed&list_uids=15615701&dopt=Abstract; printed on Aug. 22, 2006.

Knipe, David M.; Howley, Peter M.; Griffin, Diane E.; Lamb, Robert A.; Martin, Malcolm A.; Fields Virology; Dec. 1, 2006; 3177 pages; 5th edition; ISBN 0781760607; Lippincott Williams & Wilkins (not provided).

Koutny, L.; Schmalzing, D.; Salas-Solano, O.; El-Difrawy, S.; Adourian, A.; Buonocore, S.; Abbey, K.; McEwan, P.; Matsudaira, P.; Ehrlich, D.; "Eight Hundred-Base Sequencing in a Microfabricated Electrophoretic Device"; Anal. Chem.; Jul. 15, 2000; pp. 3388-3391 (p. 1); vol. 72, Issue 14; PubMed; located at: http://www.ncbi.nlm.nih.gov/entrez/query.fcgi?cmd=Retrieve&db=PubMed&list_uids=10939418&dopt=Abstract; printed on Jan. 10, 2007.

Lagally, E.T.; Medintz, I.; Mathies, R.A.; "Single-Molecule DNA Amplification and Analysis in an Integrated Microfluidic Device"; Anal. Chem.; 2001; pp. 565-570 (p.1); vol. 73, Issue 3; located at: http://pubs.acs.org/cgi-bin/abstract.cgi/ancham/2001/73/i03/abs/ac001026b.html; printed Jan. 10, 2007.

Lee, Gwo-Bin; Chen, Shu-Hui; Huang, Guan-Ruey; Sung, Wang-chou; Lin, Yen-Heng; "Microfabricated plastic chips by hot embossing methods and their applications for DNA separation and detection"; Sensors and Actuators B: Chemical; Apr. 30, 2001; pp. 142-148 (pp. 1-2); vol. 75, Issues 1-2; Elsevier Science B.V.-ScienceDirect; located at: http://www.sciencedirect.com/science?_ob=ArticleURL&_udi=B6THH-42YW4DG-T&_user=10&_coverDate=04%2F30%2F2001&_alid=526564643&_rdoc=1 &_fmt=summary&_orig=search&_cdi=5283&_sort=d&_docanchor=&view=c&_acct=C000050221&_version=1&_urlVersion=0&_userid=10&md5=bfa2c2c46253874c8198955434104969; printed on Jan. 10, 2007.

Li, JX; Xue, B; Chai, Q; Liu, ZX; Zhao, AP; Chen, LB; "Antihypertensive effect of total flavonoid fraction of Astragalus complanatus in hypertensive rats"; The Chinese Journal of Physiology; Bearing a date of Jun. 30, 2005; pp. 101-106 (pp. 1-2); vol. 48, Issue 2; PubMed; located at: http://www.ncbi.nlm.nih.gov/entrez/query.fcgi?cmd=Retrieve&db=PubMed&list_uids=16201455&dopt=Abstract; printed on Aug. 22, 2006.

Lin, RC; Guthrie, S; Xie, CY; Mai, K; Lee, DY; Lumeng, L; Li, TK; "Isoflavonoid compounds extracted from Pueraria lobata suppress alcohol preference in a pharmacogenetic rat model of alcoholism"; Alcoholism, Clinical & Experimental Research; Bearing a date of Jun. 1996; pp. 659-663 (pp. 1-2); vol. 20, Issue 4; PubMed; located at: http://www.ncbi.nlm.nih.gov/entrez/query.fcgi?CMD=Display&DB=pubmed; printed on Aug. 22, 2006.

Lu, Jiebo; Ho, Chi-Tang; Ghai, Geetha; Chen, Kuang Yu; "Differential Effects of Theaflavin Monogallates on Cell Growth, Apoptosis, and *Cox*-2 Gene Expression in Cancerous *versus* Normal Cells"; Cancer Research; Bearing a date of Nov. 15, 2000; pp. 6465-6471; vol. 60.

Lu, Jiebo; Ho, Chi-Tang; Ghai, Geetha; Chen, Kuang Yu; "Resveratrol analog, 3,4,5,4,'-tetrahydroxystilbene, differentially induces pro-apoptotic p53/Bax gene expression and inhibits the growth of transformed cells but not their normal counterparts"; Carcinogenesis; Bearing a date of 2001; pp. 321-328; vol. 22, No, 2; Oxford University Press.

Lucock, Mark; "Clinical Review: Science, Medicine, and the future—Is folic acid the ultimate functional food component for disease prevention?" BMJ; Bearing a date of Jan. 24, 2004; pp. 211-214 (pp. 1-9); vol. 328; BMJ Publishing Group Ltd.; located at: http://www.bmj.com/cgi/content/full/328/7433/211; printed on Jun. 22, 2007.

Ma, Jing; Stampfer, Meir J.; Giovannucci, Edward; Artigas, Carmen; Hunter, David J.; Fuchs, Charles; Willett, Walter C.; Selhub, Jacob; Hennekens, Charles H.; Rozen, Rima; "Methylenetetrahydrofolate Reductase Polymorphism, Dietary Interactions, and Risk of Colorectal Cancer"; Cancer Research; Bearing a date of Mar. 15, 1997; pp. 1098-1102; vol. 57.

Machha, A; Mustafa, MR; "Chronic treatment with flavonoids prevents endothelial dysfunction in spontaneously hypertensive rat aorta"; Journal of Cardiovascular Pharmacology; Bearing a date of Jul. 2005; pp. 36-40 (p. 1); vol. 46, Issue 1; PubMed; located at: http://www.ncbi.nlm.nih.gov/entrez/query.fcgi?CMD=Display&DB=pubmed; printed on Aug. 22, 2006.

Macounova, K.; Cabrera, C.R.; Yager, P.; "Concentration and Separation of Proteins in Microfluidic Channels on the Basis of Transverse IEF"; Anal. Chem.; Apr. 1, 2001; pp. 1627-1633 (p. 1); vol. 73, Issue 7; PubMed; located at: http://www.ncbi.nlm.nih.gov/entrez/query.fcgi?cmd=Retrieve&db=PubMed&list_uids=11321320&dopt=Abstract; printed on Jan. 9, 2007.

Macounova, K.; Cabrera, C.R.; Holl, M.R.; Yager, P.; "Generation of Natural pH Gradients in Microfluidic Channels for Use in Isoelectric Focusing"; Anal. Chem.; Aug. 15, 2000; pp. 3745-3751 (p. 1); vol. 72, Issue 16; PubMed; located at: http://www.ncbi.nlm.nih.gov/entrez/query.fcgi?db=pubmed&cmd=Retrieve&dopt=AbstractPlus&list_uids=10959958&query_hl=5&itool=pubmed_docsum; printed on Jan. 9, 2007.

"Magnetic Fluid"; pp. 1-3; Sigma Hi-Chemical Inc.; located at: http://www.sigma-hc.co.jp/english/magnetic_fluid.html; printed on Jan. 17, 2007.

Maizels, R.M.; Blaxter, M.L.; Robertson, B.D.; Selkirk, M.E.; Parasite Antigens, Parasite Genes: A Laboratory Manual for Molecular Parasitology; Jan. 31, 1992; 234 pages; ISBN 0521419271; Cambridge University Press (not provided).

"Male Hormone Tests"; Home Health Testing; Bearing dates of Dec. 1, 2005 and 2000; pp. 1-2; AbDiagnostics, Inc.; located at: http://www.homehealthtesting.com/male-hormonne-tests.htm; printed on Jul. 24, 2006.

Malnick, Stephen; Goland, Sorel; "Folic acid as ultimate in disease prevention Beware of vitamin B12 deficiency"; BMJ; Bearing a date of Mar. 27, 2004; pp. 1-2; vol. 328, No. 769; BMJ Publishing Group Ltd.; located at: http://www.bmj.com/cgi/content/full/328/7442/769; printed on Jun. 25, 2007.

Mangels, Reed; "Vitamin B12 in the Vegan Diet"; The Vegetarian Resource Group: Nutrition; Bearing dates of 1996-2003 and Jun. 20, 2006; pp. 1-3; The Vegetarian Resource Group; located at http://www.vrg.org/nutrition/b12.htm; printed Jul. 7, 2006.

Marshall, Marilyn M.; Naumovitz, Donna; Ortega, Ynes; Sterling, Charles R.; "Waterborne Protozoan Pathogens"; Clinical Microbiology Reviews; Jan. 1997; pp. 67-85; vol. 10, No. 1; American Society for Microbiology.

McClatchey, Kenneth D.; "Clinical Laboratory Medicine"; Bearing a date of Jan. 15, 2002; 1693 pages; 2nd Edition; ISBN No. 0683307517; Lippincott Williams & Wilkins; Philadelphia, PA (not provided).

Merril, Carl R.; Biswas, Biswajit; Carlton, Richard; Jensen, Nicole C.; Creed, G. Joseph; Zullo, Steve; Adhya, Sankar; "Long-circulating bacteriophage as antibacterial agents"; Proc. Natl. Acad. Sci.; Apr. 1996; pp. 3188-3192; vol. 93.

"Microfluidic Materials: Polymeric Laminate Technology"; Polymeric Laminates; Bearing a date of Sep. 7, 2001; pp. 1-6; located at: http://faculty.washington.edu/yagerp/microfluidicstutorial/polymericlaminates/polymericlaminates.htm; printed on Jan. 17, 2007.

Mills, JL; Kirke, PN; Molloy AM; Burke, H; Conley, MR; Lee, YJ; Mayne, PD; Weir, DG; Scott, JM; "Methylenetetrahydrofolate reductase thermolabile variant and oral clefts"; Am. J. Med. Genet.; Bearing a date of Sep. 3, 1999; pp. 71-74 (p. 1); vol. 86, No. 1; PubMed; located at: http://www.ncbi.nlm.nih.gov/sites/entrez; printed on Jun. 25, 2007.

"Mineral & Toxic Element Tests"; Home Health Testing; Bearing dates of Dec. 1, 2005 and 2000; pp. 1-3; AbDiagnostics, Inc.; located at: http://www.homehealthtestin.com/mineral-tests.htm; printed on Jul. 24, 2006.

Mondal, K.; Gupta, M.N.; "The affinity concept in bioseparation: evolving paradigms and expanding range of applications"; Biomol Eng.; Jun. 2006; pp. 59-76 (p. 1); vol. 23, Issues 2-3; located at: http://www.ncbi.nlm.nih.gov/entrez/query.fcgi?cmd=Retrieve&db=PubMed&list_uids=16527537&dopt=Abstract; printed on Jan. 10, 2007.

Moritz, R.L.; Simpson, R.J.; "Application of capillary reversed-phase high-performance liquid chromatography to high-sensitivity protein sequence analysis"; J. Chromatogr; May 22, 1992; pp. 119-130 (p. 1); vol. 599, Issues 1-2; located at: http://www.ncbi.nlm.nih.gov/entrez/query.fcgi?cmd=Retrieve&db=PubMed&list_uids=1618985&dopt=Abstract; printed on Jan. 10, 2007.

Morrow, Daniel G.; Leirer, Von O.; Andrassy, Jill M.; "Using icons to convey medication schedule information"; Abstract; Science Direct; Bearing dates of Aug. 1996, May 3, 1999 and 2000; pp. 1-2; vol. 27, Issue 4; Elsevier Ltd.; located at http://www.sciencedirect.com/science_ob=ArticleURL&_ud i=B6V1 W-3WCSSG5-5&_coverDate=08%2F31%2F1996&_alid=413837048&_rdoc=1&_fmt=&_orig=search&_qd=1&_cdi=5685&_sort=d&view=c&_acct=C000050221&_version=1&_urlVersion=0&_userid=10&md5=8a92d091167ef0d84c80fe26ae9fdbae; printed on Jun. 7, 2006.

Morrow, Daniel G.; Weiner, Michael; Young, James; Steinley, Douglas; Deer, Melissa; Murray, Michael D.; "Improving Medication Knowledge Among Older Adults with Heart Failure: A Patient-Centered Approach to Instruction Design"; The Gerontologist; Bearing a date of 2005; pp. 545-552; vol. 45, No. 4; Practice Concepts; The Gerontological Society of America.

Mullan, Brian A.; Young, Ian S.; Fee, Howard; McCance, David R.; "Ascorbic Acid Reduces Blood Pressure and Arterial Stiffness in Type 2 Diabetes"; Hypertension—Journal of the American Heart Association; Bearing dates of Oct. 21, 2002 and 2002; pp. 804-809 (pp. 1-7); vol. 40; Online ISSN 1524-4563; American Heart Association, Inc.; located at: http://hyper.ahajournals.org/cgi/content/full/40/6/804; printed on May 17, 2007.

"Nano World: Fast Flow Through Nanotube Membranes (Update)"; Physorg.com; Bearing a date of 2006; pp. 1-2; United Press International; located at: www.physorg.com/news67262683.html.

Nelson, Thomas J.; Backlund, Jr., Peter S.; Yergey, Alfred L.; Alkon, Daniel L.; "Technology: Isolation of Protein Subpopulations Undergoing Protein-Protein Interactions"; Molecular & Cellular Proteomics; Feb. 14, 2002; pp. 253-259; vol. 1, Issue 3; The American Society for Biochemistry and Molecular Biology, Inc.; located at: http://www.mcponline.org/cgi/content/abstract/1/3/253.

Nissen, David (Ed); Mosby's Drug Guide; Bearing a date of 2004; ISBN No. 0-323-02872-1; Mosby, Inc: Elsevier; St. Louis, MO (not provided).

"Occult Blood (stool)—Take-Home Test Kit—$25"; St. Vincent Healthcare; Bearing a date of 2006; p. 1; located at: http://www.svh-mt.org/services/all_health/labcheck/occult_blood.htm; printed on Jul. 10, 2006.

O'Connor, T.M.; Sheehan, S.; Cryan, B.; Brennan, N.; Bredin, C.P.; "The ligase chain reaction as a primary screening tool for the detection of culture positive tuberculosis"; Thorax; 2000; pp. 955-957; vol. 55; located at: www thorax.n1 com; printed on Jan. 9, 2007.

"OnTime-RX Medication Reminders"; Bearing dates of 2000-2004; pp. 1-4; AmeliaPlex, Inc.; Orlando, FL; located at: http://www.ontimerx.com/PDA/index.asp; printed on Nov. 13, 2005.

"Ovulation Predictor: Home Testing Kits"; Pharm.uky.edu; pp. 1-2; located at :http://www.pharm.uky.edu/hometest/Ovulate/OHP.html; printed on Jul. 10, 2006.

"Pain Relief / Injuries / Home Test Kits"; Round-Earth.com; pp. 1-2; Round Earth Publishing; located at: http://roundearth.stores.yahoo.net/relaxers.html; printed on Jul. 10, 2006.

Park, YK; Kim, JS; Kang, MH; "Concord grape juice supplementation reduces blood pressure in Korean hypertensive men: double-blind, placebo controlled intervention trial"; Biofactors; Bearing a date of 2004; pp. 145-147 (p. 1); vol. 22, Nos. 1-4; PubMed; located at: http://www.ncbi.nlm.nih.gov/sites/entrez?cmd=Retrieve&db=PubMed&dopt=Citation&list_uids=15630270; printed on May 17, 2007.

"Personal Test Kits: Hormone Saliva Test, Home Hormone Test Kit"; Womenshealth.com; Bearing a date of 2005; pp. 1-3; Women's Health America, Inc.; located at: htpt://www.womenshealth.com/personaltestkit.html; printed on Jul. 10, 2006.

PCT International Search Report; International App. No. PCT/US2005/033347; Aug. 23, 2006; 4 pages.

PCT International Search Report; International App. No. PCT/US03/41466; Aug. 26, 2004; 2 pages.

PCT International Search Report; International App. No. PCT/US01/09745; Aug. 2, 2001; 1 page.

PCT International Search Report; International App. No. PCT/IL99/00122; Aug. 30, 1999; 2 pages.

Physicians' Desk Reference; The PDR Family Guide to Nutritional Supplements: An Authoritative A-to-Z Resource on the 100 Most Popular Nutritional Therapies and Nutraceuticals; Bearing a date of Nov. 2003; 3000 pages; 58$^{th}$ Edition; ISBN No. 1563634724; Thomson PDR; Montvale, NJ (not provided).

Physicians' Desk Reference; The PDR Family Guide to Nutritional Supplements: An Authoritative A-to-Z Resource on the 100 Most Popular Nutritional Therapies and Nutraceuticals; Bearing a date of Nov. 27, 2001; 352 pages; 1$^{st}$ Edition; ISBN No. 0345433769; Ballantine Books (not provided).

Pregnancy Test, Ovulation Test, Drug Test by Medimpex; Bearing a date of 2002; pp. 1-3; Medimpex United Inc.; located at: http://www.meditests.com/; printed on Jul. 10, 2006.

Premzl, Marko; Gamulin, Vera; "Comparative Genomic Analysis of Prion Genes"; BMC Genomics; Jan. 2, 2007; pp. 1-14; vol. 8, No. 1; BioMed Central Ltd.; located at: http://www.biomedcentral.com/1471-2164/8/1.

"Probiotics Basics"; Bearing a date of 2004; pp. 1-11; CDRF, Dairy & Food Culture Technologies; located at: http://www.usprobiotics.org/basics/; printed on Jul. 7, 2006.

"Quality Standards Issued For Testing Herbal Products"; ScienceDaily; Bearing dates of Apr. 18, 2006 and 1995-2006; pp. 1-2; ScienceDaily LLC; located at: http://www.sciencedaily.com/releases/2006/04/060418011332.htm; printed on Jul. 14, 2006.

Rapport, Lisa; Lockwood, Brian; Nutraceuticals; Bearing a date of Dec. 2001; 184 pages; 1$^{st}$ Edition; ISBN No. 0 85369 503 2; Pharmaceutical Press (not provided).

"Reasonably priced and battery-driven: a pocket PCR device"; Physorg.com; Bearing a date of Apr. 24, 2007; p. 1; located at: http://www.physorg.com/news96638279.html; printed on Apr. 24, 2007.

Roberts, Arthur J.; Subak-Sharpe, Genelle; O'Brien, Mary E.; Nutraceuticals: The Complete Encyclopedia of Supplements, Herbs, Vitamins, and Healing Foods; Bearing a date of Jan. 9, 2001; 669 pages; 1$^{st}$ Edition; ISBN No. 0399526323; Perigee Trade (not provided).

Sambrook, Joseph; Russell, David W.; "Molecular Cloning: A Laboratory Manual"; Bearing a date of Jan. 15, 2001; 2,344 pages; 3 Edition; ISBN 0-87969-577-3; Cold Spring Harbor Laboratory Press (not provided).

Samuel, Buck S.; Gordon, Jeffrey I.; "A Humanized Gnotobiotic Mouse Model of Host-Archaeal-Bacterial Mutualism"; PNAS; Bearing dates of 2006, Mar. 16, 2006, May 17, 2006 and Jun. 27, 2006; pp. 10011-10016; vol. 103, No. 26; The National Academy of Sciences of the USA; located at: www.pnas.org/cgi/doi/10.1073/pnas.0602187103.

Sarkar, FH; Adsule, S; Padhye, S; Kulkarni, S; Li, Y; "The role of genistein and synthetic derivatives of isoflavone in cancer prevention and therapy"; Mini Reviews in Medicinal Chemistry; Bearing a date of Apr. 2006; pp. 401-407 (pp. 1-2); vol. 6, Issue 4; PubMed; located at: http://www.ncbi.nlm.nih.gov/entrez/query.fcgi?CMD=Display&DB=pubmed; printed on Aug. 22, 2006.

"Search Results"; Health HomeTest.com; Bearing dates of 2003-2005; pp. 1-2; B Scientific, Inc.; located at: http://www.health-hometest.com/index.php?cPath=40; printed on Jul. 24, 2006.

Shizuka, F; Kido, Y; Nakazawa, T; Kitajima, H; Aizawa, C; Kayamura, H; Ichijo, N; "Antihypertensive effect of gamma-amino butyric acid enriched soy products in spontaneously hypertensive rats"; Biofactors; Bearing a date of 2004; pp. 165-167 (p. 1); vol. 22, Nos. 1-4; PubMed; located at: http://www.ncbi.nlm.nih.gov/sites/entrez?cmd=Retrieve&db=PubMed&list_uids=15630275&dopt=Abstract; printed on May 17, 2007.

Sholl, David S.; Johnson, J. Karl; "Materials Science: Making High-Flux Membranes with Carbon Nanotubes"; Science; Bearing a date of May 19, 2006; pp. 1003-1004; vol. 312; AAAS; located at: www.sciencemag.org.

"Single Parameter Test Kits"; Hach.com; Bearing a date of 2006; pp. 1-9; Hach Company; located at: http://www.hach.com/hc/browse.exploded.product.category.catalog/PRODCAT0033/NewLinkLabel=Single+Parameter+Test+Kits/PREVIOUS_BREADCRUMB_ID=HC_SEARCH_BROWSE/SESSIONID|BkUx TIRVM05UQTVPVFEzT0NabmRXVnpkRTVEVWc9PUEwdFhNVA==|; printed on Jul. 14, 2006.

Singh-Zocchi, Mukta; Dixit, Sanhita; Ivanov, Vassili; Zocchi, Giovanni; "Single-Molecule Detection of DNA Hybridization"; Bearing a date of Jun. 24, 2003; pp. 7605-7610; vol. 100, No. 13; located at: www.pnas.org/cgi/doi/10.1073/pnas.1337215100.

"Sleep Hormone Tests"; Home Health Testing; Bearing dates of Dec. 1, 2005 and 2000; pp. 1-3; AbDiagnostics, Inc.; located at: http://www.homehealthtesting.com/sleep-tests.htm; printed on Jul. 24, 2006.

"Smart Pillbox Goes Direct to Consumer"; Health Data Management; Bearing dates of Aug. 28, 2007 and Aug. 29, 2007; pp. 1-2; Health Data Management and SourceMedia, Inc.; located at: http://healthdatamanagement.com/html/news/NewsStory.cfm?articleld=15652; printed on Aug. 29, 2007.

Smith, Ann; Heckelman, Patricia E.; O'Neil, Maryadele J. (Ed); Budavari, Susan (Ed); The Merck Index: An Encyclopedia of Chemicals, Drugs and Biologicals; Bearing a date of Oct. 2001; 2564 pages;

13th Edition; ISBN No. 0911910131; John Wiley and Sons and Merck & Co. Inc.; Whitehouse Station, NJ (not provided).

Sohn, L.L.; Saleh, O.A.; Facer, G.R.; Beavis, A.J.; Allan, R.S.; Notterman, D.A.; "Capacitance cytometry: Measuring biological cells one by one"; PNAS; Sep. 26, 2000; pp. 10687-10690; vol. 97, No. 20.

Sojourner, Russell J.; Wogalter, Michael S.; "The Influence of Pictorials on Evaluations of Prescription Medication Instructions"; Drug Information Journal; Bearing a date of 1997; pp. 963-972; vol. 31; Drug Information Association, Inc.

"Spectrophotometers and Colorimeters"; Hach.com; Bearing a date of 2006; pp. 1-2; Hach Company; located at: http://www.hach.com/hc/browse.exploded.product.category.catalog/PRODCAT0001/NewLinkLabel=Spectrophotometers+%26+Colorimeters/PREVIOUS_BREADCRUMB_ID=HC_SEARCH_BROWSE/SESSIONID|A3INVE14TnpJeUITWm5kVIZ6ZEZCWIQxZEINVEUxTIE9PUNUTQ==|; printed on Jul. 14, 2006.

Steenge, Gery R.; Verhoef, Petra; Katan, Martijn B.; "Human Nutrition and Metabolism—Betaine Supplementation Lowers Plasma Homocysteine in Healthy Men and Women"; The Journal of Nutrition; Bearing a date of 2003; pp. 1291-1295; vol. 133; American Society for Nutritional Sciences; located at jn.nutrition.org; printed on May 17, 2007.

Steffora Mutschler, Ann; "ST Prototypes Medical Diagnostic Chip"; Electronic News: EDN Network; Nov. 30, 2006; pp. 1-6; Reed Business Information-Reed Elsevier Inc.; located at: http://www.edn.com/article/CA6396045.html?ref=nbra; printed on Jan. 24, 2007.

Subbiah, MT; "Nutrigenetics and Nutraceuticals: the next wave riding on personalized medicine"; Transl Res.; Bearing a date of Feb. 2007; pp. 55-61 (pp. 1-2); vol. 149, No. 2; PubMed; located at: http://www.ncbi.nlm.nih.gov/sites/entrez; printed on Jun. 25, 2007.

"Stress Hormone Tests"; Home Health Testing; Bearing dates of Dec. 1, 2005 and 2000; pp. 1-3; AbDiagnostics, Inc.; located at: http://www.homehealthtesting.com/stress-hormone-tests.htm; printed on Jul. 24, 2006.

Swiderek, K.M.; Lee, T.D.; Shively, J.E.; Trace Structural Analysis of Proteins; Methods of Enzymology; 1996; pp. 68-86; vol. 271, Spectrum, Publisher Services (not provided).

"Talking Medicine Identifiers"; Bearing a date of Jul. 10, 2003; pp. 1-5.

Taylor, Richard; Protein Immobilization: Fundamentals and Applications; 1991; 377 pages; ISBN 0824782712; Marcel Dekker, Inc.; New York (not provided).

"The T-Sensor"; Bearing a date of Sep. 7, 2001; pp. 1-5; located at: http://faculty.washington.edu/yagerp/microfluidicstutorial/tsensor/tsensor.htm; printed on Jan. 17, 2007.

Tooley, P.W.; Hatziloukas, E.; Scott, D.L.; Carras, M.M.; "Epidemiology: Use of ligase chain reaction for enhanced detection of *Phytophthora infestans*"; Can. J. Plant Pathol.; 2002; pp. 294-301; vol. 24.

Ulrich, H.; "RNA aptamers: from basic science towards therapy"; Handb. Exp. Pharmacol.; 2006; pp. 305-326 (pp. 1-2); vol. 173; PubMed; located at: http://www.ncbi.nlm.nih.gov/entrez/query.fcgi?cmd=Retrieve&db=PubMed&list_uids=16594622&dopt=Abstract; printed on Jan. 10, 2007.

"UV-Vis-NIR Advantage Note"; Bearing a date of May 2005; No. 1; pp. 1-3; Varian, Inc.; located at: www.varianinc.com/image/vimage/docs/applications/apps/uv_anl.pdf; printed on Jul. 14, 2006.

"UV-Vis-IR-Raman Spectrophotometers"; Micro Photonics; Bearing a date of Dec. 7, 2005; pp. 1-2; Micro Photonics, Inc.; located at: http://www.microphotonics.com/spectrophotometer.html; printed on Jul. 14, 2006.

Vieira DA Costa, VA; Vianna, LM; "Effect of alpha-tocopherol supplementation on blood pressure and lipidic profile in streptozotocin-induced diabetes mellitus in spontaneously hypertensive rats"; Clin. Chim. Acta.; Bearing a date of Jan. 2005; pp. 101-104 (p. 1); vol. 351, Nos. 1-2; PubMed; located at: http://www.ncbi.nlm.nih.gov/sites/entrez; printed on May 17, 2007.

Wald, NJ; Law, MR; "A strategy to reduce cardiovascular disease by more than 80%"; BMJ; Jun. 28, 2003; pp. 1-6; vol. 326; located at: www.bmj.com.

Wallerath, T; Deckert, G; Ternes, T; Anderson, H; Li, H; Witte, K; Forstermann, U; "Resveratrol, a polyphenolic phytoalexin present in red wine, enhances expression and activity of endothelial nitric oxide synthase"; Circulation; Bearing a date of Sep. 24, 2002; pp. 1652-1658 (pp. 1-2); vol. 106, Issue 13; PubMed; located at: http://www.ncbi.nlm.nih.gov/entrez/query.fcgi?cmd=Retrieve&db=PubMed&list_uids=12270858&dopt=Abstract; printed on Aug. 22, 2006.

Walji, Rishma; "Acidophilus Effects, Benefits and Other Information"; About: Alternative Medicine; Bearing a date of 2006; p. 1; About, Inc., A part of *The New York Times Company*; located at: http://altmedicine.about.com/cs/digestiveproblems/a/Acidophilus.htm; printed on Jul. 7, 2006.

Walji, Rishma; "What are Probiotics?"; About: Alternative Medicine; Bearing a date of 2006; p. 1; About, Inc., A part of *The New York Times Company*; located at: http://altmedicine.about.com/cs/digestiveporblems/a/Acidophilus_2.htm; printed on Jul. 7, 2006.

Walter, G.; Bussow, K.; Lueking, A.; Glokler, J.; "High-throughput protein arrays: prospects for molecular diagnostics"; Trends Mol. Med.; Jun. 2002; pp. 250-253 (p. 1); vol. 8, Issue 6; PubMed; located at: http://www.ncbi.nlm.nih.gov/entrez/query.fcgi?cmd=Retrieve&db=PubMed&list_uids =12067604&dopt=Abstract; printed on Jan. 10, 2007.

Wan, Ruiqian; Camandola, Simonetta; Mattson, Mark P.; "Dietary supplementation with 2-deoxy-d-glucose improves cardiovascular and neuroendocrine stress adaptation in rats"; Am. J. Physiol Heart Circ. Physiol; Bearing dates of Oct. 10, 2003 and Apr. 26, 2004; pp. 1-13; vol. 287; American Physiological Society; located at: http://ajpheart.physiology.org/cgi/content/full/287/3/H1186; printed on May 17, 2007.

Wang, J.; Li, J.; Baca, AJ.; Hu, J.; Zhou, F.; Yan, W.; Pang, DW.; "Amplified Voltammetric Detection of DNA Hybridization via Oxidation of Ferrocene Caps on Gold Nanoparticle/Streptavidin Conjugates"; Anal. Chem.; Bearing a date of Aug. 1, 2003; pp. 3941-3945 (p. 1); vol. 75, No. 15; PubMED; located at: http://www.ncbi.nlm.nih.gov/entrez/query.fcgi?cmd=Retrieve&db=PubMed&list_uids=14572067&dopt=Abstract; printed on Nov. 29, 2006.

Warren, Erin N.; Elms, Phillip J.; Parker, Carol E.; Borchers, Christoph H.; "Development of a Protein Chip: A MS-Based Method for Quantitation of Protein Expression and Modification Levels Using an Immunoaffinity Approach"; Anal. Chem.; 2004; pp. 4082-4092 (p. 1); vol. 76, Issue 14; located at: http://pubs.acs.org/cgi-bin/abstract.cgi/ancham/2004/76/i14/abs/ac049880g.html; printed on Jan. 10, 2007.

West, SG; Likos-Krick, A; Brown, P; Mariotti, F; "Oral L-arginine improves hemodynamic responses to stress and reduces plasma homocysteine in hypercholesterolemic men"; J. Nutr.; Bearing a date of Feb. 2005; pp. 212-217 (p. 1-2); vol. 135, No. 2; PubMed; located at: http://www.ncbi.nlm.nih.gov/sites/entrez?cmd=Retrieve&db=pubmed&dopt=Abstract&list_uids=15671215; printed on Jun. 25, 2007.

"What are Probiotics?"; USProbiotics; Bearing a date of 2004; 1 page; CDRF, Dairy & Food Culture Technologies; located at: http://www.usprobiotics.org/mainpageframe.htm; printed on Jul. 7, 2006.

Widdershoven, J.; Van Munster, P.; De Abreu, R.; Bosman, H.; Van Lith, TH.; Van Der Putten-Van Meyel, M.; Motohara, K.; Matsuda, I.; "Four Methods Compared for Measuring Des-Carboxy-Prothrombin (PIVKA-II)"; Clinical Chemistry; Bearing a date of 1987; pp. 2074-2078; vol. 33, No. 11.

Wilson, A; Platt, R; Wu, Q; Leclerc, D; Christensen, B; Yang, H; Gravel, RA; Rozen, R; "A common variant in methionine synthase reductase combined with low cobalamin (vitamin B12) increases risk for spina bifida"; Mol. Genet. Metab.; Bearing a date of Aug. 1999; pp. 317-323 (p. 1); vol. 67, No. 4; PubMed; located at: http://www.ncbi.nlm.nih.gov/sites/entrez; printed on Jun. 25, 2007.

Wildman, Robert E.C.; Handbook of Nutraceuticals and Functional Foods; Bearing a date of Nov. 10, 2000; 568 pages; 1st Edition; ISBN No. 0849387345; CRC Press (not provided).

Woolley, AT et al.; "Functional integration of PCR amplification and capillary electrophoresis in a microfabricated DNA analysis device"; Anal Chem; Bearing a date of Dec. 1, 1996; pp. 4081-4086 (p. 1); vol. 68, No. 23; PubMed; located at: http://www.ncbi.nlm.nih.gov; printed on Aug. 2, 2007.

Wu, Jiaqi; Pawliszyn, Janusz; "Isoelectric focusing of proteins in a microcapillary with universal concentration gradient detection"; Journal of Microcolumn Separations; 1992; pp. 419-422 (pp. 1-2);

vol. 4, Issue 5; located at: http://www3.interscience.wiley.com/cgi-bin/abstract/110429293/ABSTRACT?CRETRY=1&SRETRY=0; printed on Jan. 10, 2007.

Wynn, Susan G.; Emerging Therapies: Using Herbs and Nutraceuticals for Small Animals; Bearing a date of 1999; 160 pages; 1st Edition; ISBN No. 1583260102; American Animal Hospital Assn Press (not provided).

Xiao, YI; Lubin, Arica A.; Baker, Brian R.; Plaxco, Kevin W.; Heeger, Alan J.; "Single-Step Electronic Detection of Femtomolar DNA by Target-Induced Strand Displacement in an Electrode-Bound Duplex"; PNAS; Bearing a date of Nov. 7, 2006; pp. 16677-16680; vol. 103, No. 45; located at: www.pnas.org/cgi/doi/10.1073/pnas.0607693103.

Xu, J.; Lee, C.S.; Locascio, L.E.; "Isoelectric focusing of green fluorescent proteins in plastic microfluidic channels"; Abstracts of Papers of the American Chemical Society; 2000; vol. 219, 9-ANYL (not provided).

Yang, Tinglu; Jung, Seung-Yong; Mao, Hanbin; Cremer, Paul S.; "Fabrication of Phospholipid Bilayer-Coated Microchannels for On-Chip Immunoassays"; Anal. Chem.; 2001; pp. 165-169 (p. 1); vol. 73, Issue 2; American Chemical Society; located at: http://pubs.acs.org/cgi-bin/abstract.cgi/ancham/2001/73/i02/abs/ac000997o.html; printed on Jan. 10, 2007.

Yang, Jun; Huang, Ying; Wang, Xiao-Bo; Becker, Frederick F.; Gascoyne, Peter R.C.; "Cell Separation on Microfabricated Electrodes Using Dielectrophoretic/Gravitational Field-Flow Fractionation"; Anal. Chem.; 1999; pp. 911-918 (p. 1); vol. 71, Issue 5; American Chemical Society; located at: http://pubs.acs.org/cgi-bin/abstract.cgi/ancham/1999/71/i05/abs/ac981250p.html; printed on Jan. 10, 2007.

Yang, Peilin; Whelan, Rebecca J.; Mao, Yingwei; Lee, Angel W.M.; Carter-Su, Christin; Kennedy, Robert T.; "Multiplexed Detection of Protein-Peptide Interaction and Inhibition Using Capillary Electrophoresis"; Anal. Chem.; ASAP Article; Bearing a date of Dec. 8, 2006; p. 1; DOI 10.1021/ac061936e S0003-2700(06)01936-6; American Chemical Society; located at: http://pubs.acs.org/cgi-bin/abstract.cgi/ancham/asap/abs/ac061936e.html; printed on Jan. 10, 2007.

PCT International Search Report; International App. No. PCT/US07/25379; May 13, 2008; 1-2.

PCT International Search Report; International App. No. PCT/US07/25417; May 14, 2008; pp. 1-3.

PCT International Search Report; International App. No. PCT/US07/25417; May 19, 2008; pp. 1-2.

PCT International Search Report; International App. No. PCT/US2007/025450; May 23, 2008; pp. 1-2.

PCT International Search Report; International App. No. PCT/US06/47835; Jul. 14, 2008; pp. 1-2.

EPA European Search Report, European App. No. EP 08 25 1104; Sep. 23, 2008; pp. 1-6.

Gehring, Andrew et al.; "Enzyme-linked immunomagnetic chemiluminescent detection of *Escherichia coli* O157:H7"; Journal of Immunological Methods; bearing a date of 2004; pp. 97-106; vol. 293; Elsevier B.V.

International Search Report; International App. No. PCT/US2008/001255; Nov. 18, 2008; pp. 1-3.

Yeung et al.; "A DNA biochip for on-the-spot multiplexed pathogen identification"; Nucleic Acids Research; bearing a date of Sep. 25, 2006; pp. e118, 1-7; vol. 34, No. 18; Oxford Journals; located at http://nar.oxfordjournals.org/cgi/content/full/34/18/e118.

PCT International Search Report; International App. No. PCT/US06/44664; Apr. 14, 2008; pp. 1-3.

PCT International Search Report; International App. No. PCT/US06/44269; Sep. 18, 2007; pp. 1-2.

Smith, Stevie; "New Chip Identifies Bird Flu in Humans"; The Tech Herald.com, WOTR Limited; 2008; located at: www.thetechherald.com/article/php200813/520/new-chip-identifies-bird-flu-in-humans; Bearing a date of Mar. 25, 2008; printed on Sep. 8, 2008; pp. 1-6.

PCT International Search Report; International App. No. PCT/US07/25451; Sep. 15, 2008; pp. 1-2.

PCT International Search Report; International App. No. PCT/US07/20272; Sep. 15, 2008; pp. 1-2.

PCT International Search Report; International App. No. PCT/US07/20305; Sep. 11, 2008; pp. 1-2.

PCT International Search Report; International App. No. PCT/US07/20283; Sep. 11, 2008; pp. 1-2.

PCT International Search Report; International App. No. PCT/US07/14994; Sep. 9, 2008; pp. 1-2.

PCT International Search Report; International App. No. PCT/US08/07993; Sep. 8, 2008; pp. 1-3.

PCT International Search Report; International App. No. PCT/US06/47451; Sep. 5, 2008; pp. 1-2.

PCT International Search Report; International App. No. PCT/US06/44658; Aug. 29, 2008; pp. 1-2.

PCT International Search Report; International App. No. PCT/US06/44279; Aug. 19, 2008; pp. 1-3.

PCT International Search Report; International App. No. PCT/US06/44283; Aug. 18, 2008; pp. 1-2.

PCT International Search Report; International App. No. PCT/US07/14266; Jul. 21, 2008; pp. 1-2.

Gelfand, Alexander; "Device Offers a Roadside Dope Test"; Technology Review; Aug. 4, 2009; pp. 1-4; Published by MIT; located at http://www.technologyreview.com/biomedicine/23111/; printed on Aug. 10, 2009.

Smith, Stevie; "New Chip Identifies Bird Flu in Humans"; The Tech Herald; Mar. 25, 2008; pp. 1-5; WOTR Limited; located at: http://www.thetechherald.com/article.php/200813/520/New-chip-identifies-bird-flu-in-humans; printed on Apr. 10, 2008.

"STMicroelectronics Introduces Flu Detection Laboratory on a Chip"; International Herald Tribune; Mar. 25, 2008; p. 1; located at: http://www.iht.com/articles/2008/03/24/business/strn.php; printed on Apr. 10, 2008.

Evans, R. Scott, Ph.D. et al., "A Computer-Assisted Management Program For Antibiotics And Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C.C., J.F.L., J.P.B.), Critical Care (T.P.C., L.K.W., J.F.O.,), and Medical Informatics (R.S.E.), LDS Hospital, Salt Lake City, UT.

EPA European Search Report, European App. No. EP 08 25 1104; May 4, 2009; pp. 1-2.

Liu, Robin Hui et al., "Validation of A Fully Integrated Microfluidic Array Device for Influenza A Subtype Identification and Sequencing"; Analytical Chemistry; bearing a date of Jun. 15, 2006; pp. 4184-4193; vol. 78, No. 12; XP0025122061 ; Issn: 0003-2700.

Liu, Wen-Tso et al., "Microfluidic Device As a New Platform For Immunofluorescent Detection of Viruses"; Lab On A Chip; bearing a date of Nov. 2005; pp. 1327-1330; vol. 5; No. 11; XP002512207; Issn: 1473-0197.

PCT International Search Report; International App. No. PCT/US 06/47436; Jan. 30, 2008; pp. 1-2.

Lagally, E.T. et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.

Leibovici, Leonard et al.; "A Causal Probabilistic Network for Optimal Treatment of Bacterial Infections"; IEEE Transactions On Knowledge And Data Engineering; bearing a date of Jul./Aug. 2000; pp. 517-528; vol. 12, No. 4; © 2000 IEEE.

UK Intellectual Property Office Examination Report Under Section 18(3); App. No. GB0915119.2; Oct. 20, 2010 (received by our Agent on Oct. 22, 2010); pp. 1-5.

Yager, Paul; "Biosensors from Membrane Proteins Reconstituted in Polymerized Lipid Bilayers"; United States Statutory Invention Registration No. H201; Published on Jan. 6, 1987; 6 Total Pages.

Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.

Sriskanthan, N. and Subramanian, K. R.; "Braille Display Terminal For Personal Computers"; IEEE Transactions on Consumer Electronics; May 1990; pp. 121-128; vol. 36, No. 2; IEEE.

Edible Science; bearing dates of 2005-2010; pp. 1-2; located at: http://www.ediblescience.com; printed on May 13, 2010.

Fightermins; bearing a date of 2010; 1 page; located at: http://www.fightermins.com/index.jsp; printed on May 13, 2010.

Ideal Health; "Custom Essentials"; "The Priva Test"; bearing a date of 2010; total of 5 pages; located at: http://www.idealhealth.com; printed on May 13, 2010; The Trump Network.

I-Vita; bearing a date of 2009; 1 page; located at: http://www.mynutrapack.com/index.html; printed on May 13, 2010.

LifeScript; bearing dates of 1998-2010; 1 page; located at: http://vitamins.lifescript.com/Begin.asp?BID=14971&PROMO=zluswiec; printed on May 13, 2010.

Mindell, Earl, Dr.; Vitaganic "Custom-Made Multivitamins"; bearing dates of 2005-2010; 1 page; located at: http://drmindell.vitaganic.com/; printed on May 13, 2010.

My Vitamin Clinic; bearing a date of 2010; 1 page; located at: http://www.myvitaminclinic.com/index.jsp; printed on May 13, 2010.

MyNutraPack; 1 page; located at: http://www.mynutrapack.com/index.html; printed on May 25, 2010.

MyVitaminRx; bearing a date of 2007; 1 page; located at: http://www.myvitaminsrx.com/CustoinNutrition/CustomNutrition,aspx?ID=MoonlightSpa; printed on May 13, 2010.

Nature Made; pp. 1-2; located at: http://www.naturemade.com/; printed on May 13, 2010.

NutriHerb; bearing dates of 2001-2009; pp. 1-2; Nutri Herb, Inc.; located at: http://www.nutriherb.net/custom_made_to_order_herbal_vitamins_supplements.html; printed on May 13, 2010.

Pharmavite LLC; 1 page; located at: http://www.pharmavite.com/index.asp; printed on May 13, 2010.

"Pharmavite LLC Launches New Diret-to-Consumer Company" Press Release; Pharmavite LLC; bearing a date of Sep. 4, 2009; 1 page; located at: http://www.pharmavite.com/MediaCenter/MC_PR.asp?ID=164; printed on May 13, 2010.

Signature Supplements; bearing a date of 2009; pp. 1-2; located at: http://www.signaturesupplements.com/jsp/main/index.jsp; printed on May 13, 2010; Signature Supplements.

Soyjoy®; bearing a date of 2010; 1 page; located at: http://www.soyjoy.com/index.aspx; printed on May 13, 2010; Pharmavite LLC.

Total Health Nutrients; pp. 1-2; located at: http://www.totalhealthnutrients.com/ph/index.html; printed on May 13, 2010.

VitaminID.com; bearing a date of 2010; 1 page; located at: http://www.vitaminid.com/webapp/wcs/stores/servlet/StoreView?storeId=201&langId=-1; printed on May 25, 2010; Pharmavite Direct LLC.

Vitamins On Demand; bearing a date of 2010; 1 page; located at: http://www.vitaminsondemand.com/?gclid=CNbygPut9aACFRYhDQodvGkivw; printed on May 13, 2010.

VitaXact; bearing a date of 2009; 1 page; located at: http://www.vitaxact.com; printed on May 13, 2010.

Weil, Andrew, M.D.; "Dr. Weil's Vitamin Advisor & Complete Program Supplements"; bearing a date of 2010; 1 page; located at: https://www.drweilvitaminadvisor.corn/drw/ecs/Va2/land_goog_08girl.html?aid=999910&aparam=TSAsGoogleApr10VA_vitamins&refed=GO000000101882154s_vitarnins&tsacr=GO3784957603&gclid=CM3NpLzm9aACFRYhDQodvGkivw; printed on May 13, 2010; Weil Lifestyle Custom Pak.

UK Intellectual Property Office Examination Report Under Section 18(3); App. No. GB1000316.8; Jul. 26, 2011; pp. 1-3.

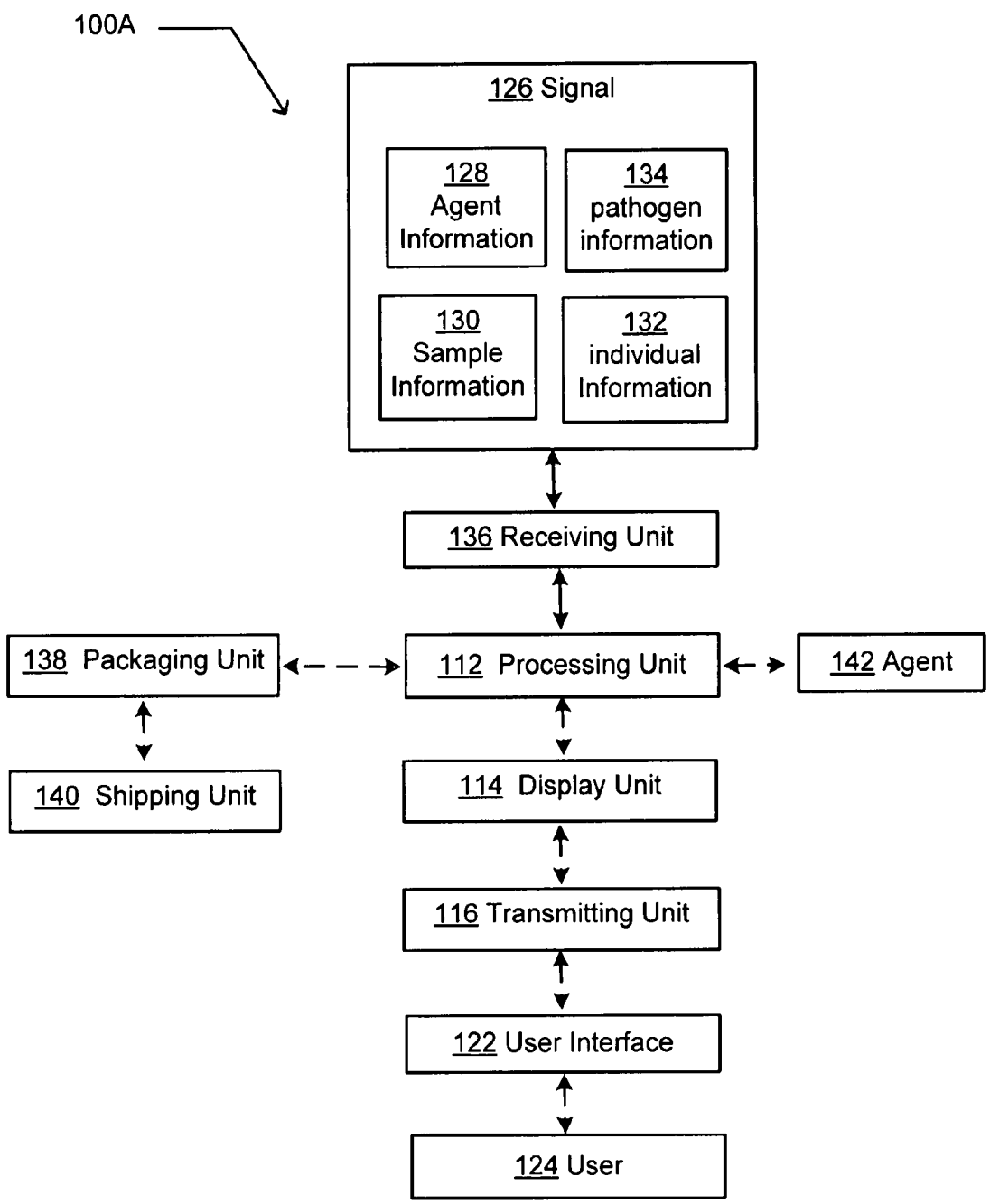

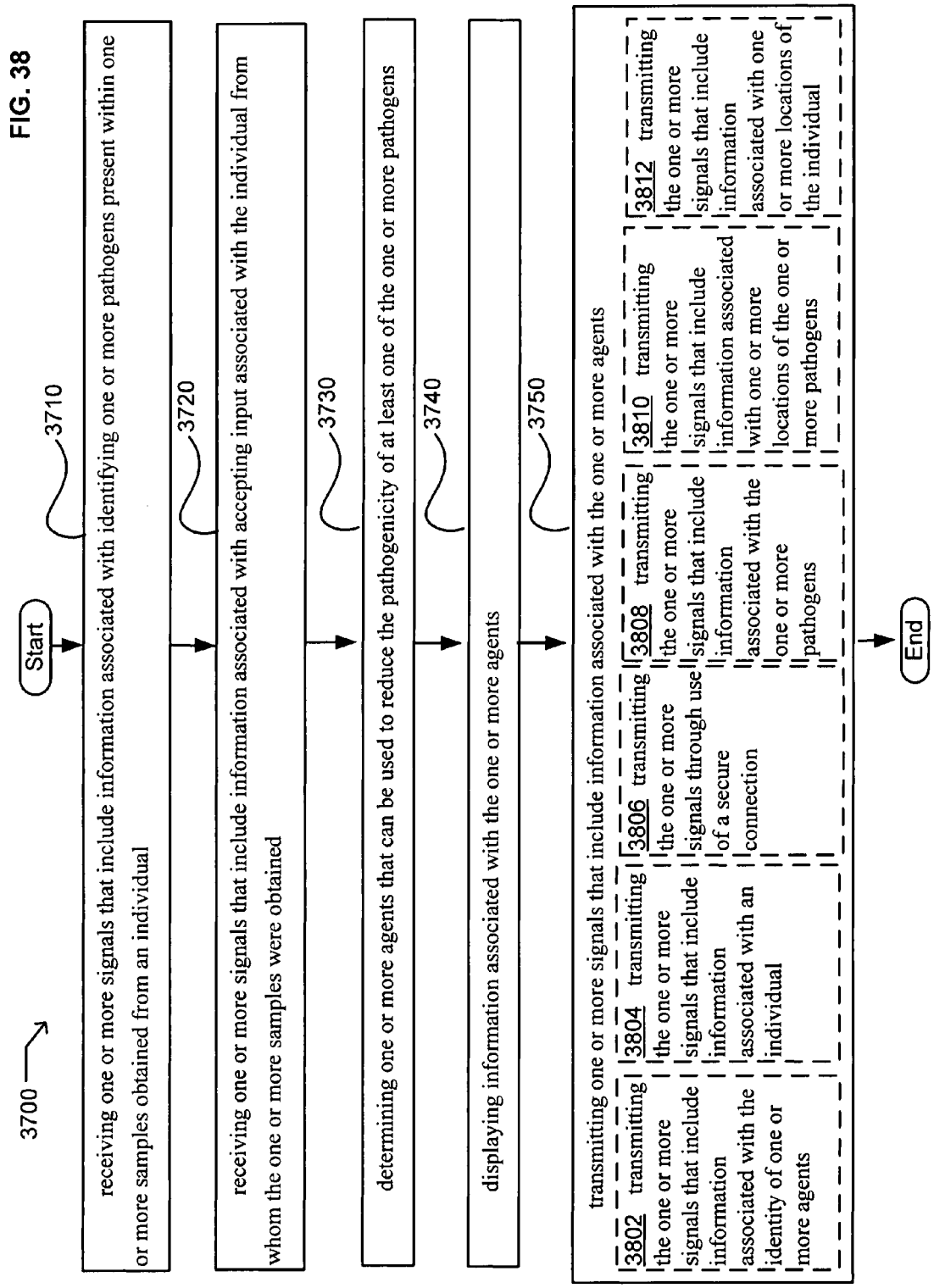

Start

↓ 3910 receiving one or more signals that include information associated with identifying one or more pathogens present within one or more samples obtained from an individual

↓ 3920 receiving one or more signals that include information associated with accepting input associated with the individual from whom the one or more samples were obtained

↓ 3930 determining one or more agents that can be used to reduce the pathogenicity of at least one of the one or more pathogens

↓ 3940 displaying information associated with the one or more agents

↓ 3950 transmitting one or more signals that include information associated with the one or more agents

↓ 3960 packaging the one or more agents

↓

End

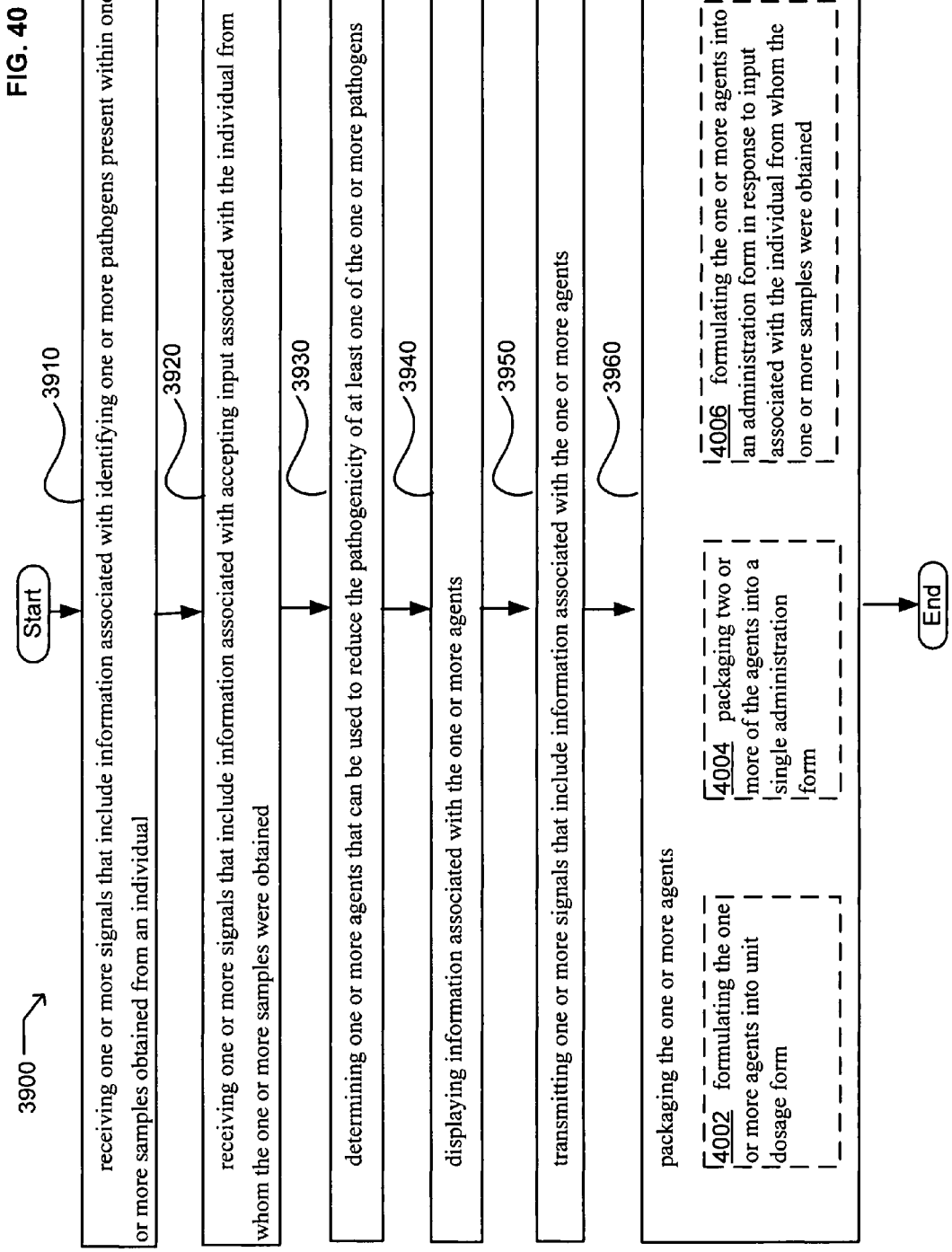

Start

4210 — receiving one or more signals that include information associated with identifying one or more pathogens present within one or more samples obtained from an individual

4220 — receiving one or more signals that include information associated with accepting input associated with the individual from whom the one or more samples were obtained

4230 — determining one or more agents that can be used to reduce the pathogenicity of at least one of the one or more pathogens

4240 — displaying information associated with the one or more agents

4250 — transmitting one or more signals that include information associated with the one or more agents

4260 — packaging the one or more agents

4270 — shipping one or more packages that include the one or more agents

End

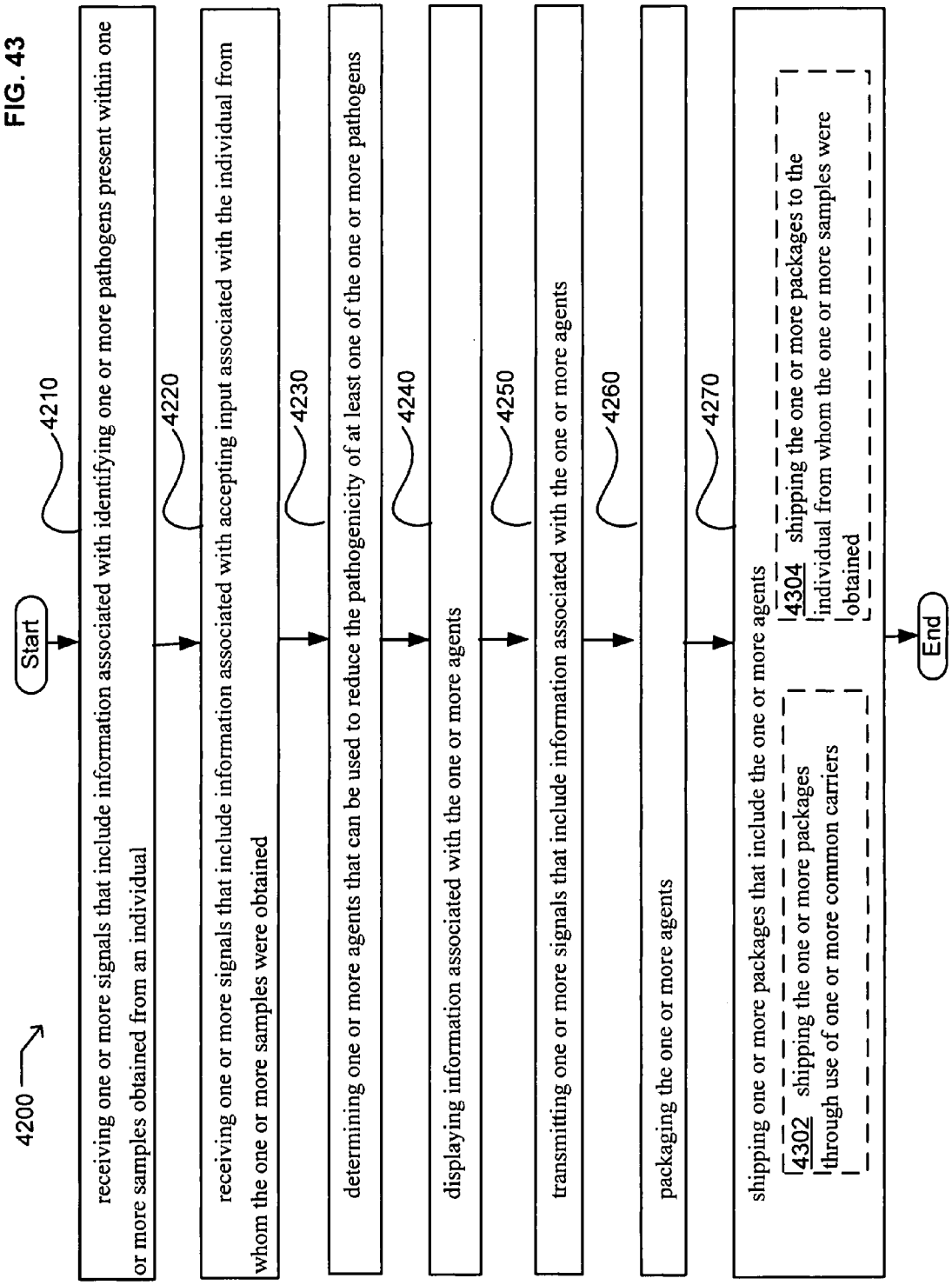

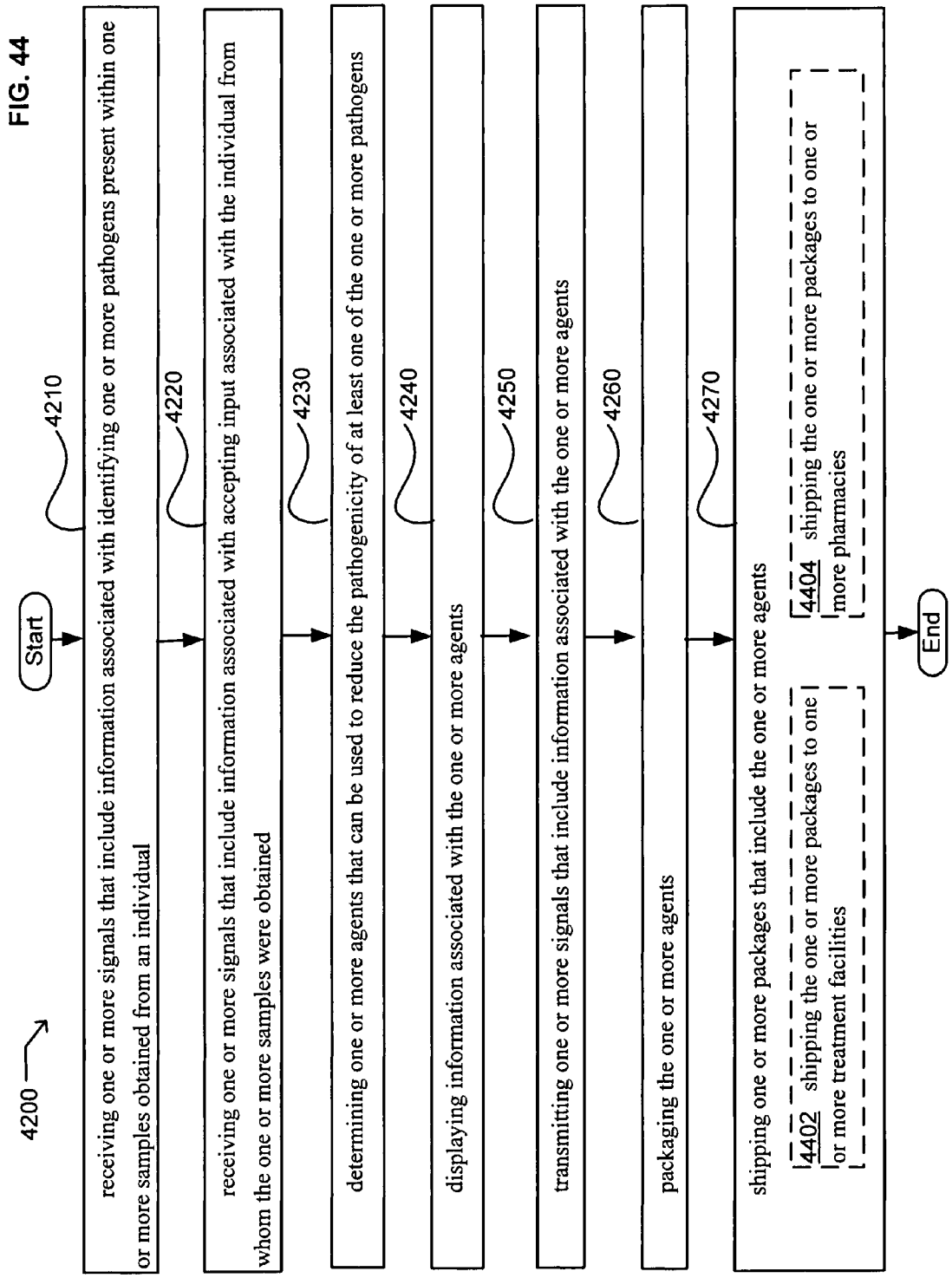

FIG. 45A

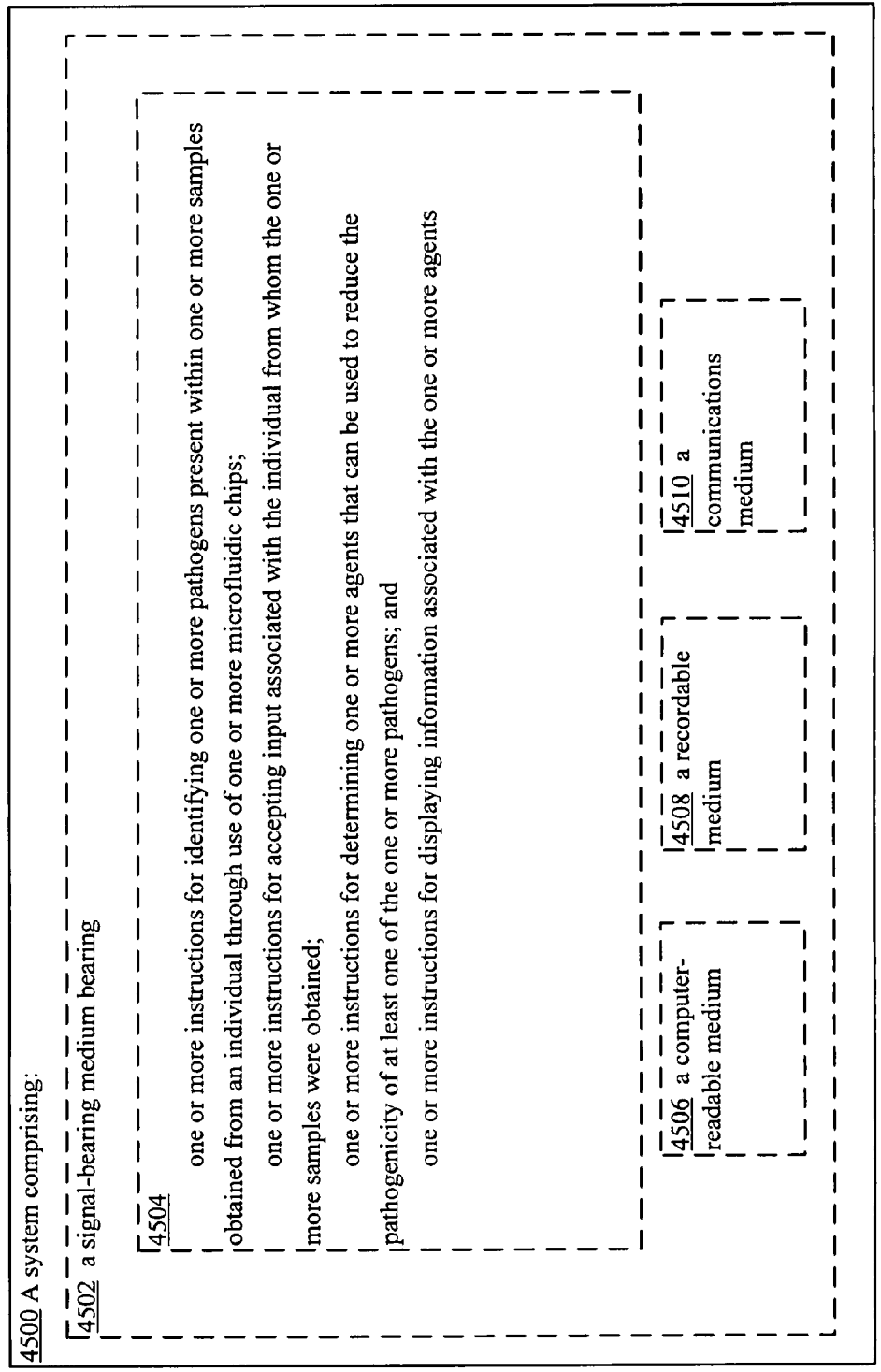

4500 A system comprising:
4502 a signal-bearing medium bearing 4504
one or more instructions for identifying one or more pathogens present within one or more samples obtained from an individual through use of one or more microfluidic chips;
one or more instructions for accepting input associated with the individual from whom the one or more samples were obtained;
one or more instructions for determining one or more agents that can be used to reduce the pathogenicity of at least one of the one or more pathogens; and
one or more instructions for displaying information associated with the one or more agents 4506 a computer-readable medium
4508 a recordable medium
4510 a communications medium

SYSTEMS AND METHODS FOR TRANSMITTING PATHOGEN RELATED INFORMATION AND RESPONDING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/900,637, entitled SYSTEMS AND METHODS FOR PATHOGEN DETECTION AND RESPONSE, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 11 Sep. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/900,649, entitled SYSTEMS AND METHODS FOR RECEIVING PATHOGEN RELATED INFORMATION AND RESPONDING, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 11 Sep. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/893,608, entitled COMPUTATIONAL SYSTEMS AND METHODS RELATED TO NUTRACEUTICALS, naming Edward K. Y. Jung, Royce A. Levien, Robert W. Lord, Mark A. Malamud, John D. Rinaldo, Jr., Clarence T. Tegreene; and Lowell L. Wood, Jr. as inventors, filed 15 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/893,606, entitled COMPUTATIONAL SYSTEMS AND METHODS RELATED TO NUTRACEUTICALS, naming Edward K. Y. Jung, Royce A. Levien, Robert W. Lord, Mark A. Malamud, John D. Rinaldo, Jr., Clarence T. Tegreene; and Lowell L. Wood, Jr. as inventors, filed 15 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/893,605, entitled COMPUTATIONAL SYSTEMS AND METHODS RELATED TO NUTRACEUTICALS, naming Edward K. Y. Jung, Royce A. Levien, Robert W. Lord, Mark A. Malamud, John D. Rinaldo, Jr., Clarence T. Tegreene; and Lowell L. Wood, Jr. as inventors, filed 15 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/888,627, entitled COMPUTATIONAL METHODS AND SYSTEMS ASSOCIATED WITH NUTRACEUTICAL RELATED ASSAYS, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 31 Jul. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/888,614, entitled METHODS AND SYSTEMS RELATED TO RECEIVING NUTRACEUTICAL ASSOCIATED INFORMATION, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 31 Jul. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/888,613, entitled METHODS AND SYSTEMS RELATED TO TRANSMISSION OF NUTRACEUTICAL ASSOCIATED INFORMATION, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 31 Jul. 2007, now U.S. Pat. No. 7,287,042, or is an application of which a currently co-pending application is entitled to the benefit of the filing date.

For purposes of the USPTO extra-statutory requirements, the present application constitutes a continuation-in-part of U.S. patent application Ser. No. 11/824,529, entitled COMPUTATIONAL SYSTEMS AND METHODS RELATED TO NUTRACEUTICALS, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 28 Jun. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/824,604, entitled COMPUTATIONAL SYSTEMS RELATED TO NUTRACEUTICALS, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 28 Jun. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/799,465, entitled FLUIDIC DEVICES, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 30 Apr. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/799,462, entitled FLU- IDIC METHODS, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 30 Apr. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/729,301, entitled METHODS FOR PATHOGEN DETECTION, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 27 Mar. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/729,276, entitled DEVICES FOR PATHOGEN DETECTION, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 27 Mar. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/729,275, entitled MICROFLUIDIC CHIPS FOR PATHOGEN DETECTION, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 27 Mar. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/729,274, entitled SYSTEMS FOR PATHOGEN DETECTION, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 27 Mar. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/637,638, entitled METHODS AND SYSTEMS FOR ANALYSIS OF NUTRACEUTICAL ASSOCIATED COMPONENTS, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 11 Dec. 2006, now U.S. Pat. No. 7,927,787, or is an application of which a currently co-pending application is entitled to the benefit of the filing date.

For purposes of the USPTO extra-statutory requirements, the present application constitutes a continuation-in-part of U.S. patent application Ser. No. 11/637,616, entitled METHODS AND SYSTEMS FOR ANALYSIS OF NUTRACEUTICAL ASSOCIATED COMPONENTS, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 11 Dec. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/523,809, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed 18 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/523,766, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed 18 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/518,540, entitled INDIVIDUALIZED PHARMACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 8 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/515,357, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed 1 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/486,998, entitled COMPUTATIONAL AND/OR CONTROL SYSTEMS RELATED TO INDIVIDUALIZED PHARMACEUTICAL AND NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/486,973, entitled COMPUTATIONAL AND/OR CONTROL SYSTEMS RELATED TO INDIVIDUALIZED PHARMACEUTICAL AND NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,341, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,296, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/474,109, entitled CUSTOMIZED VISUAL MARKING FOR MEDICATION LABELING, naming Edward K. Y. Jung, Royce A. Levien, Robert W. Lord, Mark A. Malamud, John D. Rinaldo, Jr., and Lowell L. Wood, Jr. as inventors, filed 23 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/453,571, entitled INDIVIDUALIZED PHARMACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/314,945, entitled GENERATING A REQUEST FROM A NUTRACEUTICAL INVENTORY, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 20 Dec. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/291,482, entitled GENERATING A NUTRACEUTICAL REQUEST FROM AN INVENTORY, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 30 Nov. 2005, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to methods and systems that may be used for detection of one or more pathogens and determining one or more agents in response to pathogen detection.

SUMMARY

In some embodiments one or more methods are provided that include identifying one or more pathogens present within one or more samples obtained from an individual through use of one or more microfluidic chips, accepting input associated with the individual from whom the one or more samples were obtained, and determining one or more agents that can be used to reduce the pathogenicity of at least one of the one or more pathogens. The method may optionally include displaying information associated with the one or more agents. The method may optionally include transmitting one or more signals that include information associated with the one or more agents. In addition to the foregoing, other aspects are described in the claims, drawings, and text forming a part of the present disclosure.

In some embodiments one or more methods are provided that include receiving one or more signals that include information associated with one or more agents determined in response to one or more pathogens present within one or more samples obtained from an individual and input associated with the individual from whom the one or more samples were obtained and processing the information associated with one or more agents determined in response to one or more pathogens present within one or more samples obtained from an individual and the input associated with the individual from whom the one or more samples were obtained. The method may optionally include packaging the one or more agents. The method may optionally include shipping one or more packages that include the one or more agents. In addition to the foregoing, other aspects are described in the claims, drawings, and text forming a part of the present disclosure.

In some embodiments one or more methods are provided that include identifying one or more pathogens present within one or more samples obtained from an individual through use of one or more microfluidic chips, accepting input associated with the individual from whom the one or more samples were obtained, and transmitting one or more signals that include information associated with the identifying one or more pathogens present within one or more samples obtained from an individual through use of one or more microfluidic chips and the accepting input associated with the individual from whom the one or more samples were obtained. The method may optionally include receiving one or more signals that include information associated with one or more agents that can be used to reduce the pathogenicity of at least one of the one or more pathogens. The method may optionally include displaying the information associated with the one or more agents that can be used to reduce the pathogenicity of the at least one of the one or more pathogens. In addition to the foregoing, other aspects are described in the claims, drawings, and text forming a part of the present disclosure.

In some embodiments one or more methods are provided that include receiving one or more signals that include information associated with identifying one or more pathogens present within one or more samples obtained from an individual, receiving one or more signals that include information associated with accepting input associated with the individual from whom the one or more samples were obtained, and determining one or more agents that can be used to reduce the pathogenicity of at least one of the one or more pathogens. The method may optionally include displaying information associated with the one or more agents. The method may optionally include transmitting the one or more signals that include information associated with the one or more agents. The method may optionally include packaging the one or more agents. The method may optionally include shipping one or more packages that include the one or more agents. In addition to the foregoing, other aspects are described in the claims, drawings, and text forming a part of the present disclosure.

In some embodiments a system is provided that includes a signal-bearing medium bearing one or more instructions for identifying one or more pathogens present within one or more samples obtained from an individual through use of one or more microfluidic chips; one or more instructions for accepting input associated with the individual from whom the one or more samples were obtained; and one or more instructions for determining one or more agents that can be used to reduce the pathogenicity of at least one of the one or more pathogens. The system may optionally include one or more instructions for displaying information associated with the one or more agents. The system may optionally include one or more instructions for transmitting one or more signals that include information associated with the one or more agents. In addition to the foregoing, other system aspects are described in the claims, drawings, and/or text forming a part of the present disclosure.

In some embodiments a system is provided that includes a signal-bearing medium bearing one or more instructions for receiving one or more signals that include information associated with one or more agents determined in response to one or more pathogens present within one or more samples obtained from an individual and input associated with the individual from whom the one or more samples were obtained; and one or more instructions for processing the information associated with one or more agents determined in response to one or more pathogens present within one or more samples obtained from an individual and the input associated with the individual from whom the one or more samples were obtained. The system may optionally include one or more instructions for packaging the one or more agents. The system may optionally include one or more instructions for shipping one or more packages that include the one or more agents. In addition to the foregoing, other aspects are described in the claims, drawings, and/or text forming a part of the present disclosure.

In some embodiments a system is provided that includes a signal-bearing medium bearing one or more instructions for identifying one or more pathogens present within one or more samples obtained from an individual through use of one or more microfluidic chips; one or more instructions for accepting input associated with the individual from whom the one or more samples were obtained; and one or more instructions for transmitting one or more signals that include information associated with the identifying one or more pathogens present within one or more samples obtained from an individual through use of one or more microfluidic chips and the accepting input associated with the individual from whom the one or more samples were obtained. The system may optionally include one or more instructions for receiving one or more signals that include information associated with one or more agents that can be used to reduce the pathogenicity of at least one of the one or more pathogens. The system may optionally include one or more instructions for displaying the information associated with the one or more agents that can be used to reduce the pathogenicity of at least one of the one or more pathogens. In addition to the foregoing, other system aspects are described in the claims, drawings, and/or text forming a part of the present disclosure.

In some embodiments a system is provided that includes a signal-bearing medium bearing one or more instructions for receiving one or more signals that include information associated with identifying one or more pathogens present within one or more samples obtained from an individual; one or more instructions for receiving one or more signals that include information associated with accepting input associated with the individual from whom the one or more samples were obtained; and one or more instructions for determining one or more agents that can be used to reduce the pathogenicity of at least one of the one or more pathogens. The system may optionally include one or more instructions for displaying information associated with the one or more agents. The system may optionally include one or more instructions for transmitting one or more signals that include information associated with the one or more agents. The system may optionally include one or more instructions for packaging the one or more agents. The system may optionally include one or more instructions for shipping one or more packages that include the one or more agents. In addition to the foregoing, other system aspects are described in the claims, drawings, and/or text forming a part of the present disclosure.

In some embodiments one or more systems are provided that include means for identifying one or more pathogens present within one or more samples obtained from an individual through use of one or more microfluidic chips, means for accepting input associated with the individual from whom the one or more samples were obtained; and means for determining one or more agents that can be used to reduce the pathogenicity of at least one of the one or more pathogens responsive to the means for identifying one or more pathogens present within one or more samples obtained from an individual through use of one or more microfluidic chips and the means for accepting input associated with the individual from whom the one or more samples were obtained. The system may optionally include means for displaying information associated with the one or more agents. The system may optionally include means for transmitting one or more signals that include information associated with the one or more agents. In addition to the foregoing, other system aspects are described in the claims, drawings, and/or text forming a part of the present disclosure.

In some embodiments one or more systems are provided that include means for receiving one or more signals that include information associated with one or more agents determined in response to one or more pathogens present within one or more samples obtained from an individual and input associated with the individual from whom the one or more samples were obtained and means for processing the information associated with the means for receiving one or more signals that include information associated with one or more agents determined in response to one or more pathogens present within one or more samples obtained from an individual and input associated with the individual from whom the one or more samples were obtained. The system may optionally include means for packaging the one or more agents. The system may optionally include means for shipping one or more packages that include the one or more agents. In addition to the foregoing, other system aspects are described in the claims, drawings, and/or text forming a part of the present disclosure.

In some embodiments one or more systems are provided that include means for identifying one or more pathogens present within one or more samples obtained from an individual through use of one or more microfluidic chips, means for accepting input associated with the individual from whom the one or more samples were obtained, and means for transmitting one or more signals responsive to the means for identifying one or more pathogens present within one or more samples obtained from an individual through use of one or more microfluidic chips and the means for accepting input associated with the individual from whom the one or more samples were obtained. The system may optionally include means for receiving the one or more signals that include information associated with one or more agents that can be used to reduce the pathogenicity of at least one of the one or more pathogens. The system may optionally include means for displaying the information associated with the means for receiving the one or more signals that include information associated with one or more agents that can be used to reduce the pathogenicity of at least one of the one or more pathogens. In addition to the foregoing, other system aspects are described in the claims, drawings, and/or text forming a part of the present disclosure.

In some embodiments one or more systems are provided that include means for receiving one or more signals that include information associated with identifying one or more pathogens present within one or more samples obtained from an individual, means for receiving one or more signals that include information associated with accepting input associated with the individual from whom the one or more samples were obtained, and means for determining one or more agents that can be used to reduce the pathogenicity of at least one of the one or more pathogens responsive to the means for receiving one or more signals that include information associated with identifying one or more pathogens present within one or more samples obtained from an individual and the means for receiving one or more signals that include information associated with accepting input associated with the individual from whom the one or more samples were obtained. The system may optionally include means for displaying information associated with the one or more agents. The system may optionally include means for transmitting one or more signals that include information associated with the one or more agents. The system may optionally include means for packaging the one or more agents. The system may optionally include means for shipping one or more packages that include the one or more agents. In addition to the foregoing, other system aspects are described in the claims, drawings, and/or text forming a part of the present disclosure.

In some embodiments one or more systems are provided that include circuitry for identifying one or more pathogens present within one or more samples obtained from an individual through use of one or more microfluidic chips, circuitry for accepting input associated with the individual from whom the one or more samples were obtained, circuitry for determining one or more agents that can be used to reduce the pathogenicity of at least one of the one or more pathogens responsive to the circuitry for identifying one or more pathogens present within one or more samples obtained from an individual through use of one or more microfluidic chips and the circuitry for accepting input associated with the individual from whom the one or more samples were obtained. The system may optionally include circuitry for displaying information associated with the one or more agents. The system may optionally include circuitry for transmitting one or more signals that include information associated with the one or more agents. In addition to the foregoing, other system aspects are described in the claims, drawings, and/or text forming a part of the present disclosure.

In some embodiments one or more systems are provided that include circuitry for receiving one or more signals that include information associated with one or more agents determined in response to one or more pathogens present within one or more samples obtained from an individual and input associated with the individual from whom the one or more samples were obtained and circuitry for processing the information associated with one or more agents determined in response to one or more pathogens present within one or more samples obtained from an individual and the input associated with the individual from whom the one or more samples were obtained. The system may optionally include circuitry for packaging the one or more agents. The system may optionally include circuitry for shipping one or more packages that include the one or more agents. In addition to the foregoing, other system aspects are described in the claims, drawings, and/or text forming a part of the present disclosure.

In some embodiments one or more systems are provided that include circuitry for identifying one or more pathogens present within one or more samples obtained from an individual through use of one or more microfluidic chips, circuitry for accepting input associated with the individual from whom the one or more samples were obtained, circuitry for transmitting one or more signals that include information associated with the identifying one or more pathogens present within one or more samples obtained from an individual through use of one or more microfluidic chips and the accepting input associated with the individual from whom the one or more samples were obtained. The system may optionally include circuitry for receiving one or more signals that include information associated with one or more agents that can be used to reduce the pathogenicity of at least one of the one or more pathogens. The system may optionally include circuitry for displaying the information associated with the one or more agents that can be used to reduce the pathogenicity of the at least one of the one or more pathogens. In addition to the foregoing, other system aspects are described in the claims, drawings, and/or text forming a part of the present disclosure.

In some embodiments one or more systems are provided that include circuitry for receiving one or more signals that include information associated with identifying one or more pathogens present within one or more samples obtained from an individual, circuitry for receiving one or more signals that include information associated with accepting input associated with the individual from whom the one or more samples were obtained, and circuitry for determining one or more agents that can be used to reduce the pathogenicity of at least one of the one or more pathogens responsive to the circuitry for receiving one or more signals that include information associated with identifying one or more pathogens present within one or more samples obtained from an individual and the circuitry for receiving one or more signals that include information associated with accepting input associated with the individual from whom the one or more samples were obtained. The system may optionally include circuitry for displaying information associated with the one or more agents. The system may optionally include circuitry for transmitting one or more signals that include information associated with the one or more agents. The system may optionally include circuitry for packaging the one or more agents. The system may optionally include circuitry for shipping one or more packages that include the one or more agents. In addition to the foregoing, other system aspects are described in the claims, drawings, and/or text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

BRIEF DESCRIPTION OF THE FIGURES

FIG. 1 illustrates an example system 100 in which embodiments may be implemented.

FIG. 1A illustrates an example system 100 in which embodiments may be implemented.

FIG. 1B illustrates an example system 100 in which embodiments may be implemented.

FIG. 1C illustrates an example system 100 in which embodiments may be implemented.

FIG. 2 illustrates an operational flow representing example operations related to methods and systems responsive to the detection of pathogens.

FIG. 3 illustrates alternate embodiments of the example operational flow of FIG. 2.

FIG. 4 illustrates alternate embodiments of the example operational flow of FIG. 2.

FIG. 5 illustrates alternate embodiments of the example operational flow of FIG. 2.

FIG. 6 illustrates alternate embodiments of the example operational flow of FIG. 2.

FIG. 7 illustrates an operational flow representing example operations related to methods and systems responsive to the detection of pathogens.

FIG. 8 illustrates alternate embodiments of the example operational flow of FIG. 7.

FIG. 9 illustrates alternate embodiments of the example operational flow of FIG. 7.

FIG. 10 illustrates an operational flow representing example operations related to methods and systems responsive to the detection of pathogens.

FIG. 11 illustrates alternate embodiments of the example operational flow of FIG. 10.

FIG. 12 illustrates an operational flow representing example operations related to methods and systems responsive to the detection of pathogens.

FIG. 13 illustrates alternate embodiments of the example operational flow of FIG. 12.

FIG. 14 illustrates alternate embodiments of the example operational flow of FIG. 12.

FIG. 15 illustrates an operational flow representing example operations related to methods and systems responsive to the detection of pathogens.

FIG. 16 illustrates alternate embodiments of the example operational flow of FIG. 15.

FIG. 17 illustrates alternate embodiments of the example operational flow of FIG. 15.

FIG. 18 illustrates an operational flow representing example operations related to methods and systems responsive to the detection of pathogens.

FIG. 19 illustrates alternate embodiments of the example operational flow of FIG. 18.

FIG. 20 illustrates an operational flow representing example operations related to methods and systems responsive to the detection of pathogens.

FIG. 21 illustrates alternate embodiments of the example operational flow of FIG. 20.

FIG. 22 illustrates alternate embodiments of the example operational flow of FIG. 20.

FIG. 23 illustrates alternate embodiments of the example operational flow of FIG. 20.

FIG. 24 illustrates an operational flow representing example operations related to methods and systems responsive to the detection of pathogens.

FIG. 25 illustrates alternate embodiments of the example operational flow of FIG. 24.

FIG. 26 illustrates an operational flow representing example operations related to methods and systems responsive to the detection of pathogens.

FIG. 27 illustrates alternate embodiments of the example operational flow of FIG. 26.

FIG. 28 illustrates alternate embodiments of the example operational flow of FIG. 26.

FIG. 29 illustrates an operational flow representing example operations related to methods and systems responsive to the detection of pathogens.

FIG. 30 illustrates alternate embodiments of the example operational flow of FIG. 29.

FIG. 31 illustrates alternate embodiments of the example operational flow of FIG. 29.

FIG. 32 illustrates alternate embodiments of the example operational flow of FIG. 29.

FIG. 33 illustrates alternate embodiments of the example operational flow of FIG. 29.

FIG. 34 illustrates an operational flow representing example operations related to methods and systems responsive to the detection of pathogens.

FIG. 35 illustrates alternate embodiments of the example operational flow of FIG. 34.

FIG. 38 illustrates alternate embodiments of the example operational flow of FIG. 37.

FIG. 39 illustrates an operational flow representing example operations related to methods and systems responsive to the detection of pathogens.

FIG. 40 illustrates alternate embodiments of the example operational flow of FIG. 39.

FIG. 42 illustrates an operational flow representing example operations related to methods and systems responsive to the detection of pathogens.

FIG. 43 illustrates alternate embodiments of the example operational flow of FIG. 42.

FIG. 44 illustrates alternate embodiments of the example operational flow of FIG. 42.

FIG. 45A illustrates an example system 4500 in which embodiments may be implemented.

DETAILED DESCRIPTION

Figure 1:
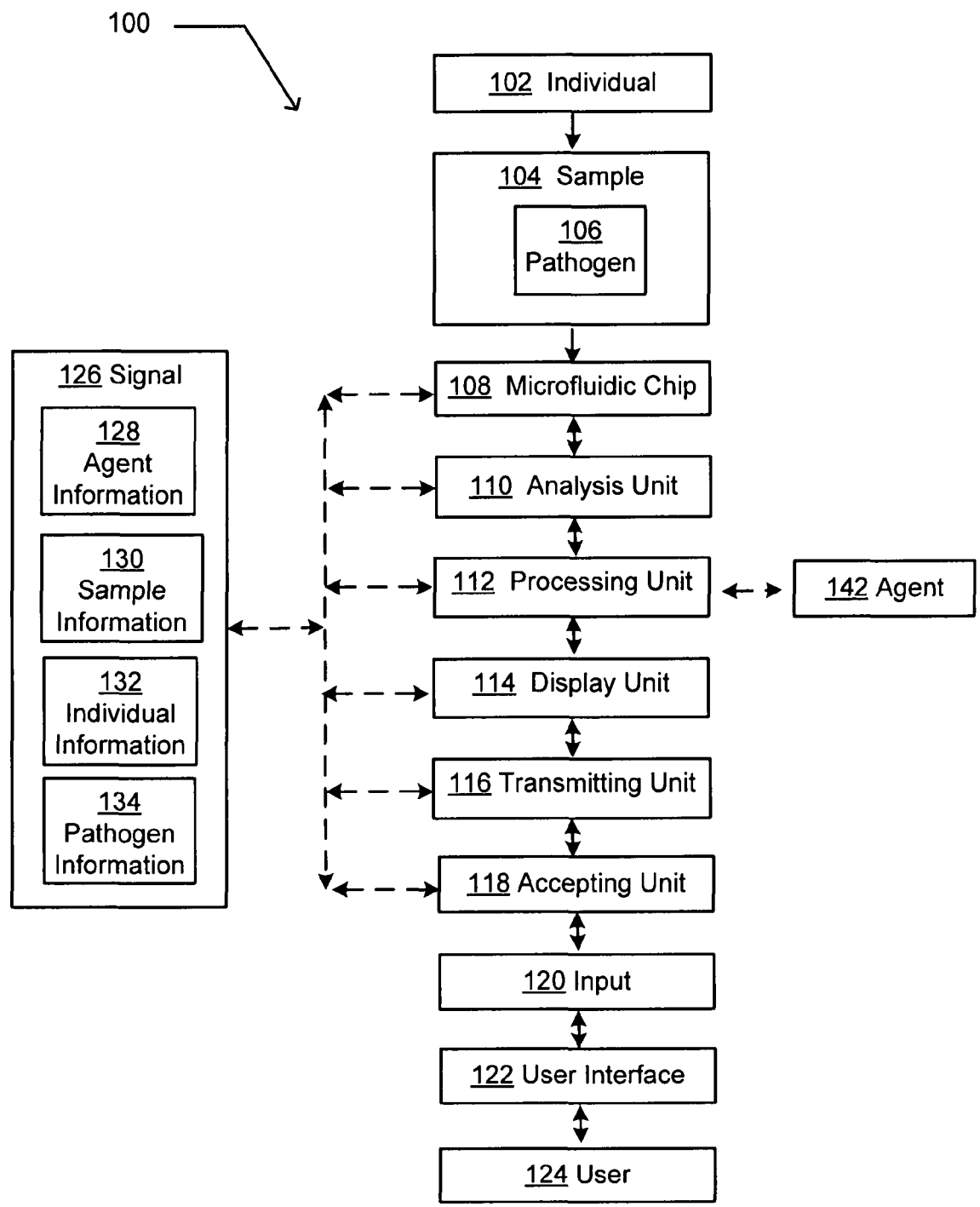

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a method that may be used to detect and respond to one or more pathogens 106. In some embodiments, one or more samples 104 may be processed with one or more microfluidic chips 108 that are configured to detect one or more pathogens 106. In some embodiments, one or more samples 104 may be processed with one or more microfluidic chips 108 that are configured to analyze one or more pathogens 106. In some embodiments, one or more samples 104 associated with an individual 102 may be processed. In some embodiments, one sample 104 associated with an individual 102 may be processed. In some embodiments, one or more microfluidic chips 108 may be used to process one or more samples 104. In some embodiments, one microfluidic chip 108 may be used to process one or more samples 104. In some embodiments, one or more microfluidic chips 108 may be used to process one or more samples 104. In some embodiments, one or more microfluidic chips 108 may be used to process one sample 104. In some embodiments, one or more microfluidic chips 108 may be configured to accept one or more samples 104. In some embodiments, one or more microfluidic chips 108 may include one or more reservoirs. In some embodiments, one or more microfluidic chips 108 may include one or more reagent inputs. In some embodiments, one or more microfluidic chips 108 may be configured to operably associate with one or more analysis units 110. In some embodiments, one or more microfluidic chips 108 may be configured to operably associate with one or more centrifugation units. In some embodiments, one or more microfluidic chips 108 may be configured to operably associate with one or more processing units 112. In some embodiments, one or more microfluidic chips 108 may be configured to operably associate with one or more transmitting units 116. In some embodiments, one or more microfluidic chips 108 may be configured to operably associate with one or more display units 114. In some embodiments, one or more analysis units 110 may be used to detect one or more pathogens 106. In some embodiments, one analysis unit 110 may be used to detect one or more pathogens 106. In some embodiments, one or more analysis units 110 may be portable analysis units 110. In some embodiments, one or more analysis units 110 may be non-portable analysis units 110. In some embodiments, one or more analysis units 110 may be handheld analysis units 110. In some embodiments, one or more analysis units 110 may include one or more user interfaces 122. In some embodiments, one or more analysis units 110 may include one user interface 122. In some embodiments, one or more analysis units 110 may include one or more user interfaces 122 that are operably associated with the one or more analysis units 110. In some embodiments, one or more analysis units 110 may include one or more display units 114. In some embodiments, one or more analysis units 110 may be operably associated with one or more display units 114. In some embodiments, one or more display units 114 may include one or more user interfaces 122. In some embodiments, one or more display units 114 may include one user interface 122. In some embodiments, one or more processing units 112 may be operably associated with one or more analysis units 110. In some embodiments, one or more processing units 112 may be operably associated with one or more display units 114. In some embodiments, one or more processing units 112 may be operably associated with one or more user inputs. In some embodiments, one or more transmitting units 116 may transmit one or more signals 126. In some embodiments, one or more transmitting units 116 may be operably associated with one or more processing units 112. In some embodiments, one or more transmitting units 116 may be operably associated with one or more display units 114. In some embodiments, one or more transmitting units 116 may be operably associated with one or more analysis units 110. In some embodiments, one or more transmitting units 116 may be operably associated with one or more accepting units 118.

FIG. 1A illustrates an example system 100A in which embodiments may be implemented. In some embodiments, the system 100A is operable to provide a method that may be used during the detection and response to one or more pathogens 106. In some embodiments, one or more signals 126 may be received by one or more receiving units 136. Such signals 126 may include numerous types of information. In some embodiments, such signals 126 may include information related to agent information 128, sample information 130, individual information 132, pathogen information 134, and the like. In some embodiments, one or more receiving units 136 may be operably associated with one or more: processing units 112, display units 114, transmitting units 116, user interfaces 122, packaging units 138, shipping units 140, or substantially any combination thereof. In some embodiments, one or more processing units 112 may process information received by one or more receiving units 136. In some embodiments, one or more processing units 112 may be operably associated with one or more: receiving units 136, display units 114, transmitting units 116, user interfaces 122, packaging units 138, shipping units 140, or substantially any combination thereof. In some embodiments, one or more display units 114 may display information received from one or more receiving units 136. In some embodiments, one or more display units 114 may display information received from one or more processing units 112. In some embodiments, one or more display units 114 may be operably associated with one or more: receiving units 136, processing units 112, transmitting units 116, user interfaces 122, packaging units 138, shipping units 140, or substantially any combination thereof. In some embodiments, one or more transmitting units 116 may transmit one or more signals 126. In some embodiments, one or more transmitting units 116 may transmit one or more signals 126 that include information received from one or more receiving units 136. In some embodiments, one or more transmitting units 116 may transmit one or more signals 126 that include information received from one or more processing units 112. In some embodiments, one or more transmitting units 116 may be operably associated with one or more: receiving units 136, processing units 112, display units 114, user interfaces 122, packaging units 138, shipping units 140, or substantially any combination thereof. In some embodiments, one or more user interfaces 122 may be operably associated with one or more: receiving units 136, processing units 112, display units 114, transmitting units 116, packaging units 138, shipping units 140, or substantially any combination thereof. In some embodiments, one or more packaging units 138 may package one or more agents 142. In some embodiments, one or more packaging units 138 may receive one or more signals 126 from one or more transmitting units 116. In some embodiments, one or more packaging units 138 may be operably associated with one or more: receiving units 136, processing units 112, display units 114, transmitting units 116, user interfaces 122, shipping units 140, or substantially any combination thereof. In some embodiments, one or more shipping units 140 may ship one or more packages that include one or more agents 142. In some embodiments, one or more shipping units 140 may receive one or more signals 126 from one or more transmitting units 116. In some embodi-ments, one or more shipping units 140 may be operably associated with one or more: receiving units 136, processing units 112, display units 114, transmitting units 116, user interfaces 122, packaging units 138, or substantially any combination thereof. In some embodiments, one or more processing units 112 may be operably associated with one or more accepting units 118.

Figure 1B:
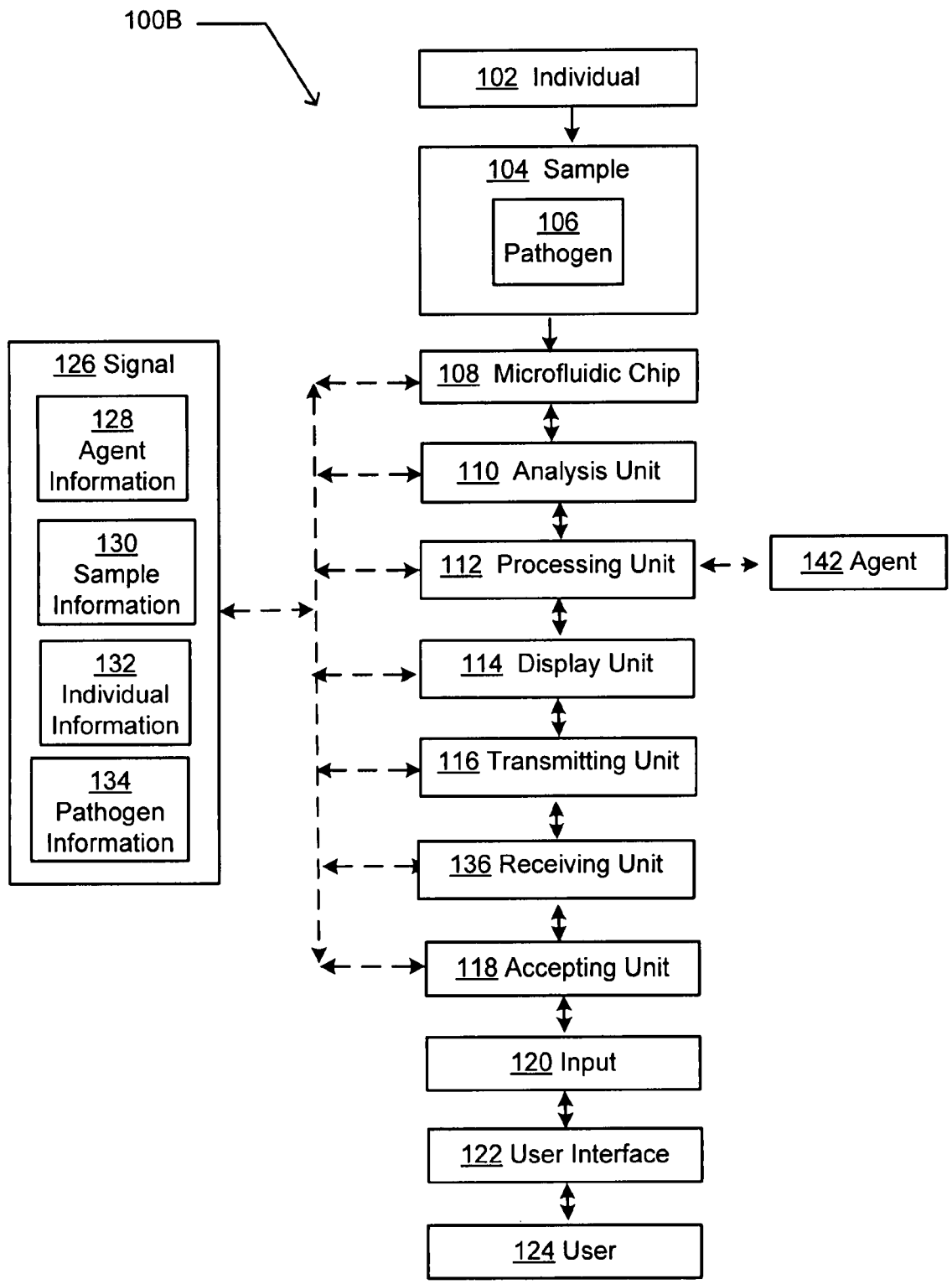

FIG. 1B illustrates an example system 100B in which embodiments may be implemented. In some embodiments, the system 100B is operable to provide a method that may be used to detect and respond to one or more pathogens 106. In some embodiments, one or more samples 104 may be processed with one or more microfluidic chips 108 that are configured to detect one or more pathogens 106. In some embodiments, one or more samples 104 may be processed with one or more microfluidic chips 108 that are configured to analyze one or more pathogens 106. In some embodiments, one or more samples 104 associated with an individual 102 may be processed. In some embodiments, one sample 104 associated with an individual 102 may be processed. In some embodiments, one or more microfluidic chips 108 may be used to process one or more samples 104. In some embodiments, one microfluidic chip 108 may be used to process one or more samples 104. In some embodiments, one or more microfluidic chips 108 may be used to process one or more samples 104. In some embodiments, one or more microfluidic chips 108 may be used to process one sample 104. In some embodiments, one or more microfluidic chips 108 may be configured to accept one or more samples 104. In some embodiments, one or more microfluidic chips 108 may include one or more reservoirs. In some embodiments, one or more microfluidic chips 108 may include one or more reagent inputs. In some embodiments, one or more microfluidic chips 108 may be configured to operably associate with one or more analysis units 110. In some embodiments, one or more microfluidic chips 108 may be configured to operably associate with one or more centrifugation units. In some embodiments, one or more microfluidic chips 108 may be configured to operably associate with one or more processing units 112. In some embodiments, one or more microfluidic chips 108 may be configured to operably associate with one or more transmitting units 116. In some embodiments, one or more microfluidic chips 108 may be configured to operably associate with one or more display units 114. In some embodiments, one or more analysis units 110 may be used to detect one or more pathogens 106. In some embodiments, one analysis unit 110 may be used to detect one or more pathogens 106. In some embodiments, one or more analysis units 110 may be portable analysis units 110. In some embodiments, one or more analysis units 110 may be non-portable analysis units 110. In some embodiments, one or more analysis units 110 may be handheld analysis units 110. In some embodiments, one or more analysis units 110 may include one or more user interfaces 122. In some embodiments, one or more analysis units 110 may include one user interface 122. In some embodiments, one or more analysis units 110 may include one or more user interfaces 122 that are operably associated with the one or more analysis units 110. In some embodiments, one or more analysis units 110 may include one or more display units 114. In some embodiments, one or more analysis units 110 may be operably associated with one or more display units 114. In some embodiments, one or more display units 114 may include one or more user interfaces 122. In some embodiments, one or more display units 114 may include one user interface 122. In some embodiments, one or more processing units 112 may be operably associated with one or more analysis units 110. In some embodiments, one or more processing units 112 may be operably associated with one or more display units 114. In some embodiments, one or more processing units 112 may be operably associated with one or more user inputs. In some embodiments, one or more processing units 112 may be operably associated with one or more accepting units 118. In some embodiments, one or more transmitting units 116 may transmit one or more signals 126. In some embodiments, one or more transmitting units 116 may be operably associated with one or more processing units 112. In some embodiments, one or more transmitting units 116 may be operably associated with one or more display units 114. In some embodiments, one or more transmitting units 116 may be operably associated with one or more analysis units 110. In some embodiments, one or more transmitting units 116 may be operably associated with one or more accepting units 118. In some embodiments, one or more receiving units 136 may receive one or more signals 126. In some embodiments, one or more receiving units 136 may be operably associated with one or more: processing units 112, display units 114, transmitting units 116, user interfaces 122, or substantially any combination thereof.

Figure 1C:
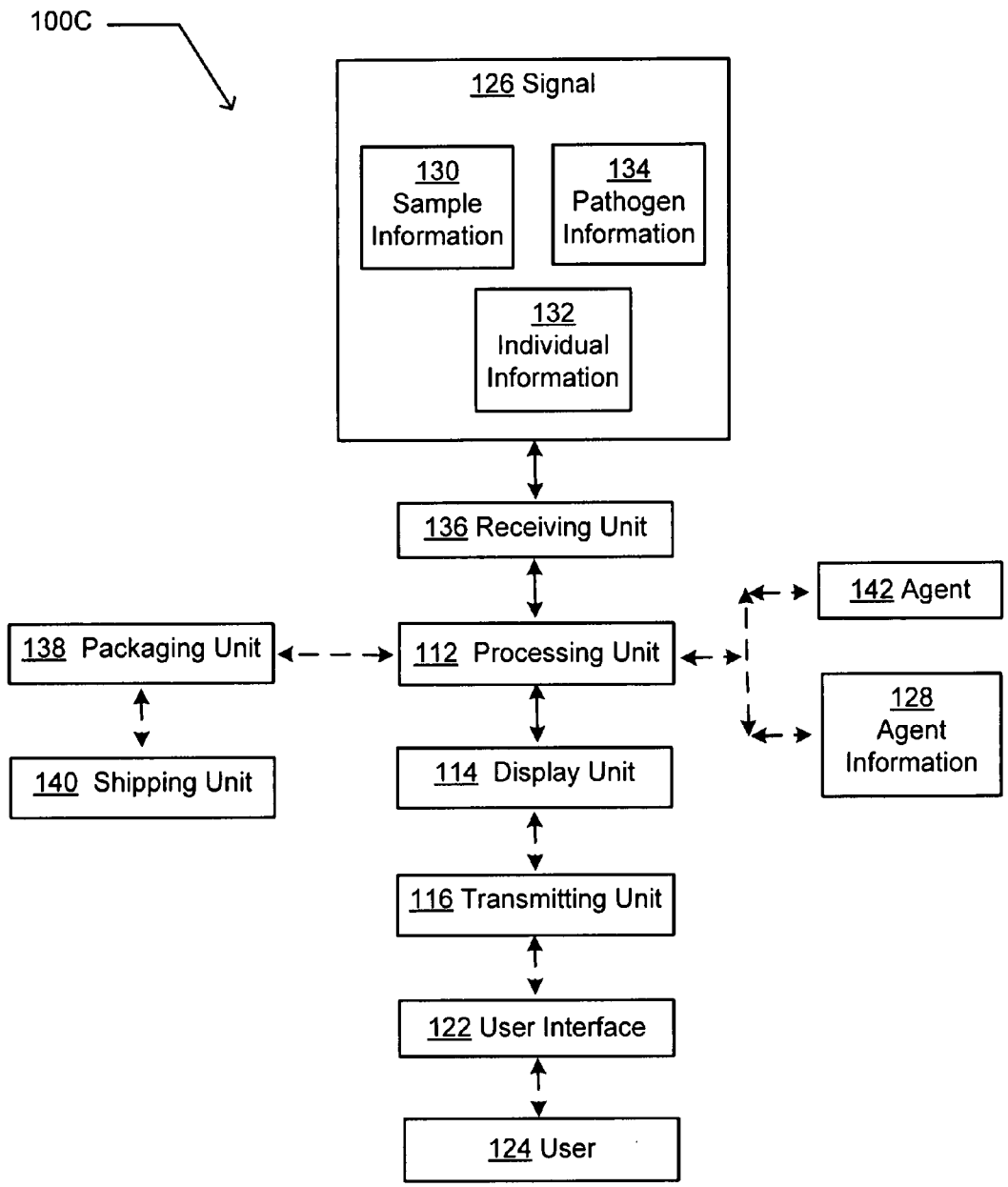

FIG. 1C illustrates an example system 100C in which embodiments may be implemented. In some embodiments, the system 100C is operable to provide a method that may be used during the detection and response to one or more pathogens 106. In some embodiments, one or more signals 126 may be received by one or more receiving units 136. Such signals 126 may include numerous types of information. In some embodiments, such signals 126 may include information related to sample information 130, individual information 132, pathogen information 134, and the like. In some embodiments, one or more receiving units 136 may be operably associated with one or more: processing units 112, display units 114, transmitting units 116, user interfaces 122, packaging units 138, shipping units 140, or substantially any combination thereof. In some embodiments, one or more processing units 112 may process information received by one or more receiving units 136. In some embodiments, one or more processing units 112 may be operably associated with one or more: receiving units 136, display units 114, transmitting units 116, user interfaces 122, packaging units 138, shipping units 140, or substantially any combination thereof. In some embodiments, one or more display units 114 may display information received from one or more receiving units 136. In some embodiments, one or more display units 114 may display information received from one or more processing units 112. In some embodiments, one or more display units 114 may be operably associated with one or more: receiving units 136, processing units 112, transmitting units 116, user interfaces 122, packaging units 138, shipping units 140, or substantially any combination thereof. In some embodiments, one or more transmitting units 116 may transmit one or more signals 126. In some embodiments, one or more transmitting units 116 may transmit one or more signals 126 that include information received from one or more receiving units 136. In some embodiments, one or more transmitting units 116 may transmit one or more signals 126 that include information received from one or more processing units 112. In some embodiments, one or more transmitting units 116 may be operably associated with one or more: receiving units 136, processing units 112, display units 114, user interfaces 122, packaging units 138, shipping units 140, or substantially any combination thereof. In some embodiments, one or more user interfaces 122 may be operably associated with one or more: receiving units 136, processing units 112, display units 114, transmitting units 116, packaging units 138, shipping units 140, or substantially any combination thereof. In some embodiments, one or more packaging units 138 may package one or more agents 142. In some embodiments, one or more packaging units 138 may receive one or more signals 126 from one or more transmitting units 116. In some embodiments, one or more packaging units 138 may be operably associated with one or more: receiving units 136, processing units 112, display units 114, transmitting units 116, user interfaces 122, shipping units 140, or substantially any combination thereof. In some embodiments, one or more shipping units 140 may ship one or more packages that include one or more agents 142. In some embodiments, one or more shipping units 140 may receive one or more signals 126 from one or more transmitting units 116. In some embodiments, one or more shipping units 140 may be operably associated with one or more: receiving units 136, processing units 112, display units 114, transmitting units 116, user interfaces 122, packaging units 138, or substantially any combination thereof.

Sample

Numerous types of samples 104 may be analyzed through use of system 100. In some embodiments, one or more samples 104 may be associated with an individual 102. In some embodiments, one or more samples 104 may be associated with one or more individuals 102. In some embodiments, an individual 102 may be a human. In some embodiments, an individual 102 may be a group of humans who share a common pathogen infection. For example, in some embodiments, system 100 may be used to diagnose an individual 102 for infection with one or more pathogens 106. In some embodiments, one or more samples 104 may include a liquid. In some embodiments, one or more samples 104 may include a solid. In some embodiments, one or more samples 104 may include a vapor. In some embodiments, one or more samples 104 may include a semi-solid. In some embodiments, one or more samples 104 may include a gas. Examples of such samples 104 include, but are not limited to, samples 104 obtained from humans (e.g., skin, breath, tissue, hair, saliva, blood, mucus, cerebrospinal fluid, urine, fecal material, tears, urogenital associated samples), samples 104 that are associated with, but not limited to, one or more toxins, viruses, bacteria, protozoans, single-celled organisms, fungus, algae, prions, microbes, cyst, eggs, pathogenic proteins, or substantially any combination thereof.

Agent

Numerous agents 142 may be selected. In some embodiments, an agent 142 may include a substance that may be used in the diagnosis, cure, mitigation, treatment, or prevention of disease in a human or another animal. Such agents are recognized in the official United States Pharmacopeia, official Homeopathic Pharmacopeia of the United States, official National Formulary or any supplement thereof.

In some embodiments, an agent 142 may include a chemical agent 142. For example, in some embodiments, an agent 142 may be an antibiotic, a steroid, an alcohol deterrent, an analgesic, an anesthetic, an antacid, an antihelmintic, an antiallergic, an antiamebic, an antiarteriosclerotic, an antibacterial, an antibacterial adjuvant, an antiharrheal, an antidiuretic, an antifungal, an antimalarial, an antiprotozoal, an antishphilitic, an antitussive, an antiviral, a chelating agent, a choleretic, a CNS stimulant, a decongestant, an antiseptic, a disinfectant, an expectorant, a glucocorticoid, an HIV fusion inhibitor, an HIV protease inhibitor, an immunomodulator, an immunosuppressant, a protease inhibitor, a pulmonary surfactant, a respiratory stimulant, a reverse transcriptase inhibitor, a sedative, a hypnotic, a serotonin noradrenaline reuptake inhibitor, a serotonin receptor agonist, a serotonin receptor antagonist, a serotonin reuptake inhibitor, a topoisomerast I inhibitor, a topoisomerase II inhibitor, a tranquilizer, a vasodilator, a vasoprotectant, and the like. Numerous agents 142 are known and have been described (e.g., Merck Index, Thirteenth Edition, Merck & Co., Inc., Whitehouse Station, N.J. (2001); Mosby's Drug Guide, An Imprint of Elsevier, St. Louis, Mo. (2004); The Merck Manual, Seventeenth Edition, Merck Research Laboratories, Whitehouse Station, N.J. (1999); Physician's Desk Reference, 58$^{th}$ Edition, Thomson Montvale, N.J. (2004)).

In some embodiments, an agent 142 may include a mechanical agent 142. Examples of mechanical agents 142 include, but are not limited to, radiation, ultraviolet light, sonication, phototherapy, and the like.

In some embodiments, an agent 142 may include a bioagent. In some embodiments, a bioagent may be found in nature. In some embodiments, an bioagent may be synthetic. For example, in some embodiments, a bioagent may be produced through use of recombinant nucleic acid technology. In some embodiments, a bioagent may be assembled in vitro. For example, in some embodiments, a bioagent may be a virus and/or bacteriophage against a pathogen that is found in nature. In some embodiments, a bioagent may be a virus and/or bacteriophage against a pathogen that is assembled in vitro. In some embodiments, a bioagent may be a virus and/or bacteriophage against a pathogen that includes recombinant nucleic acid (e.g., Merrill et al., PNAS (USA), 93:3188 (1996); Brussow, Microbiology, 151:2133-2140 (2005)). In some embodiments, an agent may include a recombinant microbe. For example, in some embodiments, *Yersinia, Listeria, Salmonella,* and/or *Shigella* may be used to deliver recombinant products through the intestinal mucosa.

In some embodiment, an agent 142 may provide a synergistic effect with another agent. In some embodiments, a first agent 142 may increase the effectiveness of a second agent 142. For example, in some embodiments, a first agent 142 may be an antibacterial adjuvant (e.g., a beta-lactamase inhibitor).

Pathogen/Pathogen Indicator

Numerous pathogens 106 may be processed, analyzed and/or detected through use of system 100. In some embodiments, pathogens 106 include intact pathogens 106 and components of pathogens 106. For example, in some embodiments, pathogens 106 may include polynucleotides and/or polypeptides that are associated with a pathogen 106. In some embodiments, pathogens 106 may include one or more products of a pathogen 106. In some embodiments, pathogens 106 may include products and/or substrates that are associated with the activity of one or more pathogen associated enzymes. Examples of pathogens 106 that may be processed, analyzed and/or detected through use of system 100 include, but are not limited to, pathogens 106 associated with plants, animals, humans, fish, birds, and the like. Examples of such pathogens 106 include, but are not limited to, viruses, bacteria, prions, protozoans, single-celled organisms, algae, eggs of pathogenic organisms, microbes, cysts, molds, fungus, worms, amoeba, pathogenic proteins, or substantially any combination thereof. Numerous pathogens 106 are known and have been described (e.g., Foodborne Pathogens: Microbiology and Molecular Biology, Caister Academic Press, eds. Fratamico, Bhunia, and Smith (2005); Maizels et al., Parasite Antigens Parasite Genes: A Laboratory Manual for Molecular Parasitology, Cambridge University Press (1991); National Library of Medicine; Physician's Desk Reference, 58$^{th}$ Edition, Thomson PDR, Montvale, N.J. (2004)).

Numerous types of viruses may be identified. Such viruses are known and have been described (e.g., U.S. Patent Appl. No.: 20060257852; Field's Virology, Knipe et al, (Fifth Edition) Lippincott Williams & Wilkins, Philadelphia, (2006)). Examples of such viruses include, but are not limited to, hepatitis, influenza, avian influenza, severe acute respiratory syndrome coronavirus (severe acute respiratory syndrome (SARS)), human immunodeficiency virus, herpes viruses, human papilloma virus, rhinovirus, rotavirus, West Nile virus, and the like.

Examples of bacteria that may be identified include, but are not limited to, *Staphylococcus aureus, Staphylococcus epidermidis, Staphylococcus* sp., *Streptococcus pneumoniae, Streptococcus agalactiae, Streptococcus pyogenes, Enterococcus* sp., *Bacillus anthracis, Bacillus cereus, Bifidobacterium bifidum, Lactobacillus* sp., *Listeria monocytogenes, Nocardia* sp., *Rhodococcus equi, Erysipelothrix rhusiopathiae, Corynebacterium diptheriae, Propionibacterium acnes, Actinomyces* sp., *Clostridium botulinum, Clostridium difficile, Clostridium perfringens, Clostridium tetani, Mobiluncus* sp., *Peptostreptococcus* sp., *Neisseria gonorrhoeae, Neisseria meningitides, Moraxella catarrhalis, Veillonella* sp., *Actinobacillus actinomycetemcomitans, Acinetobacter baumannii, Bordetella pertussis, Brucella* sp., *Campylobacter* sp., *Capnocytophaga* sp., *Cardiobacterium hominis, Eikenella corrodens, Francisella tularensis, Haemophilus ducreyi, Haemophilus influenzae, Helicobacter pylori, Kingella kingae, Legionella pneumophila, Pasteurella multocida, Klebsiella granulomatis,* Enterobacteriaceae, *Citrobacter* sp., *Enterobacter* sp., *Escherichia coli, Klebsiella pneumoniae, Proteus* sp., *Salmonella enteriditis, Salmonella typhi, Shigella* sp., *Serratia marcescens, Yersinia enterocolitica, Yersinia pestis, Aeromonas* sp., *Plesiomonas shigelloides, Vibrio cholerae, Vibrio parahaemolyticus, Vibrio vulnificus, Acinetobacter* sp., *Flavobacterium* sp., *Pseudomonas aeruginosa, Burkholderia cepacia, Burkholderia pseudomallei, Xanthomonas maltophilia, Stenotrophomonas maltophila, Bacteroides fragilis, Bacteroides* sp., *Prevotella* sp., *Fusobacterium* sp., *Spirillum minus,* or substantially any combination thereof.

Numerous prions may be identified. Examples of such prions include, but are not limited to, bovine prion protein, human prion protein, monkey prion protein, dog prion protein, and the like. The amino acid sequences and/or nucleotide sequences of numerous prions are known and have been reported (e.g., Premzl and Gamulin, BMC Genomics, 8:1 (2007)).

Numerous pathogenic worms may be identified. Examples of such worms include, but are not limited to, tapeworms, helminths, whipworms, hookworms, ringworms, roundworms, pinworms, ascarids, filarids, and the like.

In some embodiments, the eggs and/or cysts of pathogens 106 may be identified. Examples of such eggs and/or cysts include, but are not limited to, eggs and/or cysts of: parasitic worms (e.g., *Heterodera glycines, Trichinella*), amoebe (e.g., *Entamoeba histolytica, Acanthamoeba*), protozoans (e.g., *Giardia, cryptosporidium, Toxoplasma*), and the like.

Numerous protozoans may be identified. Examples of protozoans include, but are not limited to, slime molds, flagellates, ciliates, and the like (e.g., *cryptosporidium, giardia, naegleria fowleri, acanthamoeba, entamoeba histolytica, cryptosporidium parvum, cyclospora cayetanensis, isospora belli, microsporidia*) (Marshall et al., Clin, Micro. Rev., 10:67-85 (1997)).

Examples of pathogenic fungi include, but are not limited to, dimorphic fungi that may assume a mold form but may also adopt a yeast form, *histoplasma capsulatum, coccidioides immitis, candida, aspergillus*, and the like.

Pathogenic algae include, but are not limited to, *Prototheca* members, *Helicosporidiu* members, *Chattonella* members (e.g., *Chattonella marina*), and the like.

Numerous types of pathogenic proteins may be identified and include, but are not limited to, toxins (e.g., exotoxing, endotoxins), prions, and the like.

Numerous microbes may be identified. In some embodiments, microbes may be prokaryotes. In some embodiments, microbes may be eukaryotes. Examples of such microbes include, but are not limited to, *Giardia*, amoeba (e.g., *Entamoeba, Naegleria, Acanthamoeba*), trypanosomes, *Plasmodium* (e.g., *Plasmodium falciparum, Plasmodium vivax, Plasmodium ovale, Plasmodium malariae, Plasmodium knowlesi*), *Eimeria, Toxoplasma, Neospora, Mycoplasma, Leishmania*, Trichomonas, *Cryptosporidium, Isospora, Balantidium*, protozoans, *Mycoplasma hominis, Ureaplasma urealyticum*, and the like.

In some embodiments, a pathogen 106 may be a member of numerous groups of pathogens 106. For example, single-celled organisms may include microbes, protozoans, and the like. In some embodiments, a pathogen 106 may include an artificial device such an electomechanical machine, a nano-machine, a micro-machine, and the like.

Microfluidic Chip

Numerous types of microfluidic chips 108 may be utilized within system 100. Methods to construct and utilize microfluidic chips 108 have been described (e.g., U.S. Statutory Invention Registration No. H201; U.S. Pat. Nos. 6,454,945; 6,818,435; 6,812,458; 6,794,196; 6,709,869; 6,582,987; 6,482,306; 5,726,404; 7,118,910; 7,081,192; herein incorporated by reference).

In some embodiments, a microfluidic chip 108 may be configured to utilize microfluidic principles. Accordingly, in some embodiments, a microfluidic chip 108 may be configured to include one or more channels with at least one dimension that is less than 1 millimeter. However, in some embodiments, microfluidic chips 108 may be configured such that they do not utilize microfluidic principles. Accordingly, in some embodiments, microfluidic chips 108 may be configured such that there are not any components that have a dimension that is less than 1 millimeter. Accordingly, in some embodiments, microfluidic chips 108 may be configured that include components having a dimension that is less than 1 millimeter, while in other embodiments, microfluidic chips 108 may be configured with components having dimensions that are greater than 1 millimeter. In some embodiments, a microfluidic chip 108 may include at least one component that has at least one dimension that is less than 1 millimeter and at least one component having at least one dimension that is greater than 1 millimeter.

For example, microfluidic chips 108 may be configured to utilize a variety of methods to facilitate detection of one or more pathogens 106. Examples of such methods include, but are not limited to, nucleic acid (polynucleotide) hybridization based methods, immunological based methods, chromatographic based methods, affinity based methods, extraction based methods, separation based methods, isolation based methods, filtration based methods, enzyme based methods, isoelectric focusing methods, or substantially any combination thereof.

Microfluidic chips 108 may utilize numerous methods to facilitate detection of one or more pathogens 106. For example, in some embodiments, one or more microfluidic chips 108 may be configured to utilize: chemiluminescent methods (e.g., U.S. Pat. Nos. 6,090,545 and 5,093,268; herein incorporated by reference), plasmon resonance sensors (e.g., U.S. Pat. No. 7,030,989; herein incorporated by reference), nuclear magnetic resonance detectors (e.g., U.S. Pat. No. 6,194,900; herein incorporated by reference), gradient-based assays (e.g., U.S. Pat. No. 7,112,444; herein incorporated by reference), reporter beads (e.g., U.S. Pat. No. 5,747,349; herein incorporated by reference), transverse electrophoresis (e.g., Macounova et al., Analytical Chemistry, 73:1627-1633 (2001)); isoelectric focusing (e.g., Macounova et al., Analytical Chemistry, 72:3745-3751 (2000); Xu et al., Isoelectric focusing of green fluorescent proteins in plastic microfluidic channels. Abstracts of Papers of the American Chemical Society, 219:9-ANYL (2000); Macounova et al., Analytical Chemistry, 73:1627-1633 (2001)), diffusion based systems (e.g., Kamholz et al., Biophysical Journal, 80:1967-1972 (2001); Hatch et al., Nature Biotechnology, 19:461-465 (2001); U.S. Pat. Nos. 6,221,677; 5,972,710; herein incorporated by reference), high performance liquid chromatography (e.g., U.S. Pat. No. 6,923,907; herein incorporated by reference), polynucleotide analysis (e.g., Belgrader et al., Biosensors & Bioelectronics, 14:849-852 (2000); Buchholz et al., Analytical Chemistry, 73:157-164 (2001); Fan et al., Analytical Chemistry, 71:4851-4859 (1999); Koutny et al., Analytical Chemistry, 72:3388-3391 (2000); Lee et al., Microfabricated plastic chips by hot embossing methods and their applications for DNA separation and detection. Sensors and Actuators B-Chemical, 75:142-148 (2001); U.S. Pat. No. 6,958,216; herein incorporated by reference), capillary electrophoresis (e.g., Kameoka et al., Analytical Chemistry, 73:1935-1941 (2001)), immunoassays (e.g., Hatch et al., Nature Biotechnology, 19:461-465 (2001); Eteshola and Leckband, D. Development and characterization of an ELISA assay in PDMS microfluidic channels. Sensors and Actuators B-Chemical 72:129-133 (2001); Cheng et al., Analytical Chemistry, 73:1472-1479 (2001); Yang et al., Analytical Chemistry, 73:165-169 (2001)), flow cytometry (e.g., Sohn et al., Proc. Natl. Acad. Sci., 97:10687-10690 (2000)), PCR amplification (e.g., Belgrader et al., Biosensors & Bioelectronics, 14:849-852 (2000); Khandurina et al., Analytical Chemistry, 72:2995-3000 (2000); Lagally et al., Analytical Chemistry, 73:565-570 (2001)), cell manipulation (e.g., Glasgow et al., IEEE Transactions On Biomedical Engineering, 48:570-578 (2001)), cell separation (e.g., Yang et al., Analytical Chemistry, 71:911-918 (1999)), cell patterning (e.g., Chiu et al., Proc. Natl. Acad. Sci., 97:2408-2413 (2000); Folch et al., Journal of Biomedical Materials Research, 52:346-353 (2000)), chemical gradient formation (e.g., Dertinger et al., Analytical Chemistry, 73:1240-1246 (2001); Jeon et al., Langmuir, 16:8311-8316 (2000)), microcantilevers (e.g., U.S. Pat. Nos. 7,141,385; 6,935,165; 6,926,864; 6,763,705; 6,523,392; 6,325,904; herein incorporated by reference), or substantially any combination thereof.

In some embodiments, one or more microfluidic chips 108 may be configured to utilize one or more magnets that may be used during processing and/or analysis of one or more samples 104. For example, in some embodiments, ferrous metallic particles may be associated with one or more pathogens 106 that are associated with one or more samples 104 (e.g., use of antibodies, aptamers, peptides, polynucleotides, and the like that bind to one or more pathogen indicators and that are coupled to a ferrous metallic particle). The one or more pathogens 106 may be separated from the remainder of the one or more samples 104 through use of one or more magnets. In some embodiments, one or more magnets may be used to create eddy currents that may be used to process and/or analyze one or more samples 104. For example, in some embodiments, non-ferrous metallic particles may be associated with one or more pathogens 106 that are associated with one or more samples 104 (e.g., use of antibodies, aptamers, peptides, polynucleotides, and the like that bind to one or more pathogen indicators and that are coupled to a non-ferrous metallic particle). One or more microfluidic chips 108 may be configured such that passage of a non-ferrous metallic particle through a magnetic field will cause an eddy current to impart kinetic energy to the non-ferrous metallic particle and provide for separation of the associated pathogens 106 from the remainder of the one or more samples 104. In some embodiments, such methods may be combined with additional methods to provide for separation of one or more pathogens 106 from one or more samples 104. For example, magnetic separation may be used in combination with one or more methods that may include, but are not limited to, diffusion (e.g., use of an H-filter), filtration, precipitation, immunoassay, immunodiffusion, and the like.

In some embodiments, one or more microfluidic chips 108 may be configured to utilize ferrofluids to separate one or more pathogens 106 from one or more samples 104. For example, in some embodiments, a microfluidic chip 108 may include an H-filter where a sample fluid and a ferrofluid flow substantially in parallel (e.g., the sample fluid and the ferrofluid flow side-by-side through the H-filter (horizontal) and/or above and below (vertical)). In some embodiments, one or more microfluidic chips 108 may include a ferrofluid having magnetic particles such that ferrous materials contained within the sample fluid are attracted to the ferrofluid and thereby separated from the sample fluid. Accordingly, such microfluidic chips 108 may be configured to separate one or more pathogens 106 from one or more samples 104. In some embodiments, one or more microfluidic chips 108 may include a ferrofluid having ferrous particles such that magnetic materials contained within the sample fluid are attracted to the ferrofluid and thereby separated from the sample fluid. Accordingly, in such embodiments, one or more microfluidic chips 108 may be configured to utilize ferrofluids to separate one or more pathogens 106 from one or more samples 104.

Microfluidic chips 108 may be configured to process numerous types of samples 104. For example, in some embodiments, a microfluidic chip 108 may be configured to sonicate one or more samples 104. In some embodiments, a microfluidic chip 108 may include one or more ultrasonic electronic generators that produce a signal (e.g., 20 kilohertz) that can be used to drive a piezoelectric converter/transducer. This electrical signal may be converted by the transducer to a mechanical vibration due to the characteristics of the internal piezoelectric crystals. This vibration can be amplified and transmitted to one or more probes having tips that expand and contract to provide for sonication of one or more samples 104. In some embodiments, a microfluidic chip 108 may include one or more sonication probes. Such probes may be configured such that are able to operably associate with one or more vibration sources in a detachable manner. Accordingly, in some embodiments, one or more microfluidic chips 108 that include one or more probes may be configured to detachably connect with one or more vibration sources that produce a vibration that can be coupled to the one or more probes. In some embodiments, one or more microfluidic chips 108 may include one or more vibration sources.

In some embodiments, a microfluidic chip 108 may be configured to mix one or more samples 104. For example, in some embodiments, a microfluidic chip 108 may include a mixing chamber which includes one or more ferrous mixing members and electromagnets which are configured such that motion may be imparted to the one or more ferrous mixing members. In some embodiments, a microfluidic chip 108 may include one or more mixing chambers that include two or more electromagnets positioned around the one or more mixing chambers and one or more ferrous members positioned within the one or more mixing chambers and between the electromagnets. Accordingly, mixing of one or more materials within the one or more mixing chambers may be facilitated by alternating current between the electromagnets positioned around the mixing chamber. In some embodiments, a mixing chamber may include an elastomeric material that includes a ferrous material (e.g., an elastomeric-ferrous material) such that movement of the elastomeric-ferrous material may be facilitated through use of one or more magnets, such as electromagnets.

In some embodiments, elastomeric-ferrous materials may be utilized to fabricate pumps that are associated with microfluidic chips 108. For example, in some embodiments, a tube may include an elastomeric material that includes ferrous material such that movement of the elastomeric material may be facilitated through use of one or more magnets. Accordingly, valves and ferrous materials may be associated with the elastomeric tube such that expansion of a portion of the elastomeric tube through the action of a magnet, such as an electromagnetic, will act like a vacuum pump to draw fluids into the expanded portion of the elastomeric tube. In some embodiments, release of the elastomeric material from the magnetic field will cause the expanded portion of the tube to contract and will act to push the fluid from the formerly expanded portion of the elastomeric tubing. In some embodiments, valves may be positioned within the tube to provide for directional flow of fluid through the elastomeric tube. Accordingly, such pumps may be configured as vacuum pumps, propulsion type pumps, and/or both vacuum and propulsion type pumps.

In some embodiments, microfluidic chips 108 may be configured to utilize magnetically actuated fluid handling. In some embodiments, a microfluidic chip 108 may utilize magnetic fluid (e.g., ferrofluid, ferrogel, and the like) to move one or more gases and/or liquids through flow channels. For example, magnetically actuated slugs of magnetic fluid may be moved within channels of a microfluidic chip 108 to facilitate valving and/or pumping of one or more gases and/or liquids. In some embodiments, the magnets used to control gas and/or liquid movement may be individual magnets that are moved along the flow channels and/or one or more arrays of magnets that may be individually controlled to hold or move one or more magnetic slugs. In some embodiments, an array of electromagnets may be positioned along a flow channel which may be turned on and off in a predetermined pattern to move magnetic fluid slugs in desired paths in one or more flow channels. Methods to construct magnetically actuated fluid handling devices have been described (e.g., U.S. Pat. Nos. 6,408,884 and 7,110,646; herein incorporated by reference).

In some embodiments, one or more microfluidic chips 108 may process one or more samples 104 through use of polynucleotide interaction. Numerous methods based on polynucleotide interaction may be used. Examples of such methods include, but are not limited to, those based on polynucleotide hybridization, polynucleotide ligation, polynucleotide amplification, polynucleotide degradation, and the like. Methods that utilize intercalation dyes, FRET analysis, capacitive DNA detection, and nucleic acid amplification have been described (e.g., U.S. Pat. Nos. 7,118,910 and 6,960,437; herein incorporated by reference). In some embodiments, fluorescence resonance energy transfer, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100:9134-9137 (2003); U.S. Pat. Nos. 6,958,216; 5,093,268; 6,090,545; herein incorporated by reference). In some embodiments, one or more polynucleotides that include at least one carbon nanotube are combined with one or more samples 104, and/or one or more partially purified polynucleotides obtained from one or more samples 104. The one or more polynucleotides that include one or more carbon nanotubes are allowed to hybridize with one or more polynucleotides that may be present within the one or more samples 104. The one or more carbon nanotubes may be excited (e.g., with an electron beam and/or an ultraviolet laser) and the emission spectra of the excited nanotubes may be correlated with hybridization of the one or more polynucleotides that include at least one carbon nanotube with one or more polynucleotides that are included within the one or more samples 104. Methods to utilize carbon nanotubes as probes for nucleic acid interaction have been described (e.g., U.S. Pat. No. 6,821,730; herein incorporated by reference).

In some embodiments, one or more microfluidic chips 108 may be configured to facilitate detection of one or more pathogens 106 through use of protein interaction. Numerous methods based on protein interaction may be used. In some embodiments, protein interaction may be used to immobilize one or more pathogens 106. In some embodiments, protein interaction may be used to separate one or more pathogens 106 from one or more samples 104. Examples of such methods include, but are not limited to, those based on ligand binding, protein-protein binding, protein cross-linking, use of green fluorescent protein, phage display, the two-hybrid system, protein arrays, fiber optic evanescent wave sensors, chromatographic techniques, fluorescence resonance energy transfer, regulation of pH to control protein assembly and/or oligomerization, regulation of ion concentration to control protein assembly and/or oligomerization, and the like. Methods that may be used to construct protein arrays have been described (e.g., Warren et al., Anal. Chem., 76:4082-4092 (2004) and Walter et al., Trends Mol. Med., 8:250-253 (2002), U.S. Pat. No. 6,780,582; herein incorporated by reference).

In some embodiments, one or more microfluidic chips 108 may be configured to facilitate detection of one or more pathogens 106 through use of peptide interaction. Peptides are generally described as being polypeptides that include less than one hundred amino acids. For example, peptides include dipeptides, tripeptides, and the like. In some embodiments, peptides may include from two to one hundred amino acids. In some embodiments, peptides may include from two to fifty amino acids. In some embodiments, peptides may include from two to one twenty amino acids. In some embodiments, peptides may include from ten to one hundred amino acids. In some embodiments, peptides may include from ten to fifty amino acids. Accordingly, peptides can include numerous numbers of amino acids. Numerous methods based on peptide interaction may be used. In some embodiments, peptide interaction may be used to immobilize one or more pathogens 106. In some embodiments, peptide interaction may be used to separate one or more pathogens 106 from one or more samples 104. Examples of such methods include, but are not limited to, those based on ligand binding, peptide-protein binding, peptide-peptide binding, peptide-polynucleotide binding, peptide cross-linking, use of a fluorescent protein, phage display, the two-hybrid system, protein arrays, peptide arrays, fiber optic evanescent wave sensors, chromatographic techniques, fluorescence resonance energy transfer, regulation of pH to control peptide and/or protein assembly and/or oligomerization, and the like. Accordingly, virtually any technique that may be used to analyze proteins may be utilized for the analysis of peptides. In some embodiments, high-speed capillary electrophoresis may be used to detect one or more pathogens 106 through use of fluorescently labeled phosphopeptides as affinity probes (Yang et al., Anal. Chem., 10.1021/ac061936e (2006)). Methods to immobilize proteins and peptides have been reported (Taylor, Protein Immobilization: Fundamentals and Applications, Marcel Dekker, Inc., New York (1991)).

In some embodiments, one or more microfluidic chips 108 may be configured to facilitate detection of one or more pathogens 106 through use of antibody interaction. Antibodies may be raised that will bind to numerous pathogens 106 through use of known methods (e.g., Harlow and Lane, Antibodies: A Laboratory Manual, Cold Spring Harbor Laboratory Press, Cold Spring Harbor, N.Y. (1988)). Antibodies may be configured in numerous ways within one or more microfluidic chips 108 to process one or more pathogens 106. For example, in some embodiments, antibodies may be coupled to a substrate within a microfluidic chip 108. One or more samples 104 may be passed over the coupled antibodies to facilitate binding of one or more pathogens 106 to the one or more antibodies to form one or more antibody-pathogen complexes. A labeled detector antibody that binds to the pathogen 106 (or the antibody-pathogen complex) may then be passed over the one or more antibody-pathogen complexes such that the labeled detector antibody will label the pathogen 106 (or the antibody-pathogen complex). Numerous labels may be used that include, but are not limited to, enzymes, fluorescent molecules, radioactive labels, spin labels, redox labels, and the like. In other embodiments, antibodies may be coupled to a substrate within a microfluidic chip 108. One or more samples 104 may be passed over the antibodies to facilitate binding of one or more pathogens 106 to the one or more antibodies to form one or more antibody-pathogen complexes. Such binding provides for detection of the antibody-pathogen complex through use of methods that include, but are not limited to, surface plasmon resonance, conductivity, and the like (e.g., U.S. Pat. No. 7,030,989; herein incorporated by reference). In some embodiments, antibodies may be coupled to a substrate within a microfluidic chip 108 to provide for a competition assay. One or more samples 104 may be mixed with one or more reagent mixtures that include one or more labeled pathogens 106. The mixture may then be passed over the antibodies to facilitate binding of pathogens 106 in the sample 104 and labeled pathogens 106 in the reagent mixture to the antibodies. The unlabeled pathogens 106 in the sample 104 will compete with the labeled pathogens 106 in the reagent mixture for binding to the antibodies. Accordingly, the amount of label bound to the antibodies will vary in accordance with the concentration of unlabeled pathogen 106 in the sample 104. In some embodiments, antibody interaction may be used in association with microcantilevers to process one or more pathogens 106. Methods to construct microcantilevers are known (e.g., U.S. Pat. Nos. 7,141,385;

6,935,165; 6,926,864; 6,763,705; 6,523,392; 6,325,904; herein incorporated by reference). In some embodiments, one or more antibodies may be used in conjunction with one or more aptamers to process one or more samples 104. Accordingly, in some embodiments, aptamers and antibodies may be used interchangeably to process one or more samples 104.

In some embodiments, one or more microfluidic chips 108 may be configured to process one or more samples 104 through use of chemical interaction. In some embodiments, one or more microfluidic chips 108 may be configured to utilize chemical extraction to process one or more samples 104. For example, in some embodiments, one or more samples 104 may be mixed with a reagent mixture that includes one or more solvents in which the one or more pathogens 106 are soluble. Accordingly, the solvent phase containing the one or more pathogens 106 may be separated from the sample phase to provide for detection of the one or more pathogens 106. In some embodiments, one or more samples 104 may be mixed with a reagent mixture that includes one or more chemicals that cause precipitation of one or more pathogens 106. Accordingly, the sample phase may be washed away from the one or more precipitated pathogens 106 to provide for detection of the one or more pathogens 106. Accordingly, reagent mixtures that include numerous types of chemicals that interact with one or more pathogens 106 may be used.

In some embodiments, one or more microfluidic chips 108 may be configured to process one or more samples 104 through use of diffusion. In some embodiments, one or more microfluidic chips 108 may be configured to process one or more fluid samples 104 through use of an H-filter. For example, a microfluidic chip 108 may be configured to include a channel through which a fluid sample 104 and a second fluid flow such that the fluid sample 104 and the second fluid undergo substantially parallel flow through the channel without significant mixing of the sample fluid and the second fluid. As the fluid sample 104 and the second fluid flow through the channel, one or more pathogens 106 in the fluid sample 104 may diffuse through the fluid sample 104 into the second fluid. Accordingly, such diffusion provides for the separation of the one or more pathogens 106 from the sample 104. Methods to construct H-filters have been described (e.g., U.S. Pat. Nos. 6,742,661; 6,409,832; 6,007,775; 5,974,867; 5,971,158; 5,948,684; 5,932,100; 5,716,852; herein incorporated by reference). In some embodiments, diffusion based methods may be combined with immunoassay based methods to process and detect one or more pathogens 106. Methods to conduct microscale diffusion immunoassays have been described (e.g., U.S. Pat. No. 6,541,213; herein incorporated by reference). Accordingly, microfluidic chips 108 may be configured in numerous ways to process one or more pathogens 106 through use of diffusion.

In some embodiments, one or more microfluidic chips 108 may be configured to facilitate detection of one or more pathogens 106 through use of filtration. In some embodiments, one or more microfluidic chips 108 may be configured to include one or more filters that have a molecular weight cut-off. For example, a filter may allow molecules of low molecular weight to pass through the filter while disallowing molecules of high molecular weight to pass through the filter. Accordingly, one or more pathogens 106 that are contained within a sample 104 may be allowed to pass through a filter while larger molecules contained within the sample 104 are disallowed from passing through the filter. Accordingly, in some embodiments, a microfluidic chip 108 may include two or more filters that selectively retain, or allow passage, of one or more pathogens 106 through the filters. Such configurations provide for selective separation of one or more pathogens 106 from one or more samples 104. Membranes and filters having numerous molecular weight cut-offs are commercially available (e.g., Millipore, Billerica, Mass.). In some embodiments, one or more microfluidic chips 108 may be configured to provide for dialysis of one or more samples 104. For example, in some embodiments, a microfluidic chip 108 may be configured to contain one or more samples 104 in one or more sample chambers that are separated from one or more dialysis chambers by a semi-permeable membrane. Accordingly, in some embodiments, one or more pathogens 106 that are able to pass through the semi-permeable membrane may be collected in the dialysis chamber. In other embodiments, one or more pathogens 106 may be retained in the one or more sample chambers while other sample components may be separated from the one or more pathogens 106 by their passage through the semi-permeable membrane into the dialysis chamber. Accordingly, one or more microfluidic chips 108 may be configured to include two or more dialysis chambers for selective separation of one or more pathogens 106 from one or more samples 104. Semi-permeable membranes and dialysis tubing is available from numerous commercial sources (e.g., Millipore, Billerica, Mass.; Pierce, Rockford, Ill.; Sigma-Aldrich, St. Louis, Mo.). Methods that may be used for microfiltration have been described (e.g., U.S. Pat. No. 5,922,210; herein incorporated by reference).

In some embodiments, one or more microfluidic chips 108 may be configured to process one or more samples 104 through use of chromatography. Numerous chromatographic methods may be used to process one or more samples 104. Examples of such chromatographic methods include, but are not limited to, ion-exchange chromatography, affinity chromatography, gel filtration chromatography, hydroxyapatite chromatography, gas chromatography, reverse phase chromatography, thin layer chromatography, capillary chromatography, size exclusion chromatography, hydrophobic interaction media, and the like. In some embodiments, a microfluidic chip 108 may be configured to process one or more samples 104 through use of one or more chromatographic methods. In some embodiments, chromatographic methods may be used to process one or more samples 104 for one or more pathogens 106 that include one or more polynucleotides. For example, in some embodiments, one or more samples 104 may be applied to a chromatographic media to which the one or more polynucleotides bind. The remaining components of the sample 104 may be washed from the chromatographic media. The one or more polynucleotides may then be eluted from chromatographic media in a more purified state. Similar methods may be used to process one or more samples 104 for one or more pathogens 106 that include one or more proteins or polypeptides (e.g., Mondal and Gupta, Biomol. Eng., 23:59-76 (2006)). Chromatography media able to separate numerous types of molecules is commercially available (e.g., Bio-Rad, Hercules, Calif.; Qiagen, Valencia, Calif.; Pfizer, New York, N.Y.; Millipore, Billerica, Mass.; GE Healthcare Bio-Sciences Corp., Piscataway, N.J.).

In some embodiments, one or more microfluidic chips 108 may be configured to process one or more samples 104 through use of aptamer interaction. In some embodiments, one or more aptamers may include polynucleotides (e.g., deoxyribonucleic acid; ribonucleic acid; and derivatives of polynucleotides that may include polynucleotides that include modified bases, polynucleotides in which the phosphodiester bond is replaced by a different type of bond, or many other types of modified polynucleotides). In some embodiments, one or more aptamers may include peptide aptamers. Methods to prepare and use aptamers have been described (e.g., Collett et al., Methods, 37:4-15 (2005); Collet et al., Anal. Biochem., 338:113-123 (2005); Cox et al., Nucleic Acids Res., 30:20 e108 (2002); Kirby et al., Anal. Chem., 76:4066-4075 (2004); Ulrich, Handb. Exp. Pharmacol., 173:305-326 (2006); Baines and Colas, Drug Discovery Today, 11:334-341 (2006); Guthrie et al., Methods, 38:324-330 (2006); Geyer et al., Chapter 13: Selection of Genetic Agents from Random Peptide Aptamer Expression Libraries, Methods in Enzymology, Academic Press, pg. 171-208 (2000); U.S. Pat. No. 6,569,630; herein incorporated by reference). Aptamers may be configured in numerous ways within one or more microfluidic chips 108 to process one or more pathogens 106. For example, in some embodiments, aptamers may be coupled to a substrate within a microfluidic chip 108. One or more samples 104 may be passed over the aptamers to facilitate binding of one or more pathogens 106 to the one or more aptamers to form one or more aptamer-pathogen complexes. Labeled detector antibodies and/or aptamers that bind to the pathogen 106 (or the aptamer-pathogen complex) may then be passed over the one or more aptamer-pathogen complexes such that the labeled detector antibodies and/or aptamers will label the pathogen 106 (or the aptamer-pathogen complex). Numerous labels may be used that include, but are not limited to, enzymes, fluorescent molecules, radioactive labels, spin labels, redox labels, and the like. In other embodiments, aptamers may be coupled to a substrate within a microfluidic chip 108. One or more samples 104 may be passed over the aptamers to facilitate binding of one or more pathogens 106 to the one or more aptamers to form one or more aptamer-pathogen complexes. Such binding provides for detection of the aptamer-pathogen complex through use of methods that include, but are not limited to, surface plasmon resonance, conductivity, and the like (e.g., U.S. Pat. No. 7,030,989; herein incorporated by reference). In some embodiments, aptamers may be coupled to a substrate within a microfluidic chip 108 to provide for a competition assay. One or more samples 104 may be mixed with one or more reagent mixtures that include one or more labeled pathogens 106. The mixture may then be passed over the aptamers to facilitate binding of pathogens 106 in the sample 104 and labeled pathogens 106 in the reagent mixture to the aptamers. The unlabeled pathogens 106 in the sample 104 will compete with the labeled pathogens 106 in the reagent mixture for binding to the aptamers. Accordingly, the amount of label bound to the aptamers will vary in accordance with the concentration of unlabeled pathogens 106 in the sample 104. In some embodiments, aptamer interaction may be used in association with microcantilevers to process one or more pathogens 106. Methods to construct microcantilevers are known (e.g., U.S. Pat. Nos. 7,141,385; 6,935,165; 6,926,864; 6,763,705; 6,523,392; 6,325,904; herein incorporated by reference). In some embodiments, one or more aptamers may be used in conjunction with one or more antibodies to process one or more samples 104. In some embodiments, aptamers and antibodies may be used interchangeably to process one or more samples 104. Accordingly, in some embodiments, methods and/or systems for processing and/or detecting pathogen indicators may utilize antibodies and aptamers interchangeably and/or in combination.

In some embodiments, one or more microfluidic chips 108 may be configured to facilitate detection of one or more pathogens 106 through use of electrical conductivity. In some embodiments, one or more samples 104 may be processed through use of magnetism. For example, in some embodiments, one or more samples 104 may be combined with one or more tagged polynucleotides that are tagged with a ferrous material, such as a ferrous bead. The tagged polynucleotides and the polynucleotides in the one or more samples 104 may be incubated to provide hybridized complexes of the tagged polynucleotides and the sample polynucleotides. Hybridization will serve to couple one or more ferrous beads to the polynucleotides in the sample 104 that hybridize with the tagged polynucleotides. Accordingly, the mixture may be passed over an electromagnet to immobilize the hybridized complexes. Other components in the sample 104 may then be washed away from the hybridized complexes. In some embodiments, a chamber containing the magnetically immobilized hybridized complexes may be heated to release the sample polynucleotides from the magnetically immobilized tagged polynucleotides. The sample polynucleotides may then be collected in a more purified state. In other embodiments, similar methods may be used in conjunction with antibodies, aptamers, peptides, ligands, and the like. Accordingly, one or more microfluidic chips 108 may be configured in numerous ways to utilize magnetism to process one or more samples 104. In some embodiments, one or more samples 104 may be processed through use of eddy currents. Eddy current separation uses electromagnetic induction in conducting materials to separate non-ferrous metals by their different electric conductivities. An electrical charge is induced into a conductor by changes in magnetic flux cutting through it. Moving permanent magnets passing a conductor generates the change in magnetic flux. Accordingly, in some embodiments, one or more microfluidic chips 108 may be configured to include a magnetic rotor such that when conducting particles move through the changing flux of the magnetic rotor, a spiraling current and resulting magnetic field are induced. The magnetic field of the conducting particles may interact with the magnetic field of the magnetic rotor to impart kinetic energy to the conducting particles. The kinetic energy imparted to the conducting particles may then be used to direct movement of the conducting particles. Accordingly, non-ferrous particles, such as metallic beads, may be utilized to process one or more samples 104. For example, in some embodiments, one or more samples 104 may be combined with one or more tagged polynucleotides that are tagged with a non-ferrous material, such as an aluminum bead. The tagged polynucleotides and the polynucleotides in the one or more samples 104 may be incubated to provide hybridized complexes of the tagged polynucleotides and the sample polynucleotides. Hybridization will serve to couple one or more ferrous beads to the polynucleotides in the sample 104 that hybridize with the tagged polynucleotides. Accordingly, the mixture may be passed through a magnetic field to impart kinetic energy to the non-ferrous bead. This kinetic energy may then be used to separate the hybridized complex. In other embodiments, similar methods may be used in conjunction with antibodies, aptamers, peptides, ligands, and the like. Accordingly, one or more microfluidic chips 108 may be configured in numerous ways to utilize eddy currents to process one or more samples 104. One or more microfluidic chips 108 may be configured in numerous ways to utilize electrical conductivity to process one or more samples 104.

In some embodiments, one or more microfluidic chips 108 may be configured to process one or more samples 104 through use of isoelectric focusing. Methods have been described that may be used to construct capillary isoelectric focusing systems (e.g., Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989);

U.S. Pat. Nos. 7,150,813; 7,070,682; 6,730,516; herein incorporated by reference). Such systems may be modified to provide for the processing of one or more samples 104.

In some embodiments, one or more microfluidic chips 108 may be configured to facilitate detection of one or more pathogens 106 through use of electrophoresis. In some embodiments, one or more microfluidic chips 108 may be configured to process one or more samples 104 through use of one-dimensional electrophoresis. In some embodiments, one or more microfluidic chips 108 may be configured to process one or more samples 104 through use of two-dimensional electrophoresis. In some embodiments, one or more microfluidic chips 108 may be configured to process one or more samples 104 through use of gradient gel electrophoresis. In some embodiments, one or more microfluidic chips 108 may be configured to process one or more samples 104 through use of electrophoresis under denaturing conditions. In some embodiments, one or more microfluidic chips 108 may be configured to process one or more samples 104 through use of electrophoresis under native conditions. One or more microfluidic chips 108 may be configured to utilize numerous electrophoretic methods.

In some embodiments, one or more microfluidic chips 108 may be configured to facilitate detection of one or more pathogens 106 through use of immunoassay. In some embodiments, one or more microfluidic chips 108 may be configured to process one or more samples 104 through use of enzyme linked immunosorbant assay (ELISA). In some embodiments, one or more microfluidic chips 108 may be configured to process one or more samples 104 through use of radioimmuno assay (RIA). In some embodiments, one or more microfluidic chips 108 may be configured to process one or more samples 104 through use of enzyme immunoassay (EIA). In some embodiments, such methods may utilize antibodies (e.g., monoclonal antibodies, polyclonal antibodies, antibody fragments, single-chain antibodies, and the like), aptamers, or substantially any combination thereof. In some embodiments, a labeled antibody and/or aptamer may be used within an immunoassay. Numerous types of labels may be utilized in association with immunoassays. Examples of such labels include, but are not limited to, radioactive labels, fluorescent labels, enzyme labels, spin labels, magnetic labels, gold labels, colorimetric labels, redox labels, and the like. Numerous immunoassays are known and may be configured for processing one or more samples 104.

In some embodiments, one or more microfluidic chips 108 may be configured to facilitate detection of one or more pathogens 106 through use of one or more competition assays. In some embodiments, one or more microfluidic chips 108 may be configured to process one or more samples 104 through use of one or more polynucleotide based competition assays. One or more microfluidic chips 108 may be configured to include one or more polynucleotides coupled to a substrate, such as a polynucleotide array. The one or more microfluidic chips 108 may be further configured so that a sample 104 and/or substantially purified polynucleotides obtained from one or more samples 104, may be mixed with one or more reagent mixtures that include one or more labeled polynucleotides to form an analysis mixture. This analysis mixture is then passed over the substrate such that the labeled polynucleotides and the sample polynucleotides are allowed to hybridize to the polynucleotides that are immobilized on the substrate. The sample polynucleotides and the labeled polynucleotides will compete for binding to the polynucleotides that are coupled on the substrate. Accordingly, the presence and/or concentration of the polynucleotides in the sample 104 can be determined through detection of the label (e.g., the concentration of the polynucleotides in the sample 104 will be inversely related to the amount of label that is bound to the substrate). Numerous labels may be used that include, but are not limited to, enzymes, fluorescent molecules, radioactive labels, spin labels, redox labels, and the like. In some embodiments, one or more microfluidic chips 108 may be configured to include one or more antibodies, proteins, peptides, and/or aptamers that are coupled to a substrate. The one or more microfluidic chips 108 may be further configured so that a sample 104 and/or substantially purified sample polypeptides and/or sample peptides obtained from one or more samples 104, may be mixed with one or more reagent mixtures that include one or more labeled polypeptides and/or labeled peptides to form an analysis mixture. This analysis mixture can then be passed over the substrate such that the labeled polypeptides and/or labeled peptides and the sample polypeptides and/or sample peptides are allowed to bind to the antibodies, proteins, peptides, and/or aptamers that are immobilized on the substrate. The sample polypeptides and/or sample peptides and the labeled polypeptides and/or sample peptides will compete for binding to the antibodies, proteins, peptides, and/or aptamers that are coupled on the substrate. Accordingly, the presence and/or concentration of the sample polypeptides and/or sample peptides in the sample 104 can be determined through detection of the label (e.g., the concentration of the sample polypeptides and/or sample peptides in the sample 104 will be inversely related to the amount of label that is bound to the substrate). Numerous labels may be used that include, but are not limited to, enzymes, fluorescent molecules, radioactive labels, spin labels, redox labels, and the like. Microfluidic chips 108 may be configured to utilize numerous types of competition assays.

Accordingly, microfluidic chips 108 may be configured for analysis of numerous types of pathogens 106 (e.g., intact pathogen 106 and/or portion of pathogen).

Analysis Unit

System 100 may include one or more analysis units 110. Analysis units 110 may be configured for analysis of numerous types of pathogens 106. In some embodiments, one or more analysis units 110 may be configured for analysis of one or more polynucleotides, polypeptides, polysaccharides, enzyme activities, and the like. In some embodiments, one or more polynucleotides, polypeptides, polysaccharides, enzyme activities, and the like that are associated with one or more pathogens 106 may be analyzed. In some embodiments, one or more polynucleotides, polypeptides, polysaccharides, enzyme activities, and the like that are associated with pathogen 106 activity may be analyzed.

For example, in some embodiments, one or more analysis units 110 may be configured for analysis of one or more polypeptides through use of numerous techniques that include, but are not limited to, competition assays, immunological methods (e.g., sandwich assays), and the like.

In other embodiments, one or more analysis units 110 may be configured for analysis of one or more polynucleotides through use of numerous techniques that include, but are not limited to, competition assays, electron transfer assays, electrical conductivity assays, and the like.

In some embodiments, an analysis unit 110 may include one or more centrifugation units. In some embodiments, one or more centrifugation units may be configured to operably associate with one or more microfluidic chips 108. Accordingly, in some embodiments, one or more centrifugation units may be used to facilitate analysis and/or detection of one or more pathogens 106. Methods to fabricate devices that may be used to drive fluid movement through centripetal acceleration in a microfluidics system have been described (e.g., U.S. Pat. No. 6,709,869; herein incorporated by reference).

For example, in some embodiments, one or more centrifugation units may be used to facilitate the analysis of one or more polynucleotides from one or more samples 104 that are applied to one or more microfluidic chips 108 (e.g., U.S. patent application Ser. Nos. 11/699,770; 11/699,920; 11/699,747; and 11/699,774; herein incorporated by reference).

In some embodiments, one or more centrifugation units may be configured to centrifuge one or more microfluidic chips 108 to facilitate movement of one or more samples 104, one or more reagents, one or more fluids, and the like through the one or more microfluidic chips 108.

In some embodiments, one or more centrifugation units may be configured to centrifuge one or more microfluidic chips 108 to create a gradient. In some embodiments, velocity gradients may be created to facilitate analysis of one or more samples 104. For example, glycerol gradients may be used to separate polypeptides from one or more samples 104. In other embodiments, density gradients may be created to facilitate analysis of one or more samples 104. For example, cesium chloride may be used to create a density gradient to facilitate the analysis of one or more polynucleotides. In some embodiments, gradient centrifugation may be used to analyze one or more viral particles.

In some embodiments, one or more centrifugation units may be configured to centrifuge one or more microfluidic chips 108 to facilitate chromatographic separations of components within one or more samples 104. For example, chromatographic media may be packed within a microfluidic chip 108 to facilitate the separation of components, such as pathogens 106, from one or more samples 104. Such chromatographic media is commercially available (e.g., Qiagen Sciences, Germantown, Md. and Pfizer, New York, N.Y.).

In some embodiments, an analysis unit 110 may include one or more reagent delivery units. In some embodiments, one or more reagent delivery units may be configured to operably associate with one or more microfluidic chips 108. Accordingly, in some embodiments, one or more reagent delivery units may be configured to contain one or more reagents that may be used within one or more microfluidic chips 108 to analyze and/or detect one or more pathogens 106. In some embodiments, one or more reagent delivery units may include one or more pumps to facilitate delivery of one or more reagents. Numerous types of pumps may be used within a reagent delivery unit. In some embodiments, one or more reagent delivery units may be configured to operably associate with one or more centrifugation units. Accordingly, reagents may be delivered through use of centrifugal force. Reagent delivery units may be configured in numerous ways. For example, in some embodiments, reagent delivery units may include one or more reagent reservoirs, one or more waste reservoirs or substantially any combination thereof. Reagent delivery units may be configured to contain and/or deliver numerous types of reagents. Examples of such reagents include, but are not limited to, phenol, chloroform, alcohol, salt solutions, detergent solutions, solvents, reagents used for polynucleotide precipitation, reagents used for polypeptide precipitation, reagents used for polynucleotide extraction, reagents used for polypeptide extraction, reagents used for chemical extractions, and the like. Accordingly, reagent delivery units may be configured to contain and/or deliver virtually any reagent that may be used for the analysis of one or more pathogens 106.

In some embodiments, one or more analysis units 110 may be configured to facilitate detection of one or more pathogens 106 with at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, filtration, electrophoresis, use of a CCD camera, immunoassay, or substantially any combination thereof.

In some embodiments, one or more analysis units 110 may be configured to operably associate with one or more microfluidic chips 108. For example, in some embodiments, one or more microfluidic chips 108 may include a window (e.g., a quartz window, a cuvette analog, and/or the like) through which one or more analysis units 110 may determine if one or more pathogens 106 are present and/or determine the concentration of one or more pathogens 106. In such embodiments, one or more analysis units 110 may be configured to utilize numerous techniques, such as visible light spectroscopy, ultraviolet light spectroscopy, infrared spectroscopy, fluorescence spectroscopy, and the like, to detect one or more pathogens 106.

In some embodiments, one or more analysis units 110 may be configured to facilitate detection and/or analysis of one or more pathogens 106 through use of surface plasmon resonance. In some embodiments, one or more microfluidic chips 108 may include one or more antibodies, aptamers, proteins, peptides, polynucleotides, and the like, that are bound to a substrate (e.g., a metal film) that is associated with a prism through which one or more analysis units 110 may shine light to detect one or more pathogens 106 that interact with the one or more antibodies, aptamers, proteins, peptides, polynucleotides, and the like, that are bound to a substrate.

In some embodiments, one or more analysis units 110 may be configured to facilitate detection and/or analysis of one or more pathogens 106 through use of nuclear magnetic resonance (NMR). In such embodiments, the analysis units 110 may be configured to accept an NMR probe and are configured to detect one or more pathogens 106 through use of NMR spectroscopy.

In some embodiments, one or more pathogens 106 may be detected and/or analyzed through use of spectroscopy. Numerous types of spectroscopic methods may be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, one or more pathogens 106 may be detected and/or analyzed through use of electrochemical detection. In some embodiments, one or more polynucleotides may be analyzed through use of electrochemical detection. For example, in some embodiments, a polynucleotide that includes a redox label, such as ferrocene is coupled to a gold electrode. The labeled polynucleotide forms a stem-loop structure that can self-assemble onto a gold electrode by means of facile gold-thiol chemistry. Hybridization of a sample polynucleotide induces a large conformational change in the surface-confined polynucleotide structure, which in turn alters the electron-transfer tunneling distance between the electrode and the redoxable label. The resulting change in electron transfer efficiency may be measured by cyclic voltammetry (Fan et al., Proc. Natl. Acad. Sci., 100: 9134-9137 (2003); Wang et al., Anal. Chem., 75:3941-3945 (2003); Singh-Zocchi et al., Proc. Natl. Acad. Sci., 100:7605-7610 (2003)). Such methods may be used to analyze numerous polynucleotides, such as messenger ribonucleic acid, genomic deoxyribonucleic acid, fragments thereof, and the like.

In some embodiments, one or more pathogens 106 may be detected and/or analyzed through use of polynucleotide analysis. In some embodiments, one or more analysis units 110 may be configured to use polynucleotide analysis. Numerous methods may be used to analyze one or more polynucleotides. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described (e.g., U.S. Pat. Nos. 7,118,910 and 6,960,437; herein incorporated by reference). Such methods may be adapted to provide for analysis of one or more pathogens 106. In some embodiments, fluorescence quenching, molecular beacons, electron transfer, electrical conductivity, and the like may be used to analyze polynucleotide interaction. Such methods are known and have been described (e.g., Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al., Proc. Natl. Acad. Sci., 100:7605-7610 (2003); Wang et al., Anal. Chem., 75:3941-3945 (2003); Fan et al., Proc. Natl. Acad. Sci., 100: 9134-9137 (2003); U.S. Pat. Nos. 6,958,216; 5,093,268; 6,090,545; herein incorporated by reference). In some embodiments, one or more polynucleotides that include at least one carbon nanotube may be combined with one or more samples 104, and/or one or more partially purified polynucleotides obtained from one or more samples 104. The one or more polynucleotides that include one or more carbon nanotubes are allowed to hybridize with one or more polynucleotides that may be present within the one or more samples 104. The one or more carbon nanotubes may be excited (e.g., with an electron beam and/or an ultraviolet laser) and the emission spectra of the excited nanotubes may be correlated with hybridization of the one or more polynucleotides that include at least one carbon nanotube with one or more polynucleotides that are included within the one or more samples 104. Accordingly, polynucleotides that hybridize to one or more pathogens 106 may include one or more carbon nanotubes. Methods to utilize carbon nanotubes as probes for nucleic acid interaction have been described (e.g., U.S. Pat. No. 6,821,730; herein incorporated by reference). Numerous other methods based on polynucleotide analysis may be used to analyze one or more pathogens 106.

In some embodiments, one or more pathogens 106 may be detected and/or analyzed through use of fluorescence anisotropy. Fluorescence anisotropy is based on measuring the steady state polarization of sample fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy may be coupled to numerous fluorescent labels as have been described herein and as have been described.

In some embodiments, one or more pathogens 106 may be detected and/or analyzed through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detected and/or analyze one or more pathogens 106. For example, in some embodiments, an antibody may be labeled with a fluorescent donor and one or more pathogens 106 may be labeled with a fluorescent acceptor. Accordingly, such labeled antibodies and pathogens 106 may be used within competition assays to facilitate detection and/or the determination of the concentration of one or more pathogens 106 in one or more samples 104. Numerous combinations of fluorescent donors and fluorescent acceptors may be used to analyze one or more pathogens 106. Accordingly, in some embodiments, one or more microfluidic chips 108 may be configured to include a window (e.g., quartz) through which fluorescent light may pass to provide for detection of one or more pathogens 106 through use of fluorescence resonance energy transfer. Accordingly, fluorescence resonance energy transfer may be used in conjunction with competition assays and/or numerous other types of assays to analyze and/or detect one or more pathogens 106.

In some embodiments, one or more pathogens 106 may be detected and/or analyzed through use of electron transfer. Electron transfer is the process by which an electron moves from an electron donor to an electron acceptor causing the oxidation states of the electron donor and the electron acceptor to change. In some embodiments, electron transfer may occur when an electron is transferred from one or more electron donors to an electrode. In some embodiments, electron transfer may be utilized within competition assays to analyze one or more pathogens 106. For example, in some embodiments, one or more microfluidic chips 108 may include one or more polynucleotides that may be immobilized on one or more electrodes. The immobilized polynucleotides may be incubated with a reagent mixture that includes sample polynucleotides and polynucleotides that are tagged with an electron donor. Hybridization of the tagged polynucleotides to the immobilized polynucleotides allows the electron donor to transfer an electron to the electrode to produce a detectable signal 126. Accordingly, a decrease in signal due to the presence of one or more polynucleotides that are pathogens 106 in the reagent mixture indicates the presence of a pathogen 106 in the sample 104. Such methods may be used in conjunction with polynucleotides, polypeptides, peptides, antibodies, aptamers, and the like. One or more analysis units 110 may be configured to operably associate with one or more microfluidic chips 108 to utilize numerous electron transfer based assays to provide for detection of one or more pathogens 106.

In some embodiments, one or more pathogens 106 may be detected and/or analyzed through use of one or more enzyme assays. Numerous enzyme assays may be used to provide for detection of one or more pathogens 106. Examples of such enzyme assays include, but are not limited to, beta-galactosidase assays, peroxidase assays, catalase assays, alkaline phosphatase assays, and the like. In some embodiments, enzyme assays may be configured such that an enzyme will catalyze a reaction involving an enzyme substrate that produces a fluorescent product. Accordingly, one or more analysis units 110 may be configured to facilitate detection of fluorescence resulting from the fluorescent product. Enzymes and fluorescent enzyme substrates are known and are commercially available (e.g., Sigma-Aldrich, St. Louis, Mo.). In some embodiments, enzyme assays may be configured as binding assays that provide for detection of one or more pathogens 106. For example, in some embodiments, one or more microfluidic chips 108 may be configured to include a substrate to which is coupled one or more antibodies, aptamers, peptides, proteins, polynucleotides, ligands, and the like, that will interact with one or more pathogens 106. One or more samples 104 may be passed across the substrate such that one or more pathogens 106 present within the one or more samples 104 will interact with the one or more antibodies, aptamers, peptides, proteins, polynucleotides, ligands, and the like, and be immobilized on the substrate. One or more antibodies, aptamers, peptides, proteins, polynucleotides, ligands, and the like, that are labeled with an enzyme may then be passed across the substrate such that the one or more labeled antibodies, aptamers, peptides, proteins, polynucleotides, ligands, and the like, will bind to the one or more immobilized pathogens 106. An enzyme substrate may then be introduced to the one or more immobilized enzymes such that the enzymes are able to catalyze a reaction involving the enzyme substrate to produce a fluorescent product. Such assays are often referred to as sandwich assays. Accordingly, one or more analysis units 110 may be configured to provide for detection of one or more products of enzyme catalysis to provide for detection of one or more pathogens 106.

In some embodiments, one or more pathogens 106 may be detected and/or analyzed through use of electrical conductivity. In some embodiments, one or more analysis units 110 may be configured to provide for detection of one or more pathogens 106 through use of electrical conductivity. In some embodiments, microfluidic chips 108 may be configured to operably associate with one or more analysis units 110 such that the one or more analysis units 110 can detect one or more pathogens 106 through use of electrical conductivity. In some embodiments, one or more microfluidic chips 108 may be configured to include two or more electrodes that are each coupled to one or more detector polynucleotides. Interaction of a pathogen associated polynucleotide, such as hybridization, with two detector polynucleotides that are coupled to two different electrodes will complete an electrical circuit. This completed circuit will provide for the flow of a detectable electrical current between the two electrodes and thereby provide for detection of one or more pathogen associated polynucleotides that indicate the presence of one or more pathogens 106. In some embodiments, the electrodes may be carbon nanotubes (e.g., U.S. Pat. No. 6,958,216; herein incorporated by reference). In some embodiments, electrodes may include, but are not limited to, one or more conductive metals, such as gold, copper, iron, silver, platinum, and the like; one or more conductive alloys; one or more conductive ceramics; and the like. In some embodiments, electrodes may be selected and configured according to protocols typically used in the computer industry that include, but are not limited to, photolithography, masking, printing, stamping, and the like. In some embodiments, other molecules and complexes that interact with one or more pathogens 106 may be used to detect the one or more pathogens 106 through use of electrical conductivity. Examples of such molecules and complexes include, but are not limited to, proteins, peptides, antibodies, aptamers, and the like. For example, in some embodiments, two or more antibodies may be immobilized on one or more electrodes such that contact of the two or more antibodies with a pathogen 106, such as a spore, a bacterium, a virus, an egg, a worm, a cyst, a protozoan, a single-celled organism, a fungus, an algae, and the like, will complete an electrical circuit and facilitate the production of a detectable electrical current.

In some embodiments, one or more pathogens 106 may be detected and/or analyzed through use of isoelectric focusing. In some embodiments, analysis units 110 may be configured to provide for detection of one or more pathogens 106 through use of isoelectric focusing. In such embodiments, one or more analysis units 110 may be configured to associate with one or more microfluidic chips 108 that are configured to utilize isoelectric focusing to detect and/or analyze one or more pathogens 106. In some embodiments, native isoelectric focusing may be utilized. In some embodiments, denaturing isoelectric focusing may be utilized. Methods to construct microfluidic channels that may be used for isoelectric focusing have been reported (e.g., Macounova et al., Anal Chem., 73:1627-1633 (2001); Macounova et al., Anal Chem., 72:3745-3751 (2000); Herr et al., Investigation of a miniaturized capillary isoelectric focusing (cIEF) system using a full-field detection approach, Mechanical Engineering Department, Stanford University, Stanford, Calif.; Wu and Pawliszyn, Journal of Microcolumn Separations, 4:419-422 (1992); Kilar and Hjerten, Electrophoresis, 10:23-29 (1989); U.S. Pat. Nos. 7,150,813; 7,070,682; 6,730,516; herein incorporated by reference). In some embodiments, one or more analysis units 110 may be configured to include one or more CCD cameras that can be used to detect one or more pathogens 106 that are analyzed through isoelectric focusing. In some embodiments, one or more analysis units 110 may be configured to include one or more spectrometers that can be used to detect one or more pathogens 106. Numerous types of spectrometers may be utilized to detect one or more pathogens 106 following isoelectric focusing. In some embodiments, one or more analysis units 110 may be configured to utilize refractive index to detect one or more pathogens 106.

In some embodiments, one or more pathogens 106 may be detected and/or analyzed through use of chromatographic methodology alone or in combination with additional analysis and/or detection methods. In some embodiments, one or more analysis units 110 may be configured for use with chromatographic methods. Accordingly, in some embodiments, one or more analysis units 110 may be configured to operably associate with one or more microfluidic chips 108 and detect one or more pathogens 106 that were analyzed through use of chromatographic methods. In some embodiments, the one or more analysis units 110 may be configured to operably associate with one or more microfluidic chips 108 and supply solvents and other reagents to the one or more microfluidic chips 108. For example, in some embodiments, one or more analysis units 110 may include pumps and solvent/buffer reservoirs that are configured to supply solvent/buffer flow through chromatographic media (e.g., a chromatographic column) that is operably associated with one or more microfluidic chips 108. Numerous types of chromatographic methods and media may be used to analyze one or more samples 104 and provide for detection of one or more pathogens 106. Chromatographic methods include, but are not limited to, low pressure liquid chromatography, high pressure liquid chromatography (HPLC), microcapillary low pressure liquid chromatography, microcapillary high pressure liquid chromatography, ion exchange chromatography, affinity chromatography, gel filtration chromatography, size exclusion chromatography, thin layer chromatography, paper chromatography, gas chromatography, and the like. Methods that may be used to prepare microcapillary HPLC columns (e.g., columns with a 100 micrometer-500 micrometer inside diameter) have been described (e.g., Davis et al., Methods, A Companion to Methods in Enzymology, 6: Micromethods for Protein Structure Analysis, ed. by John E. Shively, Academic Press, Inc., San Diego, 304-314 (1994); Swiderek et al., Trace Structural Analysis of Proteins. Methods of Enzymology, ed. by Barry L. Karger & William S. Hancock, Spectrum, Publisher Services, 271, Chap. 3, 68-86 (1996); Moritz and Simpson, J. Chromatogr., 599:119-130 (1992)). Methods to prepare affinity columns have been described. Briefly, a biotinylated site may be engineered into a polypeptide, peptide, aptamer, antibody, or the like. The biotinylated protein may then be incubated with avidin coated polystyrene beads and slurried in Tris buffer. The slurry may then be packed into a capillary affinity column through use of high pressure packing. Affinity columns may be prepared that may include one or more molecules and/or complexes that interact with one or more pathogens 106. For example, in some embodiments, one or more aptamers that bind to one or more pathogens 106 may be used to construct an affinity column. Accordingly, numerous chromatographic methods may be used alone, or in combination with additional methods, to process and detect one or more pathogens 106. Numerous detection methods may be used in combination with numerous types of chromatographic methods. Accordingly, one or more analysis units 110 may be configured to utilize numerous detection methods to detect one or more pathogens 106 that are analyzed through use of one or more chromatographic methods. Examples of such detection methods include, but are not limited to, conductivity detection, use of ion-specific electrodes, refractive index detection, colorimetric detection, radiological detection, detection by retention time, detection through use of elution conditions, spectroscopy, and the like. For example, in some embodiments, one or more chromatographic markers may be added to one or more samples 104 prior to the samples 104 being applied to a chromatographic column. One or more analysis units 110 that are operably associated with one or more microfluidic chips 108 that include a chromatographic column may be configured to detect the one or more chromatographic markers and use the elution time and/or position of the chromatographic markers as a calibration tool for use in detecting one or more pathogens 106. Accordingly, chromatographic methods may be used in combination with additional methods and in combination with numerous types of detection methods.

In some embodiments, one or more pathogens 106 may be detected and/or analyzed through use of immunoprecipitation. In some embodiments, one or more analysis units 110 may be configured to provide for detection of one or more pathogens 106 through use of immunoprecipitation. In some embodiments, an analysis unit 110 may be configured to associated with one or more microfluidic chips 108 that are configured to utilize immunoprecipitation to analyze one or more pathogens 106. In some embodiments, immunoprecipitation may be utilized in combination with additional analysis and/or detection methods to analyze and/or detect one or more pathogens 106. In some embodiments, one or more analysis units 110 may be configured to analyze one or more samples 104 through use of immunoprecipitation. For example, in some embodiments, one or more samples 104 may be combined with one or more antibodies that bind to one or more pathogens 106 to form one or more antibody-pathogen complexes. An insoluble form of an antibody binding constituent, such as protein A (e.g., protein A-sepharose bead, protein A-magnetic bead, protein A-ferrous bead, protein A-non-ferrous bead, and the like), Protein G, a second antibody, an aptamer, and the like, may then be mixed with the antibody-pathogen complex such that the insoluble antibody binding constituent binds to the antibody-pathogen complex and provides for precipitation of the antibody-pathogen complex. Such complexes may be separated from other sample components to provide for detection of one or more pathogens 106. For example, in some embodiments, sample components may be washed away from the precipitated antibody-pathogen complexes. In some embodiments, one or more analysis units 110 that are configured for immunoprecipitation may include one or more centrifugation units to assist in precipitating one or more antibody-pathogen complexes. In some embodiments, aptamers (polypeptide and/or polynucleotide) may be used in combination with antibodies or in place of antibodies. Accordingly, one or more analysis units 110 may be configured to detect one or more pathogens 106 through use of numerous detection methods in combination with immunoprecipitation based methods.

In some embodiments, one or more pathogens 106 may be analyzed through use of immunoseparation. In some embodiments, one or more analysis units 110 may be configured to analyze one or more pathogens 106 through use of immunoseparation. For example, in some embodiments, an analysis unit 110 may be configured to associate with one or more microfluidic chips 108 that are configured to analyze one or more pathogens 106 through use of immunoseparation. In some embodiments, immunoseparation may be utilized in combination with additional analysis and/or detection methods to detect one or more pathogens 106. In some embodiments, one or more analysis units 110 may be configured to analyze one or more samples 104 through use of immunoseparation. For example, in some embodiments, one or more samples 104 may be combined with one or more antibodies that bind to one or more pathogens 106 to form one or more antibody-pathogen complexes. An antibody binding constituent may be added that binds to the antibody-pathogen complex. Examples of such antibody binding constituents that may be used alone or in combination include, but are not limited to, protein A (e.g., protein A-sepharose bead, protein A-magnetic bead, protein A-ferrous bead, protein A-non-ferrous bead, and the like), Protein G, a second antibody, an aptamer, and the like. Such antibody binding constituents may be mixed with an antibody-pathogen complex such that the antibody binding constituent binds to the antibody-pathogen complex and provides for separation of the antibody-pathogen complex. In some embodiments, the antibody binding constituent may include a tag that allows the antibody binding constituent and complexes that include the antibody binding constituent to be separated from other components in one or more samples 104. In some embodiments, the antibody binding constituent may include a ferrous material. Accordingly, antibody-pathogen complexes may be separated from other sample components through use of a magnet, such as an electromagnet. In some embodiments, an antibody binding constituent may include a non-ferrous metal. Accordingly, antibody-pathogen complexes may be separated from other sample components through use of an eddy current to direct movement of one or more antibody-pathogen complexes. In some embodiments, two or more forms of an antibody binding constituents may be used to detect one or more pathogens 106. For example, in some embodiments, a first antibody binding constituent may be coupled to a ferrous material and a second antibody binding constituent may be coupled to a non-ferrous material. Accordingly, the first antibody binding constituent and the second antibody binding constituent may be mixed with antibody-pathogen complexes such that the first antibody binding constituent and the second antibody binding constituent bind to antibody-pathogen complexes that include different pathogens 106. Accordingly, in such embodiments, different pathogens 106 from a single sample 104 and/or a combination of samples 104 may be separated through use of direct magnetic separation in combination with eddy current based separation. In some embodiments, one or more samples 104 may be combined with one or more antibodies that bind to one or more pathogens 106 to form one or more antibody-pathogen complexes. In some embodiments, the one or more antibodies may include one or more tags that provide for separation of the antibody-pathogen complexes. For example, in some embodiments, an antibody may include a tag that includes one or more magnetic beads, a ferrous material, a non-ferrous metal, an affinity tag, a size exclusion tag (e.g., a large bead that is excluded from entry into chromatographic media such that antibody-pathogen complexes pass through a chromatographic column in the void volume), and the like. Accordingly, one or more analysis units 110 may be configured to analyze one or more pathogens 106 through use of numerous analysis methods in combination with immunoseparation based methods. In some embodiments, aptamers (polypeptide and/or polynucleotide) may be used in combination with antibodies or in place of antibodies.

In some embodiments, one or more pathogens 106 may be analyzed through use of aptamer binding. In some embodiments, one or more analysis units 110 may be configured to analyze one or more pathogens 106 through use of aptamer binding. In some embodiments, aptamer binding may be utilized in combination with additional analysis and/or detection methods to detect one or more pathogens 106. For example, in some embodiments, one or more samples 104 may be combined with one or more aptamers that bind to one or more pathogens 106 to form one or more aptamer-pathogen complexes. Such complexes may be detected through use of numerous methods that include, but are not limited to, fluorescence resonance energy transfer, fluorescence quenching, surface plasmon resonance, and the like. In some embodiments, aptamer binding constituents may be added that bind to the aptamer-pathogen complex. Numerous aptamer binding constituents may be utilized. For example, in some embodiments, one or more aptamers may include one or more tags to which one or more aptamer binding constituents may bind. Examples of such tags include, but are not limited to, biotin, avidin, streptavidin, histidine tags, nickel tags, ferrous tags, non-ferrous tags, and the like. In some embodiments, one or more tags may be conjugated with a label to provide for detection of one or more complexes. Examples of such tag-label conjugates include, but are not limited to, Texas red conjugated avidin, alkaline phosphatase conjugated avidin, CY2 conjugated avidin, CY3 conjugated avidin, CY3.5 conjugated avidin, CY5 conjugated avidin, CY5.5 conjugated avidin, fluorescein conjugated avidin, glucose oxidase conjugated avidin, peroxidase conjugated avidin, rhodamine conjugated avidin, agarose conjugated anti-protein A, alkaline phosphatase conjugated protein A, anti-protein A, fluorescein conjugated protein A, IRDye® 800 conjugated protein A, peroxidase conjugated protein A, sepharose protein A, alkaline phosphatase conjugated streptavidin, AMCA conjugated streptavidin, anti-streptavidin (*Streptomyces avidinii*) (rabbit) IgG Fraction, beta-galactosidase conjugated streptavidin, CY2 conjugated streptavidin, CY3 conjugated streptavidin, CY3.5 conjugated streptavidin, CY5 conjugated streptavidin, CY5.5 conjugated streptavidin, fluorescein conjugated streptavidin, IRDye® 700DX conjugated streptavidin, IRDye® 800 conjugated streptavidin, IRDye® 800CW conjugated streptavidin, peroxidase conjugated streptavidin, phycoerythrin conjugated streptavidin, rhodamine conjugated streptavidin, Texas red conjugated streptavidin, alkaline phosphatase conjugated biotin, anti-biotin (rabbit) IgG fraction, beta-galactosidase conjugated biotin, glucose oxidase conjugated biotin, peroxidase conjugated biotin, alkaline phosphatase conjugated protein G, anti-protein G (rabbit) Agarose conjugated, anti-protein G (Rabbit) IgG fraction, fluorescein conjugated protein G, IRDye® 800 conjugated protein G, peroxidase conjugated protein G, and the like. Many such labeled tags are commercially available (e.g., Rockland Immunochemicals, Inc., Gilbertsville, Pa.). Such labels may also be used in association with other methods to analyze and detect one or more pathogens 106. Aptamer binding constituents may be mixed with an aptamer-pathogen complex such that the aptamer binding constituent binds to the aptamer-pathogen complex and provides for separation of the aptamer-pathogen complex. In some embodiments, the aptamer binding constituent may include a tag that allows the aptamer binding constituent and complexes that include the aptamer binding constituent to be separated from other components in one or more samples 104. In some embodiments, the aptamer binding constituent may include a ferrous material. Accordingly, aptamer-pathogen complexes may be separated from other sample components through use of a magnet, such as an electromagnet. In some embodiments, an aptamer binding constituent may include a non-ferrous metal. Accordingly, aptamer-pathogen complexes may be separated from other sample components through use of an eddy current to direct movement of one or more aptamer-pathogen complexes. In some embodiments, two or more forms of aptamer binding constituents may be used to analyze one or more pathogens 106. For example, in some embodiments, a first aptamer binding constituent may be coupled to a ferrous material and a second aptamer binding constituent may be coupled to a non-ferrous material. Accordingly, the first aptamer binding constituent and the second aptamer binding constituent may be mixed with aptamer-pathogen complexes such that the first aptamer binding constituent and the second aptamer binding constituent bind to aptamer-pathogen complexes that include different pathogens 106. Accordingly, in such embodiments, different pathogens 106 from a single sample 104 and/or a combination of samples 104 may be separated through use of direct magnetic separation in combination with eddy current based separation. In some embodiments, one or more samples 104 may be combined with one or more aptamers that bind to one or more pathogens 106 to form one or more aptamer-pathogen complexes. In some embodiments, the one or more aptamers may include one or more tags that provide for separation of the aptamer-pathogen complexes. For example, in some embodiments, an aptamer may include a tag that includes one or more magnetic beads, a ferrous material, a non-ferrous metal, an affinity tag, a size exclusion tag (e.g., a large bead that is excluded from entry into chromatographic media such that antibody-pathogen complexes pass through a chromatographic column in the void volume), and the like. Accordingly, one or more analysis units 110 may be configured to detect one or more pathogens 106 in combination with numerous analysis methods. In some embodiments, antibodies may be used in combination with aptamers and/or in place of aptamers.

In some embodiments, one or more pathogens 106 may be analyzed through use of electrophoresis. In some embodiments, one or more analysis units 110 may be configured to analyze one or more samples 104 through use of electrophoresis. In some embodiments, such analysis units 110 may be configured to operably associate with one or more microfluidic chips 108 that are configured to detect and/or analyze one or more pathogens 106 through use of electrophoresis. Numerous electrophoretic methods may be utilized to analyze and/or detect one or more pathogens 106. Examples of such electrophoretic methods include, but are not limited to, capillary electrophoresis, one-dimensional electrophoresis, two-dimensional electrophoresis, native electrophoresis, denaturing electrophoresis, polyacrylamide gel electrophoresis, agarose gel electrophoresis, and the like. Numerous detection methods may be used in combination with one or more electrophoretic methods to detect one or more pathogens 106. In some embodiments, one or more pathogens 106 may be detected according to the position to which the one or more pathogens 106 migrate within an electrophoretic field (e.g., a capillary and/or a gel). In some embodiments, the position of one or more pathogens 106 may be compared to one or more standards. For example, in some embodiments, one or more samples 104 may be mixed with one or more molecular weight markers prior to gel electrophoresis. The one or more samples 104 that include the one or more molecular weight markers, may be subjected to electrophoresis and then the gel may be stained. In some embodiments, refraction, absorbance, and/or fluorescence may be used to determine the position of sample components within a gel. In such embodiments, the molecular weight markers may be used as a reference to detect one or more pathogens 106 present within the one or more samples 104. In some embodiments, one or more components that are known to be present within one or more samples 104 may be used as a reference to detect one or more pathogens 106 present within the one or more samples 104. In some embodiments, gel shift assays may be used to detect one or more pathogens 106. For example, in some embodiments, a sample 104 (e.g., a single sample 104 or combination of multiple samples 104) may be split into a first sample 104 and a second sample 104. The first sample 104 may be mixed with an antibody, aptamer, ligand, or other molecule and/or complex that binds to the one or more pathogens 106. The first and second samples 104 may then be subjected to electrophoresis. The gels corresponding to the first sample 104 and the second sample 104 may then be analyzed to determine if one or more pathogens 106 are present within the one or more samples 104. Analysis units 110 may be configured in numerous ways to analyze and detect one or more pathogens 106 through use of electrophoresis.

In some embodiments, one or more pathogens 106 may be detected and/or analyzed through use of one or more charge-coupled device (CCD) cameras. In some embodiments, one or more analysis units 110 that include one or more CCD cameras may be configured to operably associate with one or more microfluidic chips 108. Such analysis units 110 may be utilized in combination with numerous analysis methods. Examples of such methods include, but are not limited to, electrophoresis; competition assays; methods based on polynucleotide interaction, protein interaction, peptide interaction, antibody interaction, aptamer interaction, immunoprecipitation, immunoseparation, and the like. For example, in some embodiments, one or more analysis units 110 may be configured to analyze one or more samples 104 through use of immunoprecipitation. In some embodiments, one or more antibodies may be conjugated to a fluorescent label such that binding of one or more labeled antibodies to one or more pathogens 106 included within one or more samples 104 will form a fluorescently labeled antibody-pathogen complex. One or more insoluble pathogen binding constituents, such as a sepharose bead that includes an antibody or aptamer that binds to the one or more pathogens 106, may be bound to the fluorescently labeled antibody-pathogen complex and used to precipitate the complex. One or more analysis units 110 that include a CCD camera that is configured to detect fluorescent emission from the one or more fluorescent labels may be used to detect the one or more pathogens 106. In some embodiments, one or more CCD cameras may be configured to utilize dark frame subtraction to cancel background and increase sensitivity of the camera. In some embodiments, one or more analysis units 110 may include one or more filters to select and/or filter wavelengths of energy that can be detected by one or more CCD cameras (e.g., U.S. Pat. No. 3,971,065; herein incorporated by reference). In some embodiments, one or more analysis units 110 may include polarized lenses. One or more analysis units 110 may be configured in numerous ways to utilize one or more CCD cameras to detect one or more pathogens 106.

In some embodiments, one or more pathogens 106 may be analyzed through use of immunoassay. In some embodiments, one or more analysis units 110 may be configured to analyze one or more samples 104 through use of immunoassay. In some embodiments, one or more analysis units 110 may be configured to operably associate with one or more microfluidic chips 108 that are configured to analyze one or more samples 104 through use of immunoassay. Numerous types of detection methods may be used in combination with immunoassay based methods. In some embodiments, a label may be used within one or more immunoassays that may be detected by one or more analysis units 110. Examples of such labels include, but are not limited to, fluorescent labels, spin labels, fluorescence resonance energy transfer labels, radiolabels, electrochemiluminescent labels (e.g., U.S. Pat. Nos. 5,093,268; 6,090,545; herein incorporated by reference), and the like. In some embodiments, electrical conductivity may be used in combination with immunoassay based methods.

In some embodiments, an analysis unit 110 may be configured to utilize numerous detection methods. Examples of such detection methods include, but are not limited to, colorimetric methods, spectroscopic methods, resonance based methods, electron transfer based methods (redox), conductivity based methods, gravimetric based assays, turbidity based methods, ion-specific based methods, refractive index based methods, radiological based methods, or substantially any combination thereof.

Processing Unit

The system 100 may include one or more processing units 112. In some embodiments, one or more processing units 112 may include memory and/or one or more databases that include information related to agents 142. In some embodiments, one or more processing units 112 may access memory and/or one or more databases that include information related to agents 142. Such information may include: identities of agents 142, contraindications of agents 142, dosages for use of agents 142, administration schedules for agents 142, methods of administration for agents 142, cost of agents 142, coverage of agents 142 by insurance companies, coverage of agents 142 by health care providers, chemical structures for agents 142, generic names for agents 142, brand names for agents 142, geographical distributions for agents 142, regulatory restrictions related to agents 142, alternatives to agents 142, side-effects of agents 142, agents 142 that reduce the pathogenicity of pathogens 106, stability of agents 142, shelf-life of agents 142, recommended shipping procedures for agents 142, and the like. Accordingly, one or more processing units 112 may access memory and/or one or more databases to determine one or more agents 142 that may be used to reduce the pathogenicity of one or more detected pathogens 106. In some embodiments, one or more processing units 112 may access one or more remote databases. For example, in some embodiments, one or more processing units 112 may access one or more databases at pharmaceutical companies, pharmacies, health care facilities, and the like. Accordingly, in some embodiments, one or more processing units 112 may include a computer. In some embodiments, one or more processing units 112 may perform numerous types of calculations. For example, in some embodiments, one or more processing units 112 may calculate one or more dosages of one or more agents 142 for administration to one or more individuals 102. Accordingly, in some embodiments, one or more processing units 112 may perform numerous types of calculations in response to information related to one or more individuals 102. For example, in some embodiments, one or more processing units 112 may calculate dosages of one or more agents 142 for administration to one or more specific individuals 102.

Display Unit

The system 100 may include one or more display units 114. Numerous types of display units 114 may be used in association with system 100. Examples of such display units 114 include, but are not limited to, liquid crystal displays, printers, audible displays, cathode ray displays, plasma display panels, Braille displays, passive displays, chemical displays, active displays, and the like. In some embodiments, display units 114 may display information in numerous languages. Examples of such languages include, but are not limited to, English, Spanish, German, Japanese, Chinese, Italian, and the like. In some embodiments, display units 114 may display information pictographically, calorimetrically, and/or physically, such as displaying information in Braille.

In some embodiments, one or more display units 114 may be physically coupled to one or more microfluidic chips 108. In some embodiments, one or more display units 114 may be remotely coupled to one or more microfluidic chips 108. In some embodiments, one or more display units 114 may be physically coupled to one or more analysis units 110. In some embodiments, one or more display units 114 may be remotely coupled to one or more analysis units 110. In some embodiments, one or more display units 114 may be physically coupled to one or more detection units. In some embodiments, one or more display units 114 may be remotely coupled to one or more detection units. Accordingly, one or more display units 114 may be positioned in one or more locations that are remote from the position where analysis of one or more pathogens 106 takes place. Examples of such remote locations include, but are not limited to, the offices of physicians, nurses, pharmacists, and the like.

Signal

Numerous types of signals 126 may be used in association with system 100. Examples of such signals 126 include, but are not limited to, optical signals 126, radio signals 126, wireless signals 126, hardwired signals 126, infrared signals 126, ultrasonic signals 126, and the like.

In some embodiments, one or more signals 126 may not be encrypted. In some embodiments, one or more signals 126 may be encrypted. In some embodiments, one or more signals 126 may be sent through use of a secure mode of transmission. For example, in some embodiments, one or more signals 126 may be transmitted to a specified individual. In some embodiments, one or more signals 126 may be transmitted to a specified group. In some embodiments, one or more signals 126 may include code that is specific for an individual. In some embodiments, such code may include anonymous code that is specific for an individual. Accordingly, information included within one or more signals 126 may be protected against being accessed by others who are not the intended recipient. In some embodiments, one or more signals 126 may include information that includes statements regarding non-disclosure of information included within the one or more signals 126 (e.g., statements against copying information, statements against unauthorized dissemination of information, statements about unauthorized opening of an information packet by an unintended recipient, and the like). In some embodiments, one or more signals 126 may be sent in a manner that conforms with privacy regulations as set forth by law. For example, in some embodiments, one or more signals 126 may be transmitted in accordance with the Health Information Privacy and Protection Act.

Transmitting Unit

The system 100 may include one or more transmitting units 116. Numerous types of transmitting units 116 may be used in association with system 100. Examples of such transmitting units 116 include, but are not limited to, transmitters that transmit one or more optical signals, radio signals, wireless signals, hardwired signals, infrared signals, ultrasonic signals, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitting units 116 may transmit one or more signals 126 that are encrypted. Numerous types of transmitters are known and have been described (e.g., U.S. Pat. Nos. and Published U.S. Patent Applications: 7,236,595; 7,260,155; 7,227,956; US2006/0280307; herein incorporated by reference).

Receiving Unit

The system 100 may include one or more receiving units 136. Numerous types of receiving units 136 may be used in association with system 100. Examples of such receiving units 136 include, but are not limited to, receivers that receive one or more optical signals, radio signals, wireless signals, hardwired signals, infrared signals, ultrasonic signals, and the like. Such receivers are known and have been described (e.g., U.S. Pat. Nos. RE39,785; 7,218,900; 7,254,160; 7,245,894; 7,206,605; herein incorporated by reference).

Accepting Unit

The system 100 may include one or more accepting units 118. In some embodiments, one or more accepting units 118 may accept input 120 from one or more users 124. In some embodiments, the user 124 may be an individual 102 from whom one or more samples 104 were obtained. In some embodiments, the user 124 may be someone other than an individual 102 from whom one or more samples 104 were obtained. In some embodiments, input 120 may be entered into one or more accepting units 118 through use of a user interface 122. For example, in some embodiments, input 120 may be entered into an accepting unit 118 through use of a keyboard, a keypad, an audio based system, a wireless system, and the like. In some embodiments, one or more users 124 may enter input 120 into an accepting unit 118 through use of a wireless device, such as a mobile telephone, personal data assistant, a radio transmitter, and the like. In some embodiments, one or more accepting units 118 may include a touch screen on which informational choices are displayed. For example, a touch screen may display a series of questions that a user 124 may answer. Such questions may include questions pertaining to an individual's 102 height, weight, blood pressure, exercise habits, substance use habits, sleep habits, occupation, insurance provider, health care provider, financial information, location, cholesterol level, metabolic indicators, and the like. In some embodiments, an accepting unit 118 may include memory in which input 120 may be stored. In some embodiments, an accepting unit 118 may include a database in which input 120 may be stored. In some embodiments, an accepting unit 118 may include a receiver that is configured to receive wireless signals 126. In some embodiments, an accepting unit 118 may include a receiver that is configured to operably connect to a telephone connection, a data port, a digital cable, an optical cable, and the like.

Input

Numerous types of input 120 may be entered into system 100. Examples of such input 120 include, but are not limited to, an individual's 102 height, weight, blood pressure, exercise habits, substance use habits, sleep habits, occupation, insurance provider, health care provider, financial information, location, cholesterol level, metabolic indicators, and the like.

Packaging Unit

The system 100 may include one or more packaging units 138. In some embodiments, packaging units 138 may be configured to package one or more agents 142 in unit dosage form. In some embodiments, packaging units 138 may be configured to package one or more agents 142 in numerous types of administration forms. For example, in some embodiments, one or more packaging units 138 may package one or more agents 142 in packaging material that provides for release of the one or more agents 142 at selected positions within an individual 102 (e.g., stomach, intestine, eye, nose, lungs, etc.). In some embodiments, one or more packaging units 138 may package one or more agents 142 in packaging material that provides for administration of the one or more agents 142. For example, in some embodiments, one or more packaging units 138 may package one or more agents 142 for interperitoneal administration, nasal administration, pulmonary administration, intravenous administration, intraperitoneal administration, and the like. In some embodiments, one or more packaging units 138 may package one or more agents 142 with one or more pharmaceutically acceptable carriers or excipients.

Shipping Unit

The system 100 may include one or more shipping units 140. In some embodiments, one or more shipping units 140 may address one or more packages for delivery to a destination. Examples of such destinations include, but are not limited to, the residence of an individual 102, a hospital, a medical field station, a ship, a health care facility, a pharmacy, and the like. In some embodiments, a shipping unit 140 may include circuitry and program instructions that provide for access to shipping schedules and routes used by shipping companies. Accordingly, in some embodiments, a shipping unit 140 may determine a route for shipping one or more packages that is responsive to the identity of one or more agents 142 that are to be shipped. For example, in some embodiments, an agent 142 may need to be packaged in dry ice to preserve the agent 142. Accordingly, a shipping unit 140 may select overnight delivery to a destination to preserve the integrity of the agent 142. Accordingly, one or more shipping units 140 may select a schedule and route that is appropriate for an agent 142 that is to be shipped.

User Interface/User

Numerous types of users 124 may interact with system 100. In some embodiments, a user 124 may be human. In some embodiments, a user 124 may be non-human. In some embodiments, a user 124 may interact with one or more microfluidic chips 108, one or more reagent delivery units, one or more centrifugation units, one or more analysis units 110, one or more detection units, one or more display units 114, one or more user interfaces 122, or substantially any combination thereof. The user can interact through use of numerous types of user interfaces 122. For example, one or more users 124 may interact through use of numerous user interfaces 122 that utilize hardwired methods, such as through use of a keyboard, use of wireless methods, use of the internet, and the like. In some embodiments, a user 124 may be a health-care worker. Examples of such health-care workers include, but are not limited to, physicians, nurses, pharmacists, and the like. In some embodiments, a user 124 may be a hiker, a farmer, a food inspector, a cook, a traveler, and the like.

Figure 2:
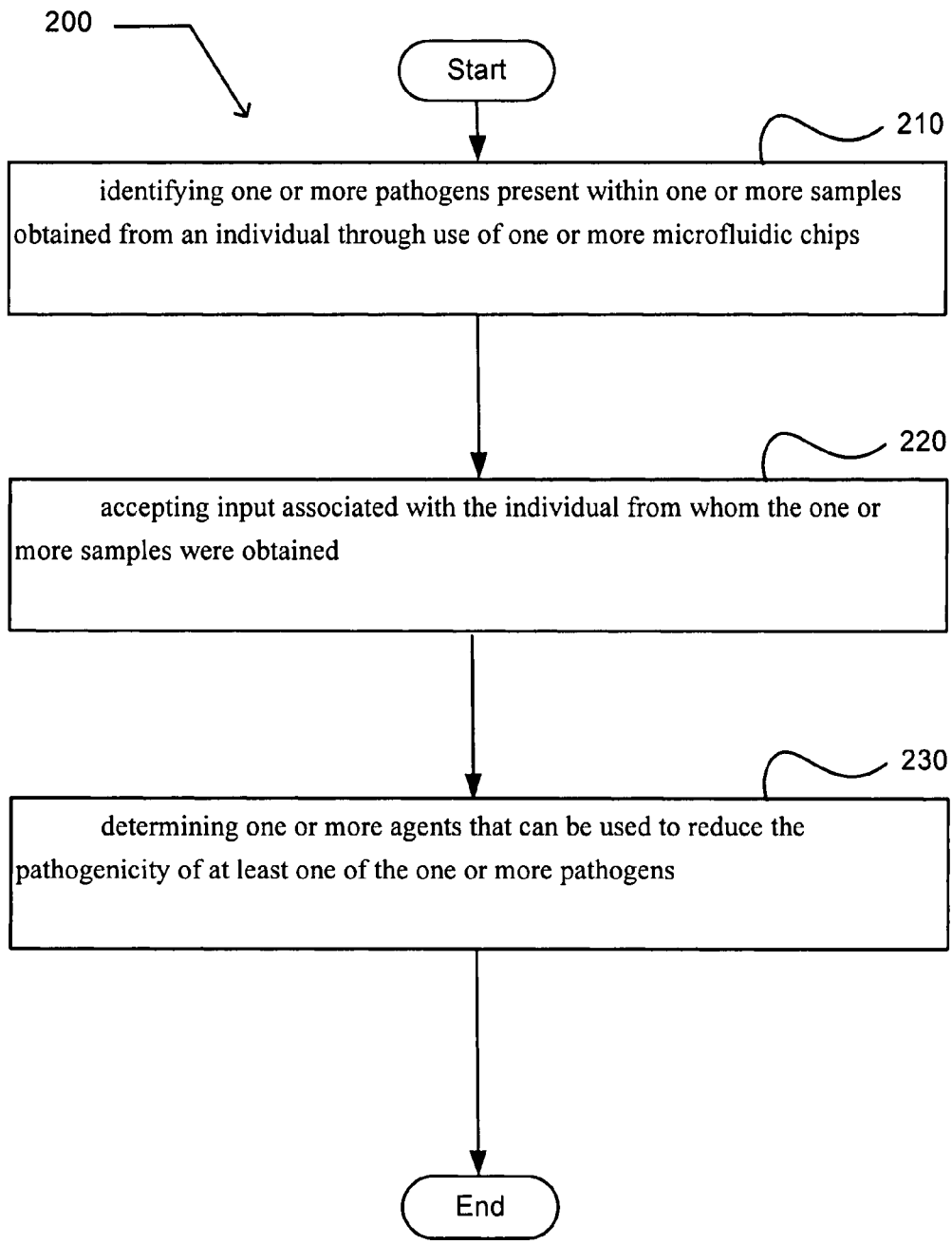

FIG. 2 illustrates an operational flow 200 representing examples of operations that are related to the performance of a method for identifying one or more pathogens 106 and determining one or more agents 142 that may be used to reduce the pathogenicity of at least one of the one or more pathogens 106. In FIG. 2 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 200 includes an identifying operation 210 involving identifying one or more pathogens present within one or more samples obtained from an individual through use of one or more microfluidic chips. In some embodiments, one or more analysis units 110 may be used to identify one or more pathogens 106 present within one or more samples 104 obtained from an individual 102 through use of one or more microfluidic chips 108.

After a start operation, the operational flow 200 includes an accepting operation 220 involving accepting input associated with the individual from whom the one or more samples were obtained. In some embodiments, one or more accepting units 118 may be used to accept input 120 associated with an individual 102 from whom one or more samples 104 were obtained.

After a start operation, the operational flow 200 includes a determining operation 230 involving determining one or more agents that can be used to reduce the pathogenicity of at least one of the one or more pathogens. In some embodiments, one or more processing units 112 may be used to determine one or more agents 142 that can be used to reduce the pathogenicity of at least one of one or more pathogens 106.

Figure 3:
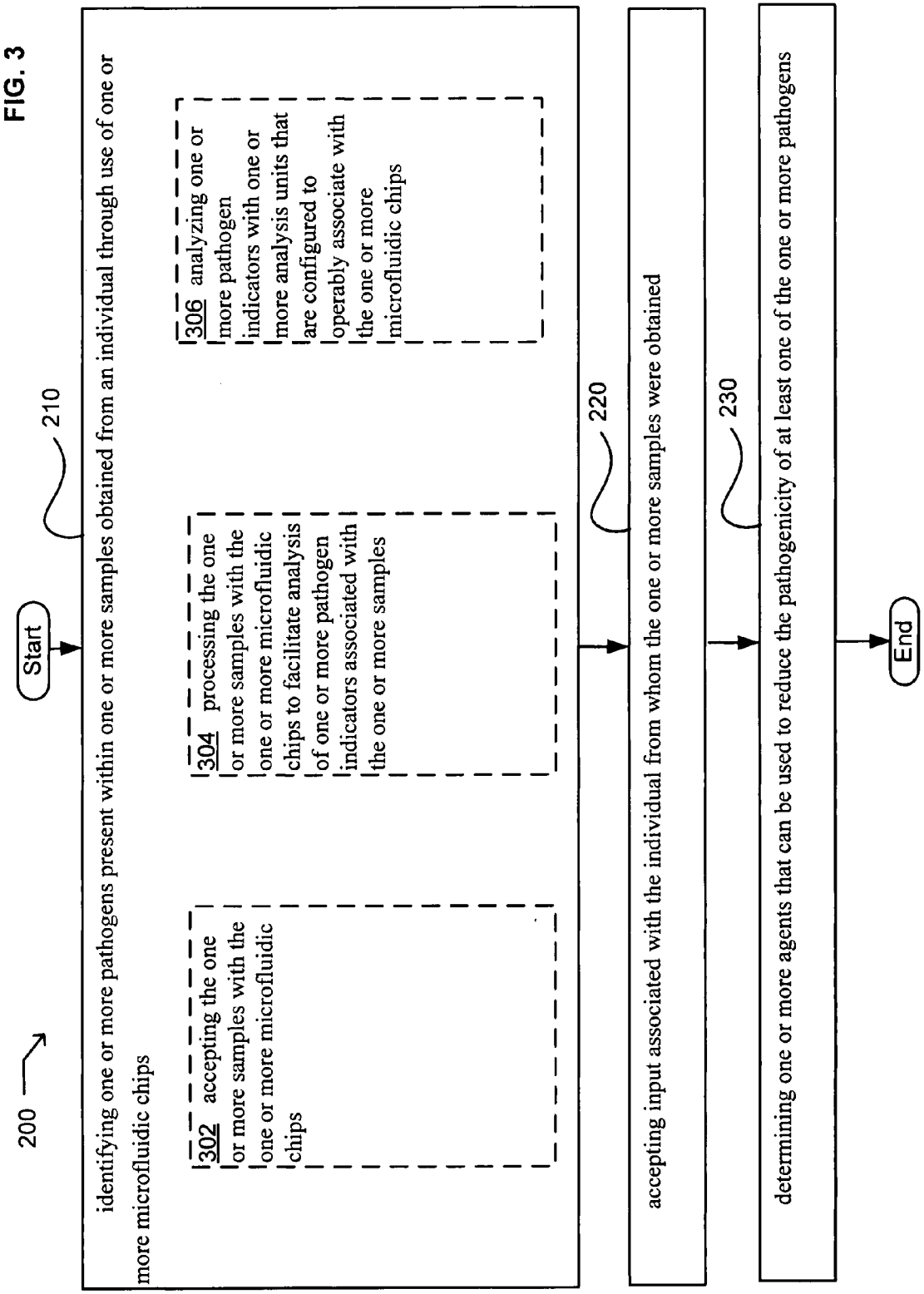

FIG. 3 illustrates alternative embodiments of the example operational flow 200 of FIG. 2. FIG. 3 illustrates example embodiments where the identifying operation 210 may include at least one additional operation. Additional operations may include an operation 302, operation 304, and/or operation 306.

At operation 302, the identifying operation 210 may include accepting the one or more samples with the one or more microfluidic chips. In some embodiments, one or more microfluidic chips 108 may accept one or more samples 104. In some embodiments, one or more microfluidic chips 108 may accept one or more samples 104 that include one or more liquids. In some embodiments, one or more microfluidic chips 108 may accept one or more samples 104 that include one or more solids. In some embodiments, one or more microfluidic chips 108 may accept one or more samples 104 that include one or more gases. In some embodiments, one or more microfluidic chips 108 may accept one or more samples 104 that include one or more biological samples 104. Examples of biological samples 104 include, but are not limited to, blood, cerebrospinal fluid, mucus, breath, urine, fecal material, skin, tissue, tears, hair, and the like.

At operation 304, the identifying operation 210 may include processing the one or more samples with the one or more microfluidic chips to facilitate analysis of one or more pathogen indicators associated with the one or more samples. In some embodiments, the identifying operation 210 may include processing one or more samples 104 with one or more microfluidic chips 108 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof.

At operation 306, the identifying operation 210 may include analyzing one or more pathogen indicators with one or more analysis units that are configured to operably associate with the one or more microfluidic chips. In some embodiments, identifying operation 210 may include analyzing the one or more pathogen indicators with one or more analysis units 110 through use of at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, immunoassay, or substantially any combination thereof.

Figure 4:
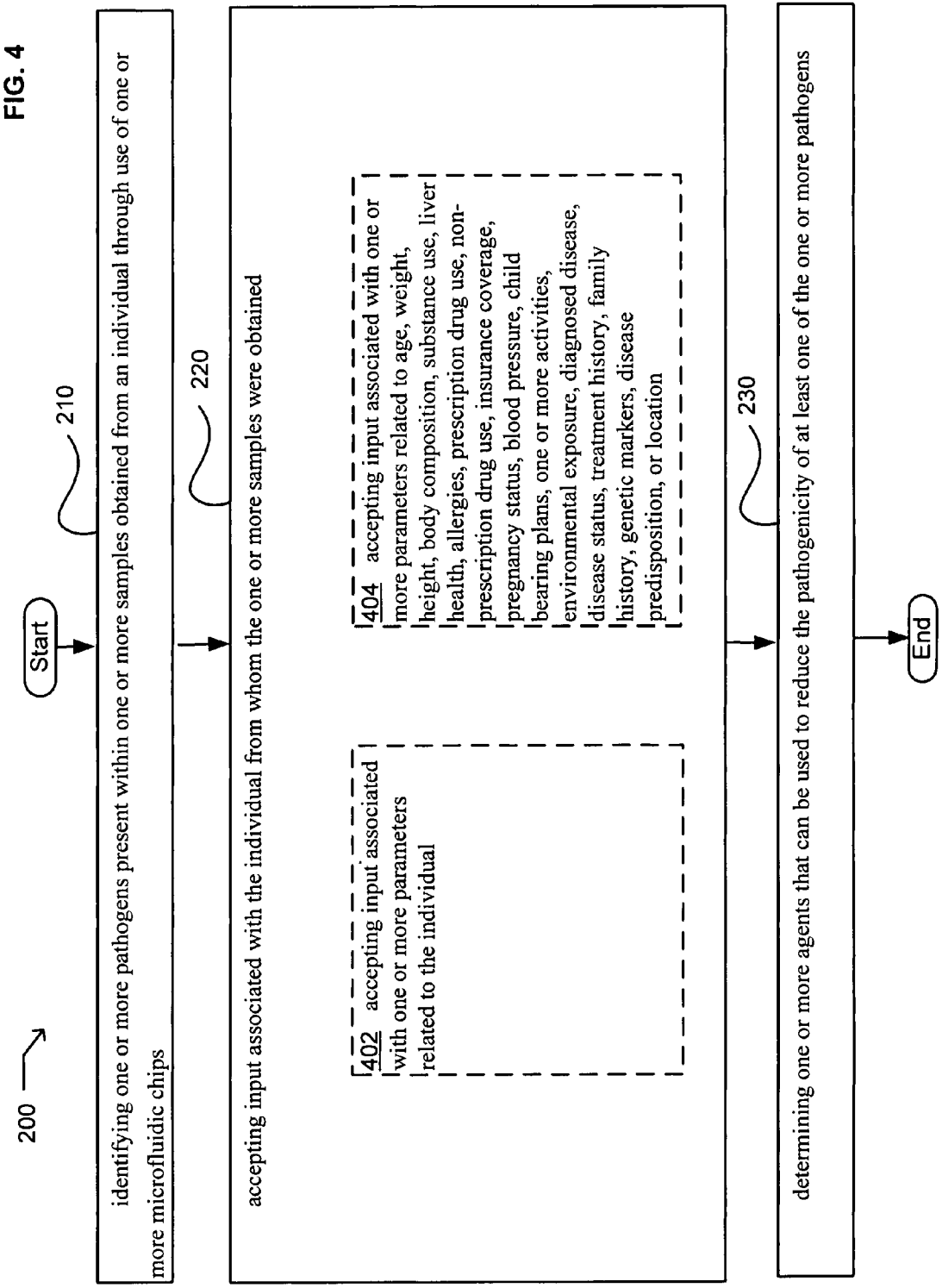

FIG. 4 illustrates alternative embodiments of the example operational flow 200 of FIG. 2. FIG. 4 illustrates example embodiments where the accepting operation 220 may include at least one additional operation. Additional operations may include an operation 402, and/or operation 404.

At operation 402, the accepting operation 220 may include accepting input associated with one or more parameters related to the individual. In some embodiments, one or more accepting units 118 may accept input 120 associated with one or more parameters related to an individual 102. In some embodiments, the one or more parameters may be physical parameters. In some embodiments, the one or more parameters may be psychological parameters. In some embodiments, the one or more parameters may be financial parameters. In some embodiments, the one or more parameters may be health care provided related parameters (e.g., physician's name, insurance provider, HMO name, prescription plan, etc.).

At operation 404, the accepting operation 220 may include accepting input associated with one or more parameters related to age, weight, height, body composition, substance use, liver health, allergies, prescription drug use, non-prescription drug use, insurance coverage, pregnancy status, blood pressure, child bearing plans, one or more activities, environmental exposure, diagnosed disease, disease status, treatment history, family history, genetic markers, disease predisposition, or location. In some embodiments, one or more accepting units 118 may accept input 120 associated with one or more parameters related to age, weight, height, body composition (e.g., body mass index, fat percentage), substance use (e.g., alcohol, tobacco, illicit drugs), liver health, allergies, prescription drug use, non-prescription drug use, insurance coverage (e.g., prescription plan, insurance limits, limitations on providers, HMO limitations), pregnancy status (e.g., pregnant, not pregnant, unknown), blood pressure, child bearing plans (e.g., yes, no, time when planning to become pregnant), one or more activities (e.g., travel, athletic activities, occupational activities, driving), location (e.g., travel to foreign nation, local address, town, city), or substantially any combination thereof.

Figure 5:
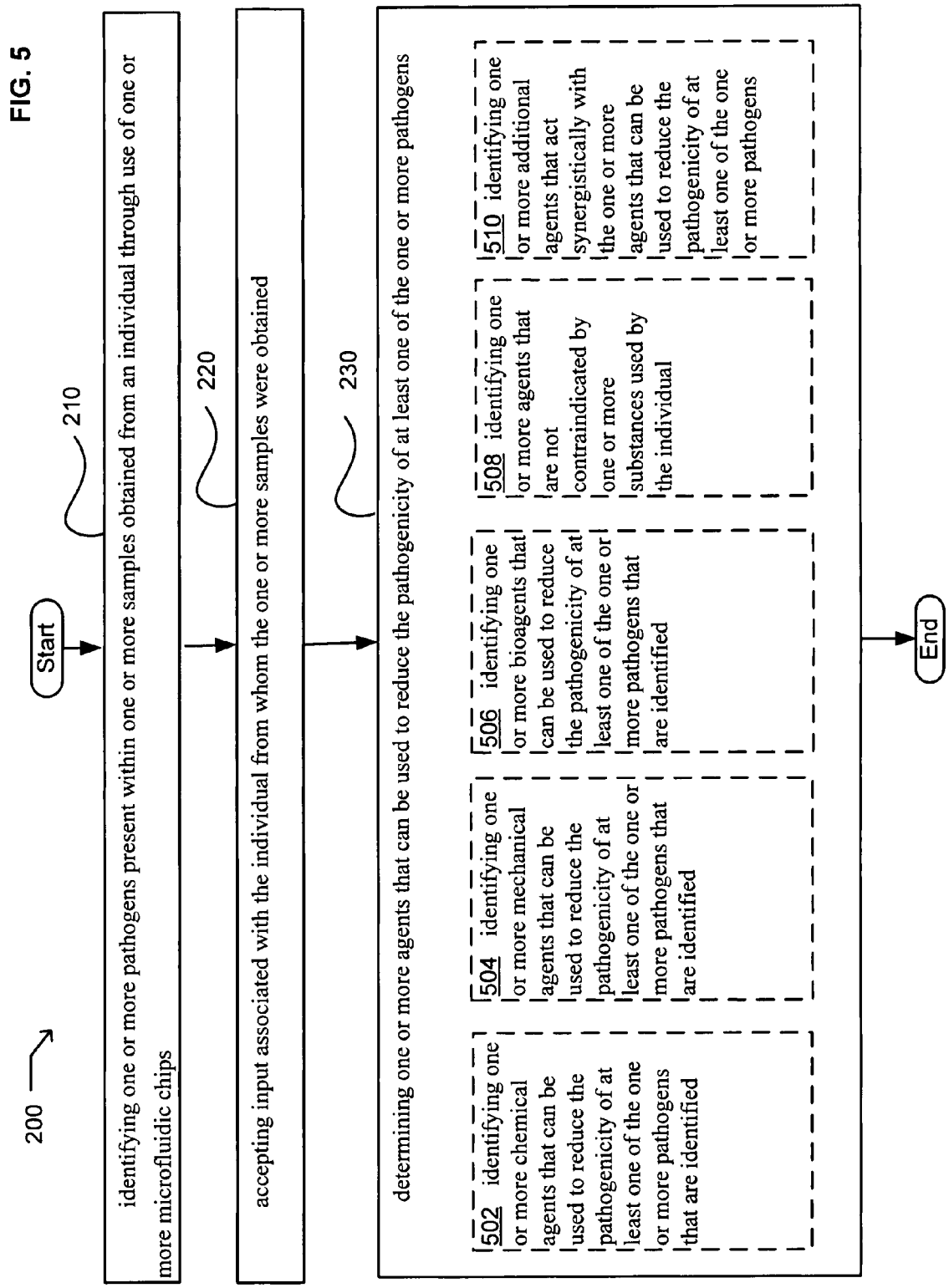

FIG. 5 illustrates alternative embodiments of the example operational flow 200 of FIG. 2. FIG. 5 illustrates example embodiments where the determining operation 230 may include at least one additional operation. Additional operations may include an operation 502, operation 504, operation 506, operation 508, and/or operation 510.

At operation 502, the determining operation 230 may include identifying one or more chemical agents that can be used to reduce the pathogenicity of the at least one of the one or more pathogens that are identified. In some embodiments, one or more processing units 112 may identify one or more chemical agents 142 that can be used to reduce the pathogenicity of at least one pathogen 106 that is identified. Numerous chemical agents 142 may be identified. Examples of such chemical agents 142 include, but are not limited to, antibiotics, ozone, peroxides, chlorinated compounds, acids, bases, alcohols, and the like (e.g., Merck Index, Thirteenth Edition, Merck & Co., Inc., Whitehouse Station, N.J. (2001) and Mosby's Drug Guide, An Imprint of Elsevier, St. Louis, Mo. (2004)). In some embodiments, such chemical agents 142 may be identified that are specific for one or more identified pathogens 106.

At operation 504, the determining operation 230 may include identifying one or more mechanical agents that can be used to reduce the pathogenicity of the at least one of the one or more pathogens that are identified. In some embodiments, one or more processing units 112 may identify one or more mechanical agents 142 that can be used to reduce the pathogenicity of at least one pathogen 106 that is identified. Numerous mechanical agents 142 may be identified. Examples of such mechanical agents 142 include, but are not limited to, ultraviolet light, irradiation, and the like. In some embodiments, such mechanical agents 142 may be identified that are specific for one or more identified pathogens 106.

At operation 506, the determining operation 230 may include identifying the one or more bioagents that can be used to reduce the pathogenicity of at least one of the one or more pathogens that are identified. In some embodiments, one or more processing units 112 may identify one or more bioagents that can be used to reduce the pathogenicity of at least one of the one or more pathogens 106 that are identified. For example, in some embodiments, one or more processing units 112 may identify one or more bacteriophages that may be used to reduce the disease causing ability of a bacteria. In some embodiments, one or more processing units 112 may identify one or more invasive recombinant bacteria that may be used to deliver a gene product that may be used to reduce the disease causing ability of one or more pathogens. For example, in some embodiments, such recombinant bacteria may be engineered to produce an antibiotic. In some embodiments, one or more processing units 112 may identify one or more inactivated pathogens (e.g., viruses, bacteria, fungi) that may be used to induce an immune response against one or more pathogens.

At operation 508, the determining operation 230 may include identifying the one or more agents that are not contraindicated by one or more substances used by the individual. In some embodiments, one or more processing units 112 may identify one or more agents 142 that are not contraindicated by one or more substances used by an individual 102. For example, in some embodiments, an individual 102 may use one or more prescription medications. In such embodiments, one or more processing units 112 may identify one or more agents 142 that do not contraindicate the one or more prescription medications. In some embodiments, an individual 102 may use one or more substances such as tobacco or alcohol that may contraindicate an agent 142. Accordingly, one or more processing units 112 may identify one or more agents 142 that are not affected by one or more substances used by an individual 102 and/or that do not affect one or more substances used by an individual 102. Accordingly, one or more processing units 112 may identify one or more agents 142 with regard to numerous types of substances used by an individual 102.

At operation 510, the determining operation 230 may include identifying the one or more additional agents that act synergistically with the one or more agents that can be used to reduce the pathogenicity of at least one of the one or more pathogens. In some embodiments, one or more processing units 112 may identify one or more additional agents 142 that act synergistically with the one or more agents 142 that can be used to reduce the pathogenicity of at least one of the one or more pathogens. In some embodiments, one or more processing units 112 may identify one or more additional agents 142 that increase the effectiveness of one or more antibiotics. For example, in some embodiments, one or more processing units 112 may identify one or more antibacterial adjuvants (e.g., beta-lactamase inhibitors) that may act synergistically with one or more antibiotics. In some embodiments, one or more processing units 112 may identify one or more agents 142 that up regulate an immune response against a pathogen that may act synergistically with one or more other agents 142. In some embodiments, one or more processing units 112 may identify one or more agents 142 that down regulate an immune response against a pathogen that may act synergistically with one or more other agents 142.

Figure 6:
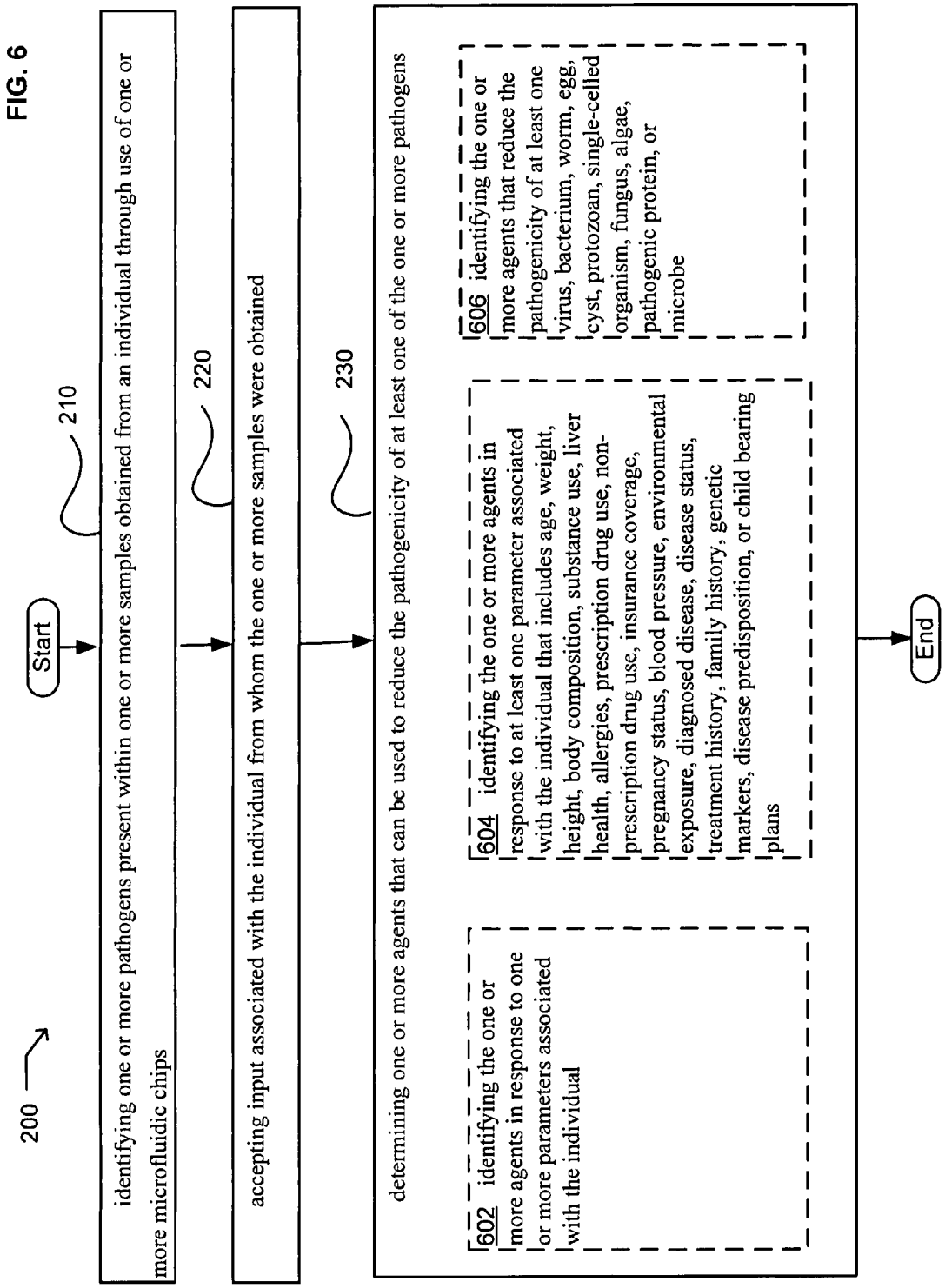

FIG. 6 illustrates alternative embodiments of the example operational flow 200 of FIG. 2. FIG. 6 illustrates example embodiments where the determining operation 230 may include at least one additional operation. Additional operations may include an operation 602, operation 604, and/or operation 606.

At operation 602, the determining operation 230 may include identifying the one or more agents in response to one or more parameters associated with the individual. In some embodiments, one or more processing units 112 may identify one or more agents 142 in response to one or more parameters associated with the individual 102. Accordingly, in some embodiments, one or more agents 142 may be identified for application to a specific individual 102. Such embodiments provide for personalized selection and dosing of agents 142 that may be used to treat pathogen infection. Numerous parameters associated with an individual 102 may be considered. Examples of such parameters include, but are not limited to, size, weight, allergies, body composition, substance use, and the like.

At operation 604, the determining operation 230 may include identifying one or more agents in response to at least one parameter associated with the individual that includes age, weight, height, body composition, substance use, liver health, allergies, prescription drug use, non-prescription drug use, insurance coverage, pregnancy status, blood pressure, environmental exposure, diagnosed disease, disease status, treatment history, family history, genetic markers, disease predisposition, or child bearing plans. In some embodiments, one or more processing units 112 may identify one or more agents 142 in response to at least one parameter associated with the individual 102 that includes age, weight, height, body composition, substance use, liver health, allergies, prescription drug use, non-prescription drug use, insurance coverage, pregnancy status, blood pressure, child bearing plans, or substantially any combination thereof.

At operation 606, the determining operation 230 may include identifying one or more agents that reduce the pathogenicity of at least one virus, bacterium, worm, egg, cyst, protozoan, single-celled organism, fungus, algae, pathogenic protein, or microbe. In some embodiments, one or more processing units 112 may identify one or more agents 142 that reduce the pathogenicity of at least one virus, bacterium, worm, egg, cyst, protozoan, single-celled organism, fungus, algae, pathogenic protein, or microbe. Numerous agents 142 are known that will reduce the pathogenicity of one or more pathogens 106 (The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, 58th Edition, Thompson, PDR, Montvale, N.J. 2004).

Figure 7:
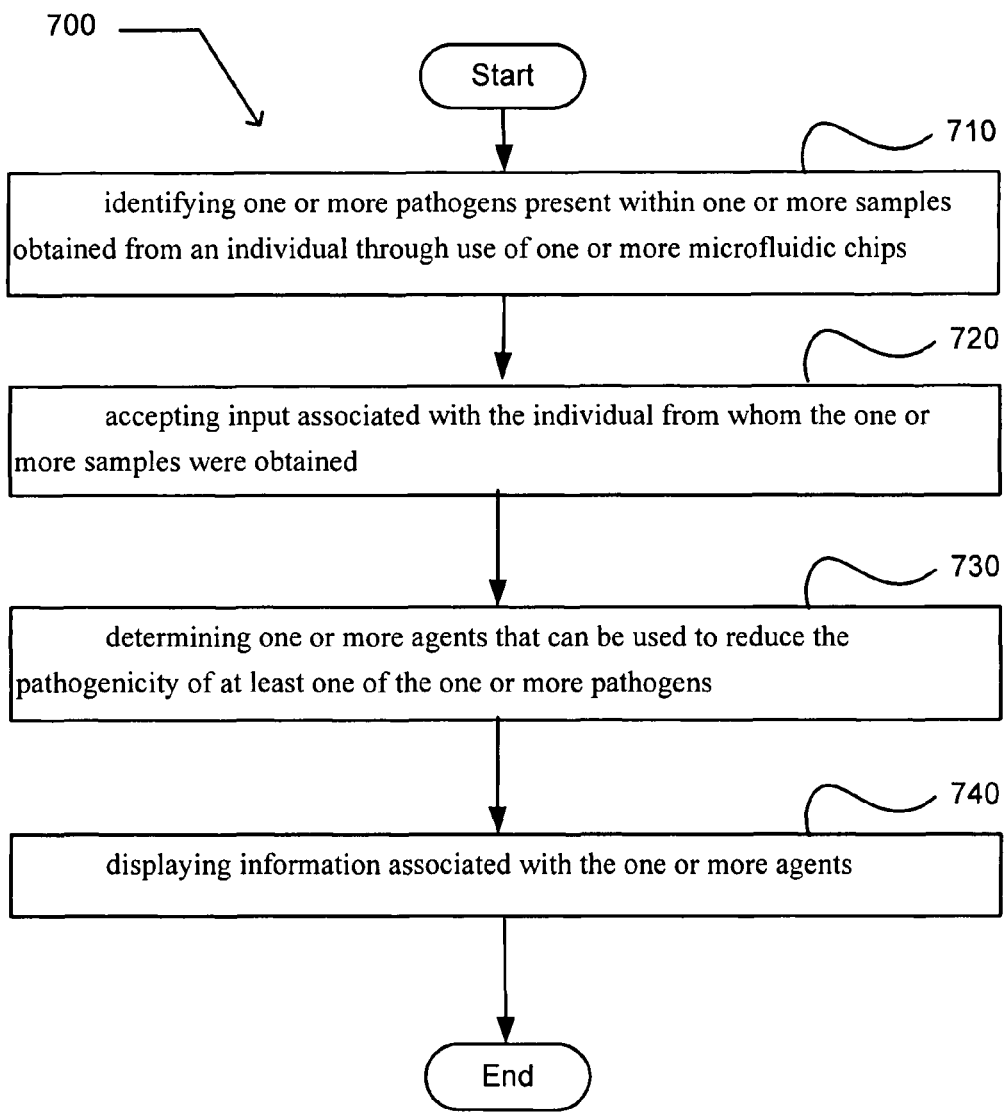

FIG. 7 illustrates operational flow 700 that includes operations 710, 720, and 730, that correspond to operations 210, 220, and 230 as illustrated in FIG. 2, with an optionally included displaying operation 740 and represents examples of operations that are related to the performance of a method for identifying one or more pathogens 106 and determining one or more agents 142 that may be used to reduce the pathogenicity of at least one of the one or more pathogens 106. In FIG. 7 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 700 optionally includes a displaying operation 740 involving displaying information associated with the one or more agents. In some embodiments, one or more display units 114 may be used to display information associated with one or more agents 142. Numerous types of display units 114 may be used to display information. Examples of such display units 114 include, but are not limited to, liquid crystal displays, light emitting diode displays, audio displays, Braille displays, graphical displays, and the like. Numerous types of information may be displayed. Examples of such types of information include, but are not limited to, the identity of one or more agents 142, the dosage of one or more agents 142, contraindications associated with the one or more agents 142, administration method to be used with one or more agents 142, administration schedule associated with one or more agents 142, and the like.

Figure 8:
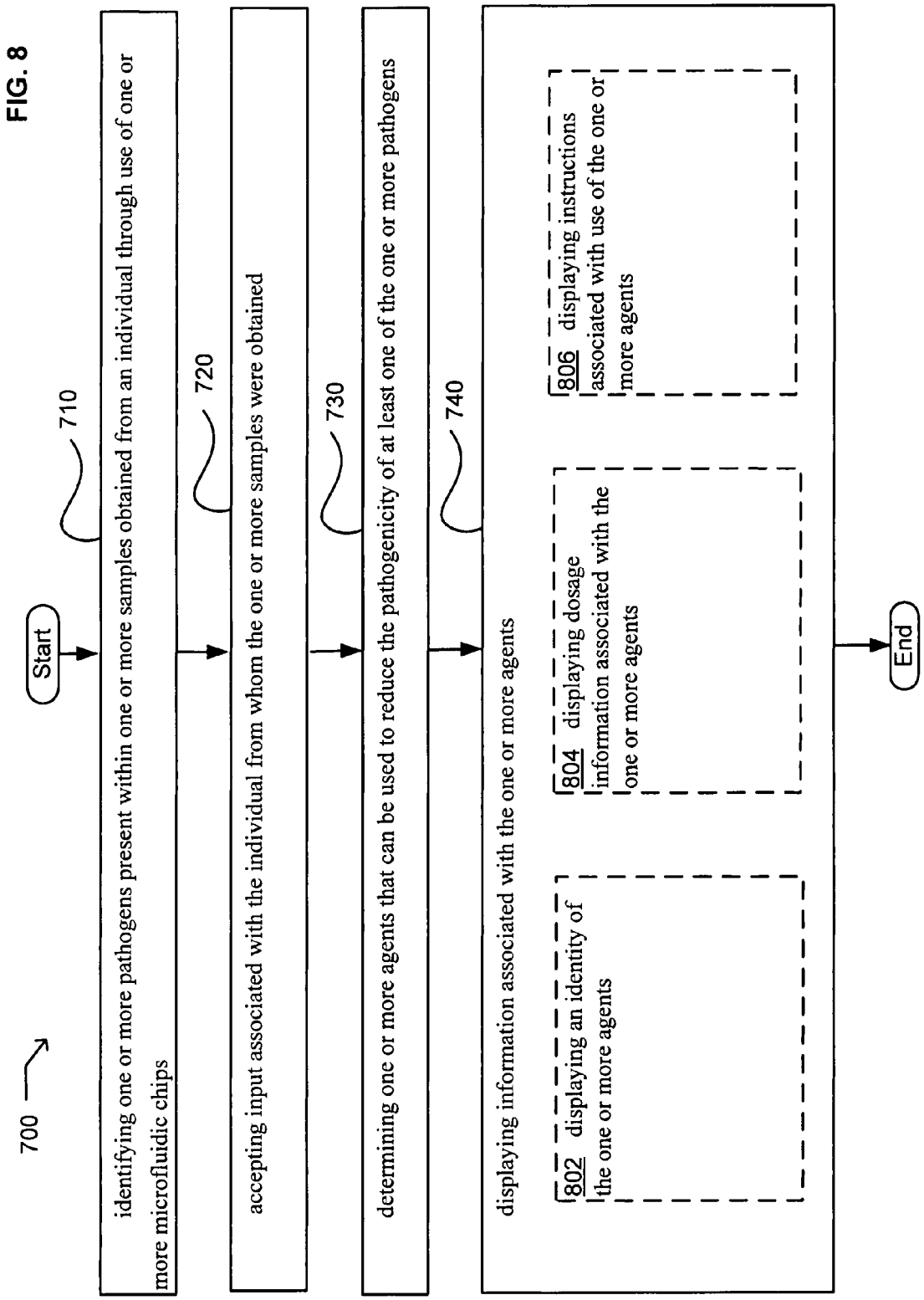

FIG. 8 illustrates alternative embodiments of the example operational flow 700 of FIG. 7. FIG. 8 illustrates example embodiments where the displaying operation 740 may include at least one additional operation. Additional operations may include an operation 802, operation 804, and/or operation 806.

At operation 802, the displaying operation 740 may include displaying an identity of the one or more agents. In some embodiments, one or more display units 114 may be used to display an identity of one or more agents 142. In some embodiments, one or more display units 114 may display the identity of one or more agents 142 in numerous languages (e.g., English, French, Spanish, Italian, Japanese, etc.). In some embodiments, one or more display units 114 may display the identity of one or more agents 142 according to chemical name, brand name, generic name, name according to location (e.g., name in a given country), and the like.

At operation 804, the displaying operation 740 may include displaying dosage information associated with the one or more agents. In some embodiments, one or more display units 114 may be used to display dosage information associated with one or more agents 142. In some embodiments, dosage may be displayed with reference to a schedule. For example, in some embodiments, an agent 142 may be administered more often at a lower dosage while in other embodiments the agent 142 may be administered less often at a higher dose. In some embodiments, a dosage of one or more agents 142 may depend upon the method used to administer the one or more agents 142. For example, in some embodiments, an agent 142 may be administered orally, intravenously, or nasally. Accordingly, the dosage that is displayed may depend on the methods used to administer the agent 142.

At operation 806, the displaying operation 740 may include displaying instructions associated with use of the one or more agents. In some embodiments, one or more display units 114 may be used to display instructions associated with use of one or more agents 142. In some embodiments, one or more display units 114 may display a schedule for administration of one or more agents 142. In some embodiments, one or more display units 114 may display instructions with regard to routes for administration of one or more agents 142. In some embodiments, one or more display units 114 may display instructions for food and/or beverage consumption during administration of one or more agents 142. Accordingly, numerous types of information may be displayed by one or more display units 114.

Figure 9:
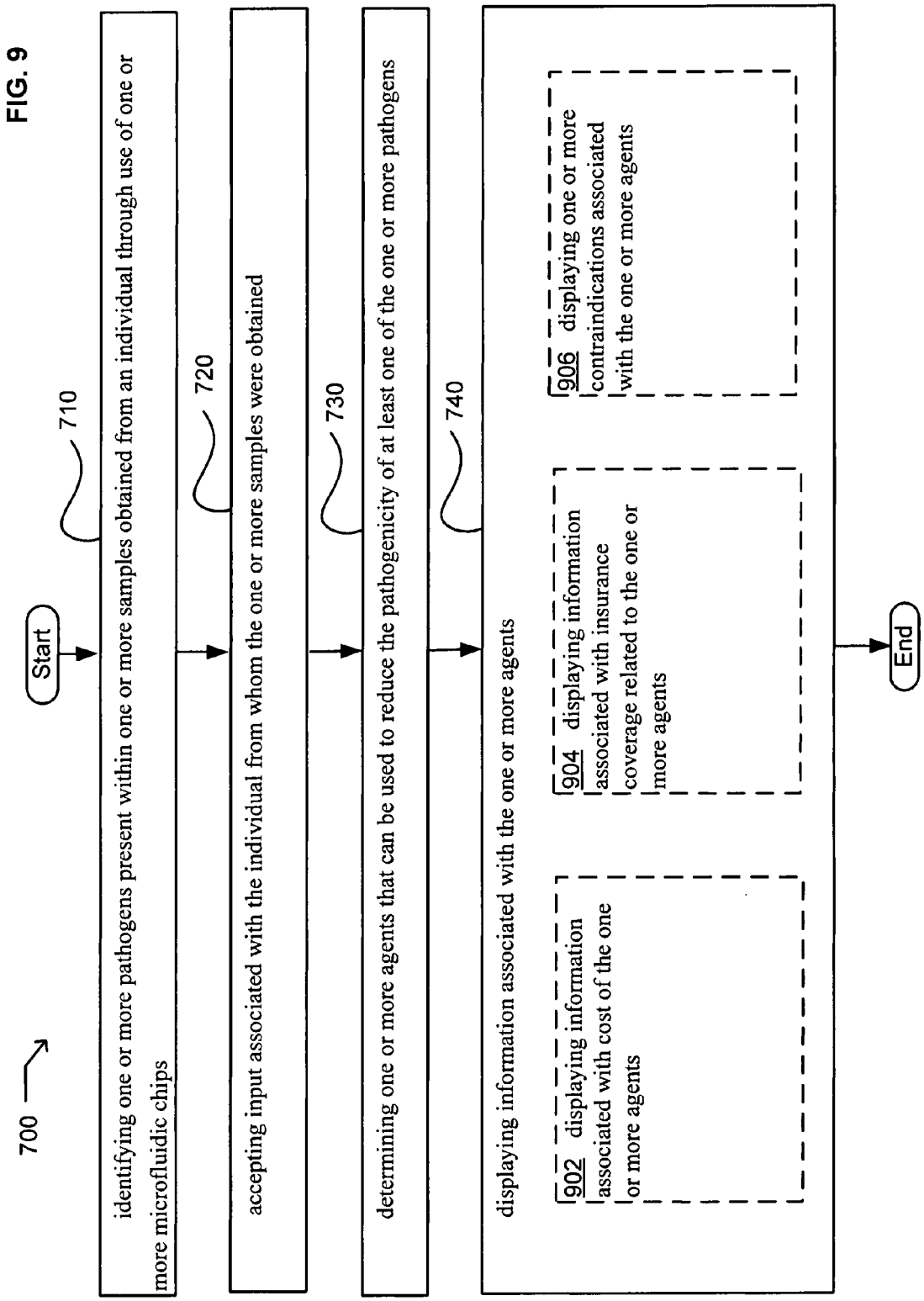

FIG. 9 illustrates alternative embodiments of the example operational flow 700 of FIG. 7. FIG. 9 illustrates example embodiments where the displaying operation 740 may include at least one additional operation. Additional operations may include an operation 902, operation 904, and/or operation 906.

At operation 902, the displaying operation 740 may include displaying information associated with cost of the one or more agents. In some embodiments, one or more display units 114 may be used to display information associated with the cost of one or more agents 142. In some embodiments, one or more display units 114 may display a combination of agents 142 based on the combined cost of the agents 142. For example, in some embodiments, two or more agents 142 may be displayed that are compatible with each other and an individual 102 as well as providing the lowest cost when compared to other comparable agents 142. In some embodiments, one or more display units 114 may display a group of agents 142 and their associated cost. In some embodiments, one or more display units 114 may display a group of agents 142 and information related to whether the cost of the agents 142 will be paid by an individual's health care plan or insurance. Numerous types of information may be displayed with regard to the cost of one or more agents 142.

At operation 904, the displaying operation 740 may include displaying information associated with insurance coverage related to the one or more agents. In some embodiments, one or more display units 114 may be used to display information associated with insurance coverage related to one or more agents 142. In some embodiments, one or more display units 114 may display a group of agents 142 and information related to which of the agents 142 are included within a health care or insurance plan. In some embodiments, one or more display units 114 may display alternative health care or insurance plans under which the cost of one or more agents 142 will be covered. Accordingly, in such embodiments, an individual 102 may be presented with information that allows the individual 102 to select an insurance or health care plan under which the cost of one or more agents 142 will be covered.

At operation 906, the displaying operation 740 may include displaying one or more contraindications associated with the one or more agents. In some embodiments, one or more display units 114 may be used to display one or more contraindications associated with one or more agents 142. In some embodiments, one or more display units 114 may display one or more selected agents 142 and additional agents 142 that contraindicate the selected agents 142. In some embodiments, one or more display units 114 may display activities that are contraindicated by one or more selected agents 142. For example, in some embodiments, one or more display units 114 may indicate that an individual 102 should not drive or operate machinery following administration of one or more agents 142. Accordingly, numerous types of information may be displayed.

Figure 10:
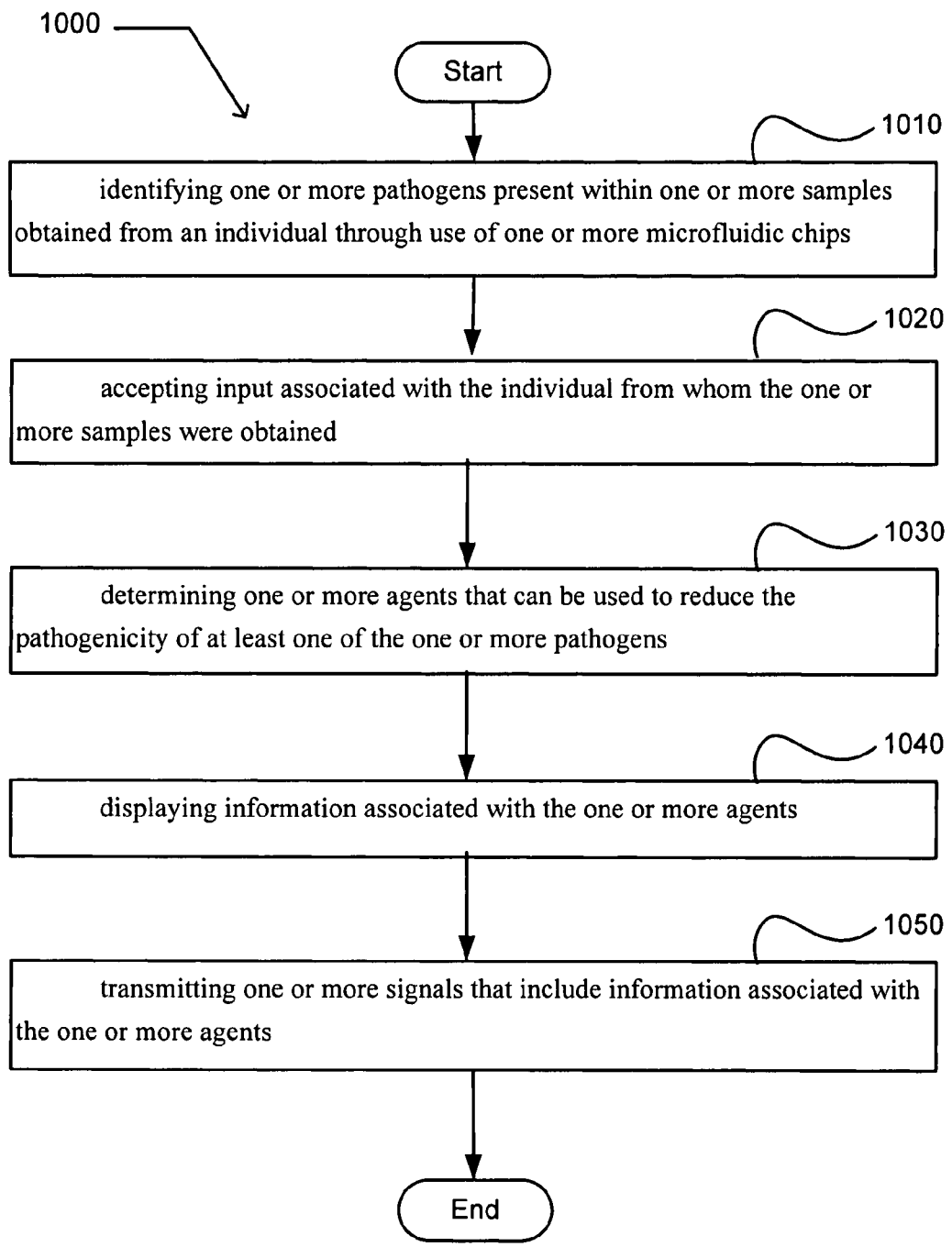

FIG. 10 illustrates operational flow 1000 that includes operations 1010, 1020, 1030, and 1040 that correspond to operations 710, 720, 730, and 740 as illustrated in FIG. 7 with an optionally included transmitting operation 1050 and represents examples of operations that are related to the performance of a method for identifying one or more pathogens 106 and determining one or more agents 142 that may be used to reduce the pathogenicity of at least one of the one or more pathogens 106. In FIG. 10 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 1000 optionally includes a transmitting operation 1050 involving transmitting one or more signals that include information associated with the one or more agents. In some embodiments, one or more transmitting units 116 may be used to transmit one or more signals 126 that include information associated with one or more agents 142. The one or more transmitting units 116 may transmit signals 126 through use of numerous technologies. For example, such signals 126 may be transmitted through use of the internet, radio waves, optical cables, cellular telephone connections, telephone connections, satellite telephone connections, and the like. The one or more signals 126 may be transmitted to, and received by, numerous types of receivers. For example, one or more signals 126 may be received by pharmacies, hospitals, pharmaceutical companies, health care providers, nutraceutical companies, and the like.

Figure 11:
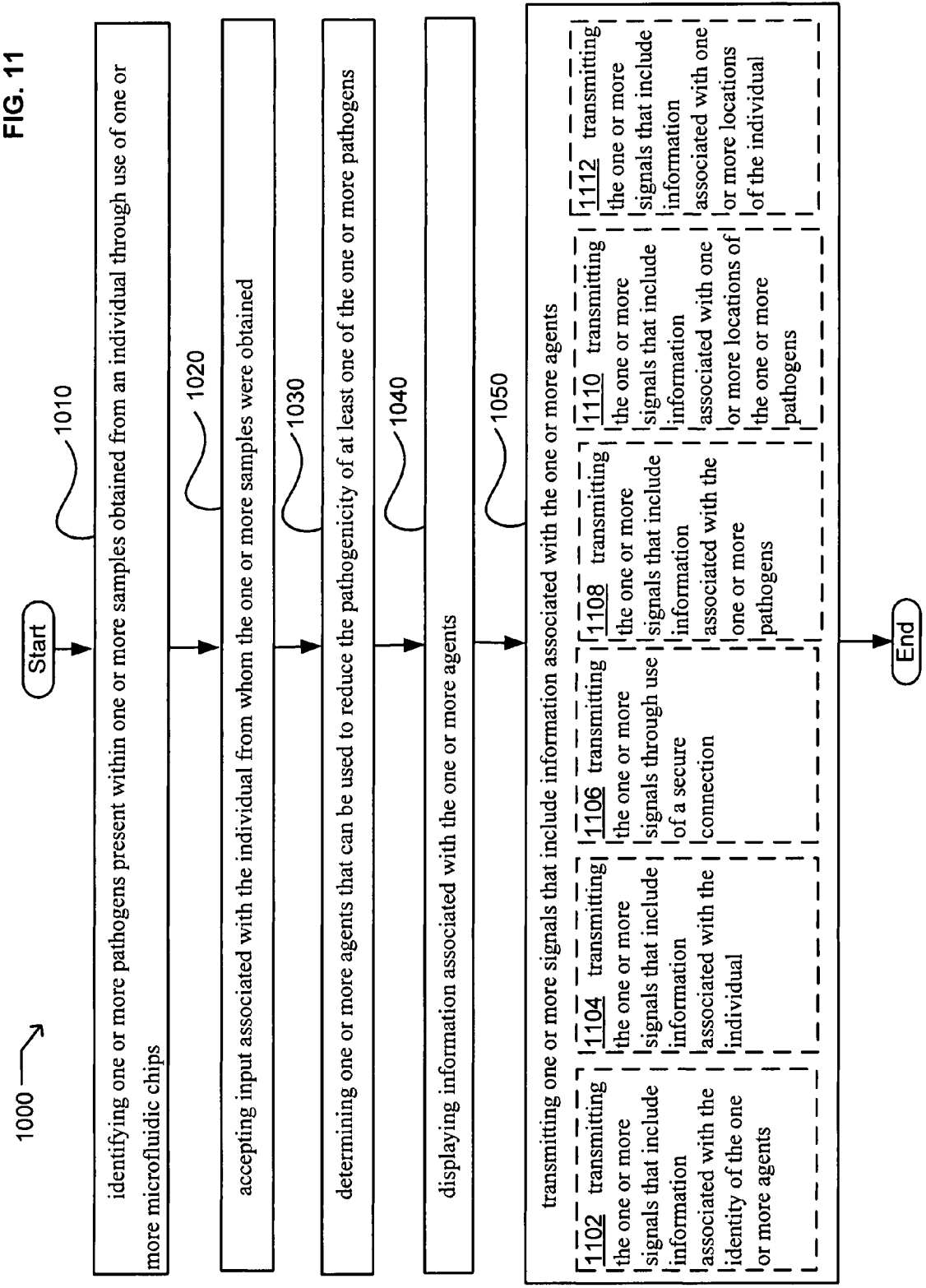

FIG. 11 illustrates alternative embodiments of the example operational flow 1000 of FIG. 10. FIG. 11 illustrates example embodiments where the transmitting operation 1050 may include at least one additional operation. Additional operations may include an operation 1102, operation 1104, operation 1106, operation 1108, operation 1110, and/or operation 1112.

At operation 1102, the transmitting operation 1050 may include transmitting the one or more signals that include information associated with the identity of one or more agents. In some embodiments, one or more transmitting units 116 may transmit one or more signals 126 that include information associated with the identity of one or more agents 142. For example, in some embodiments, one or more transmitting units 116 may transmit one or more signals 126 that include information associated with the brand name, the generic name, the chemical name, the structure, identifiers associated with an agent 142, or substantially any combination thereof.

At operation 1104, the transmitting operation 1050 may include transmitting the one or more signals that include information associated with the individual. In some embodiments, one or more transmitting units 116 may transmit one or more signals 126 that include information associated with an individual 102. One or more signals 126 that include numerous types of information associated with an individual 102 may be transmitted. Examples of such information include, but are not limited to, height, weight, age, substances used by an individual 102 (e.g., alcohol, tobacco, prescription medication, non-prescription medication, illicit drugs, etc.), body composition, allergies, physical characteristics (e.g., blood pressure, heart rate, intraocular pressure, etc.), activities, and the like.

At operation 1106, the transmitting operation 1050 may include transmitting the one or more signals through use of a secure connection. In some embodiments, one or more transmitting units 116 may transmit one or more signals 126 through use of a secure connection. For example, in some embodiments, one or more signals may be encrypted. In some embodiments, one or more signals may be sent through use of a secure mode of transmission. For example, in some embodiments, one or more signals may be transmitted to a specified individual. In some embodiments, one or more signals may be transmitted to a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be sent in a manner that conforms with privacy regulations as set forth by law. For example, in some embodiments, one or more signals may be transmitted in accordance with the Health Information Privacy and Protection Act. In some embodiments, one or more signals may be sent with information that includes a request for a return receipt.

At operation 1108, the transmitting operation 1050 may include transmitting the one or more signals that include information associated with the one or more pathogens. In some embodiments, one or more transmitting units 116 may transmit one or more signals 126 that include information associated with the one or more pathogens 106. The one or more signals 126 may include numerous types of information associated with one or more pathogens 106. Examples of such information include the identity of a pathogen 106, the concentration of a pathogen 106, drug resistance characteristics of a pathogen 106, and the like. In some embodiments, one or more transmitting units 116 may transmit one or more signals 126 that include information associated with the virulence of one or more pathogens 106. For example, some pathogenic strains of *E. coli* exhibit increased virulence relative to other strains of *E. coli*. Such virulent strains may be identified by the presence of virulence determinants. Examples of such virulence determinants include, but are not limited to, adhesions (e.g., CFAI/CFAII, type 1 fimbriae, P fimbriae, S fimbriae, Intimin), invasions (e.g., hemolysisn, siderophores and siderophore uptake systems, *Shigella*-like "invasins" for intracellular invasion and spread), toxins (e.g., LT toxin, ST toxin, Shiga-like toxin, cytotoxins, endotoxin LPS), antiphagocytic surface properties (e.g., capsules, K antigens, lipopolysaccharides), somatic antigens, flagellar antigens, and the like. Accordingly, one or more signals may include information related to numerous types of virulence indicators.

At operation 1110, the transmitting operation 1050 may include transmitting the one or more signals that include information associated with one or more locations of the one or more pathogens. In some embodiments, one or more transmitting units 116 may transmit one or more signals 126 that include information associated with one or more locations of the one or more pathogens 106. For example, in some embodiments, one or more transmitting units 116 may transmit one or more signals 126 that include information associated with where an individual 102 is physically experiencing a pathogen infection (e.g., eye infection, nasal infection, gastrointestinal tract infection, etc). In some embodiments, one or more transmitting units 116 may transmit one or more signals 126 that include information associated with the geographical location of the pathogen 106. For example, one or more signals 126 may include information that indicates where the pathogen 106 and/or individual 102 who is infected with the pathogen 106 is located (e.g., United States, Canada, Europe, Asia, Middle East, etc.). In some embodiments, the one or more signals 126 may include global positioning system (GPS) coordinates.

At operation 1112, the transmitting operation 1050 may include transmitting the one or more signals that include information associated with one or more locations of the individual. In some embodiments, one or more transmitting units 116 may transmit one or more signals 126 that include information associated with one or more locations of the individual 102. In some embodiments, one or more transmitting units 116 may transmit one or more signals 126 that include information associated with the geographical location of an individual 102. For example, one or more signals 126 may include information that indicates where an individual 102 is located (e.g., United States, Canada, Europe, Asia, Middle East, etc.). In some embodiments, the one or more signals 126 may include global positioning system (GPS) coordinates.

Figure 12:
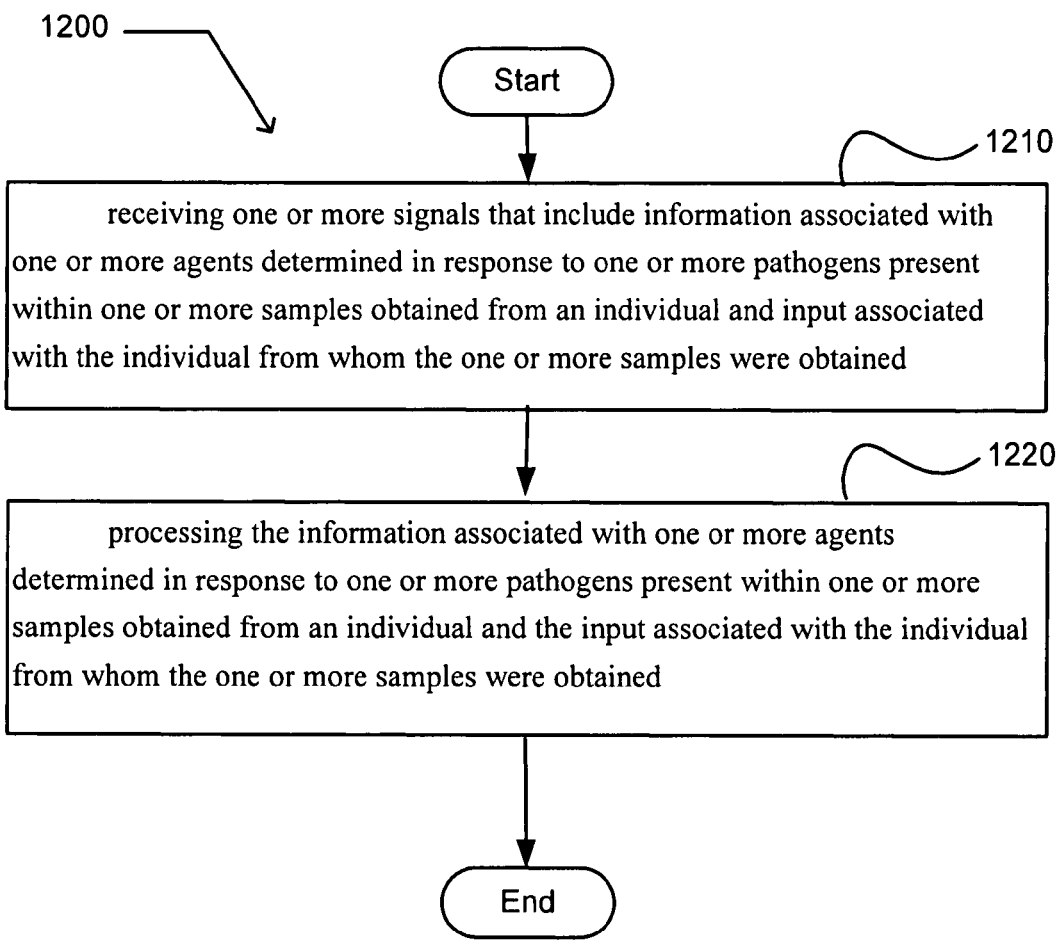

FIG. 12 illustrates an operational flow 1200 representing examples of operations that are related to the performance of a method for identifying one or more pathogens 106 and determining one or more agents 142 that may be used to reduce the pathogenicity of at least one of the one or more pathogens 106. In FIG. 12 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 1200 includes a receiving operation 1210 involving receiving one or more signals that include information associated with one or more agents determined in response to one or more pathogens present within one or more samples obtained from an individual and input associated with the individual from whom the one or more samples were obtained. In some embodiments, one or more receiving units 136 may be used to receive one or more signals 126 that include information associated with one or more agents 142 determined in response to one or more pathogens 106 present within one or more samples 104 obtained from an individual 102 and input 120 associated with the individual 102 from whom the one or more samples 104 were obtained. In some embodiments, the one or more signals 126 may include information associated with the identity of one or more agents 142, the dosage of one or more agents 142, the method of administration for one or more agents 142, contraindications associated with the one or more agents 142, an administration schedule associated with the one or more agents 142, and the like. In some embodiments, the one or more signals 126 may include information associated with an individual 102 that includes, but is not limited to, physical characteristics of the individual 102 (e.g., height, weight, body composition, heart rate, blood pressure, etc.), mental characteristics of an individual 102 (e.g., mood, depression, mental disorders, predisposition toward suicide, etc.), physiological characteristics (e.g., allergic responses, blood pressure drop in response to medication, etc.), and the like.

After a start operation, the operational flow 1200 includes a processing operation 1220 involving processing the information associated with one or more agents determined in response to one or more pathogens present within one or more samples obtained from an individual and the input associated with the individual from whom the one or more samples were obtained. In some embodiments, one or more processing units 112 may be used to process information associated with one or more agents 142 determined in response to one or more pathogens 106 present within one or more samples 104 obtained from an individual 102 and input 120 associated with the individual 102 from whom the one or more samples 104 were obtained. In some embodiments, one or more processing units 112 may search one or more databases to determine one or more agents 142 that may be utilized to reduce the pathogenicity of the one or more pathogens 106. In some embodiments, one or more processing units 112 may search one or more databases to determine one or more agents 142 that may be alternatives to an identified agent 142. In some embodiments, one or more processing units 112 may determine if the cost of one or more agents 142 is covered by a health care plan or insurance of an individual 102. In some embodiments, one or more processing units 112 may determine if the cost of one or more agents 142 is covered by a health care plan or the insurance of an individual 102 and identify alternative agents 142 that are covered. In some embodiments, one or more processing units 112 may determine if the one or more agents 142 are available in the location of the individual 102. In some embodiments, one or more processing units 112 may determine alternative agents 142 that are available at the location of the individual 102.

Figure 13:
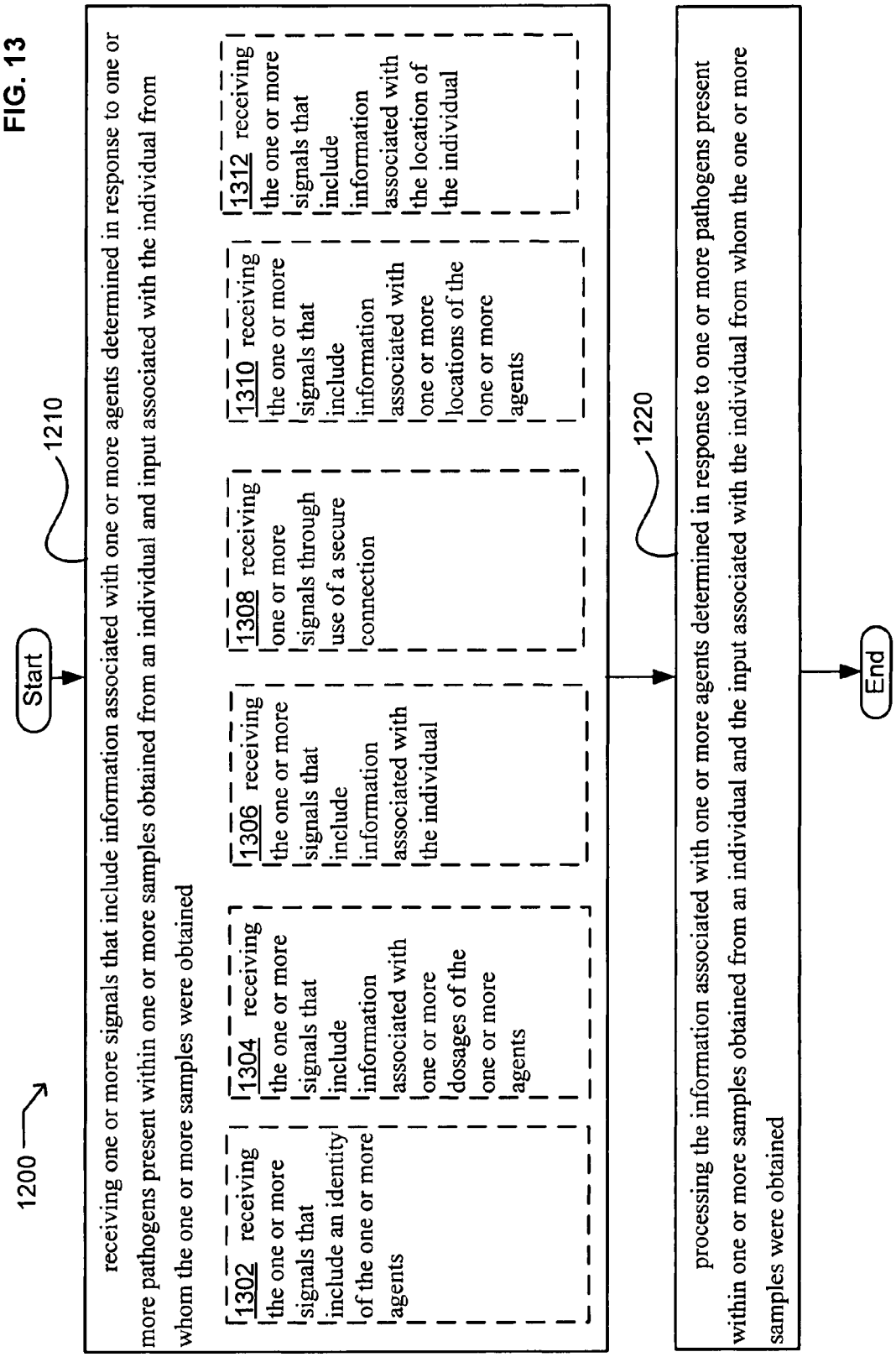

FIG. 13 illustrates alternative embodiments of the example operational flow 1200 of FIG. 12. FIG. 13 illustrates example embodiments where the receiving operation 1210 may include at least one additional operation. Additional operations may include an operation 1302, operation 1304, operation 1306, operation 1308, operation 1310, and/or operation 1312.

At operation 1302, the receiving operation 1210 may include receiving the one or more signals that include an identity of the one or more agents. In some embodiments, one or more receiving units 136 may receive one or more signals 126 that include an identity of one or more agents 142. For example, in some embodiments, one or more receiving units 136 may receive one or more signals 126 that include information associated with the brand name, the generic name, the chemical name, the structure, identifiers associated with an agent 142, or substantially any combination thereof.

At operation 1304, the receiving operation 1210 may include receiving the one or more signals that include information associated with one or more dosages of the one or more agents. In some embodiments, one or more receiving units 136 may receive one or more signals 126 that include information associated with one or more dosages of the one or more agents 142. In some embodiments, the one or more dosages may be commercially available dosages. In some embodiments, the one or more dosages may be specific for an individual 102 (e.g., dosages that are determined based on the physical characteristics of the individual 102, the metabolic characteristics of the individual 102, etc.).

At operation 1306, the receiving operation 1210 may include receiving the one or more signals that include information associated with the individual. In some embodiments, one or more receiving units 136 may receive one or more signals 126 that include information associated with an individual 102. One or more signals 126 that include numerous types of information associated with an individual 102 may be received. Examples of such information include, but are not limited to, height, weight, age, substances used by an individual 102 (e.g., alcohol, tobacco, prescription medication, non-prescription medication, illicit drugs, etc.), body composition, allergies, physical characteristics (e.g., blood pressure, heart rate, intraocular pressure, etc.), activities, and the like.

At operation 1308, the receiving operation 1210 may include receiving one or more signals through use of a secure connection. In some embodiments, one or more receiving units 136 may receive one or more signals 126 through use of a secure connection. For example, in some embodiments, one or more signals may be received that are encrypted. In some embodiments, one or more signals may be received through use of a secure mode. For example, in some embodiments, one or more signals may only be received by a specified individual. In some embodiments, one or more signals may be received by a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be received in a manner that conforms with privacy regulations as set forth by law. For example, in some embodiments, one or more signals may be received in accordance with the Health Information Privacy and Protection Act. In some embodiments, receipt of one or more signals will cause a return receipt to be sent that confirms receipt of the one or more signals.

At operation 1310, the receiving operation 1210 may include receiving the one or more signals that include information associated with one or more locations of the one or more agents. In some embodiments, one or more receiving units 136 may receive one or more signals 126 that include information associated with one or more locations of one or more agents 142. For example, in some embodiments, one or more signals 126 may include information associated with a specific pharmaceutical company, pharmaceutical distributor, hospital, pharmacy, health care facility, and the like, that have a supply of one or more agents 142. Accordingly, in some embodiments, such signals 126 may be transmitted by one or more transmitting units 116 that are associated with one or more processing units 112 that are able to access one or more databases that provide location information for agents 142.

At operation 1312, the receiving operation 1210 may include receiving the one or more signals that include information associated with the location of the individual. In some embodiments, one or more receiving units 136 may receive one or more signals 126 that include information associated with one or more locations of the individual 102. In some embodiments, one or more receiving units 136 may receive one or more signals 126 that include information associated with the geographical location of an individual 102. For example, one or more signals 126 may include information that indicates where an individual 102 is located (e.g., United States, Canada, Europe, Asia, Middle East, etc.). In some embodiments, the one or more signals 126 may include global positioning system (GPS) coordinates.

Figure 14:
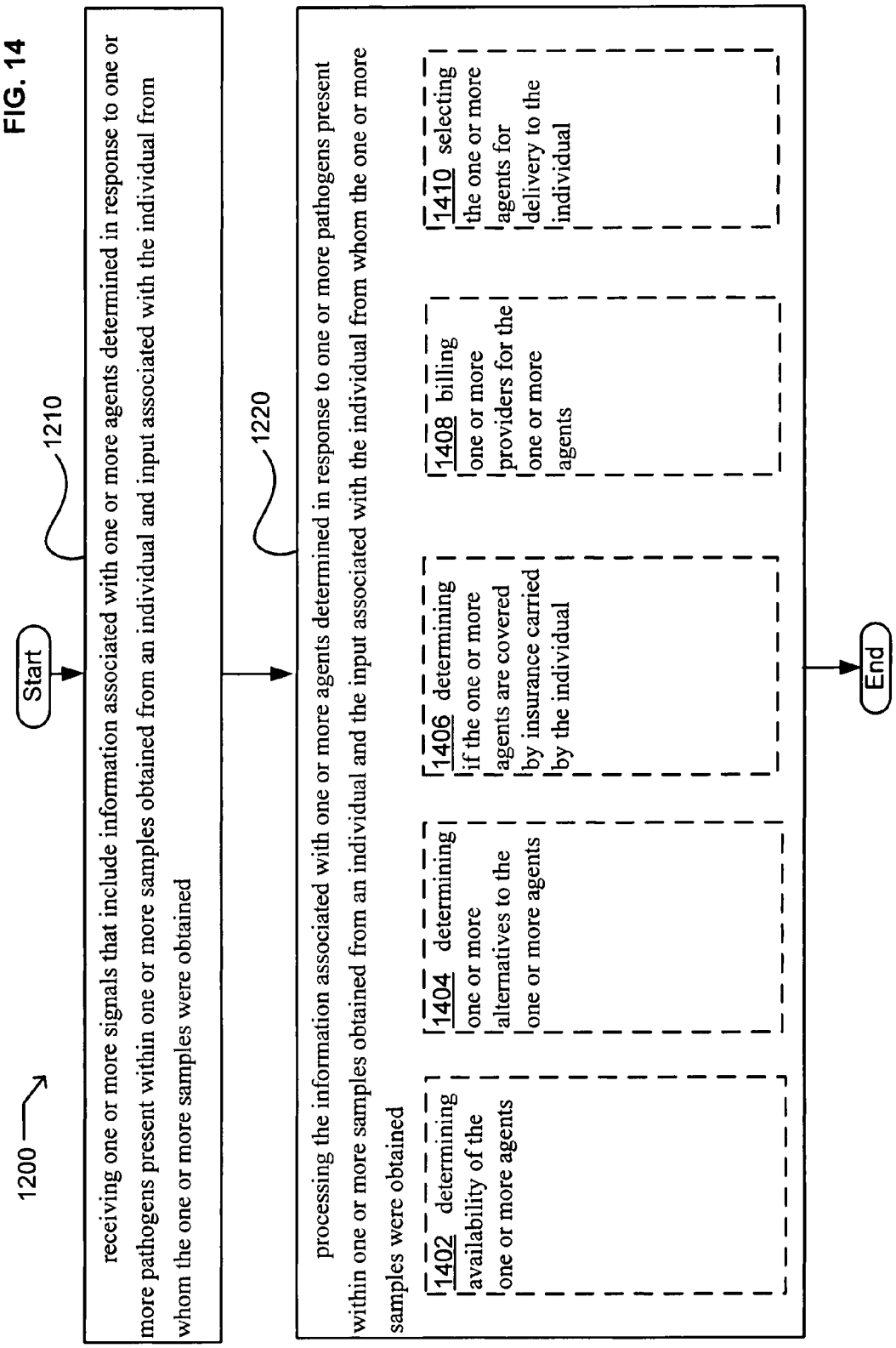

FIG. 14 illustrates alternative embodiments of the example operational flow 1200 of FIG. 12. FIG. 14 illustrates example embodiments where the processing operation 1220 may include at least one additional operation. Additional operations may include an operation 1402, operation 1404, operation 1406, operation 1408, and/or operation 1410.

At operation 1402, the processing operation 1220 may include determining availability of the one or more agents. In some embodiments, one or more processing units 112 may determine the availability of one or more agents 142. In some embodiments, one or more processing units 112 may access one or more databases to determine the availability of one or more agents 142. For example, in some embodiments, one or more processing units 112 may access one or more databases associated with a pharmaceutical company, a pharmacy, a pharmaceutical distributor, a health care facility, a health care provider, and the like, to determine if one or more agents 142 are available.

At operation 1404, the processing operation 1220 may include determining one or more alternatives to the one or more agents. In some embodiments, one or more processing units 112 may determine one or more alternatives to one or more agents 142. In some embodiments, one or more processing units 112 may determine that an identified agent 142 is not available and therefore select an alternative agent 142 that is available. Accordingly, in some embodiments, one or more processing units 112 may have access to databases of available agents 142 such as those at pharmacies, hospitals, health care facilities, pharmaceutical distributors, pharmaceutical companies, and the like. In some embodiments, one or more processing units 112 may select an alternative agent 142 based on the insurance or health plan associated with an individual 102. In some embodiments, one or more processing units 112 may select an alternative agent 142 that does not contraindicate another substance or medication that an individual 102 is using.

At operation 1406, the processing operation 1220 may include determining if the one or more agents are covered by insurance carried by the individual. In some embodiments, one or more processing units 112 may determine if the one or more agents 142 are covered by insurance carried by the individual 102. For example, one or more processing units 112 may access a database that contains information related to health care plans or insurance policies so that the one or more processing units 112 may be used to determine if the cost of one or more agents 142 will be covered by the plan and/or policy. In some embodiments, one or more processing units 112 may determine that the cost of an agent 142 is not covered by a plan or policy and may therefore determine a suitable alternative agent 142 that is covered by the plan or policy associated with an individual 102.

At operation 1408, the processing operation 1220 may include billing one or more providers for the one or more agents. In some embodiments, one or more processing units 112 may bill one or more providers for the one or more agents 142. Numerous providers may be billed for one or more agents 142. Examples of such providers include, but are not limited to, insurance companies, flex spending accounts, Medicare, Blue Cross, Blue Shield, health maintenance organizations, and the like.

At operation 1410, the processing operation 1220 may include selecting the one or more agents for delivery to the individual. In some embodiments, one or more processing units 112 may select one or more agents 142 for delivery to an individual 102. In some embodiments, one or more processing units 112 may select the one or more agents 142 indicated in one or more received signals 126 for delivery to an individual 102. In some embodiments, one or more processing units 112 may select an alternative to the one or more agents 142 indicated in one or more received signals 126 for delivery to an individual 102.

Figure 15:
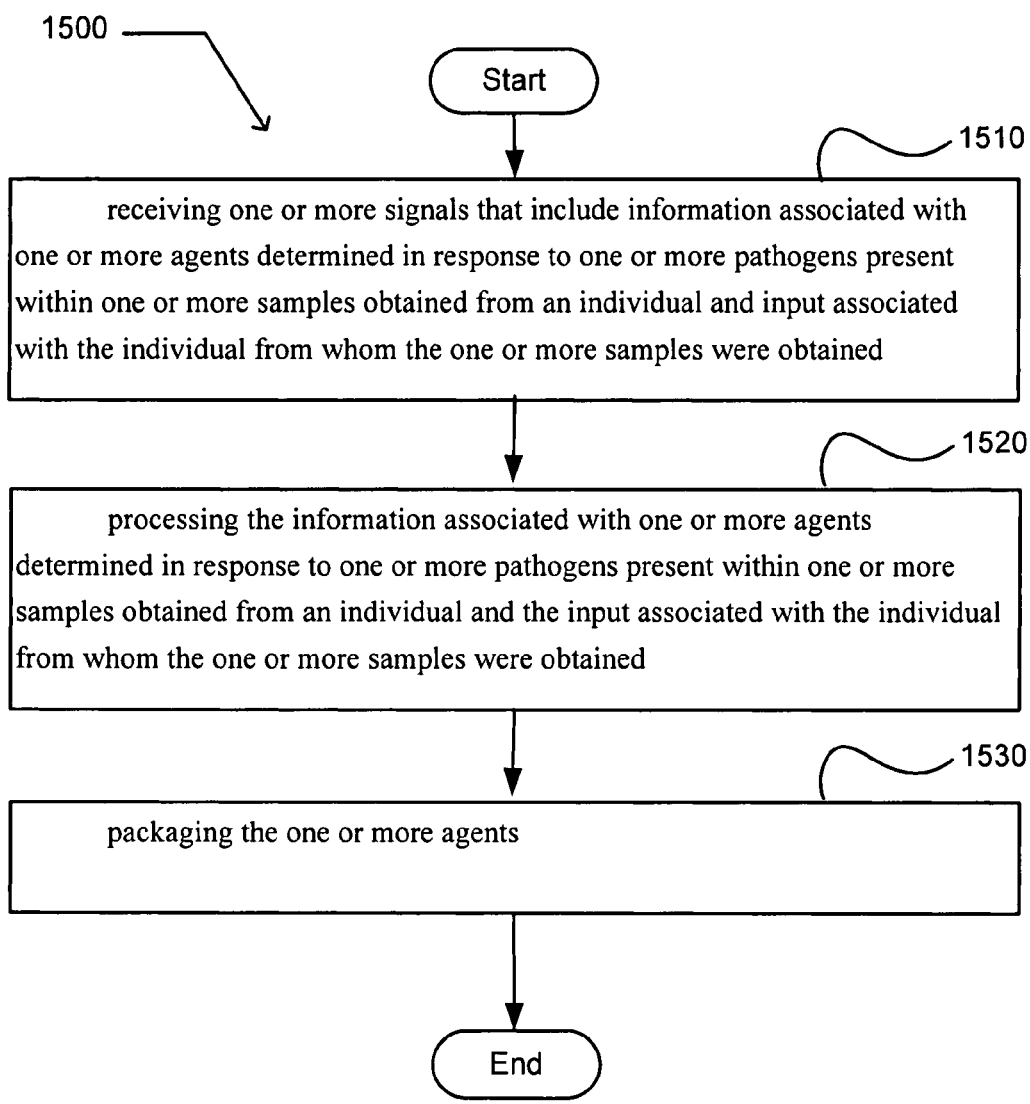

FIG. 15 illustrates operational flow 1500 that includes operations 1510 and 1520, that correspond to operations 1210 and 1220 as illustrated in FIG. 12, with an optionally included packaging operation 1530 and represents examples of operations that are related to the performance of a method for identifying one or more pathogens 106 and determining one or more agents 142 that may be used to reduce the pathogenicity of at least one of the one or more pathogens 106. In FIG. 15 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 1500 optionally includes a packaging operation 1530 involving packaging the one or more agents. In some embodiments, one or more packaging units 138 may be used to package one or more agents 142. In some embodiments, one or more packaging units 138 may be used to package one or more agents 142 in packaging material. In some embodiments, one or more packaging units 138 may package one or more agents 142 for administration to an individual 102. For example, in some embodiments, one or more packaging units 138 may package individual dosages of one or more agents 142 for a specific individual 102. Accordingly, in such embodiments, a packaging unit 138 may be used for individualized agent 142 packaging.

Figure 16:
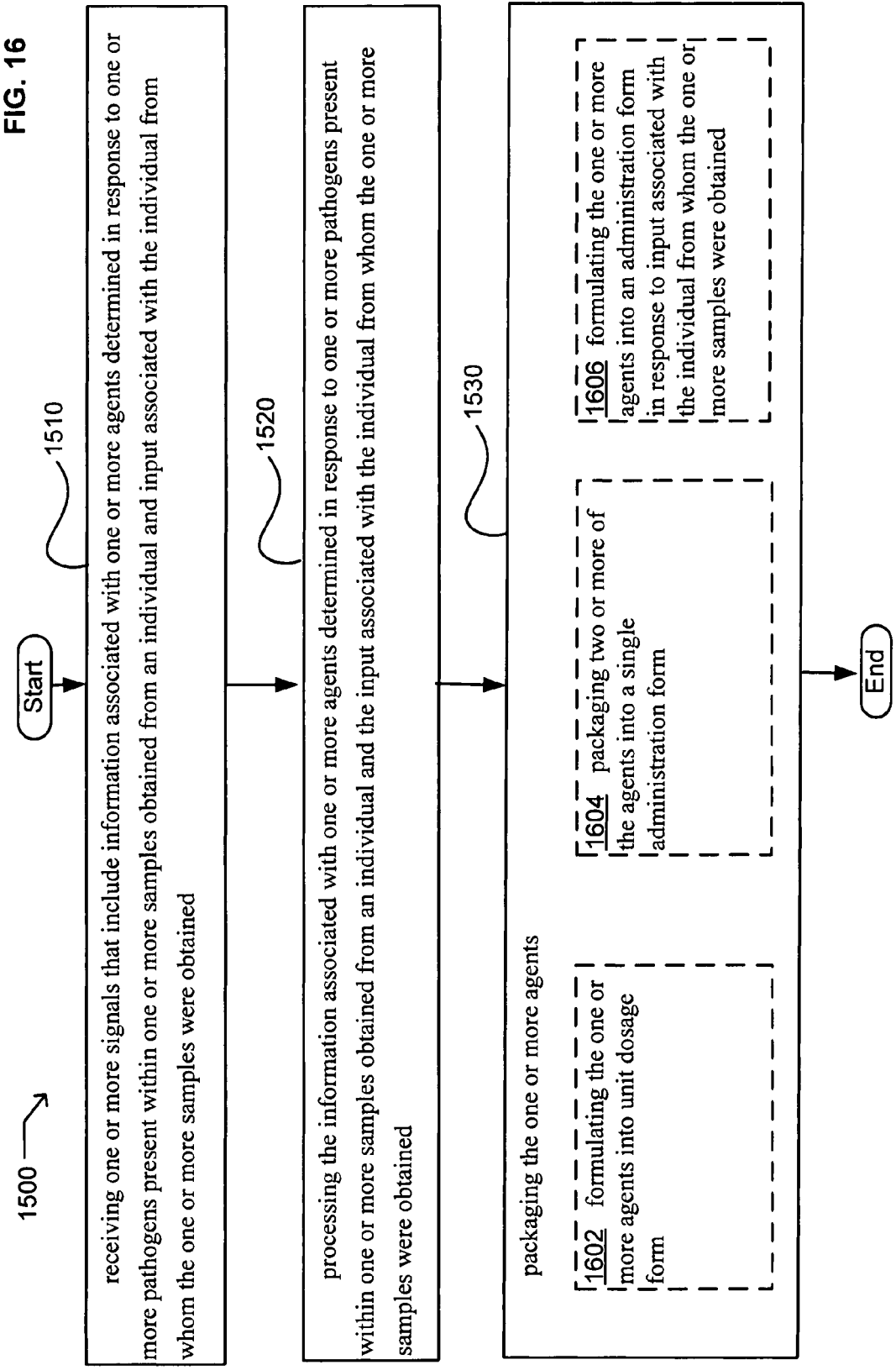

FIG. 16 illustrates alternative embodiments of the example operational flow 1500 of FIG. 15. FIG. 16 illustrates example embodiments where the packaging operation 1530 may include at least one additional operation. Additional operations may include an operation 1602, operation 1604, and/or operation 1606.

At operation 1602, the packaging operation 1530 may include formulating the one or more agents into unit dosage form. In some embodiments, one or more packaging units 138 may formulate one or more agents 142 into unit dosage form. In some embodiments, a unit dosage form may include one or more amounts of one or more agents 142, such as pharmaceutical agents 142, that are suitable as unitary dosages for an individual 102 with each unit containing a predetermined quantity of at least one agent 142 calculated to produce a desired effect, such as a therapeutic effect, in association with one or more suitable pharmaceutical carriers. Such unit dosage forms may be packaged in numerous configurations that include, but are not limited to, tablets, capsules, ampoules, and other administration forms known in the art and described herein. In some embodiments, two or more unit dosage forms of one or more agents 142 may be packaged into an administration form. For example, in some embodiments, two unit dosage forms may be wrapped into an administration form through use of a continuous wrapper such that they are released at different times following administration to an individual 102. In such an example, two unit dosage forms are included within one administration form.

At operation 1604, the packaging operation 1530 may include packaging two or more of the agents into a single administration form. In some embodiments, one or more packaging units 138 may package two or more agents 142 into a single administration form. For example, in some embodiments, two agents 142 may be wrapped into a single administration form through use of a continuous wrapper such that they are released at different times following administration to an individual 102. In some examples, two unit dosage forms may be included within one administration form.

At operation 1606, the packaging operation 1530 may include formulating the one or more agents into an administration form in response to input associated with the individual from whom the one or more samples were obtained. In some embodiments, one or more packaging units 138 may formulate one or more agents 142 into an administration form in response to input 120 associated with an individual 102 from whom one or more samples 104 were obtained. For example, in some embodiments, an individual 102 may work at night where an agent 142 may interfere with the individual's function. Accordingly, one or more agents 142 may be formulated to be released during the day when the individual 102 is not working. In some embodiments, one or more agents 142 may be formulated for oral administration according to a preference of an individual 102. Accordingly, one or more agents 142 may be formulated in numerous ways in response to input 120 associated with an individual 102.

Figure 17:
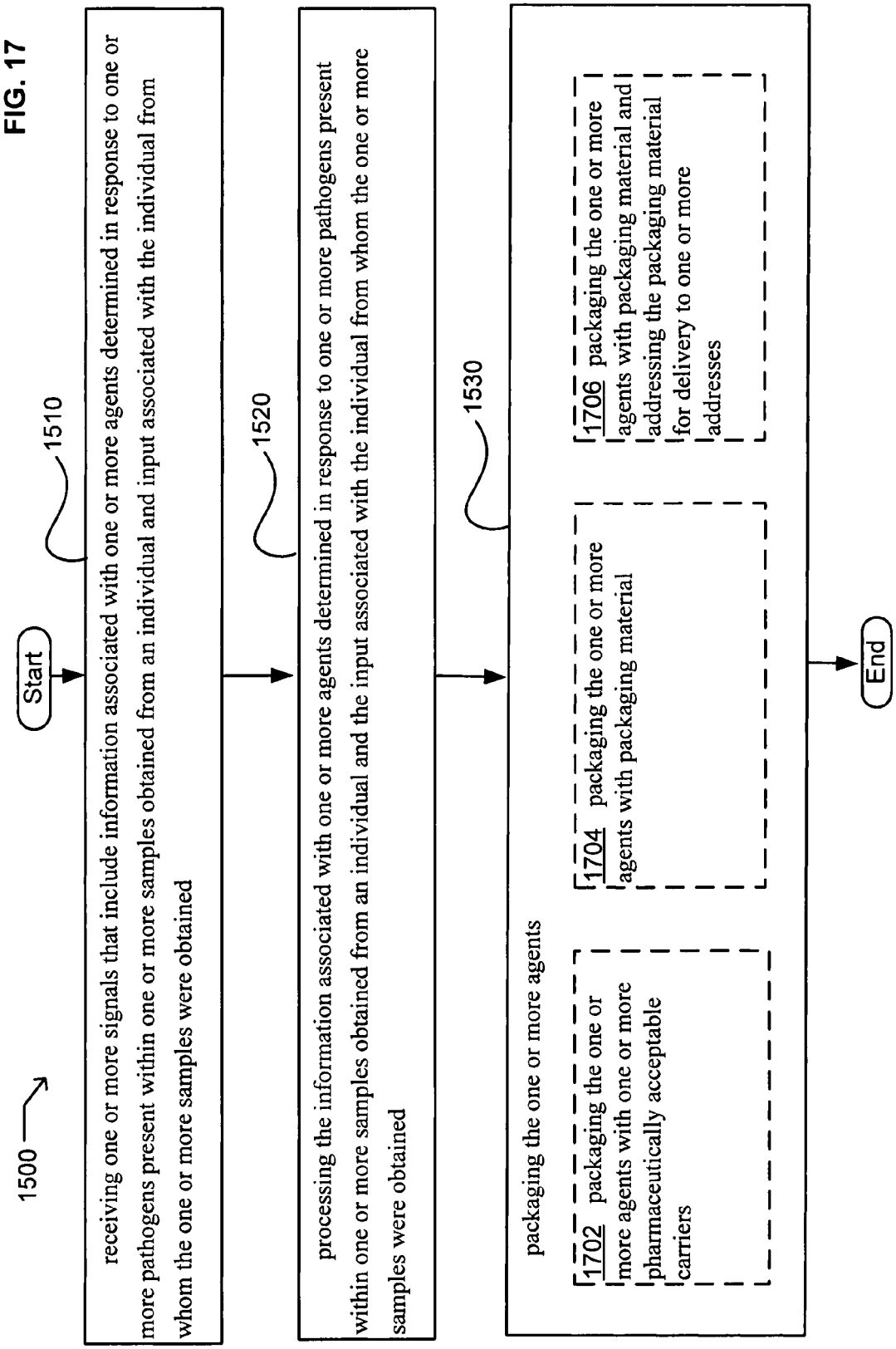

FIG. 17 illustrates alternative embodiments of the example operational flow 1500 of FIG. 15. FIG. 17 illustrates example embodiments where the packaging operation 1530 may include at least one additional operation. Additional operations may include an operation 1702, operation 1704, and/or operation 1706.

At operation 1702, the packaging operation 1530 may include packaging the one or more agents with one or more pharmaceutically acceptable carriers. In some embodiments, one or more packaging units 138 may package one or more agents 142 with one or more pharmaceutically acceptable carriers. In some embodiments, one or more agents 142 (e.g., pharmaceuticals) may be packaged with one or more solid or gel phase carriers or excipients. Examples of such carriers or excipients include, but are not limited to, croscarmellose sodium, providone, microcrystalline cellulose, calcium carbonate, calcium phosphate, various sugars, starches, cellulose derivatives, gelatin, pregelatinized starch, polymers such as polyethylene glycols, lactose, lactose monohydrate, sucrose, talc, gelatin, agar, pectin, acacia, magnesium stearate, stearic acid and substantially any combination thereof. If a solid carrier is used, the one or more agents 142 may be tableted, placed in a hard gelatin capsule in powder or pellet form, packaged in the form of a troche or lozenge, and the like.

In some embodiments, one or more agents 142 may be packaged with a liquid carrier or excipient. Examples of such liquid carriers include syrup, peanut oil, olive oil, water, physiologically compatible buffers (i.e., Hanks solution and Ringers solution), physiological saline buffer, and the like. If a liquid carrier is used, the administration form may be in the form of a syrup, emulsion, drop, soft gelatin capsule, sterile injectable solution, suspension in an ampoule or vial, non-aqueous liquid suspension, and the like.

One or more agents 142 may be packaged in stable water-soluble administration forms. For example, in some embodiments, a pharmaceutically acceptable salt of one or more agents 142 may be dissolved in an aqueous solution of an organic or inorganic acid, such as 0.3M solution of succinic acid or citric acid. If a soluble salt form is not available, an agent 142 may be dissolved in a suitable cosolvent or combination of cosolvents. Examples of suitable cosolvents include, but are not limited to, alcohol, propylene glycol, polyethylene glycol 300, polysorbate 80, glycerin and the like in concentrations ranging from 0-60% of the total volume. In some embodiments, one or more agents 142 may be dissolved in DMSO and diluted with water. The administration form may also be in the form of a solution of a salt form of one or more agents 142 in an appropriate aqueous vehicle such as water or isotonic saline or dextrose solution.

In some embodiments, agents 142 that are hydrophobic may be packaged through use of a cosolvent system comprising benzyl alcohol, a nonpolar surfactant, a water-miscible organic polymer, and an aqueous phase. The cosolvent system may be the VPD co-solvent system. VPD is a solution of 3 percent weight/volume benzyl alcohol, 8 percent weight/volume of the nonpolar surfactant polysorbate 80, and 65 percent weight/volume polyethylene glycol 300, made up to volume in absolute ethanol. The VPD co-solvent system (VPD:5W) consists of VPD diluted 1:1 with a 5 percent dextrose in water solution. This co-solvent system dissolves hydrophobic agents 142, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol (i.e., polyvinyl pyrrolidone; and other sugars or polysaccharides may substitute for dextrose). Many other delivery systems may be used to administer hydrophobic agents 142 as well. For example, liposomes and emulsions are well known examples of delivery vehicles or carriers for hydrophobic drugs. Certain organic solvents such as dimethylsulfoxide also may be employed, although usually at the cost of greater toxicity.

Some agents 142 may be packaged as salts with pharmaceutically compatible counter ions. Pharmaceutically compatible salts may be formed with many acids, including hydrochloric, sulfuric, acetic, lactic, tartaric, malic, succinic, etc. Salts of agents 142 tend to be more soluble in aqueous or other protonic solvents than are the corresponding free-base forms.

Numerous carriers and excipients are known and are commercially available (i.e., The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, 58th Edition, Thompson, PDR, Montvale, N.J. 2004; U.S. Pat. Nos. 6,773,721; 7,053,107; 7,049,312 and Published U.S. Patent Application No. 20040224916; herein incorporated by reference).

In addition, in some embodiments, one or more agents 142 may be packaged with pharmaceutically acceptable poloxamers, humectants, binders, disintegrants, fillers, diluents, lubricants, glidants, flow enhancers, compression aids, coloring agents, sweeteners, preservatives, suspending agents, dispersing agents, film formers, coatings, flavoring agents, printing inks, or substantially any combination thereof.

At operation 1704, the packaging operation 1530 may include packaging the one or more agents with packaging material. In some embodiments, one or more packaging units 138 may package one or more agents 142 with packaging material. One or more agents 142 (e.g., pharmaceuticals) may be packaged in numerous types of packaging material. Examples of packaging material include, but are not limited to, containers, boxes, ampoules, vials, syringes, and the like. In some embodiments, packaging material may include advertising. In some embodiments, packaging material may include instructions for administration. Such instructions may include time for administration, route of administration, the name of the individual 102 to whom the one or more agents 142 are to be administered, the identity of the one or more agents 142, the dosage of the one or more agents 142, appropriate buffers for suspension of the one or more agents 142, the source of the one or more agents 142, the name of a physician or physicians who prescribed the one or more agents 142, the date when the one or more agents 142 were prescribed, the date when the one or more agents 142 were packaged, the date when the one or more agents 142 were manufactured, the expiration date of the one or more agents 142, and the like.

At operation 1706, the packaging operation 1530 may include packaging the one or more agents with packaging material and addressing the packaging material for delivery to one or more addresses. In some embodiments, one or more packaging units 138 may package one or more agents 142 with packaging material and address the packaging material for delivery to one or more addresses. For example, in some embodiments, one or more packaging units 138 may package one or more agents 142 in one or more dispensing containers (e.g., a box, ampoule, vial, syringe, etc.), and then package the one or more dispensing containers in packaging material (e.g., boxes, crates, envelopes, pouches, etc.) that is addressed for delivery to one or more addresses. In some embodiments, one or more packaging units 138 may package one or more prepackaged agents 142 in one or more shipping containers (e.g., boxes, crates, envelopes, pouches, etc.) and addressing the one or more shipping containers for delivery to one or more addresses. Numerous addresses could be used. Examples of such addresses include, but are not limited to, addresses to hospitals, military field stations, pharmacies, individuals, health care facilities, and the like.

Figure 18:
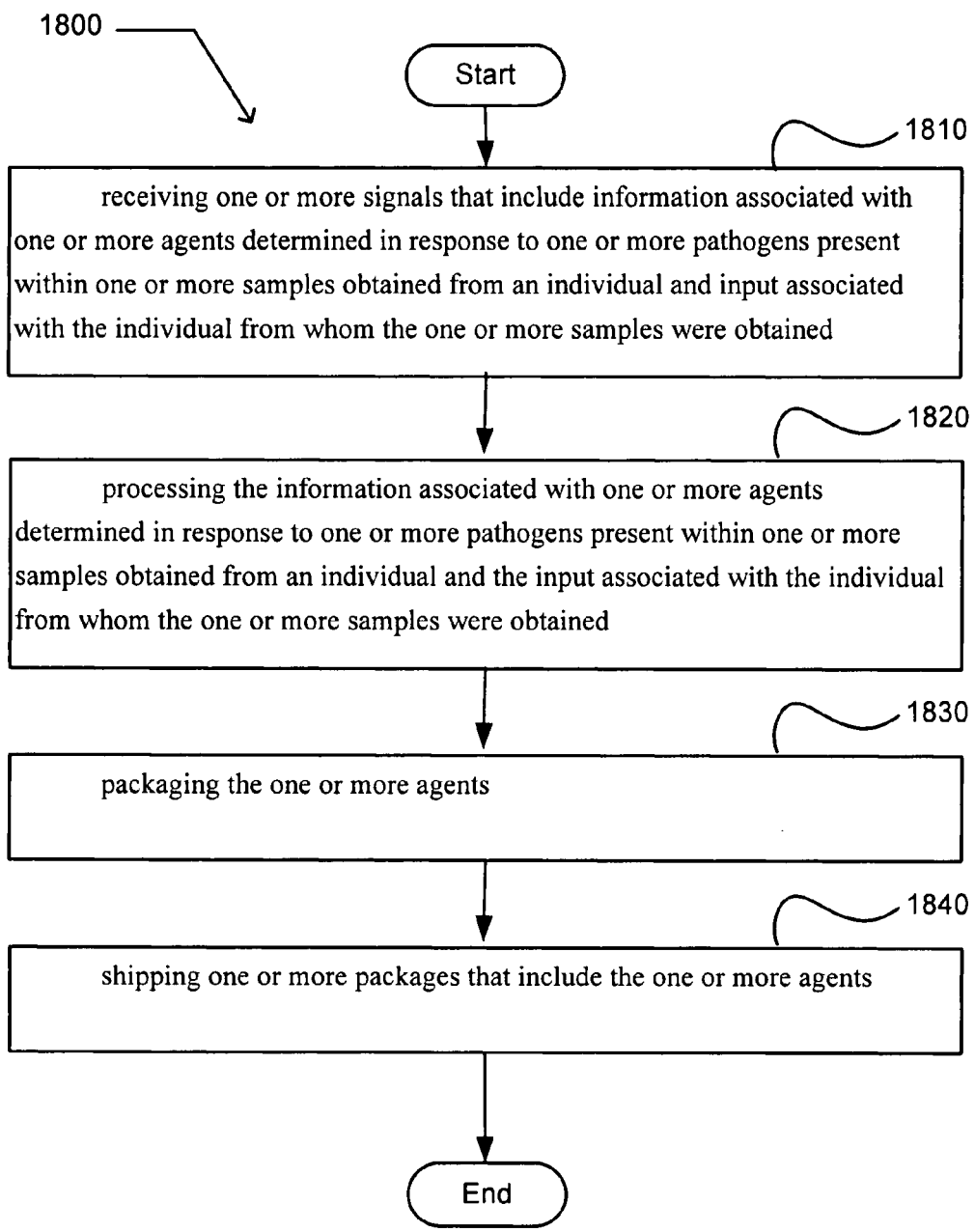

FIG. 18 illustrates operational flow 1800 that includes operations 1810, 1820, and 1830, that correspond to operations 1510, 1520, and 1530 as illustrated in FIG. 15, with an optionally included shipping operation 1840 and represents examples of operations that are related to the performance of a method for identifying one or more pathogens 106 and determining one or more agents 142 that may be used to reduce the pathogenicity of at least one of the one or more pathogens 106. In FIG. 18 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 1800 optionally includes a shipping operation 1840 involving shipping one or more packages that include the one or more agents. In some embodiments, one or more shipping units 140 may be used to ship one or more packages that include one or more agents 142. In some embodiments, a shipping unit 140 may include logic that selects one or more routes that may be used to deliver one or more packages that include one or more agents 142. For example, in some embodiments, a shipping unit 140 may select a shipping route through the Southern United States in the winter time to avoid shipping delays due to snowfall. Accordingly, one or more shipping units 140 may select from numerous routes to ship one or more packages. In some embodiments, a shipping unit 140 may select a service to ship a package. Examples of such shipping services include, but are not limited to, United States Postal Service, United Postal Service, Federal Express, and the like.

Figure 19:
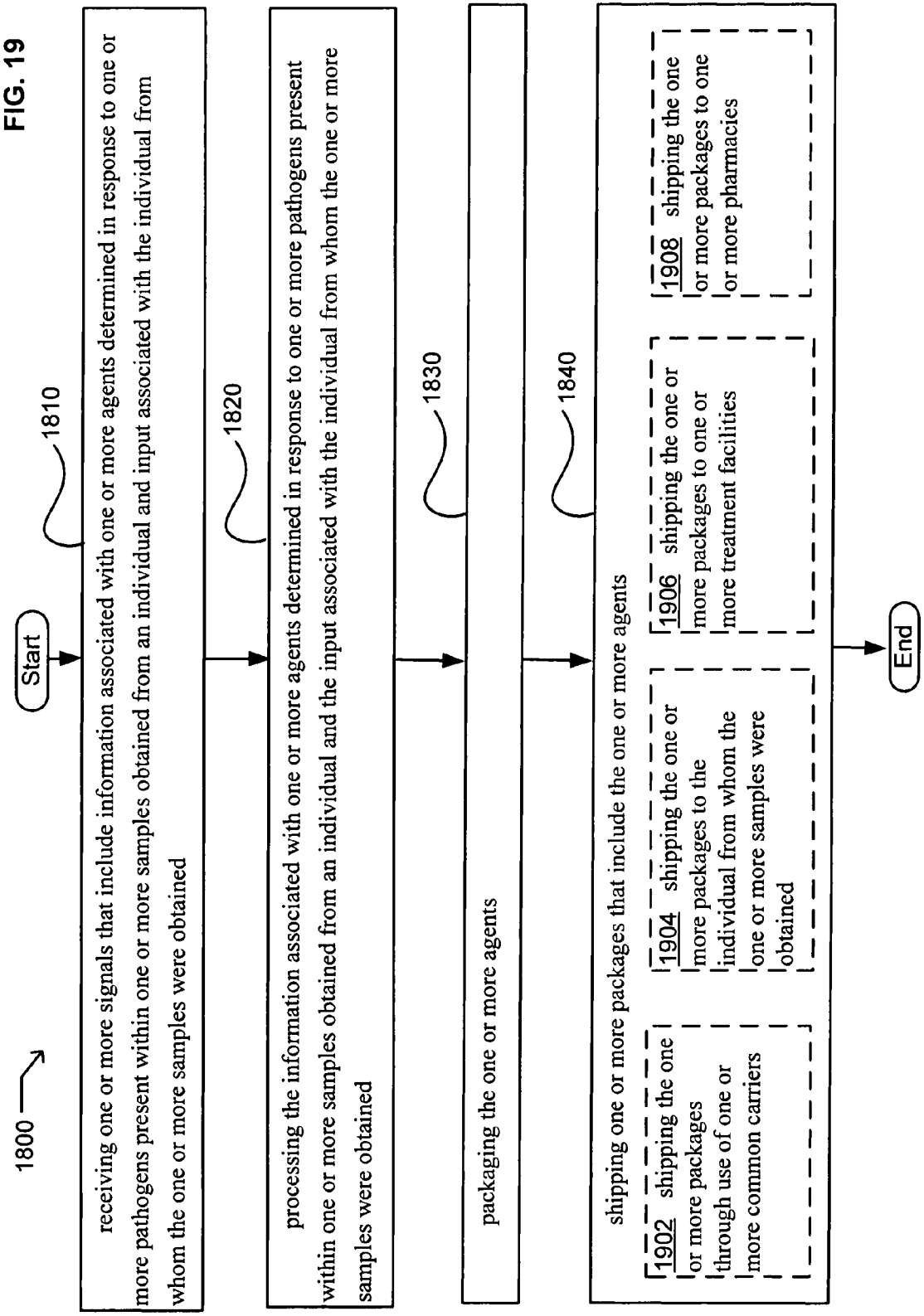

FIG. 19 illustrates alternative embodiments of the example operational flow 1800 of FIG. 18. FIG. 19 illustrates example embodiments where the shipping operation 1840 may include at least one additional operation. Additional operations may include an operation 1902, operation 1904, operation 1906, and/or operation 1908.

At operation 1902, the shipping operation 1840 may include shipping the one or more packages through use of one or more common carriers. In some embodiments, one or more shipping units 140 may be used to ship one or more packages through use of one or more common carriers. In some embodiments, one or more shipping units 140 may include logic that selects one or more common carriers for shipping one or more packages. Examples of common carriers include, but are not limited to, airline shipping services, ground shipping services, nautical shipping services, and the like.

At operation 1904, the shipping operation 1840 may include shipping the one or more packages to the individual from whom the one or more samples were obtained. In some embodiments, one or more shipping units 140 may be used to ship one or more packages to an individual 102 from whom one or more samples 104 were obtained.

At operation 1906, the shipping operation 1840 may include shipping the one or more packages to one or more treatment facilities. In some embodiments, one or more shipping units 140 may be used to ship one or more packages to one or more treatment facilities. Examples of treatment facilities include, but are not limited to, hospitals, clinics, military field hospitals, ship infirmaries, and the like.

At operation 1908, the shipping operation 1840 may include shipping the one or more packages to one or more pharmacies. In some embodiments, one or more shipping units 140 may be used to ship one or more packages to one or more pharmacies.

Figure 20:
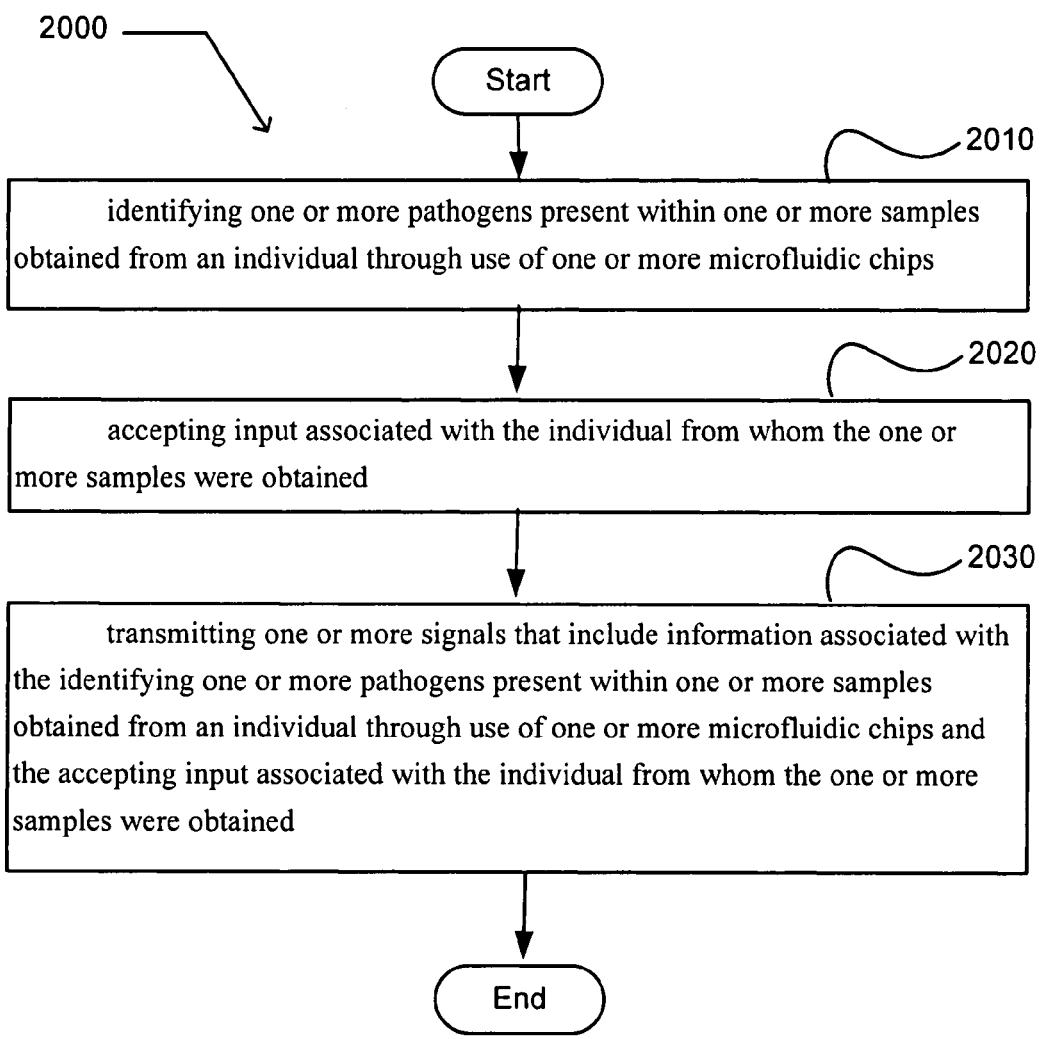

FIG. 20 illustrates an operational flow 2000 representing examples of operations that are related to the performance of a method for identifying one or more pathogens 106 and determining one or more agents 142 that may be used to reduce the pathogenicity of at least one of the one or more pathogens 106. In FIG. 20 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 2000 includes an identifying operation 2010 involving identifying one or more pathogens present within one or more samples obtained from an individual through use of one or more microfluidic chips. In some embodiments, one or more analysis units 110 may be used to identify one or more pathogens 106 present within one or more samples 104 obtained from an individual 102 through use of one or more microfluidic chips 108.

After a start operation, the operational flow 2000 includes an accepting operation 2020 involving accepting input associated with the individual from whom the one or more samples were obtained. In some embodiments, one or more accepting units 118 may be used to accept input 120 associated with an individual 102 from whom one or more samples 104 were obtained.

After a start operation, the operational flow 2000 includes a transmitting operation 2030 involving transmitting one or more signals that include information associated with the identifying one or more pathogens present within one or more samples obtained from an individual through use of one or more microfluidic chips and the accepting input associated with the individual from whom the one or more samples were obtained. In some embodiments, one or more transmitting units 116 may be used to transmit one or more signals 126 that include information associated with identifying one or more pathogens 106 present within one or more samples 104 obtained from an individual 102 through use of one or more microfluidic chips 108 and accepting input 120 associated with the individual 102 from whom the one or more samples 104 were obtained.

Figure 21:
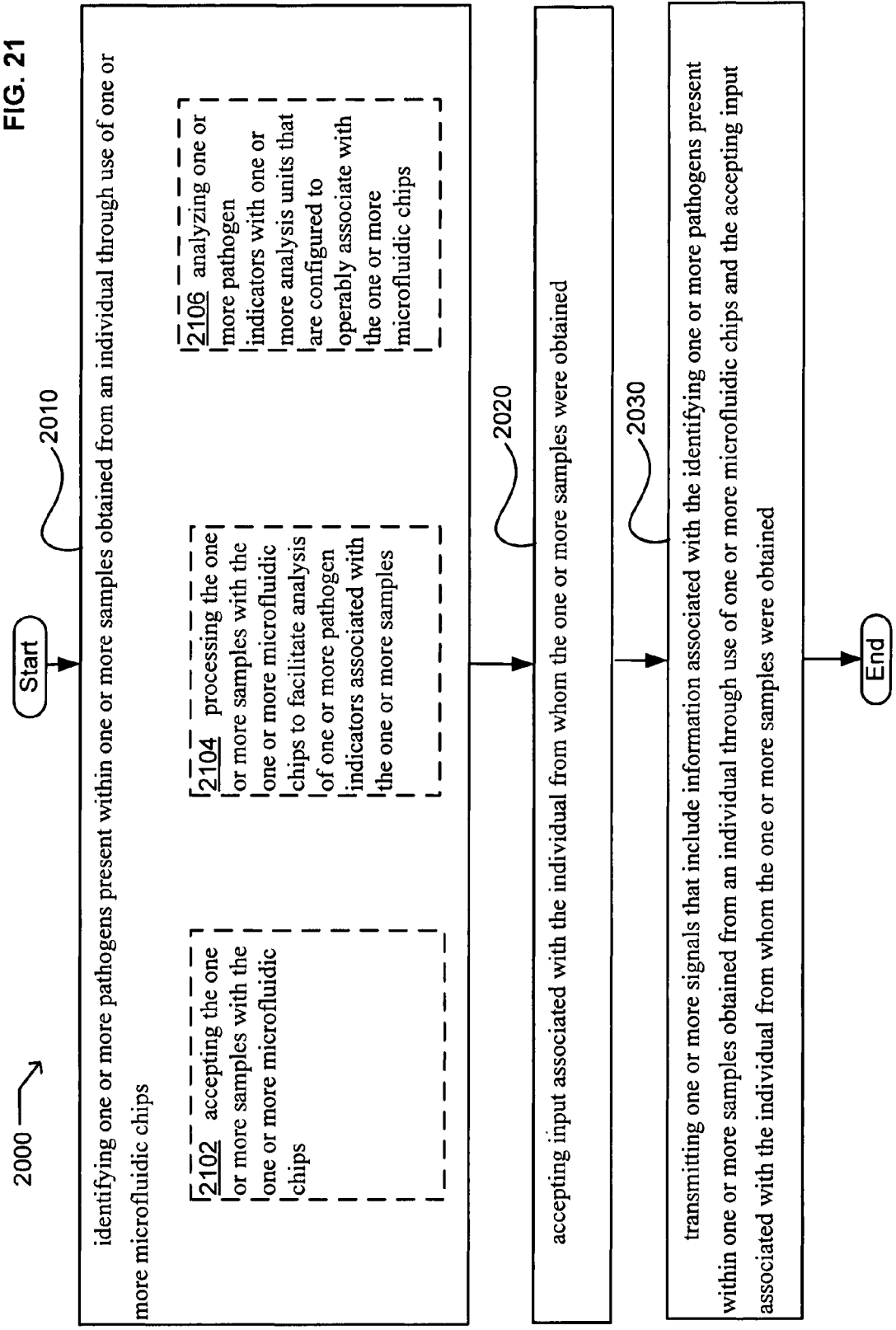

FIG. 21 illustrates alternative embodiments of the example operational flow 2000 of FIG. 20. FIG. 21 illustrates example embodiments where the identifying operation 2010 may include at least one additional operation. Additional operations may include an operation 2102, operation 2104, and/or operation 2106.

At operation 2102, the identifying operation 2010 may include accepting the one or more samples with the one or more microfluidic chips. In some embodiments, one or more microfluidic chips 108 may accept one or more samples 104. In some embodiments, one or more microfluidic chips 108 may accept one or more samples 104 that include one or more liquids. In some embodiments, one or more microfluidic chips 108 may accept one or more samples 104 that include one or more solids. In some embodiments, one or more microfluidic chips 108 may accept one or more samples 104 that include one or more gases. In some embodiments, one or more microfluidic chips 108 may accept one or more samples 104 that include one or more biological samples 104. Examples of biological samples 104 include, but are not limited to, blood, cerebrospinal fluid, mucus, breath, urine, fecal material, skin, tissue, tears, hair, and the like.

At operation 2104, the identifying operation 2010 may include processing the one or more samples with the one or more microfluidic chips to facilitate analysis of one or more pathogen indicators associated with the one or more samples. In some embodiments, the identifying operation 2010 may include processing one or more samples 104 with one or more microfluidic chips 108 through use of polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof.

At operation 2106, the identifying operation 2010 may include analyzing one or more pathogen indicators with one or more analysis units that are configured to operably associate with the one or more microfluidic chips. In some embodiments, identifying operation 2010 may include analyzing the one or more pathogen indicators with one or more analysis units 110 through use of at least one technique that includes spectroscopy, electrochemical detection, polynucleotide detection, fluorescence anisotropy, fluorescence resonance energy transfer, electron transfer, enzyme assay, electrical conductivity, isoelectric focusing, chromatography, immunoprecipitation, immunoseparation, aptamer binding, electrophoresis, use of a CCD camera, immunoassay, or substantially any combination thereof.

Figure 22:
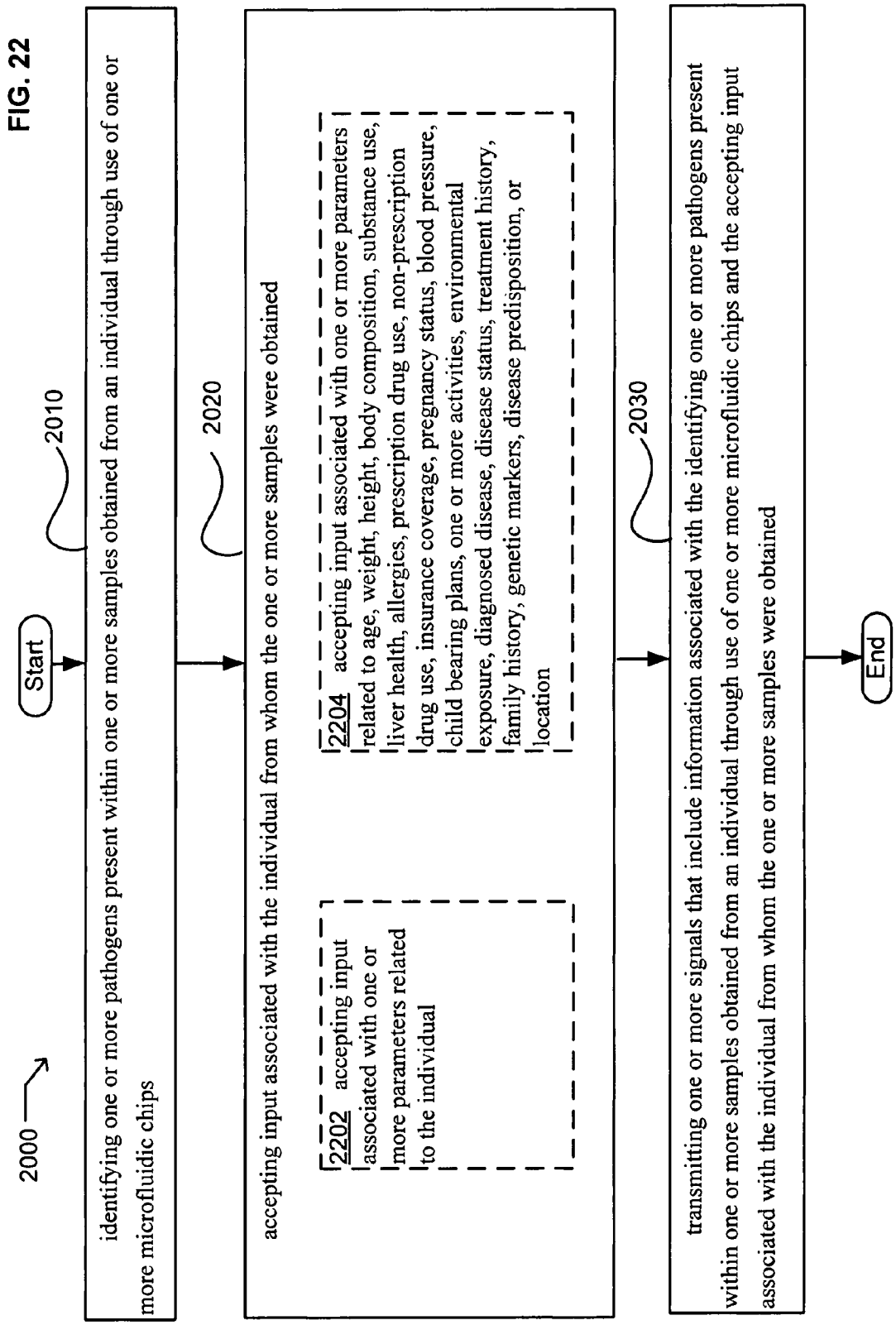

FIG. 22 illustrates alternative embodiments of the example operational flow 2000 of FIG. 20. FIG. 22 illustrates example embodiments where the accepting operation 2020 may include at least one additional operation. Additional operations may include an operation 2202, and/or operation 2204.

At operation 2202, the accepting operation 2020 may include accepting input associated with one or more parameters related to the individual. In some embodiments, one or more accepting units 118 may accept input 120 associated with one or more parameters related to an individual 102. In some embodiments, the one or more parameters may be physical parameters. In some embodiments, the one or more parameters may be psychological parameters. In some embodiments, the one or more parameters may be financial parameters. In some embodiments, the one or more parameters may be health care provided related parameters (e.g., physician's name, insurance provider, HMO name, prescription plan, etc.).

At operation 2204, the accepting operation 2020 may include accepting input associated with one or more parameters related to age, weight, height, body composition, substance use, liver health, allergies, prescription drug use, non-prescription drug use, insurance coverage, pregnancy status, blood pressure, child bearing plans, one or more activities, environmental exposure, diagnosed disease, disease status, treatment history, family history, genetic markers, disease predisposition, or location. In some embodiments, one or more accepting units 118 may accept input 120 associated with one or more parameters related to age, weight, height, body composition (e.g., body mass index, fat percentage), substance use (e.g., alcohol, tobacco, illicit drugs), liver health, allergies, prescription drug use, non-prescription drug use, insurance coverage (e.g., prescription plan, insurance limits, limitations on providers, HMO limitations), pregnancy status (e.g., pregnant, not pregnant, unknown), blood pressure, child bearing plans (e.g., yes, no, time when planning to become pregnant), one or more activities (e.g., travel, athletic activities, occupational activities, driving), location (e.g., travel to foreign nation, local address, town, city), or substantially any combination thereof.

Figure 23:
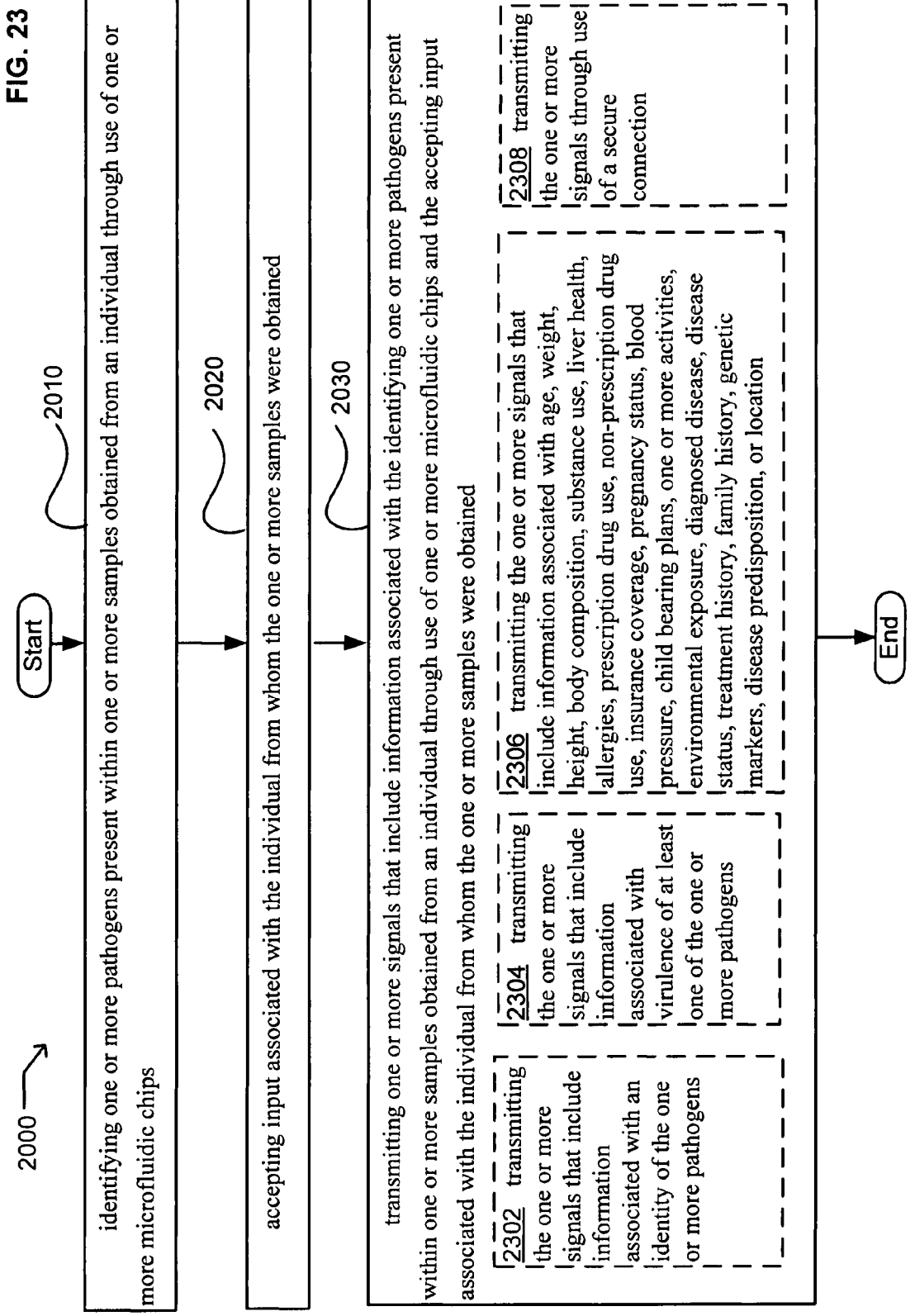

FIG. 23 illustrates alternative embodiments of the example operational flow 2000 of FIG. 20. FIG. 23 illustrates example embodiments where the transmitting operation 2030 may include at least one additional operation. Additional operations may include an operation 2302, operation 2304, operation 2306, and/or operation 2308.

At operation 2302, the transmitting operation 2030 may include transmitting the one or more signals that include information associated with an identity of the one or more pathogens. In some embodiments, one or more transmitting units 116 may transmit one or more signals 126 that include information associated with an identity of one or more pathogens 106. In some embodiments, one or more transmitting units 116 may transmit one or more signals 126 that include information associated with a particular strain of one or more pathogens 106. For example, in some embodiments, one or more transmitting units 116 may transmit one or more signals 126 that include information associated with one or more pathogens 106 that are resistant to one or more antibiotics.

At operation 2304, the transmitting operation 2030 may include transmitting the one or more signals that include information associated with virulence of at least one of the one or more pathogens. In some embodiments, one or more transmitting units 116 may transmit one or more signals 126 that include information associated with virulence of at least one of the one or more pathogens 106. For example, some pathogenic strains of *E. coli* exhibit increased virulence relative to other strains of *E. coli*. Such virulent strains may be identified by the presence of virulence determinants. Examples of such virulence determinants include, but are not limited to, adhesions (e.g., CFAI/CFAII, type 1 fimbriae, P fimbriae, S fimbriae, Intimin), invasions (e.g., hemolysisn, siderophores and siderophore uptake systems, *Shigella*-like "invasins" for intracellular invasion and spread), toxins (e.g., LT toxin, ST toxin, Shiga-like toxin, cytotoxins, endotoxin LPS), antiphagocytic surface properties (e.g., capsules, K antigens, lipopolysaccharides), somatic antigens, flagellar antigens, and the like. Accordingly, one or more signals may include information related to numerous types of virulence indicators.

At operation 2306, the transmitting operation 2030 may include transmitting the one or more signals that include information associated with age, weight, height, body composition, substance use, liver health, allergies, prescription drug use, non-prescription drug use, insurance coverage, pregnancy status, blood pressure, child bearing plans, one or more activities, environmental exposure, diagnosed disease, disease status, treatment history, family history, genetic markers, disease predisposition, or location. In some embodiments, one or more transmitting units 116 may transmit one or more signals 126 that include information associated with the age, weight, height, body composition, substance use, liver health, allergies, prescription drug use, non-prescription drug use, insurance coverage, pregnancy status, blood pressure, child bearing plans, one or more activities, location, or substantially any combination thereof, that is associated with an individual 102.

At operation 2308, the transmitting operation 2030 may include transmitting the one or more signals through use of a secure connection. In some embodiments, one or more transmitting units 116 may transmit one or more signals 126 through use of a secure connection. For example, in some embodiments, one or more signals may be encrypted. In some embodiments, one or more signals may be sent through use of a secure mode of transmission. For example, in some embodiments, one or more signals may be transmitted to a specified individual. In some embodiments, one or more signals may be transmitted to a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be sent in a manner that conforms with privacy regulations as set forth by law. For example, in some embodiments, one or more signals may be transmitted in accordance with the Health Information Privacy and Protection Act. In some embodiments, one or more signals may be sent with information that includes a request for a return receipt.

Figure 24:
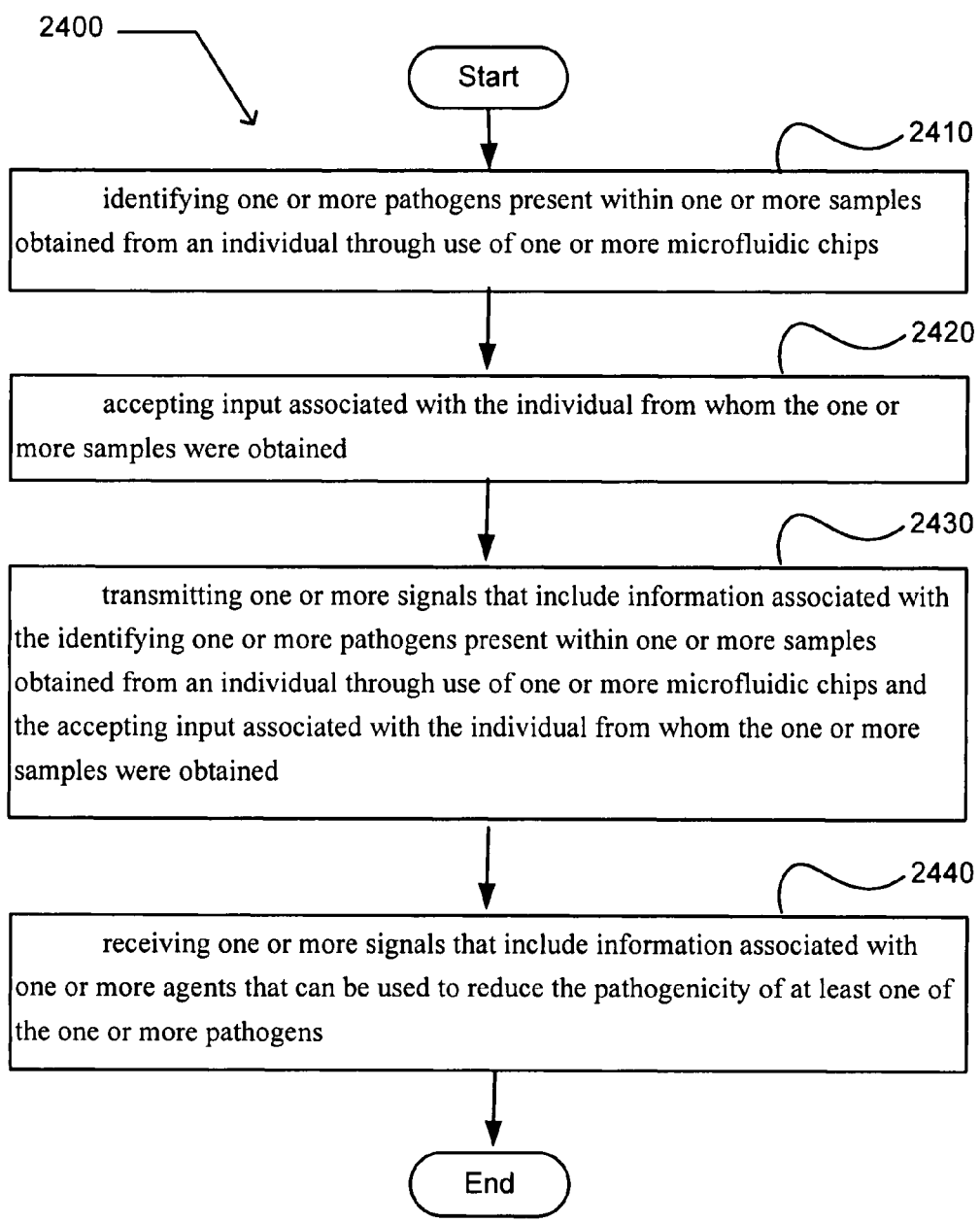

FIG. 24 illustrates operational flow 2400 that includes operations 2410, 2420, and 2430, that correspond to operations 2010, 2020, and 2030 as illustrated in FIG. 20, with an optionally included receiving operation 2440 and represents examples of operations that are related to the performance of a method for identifying one or more pathogens 106 and determining one or more agents 142 that may be used to reduce the pathogenicity of at least one of the one or more pathogens 106. In FIG. 24 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 2400 optionally includes a receiving operation 2440 involving receiving one or more signals that include information associated with one or more agents that can be used to reduce the pathogenicity of at least one of the one or more pathogens. In some embodiments, one or more receiving units 136 may receive one or more signals 126 that include information associated with one or more agents 142 that can be used to reduce the pathogenicity of at least one of one or more pathogens 106. In some embodiments, one or more receiving units 136 may receive one or more signals 126 that include the identity of one or more chemical agents 142 that can be used to reduce the pathogenicity of at least one pathogen 106. Numerous chemical agents 142 may be identified. Examples of such chemical agents 142 include, but are not limited to, antibiotics, ozone, peroxides, chlorinated compounds, acids, bases, alcohols, and the like (e.g., Merck Index, Thirteenth Edition, Merck & Co., Inc., Whitehouse Station, N.J. (2001) and Mosby's Drug Guide, An Imprint of Elsevier, St. Louis, Mo. (2004)). In some embodiments, such chemical agents 142 may be identified that are specific for one or more identified pathogens 106.

Figure 25:
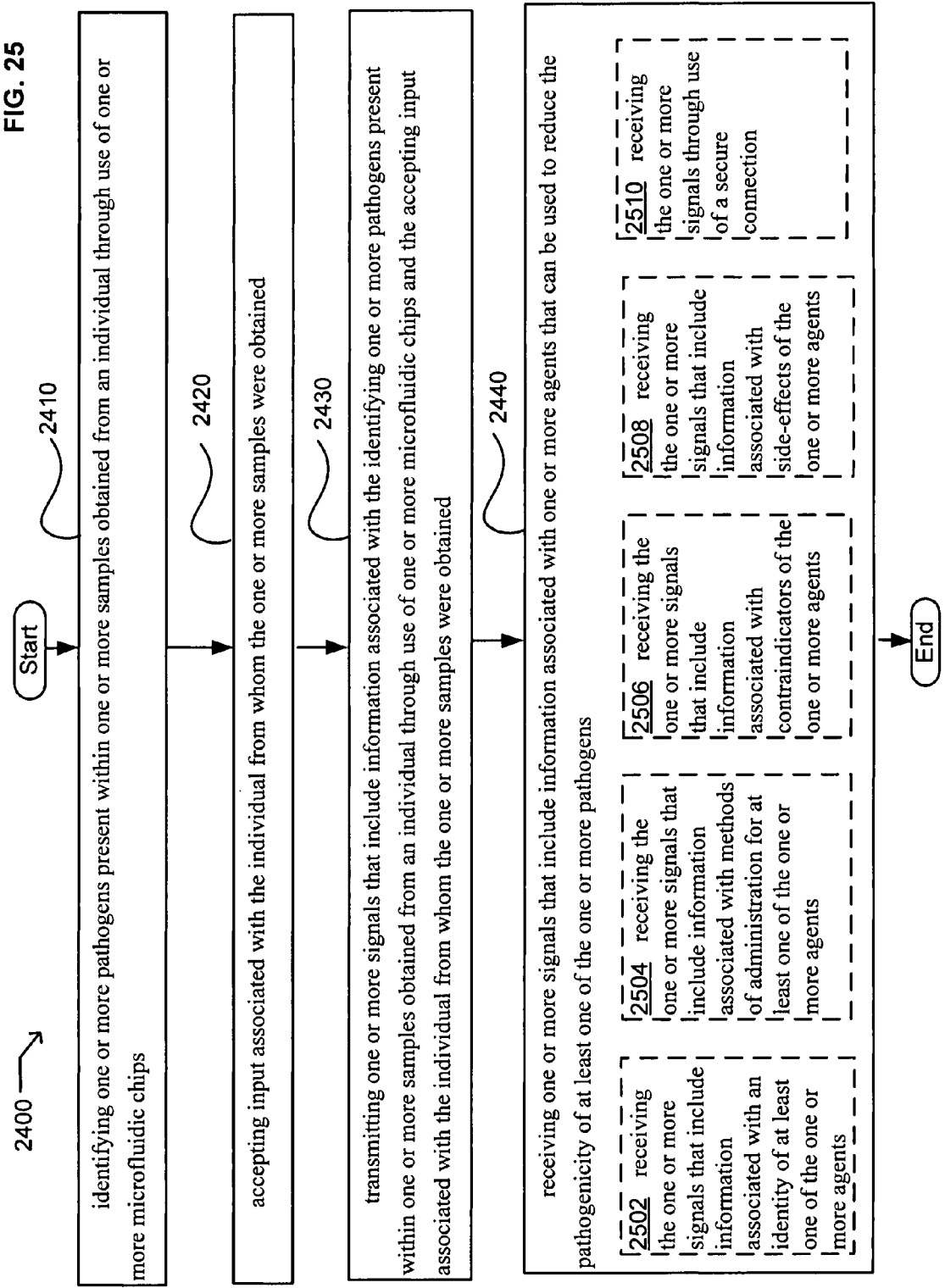

FIG. 25 illustrates alternative embodiments of the example operational flow 2400 of FIG. 24. FIG. 25 illustrates example embodiments where the receiving operation 2440 may include at least one additional operation. Additional operations may include an operation 2502, operation 2504, operation 2506, operation 2508, and/or operation 2510.

At operation 2502, the receiving operation 2440 may include receiving the one or more signals that include information associated with an identity of at least one of the one or more agents. In some embodiments, one or more receiving units 136 may receive one or more signals 126 that include information associated with an identity of at least one of the one or more agents 142. For example, in some embodiments, one or more receiving units 136 may receive one or more signals 126 that include information associated with the brand name, the generic name, the chemical name, the structure, identifiers associated with an agent 142, or substantially any combination thereof.

At operation 2504, the receiving operation 2440 may include receiving the one or more signals that include information associated with methods of administration for at least one of the one or more agents. In some embodiments, one or more receiving units 136 may receive one or more signals 126 that include information associated with methods of administration for at least one of one or more agents 142. Examples of methods of administration include, but are not limited to, oral administration, intravenous administration, transdermal administration, intraperitoneal administration, intraocular administration, nasal administration, pulmonary administration, rectal administration, vaginal administration, and the like.

At operation 2506, the receiving operation 2440 may include receiving the one or more signals that include information associated with contraindicators of the one or more agents. In some embodiments, one or more receiving units 136 may receive one or more signals 126 that include information associated with contraindicators of the one or more agents 142. In some embodiments, contraindicators may include prescription pharmaceutical agents 142 (e.g., opiates, psychotropic drugs, selective serotonin reuptake inhibitors, lithium, alpha-blockers, beta-blockers, antibiotics, cholesterol lowering drugs, heart medications). In some embodiments, contraindicators may include non-prescription pharmaceutical agents 142 (e.g., antacids, acetaminophen, aspirin, cold medications, anti-histamines). In some embodiments, contraindicators may include substances such as nicotine, alcohol, nutraceuticals, and the like. For example, in some embodiments, Saint John's Wort may be indicated as a contraindicator of selective serotonin reuptake inhibitors.

At operation 2508, the receiving operation 2440 may include receiving the one or more signals that include information associated with side-effects of the one or more agents. In some embodiments, one or more receiving units 136 may receive one or more signals 126 that include information associated with side-effects of the one or more agents 142. For example, in some embodiments, one or more signals 126 may include information associated with lower potassium levels associated with diuretic usage. Signals 126 may include information associated with numerous side-effects that include mental side-effects (e.g., excitability, depression, irritability), physical side-effects (e.g., drowsiness, insomnia, dizziness, reduced coordination, increased blood pressure), and the like.

At operation 2510, the receiving operation 2440 may include receiving the one or more signals through use of a secure connection. In some embodiments, one or more receiving units 136 may receive one or more signals 126 through use of a secure connection. For example, in some embodiments, one or more signals may be received that are encrypted. In some embodiments, one or more signals may be received through use of a secure mode. For example, in some embodiments, one or more signals may only be received by a specified individual. In some embodiments, one or more signals may be received by a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be received in a manner that conforms with privacy regulations as set forth by law. For example, in some embodiments, one or more signals may be received in accordance with the Health Information Privacy and Protection Act. In some embodiments, receipt of one or more signals will cause a return receipt to be sent that confirms receipt of the one or more signals.

Figure 26:
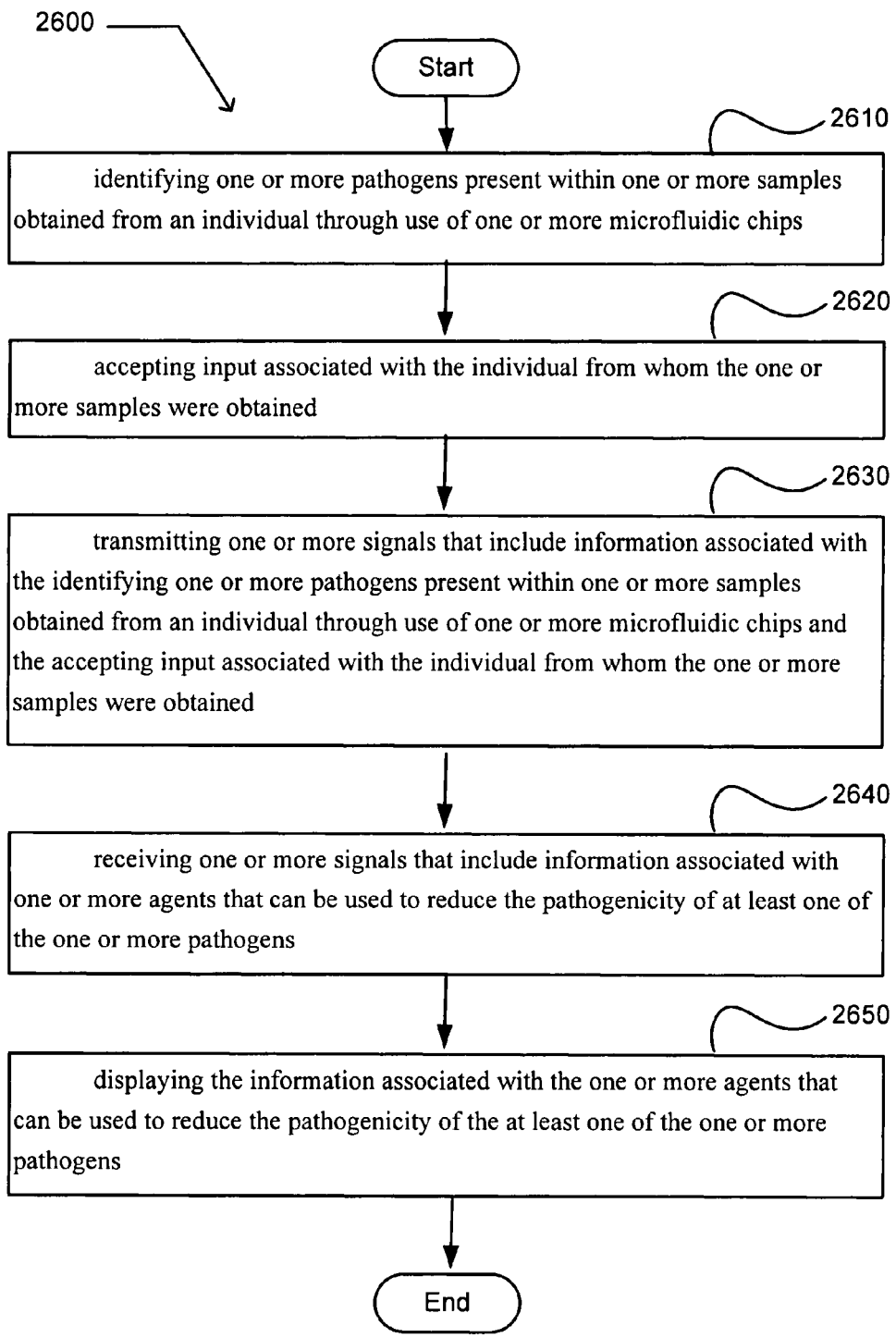

FIG. 26 illustrates operational flow 2600 that includes operations 2610, 2620, 2630, and 2640, that correspond to operations 2410, 2420, 2430, and 2440 as illustrated in FIG. 24, with an optionally included displaying operation 2650 and represents examples of operations that are related to the performance of a method for identifying one or more pathogens 106 and determining one or more agents 142 that may be used to reduce the pathogenicity of at least one of the one or more pathogens 106. In FIG. 26 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 2600 optionally includes a displaying operation 2650 involving displaying the information associated with the one or more agents that can be used to reduce the pathogenicity of the at least one of the one or more pathogens. In some embodiments, one or more display units 114 may display information associated with one or more agents 142 that can be used to reduce the pathogenicity of at least one of one or more pathogens 106. Numerous types of information may be displayed. Examples of such information include, but are not limited to, the identity of an agent 142, dosage of an agent 142, method of administration for an agent 142, and the like.

Figure 27:
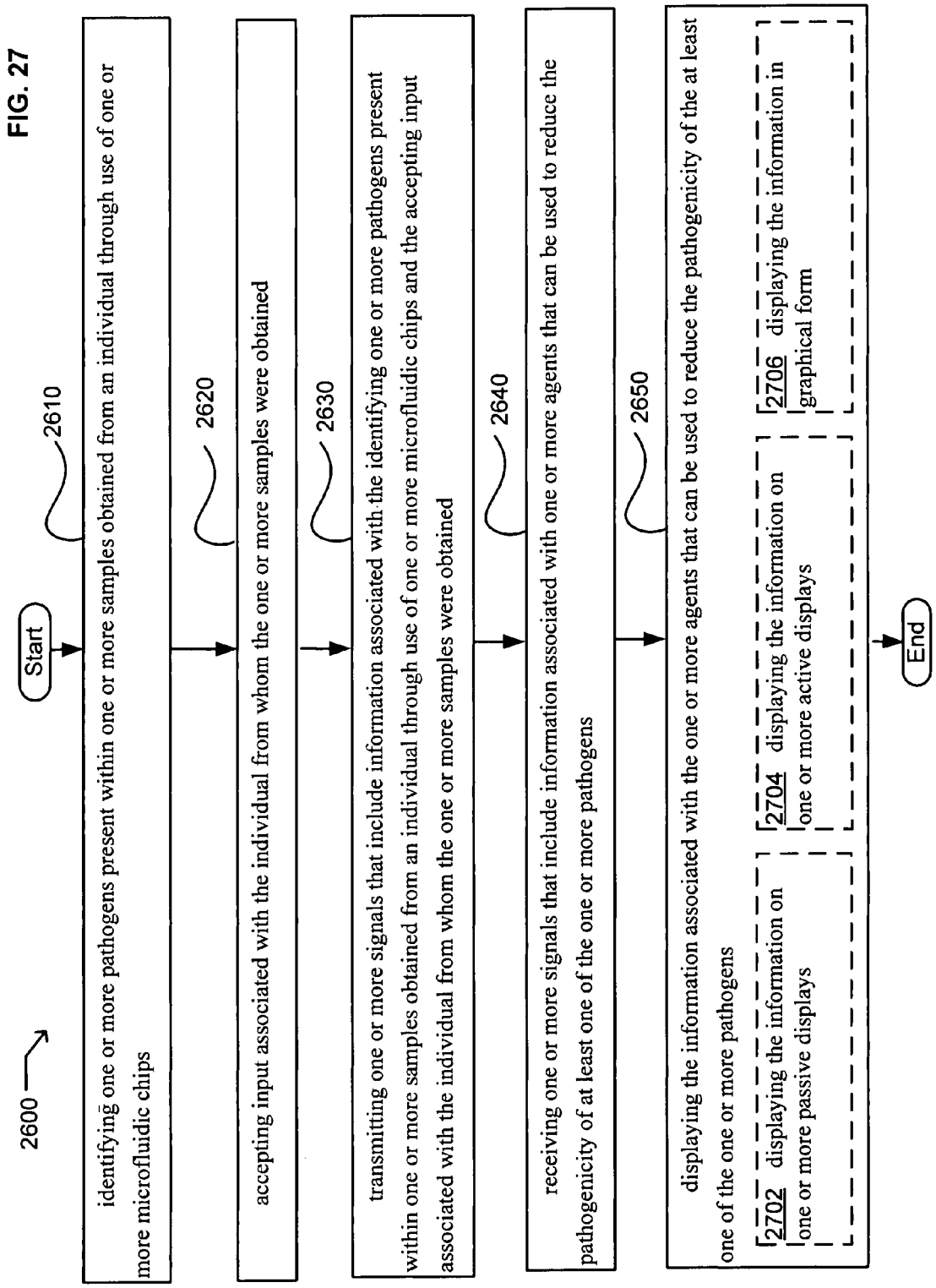

FIG. 27 illustrates alternative embodiments of the example operational flow 2600 of FIG. 26. FIG. 27 illustrates example embodiments where the displaying operation 2650 may include at least one additional operation. Additional operations may include an operation 2702, operation 2704, and/or operation 2706.

At operation 2702, the displaying operation 2650 may include displaying the information on one or more passive displays. In some embodiments, one or more display units 114 may display information on one or more passive displays. In some embodiments, one or more display units 114 may include one or more liquid crystal displays (LCD). Methods to construct passive displays have been described (e.g., U.S. Pat. Nos. 4,807,967; 4,729,636; 4,436,378; 4,257,041; herein incorporated by reference).

At operation 2704, the displaying operation 2650 may include displaying the information on one or more active displays. In some embodiments, one or more display units 114 may display information on one or more active displays. Numerous active display units 114 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), and wide ultra extended graphics array (WUXGA).

At operation 2706, the displaying operation 2650 may include displaying the information in graphical form. In some embodiments, one or more display units 114 may display information in graphical form. Numerous types of graphical formats may be used. Examples of such graphical formats include, but are not limited to, use of shapes, use of colors, use of symbols (e.g., smiley face, frowny face, thumbs up sign, thumbs down sign, histograms, bar graphs, pie charts, and the like).

Figure 28:
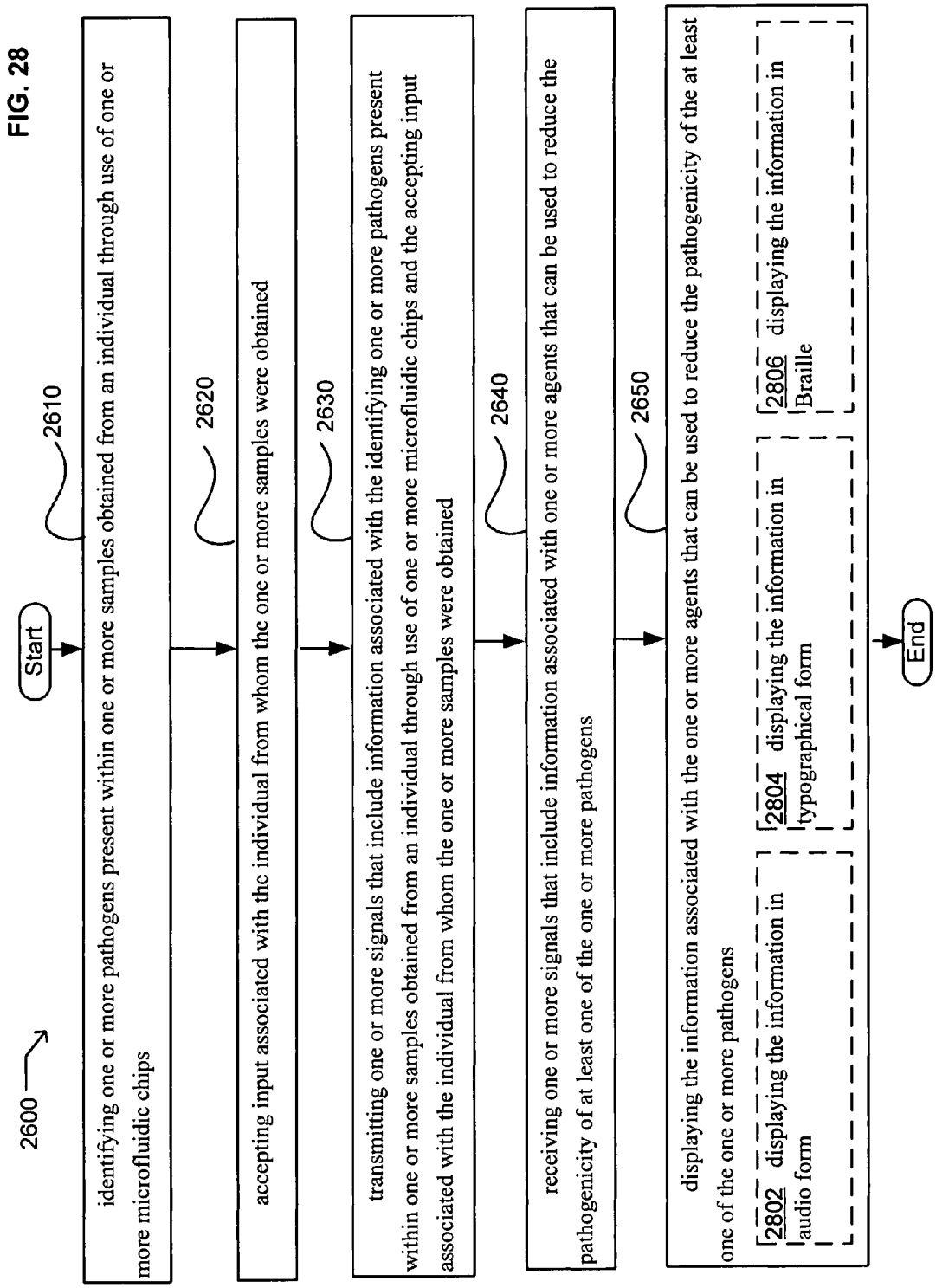

FIG. 28 illustrates alternative embodiments of the example operational flow 2600 of FIG. 26. FIG. 28 illustrates example embodiments where the displaying operation 2650 may include at least one additional operation. Additional operations may include an operation 2802, operation 2804, and/or operation 2806.

At operation 2802, the displaying operation 2650 may include displaying the information in audio form. In some embodiments, one or more display units 114 may display information in audio form. In some embodiments, one or more display units 114 may display information in voice format. For example, in some embodiments, a human voice may indicate the identity of one or more agents 142 that may be used to reduce the pathogenicity of one or more pathogens 106. Numerous types of information may be presented in audio format.

At operation 2804, the displaying operation 2650 may include displaying the information in typographical form. In some embodiments, one or more display units 114 may display information in typographical form. Information may be presented in numerous languages (e.g., Italian, Spanish, English, Japanese). In some embodiments, the typographical form may include numbers.

At operation 2806, the displaying operation 2650 may include displaying the information in Braille. In some embodiments, one or more display units 114 may display information in Braille. Accordingly, in some embodiments, one or more display units 114 may include a pad on which messages in Braille may be displayed. In some embodiments, such pads may be constructed of an elastomeric material that is positioned relative to a series of movable rods such that the rods may be positioned to create messages in Braille. In some embodiments, one or more display units 114 may print information in Braille.

Figure 29:
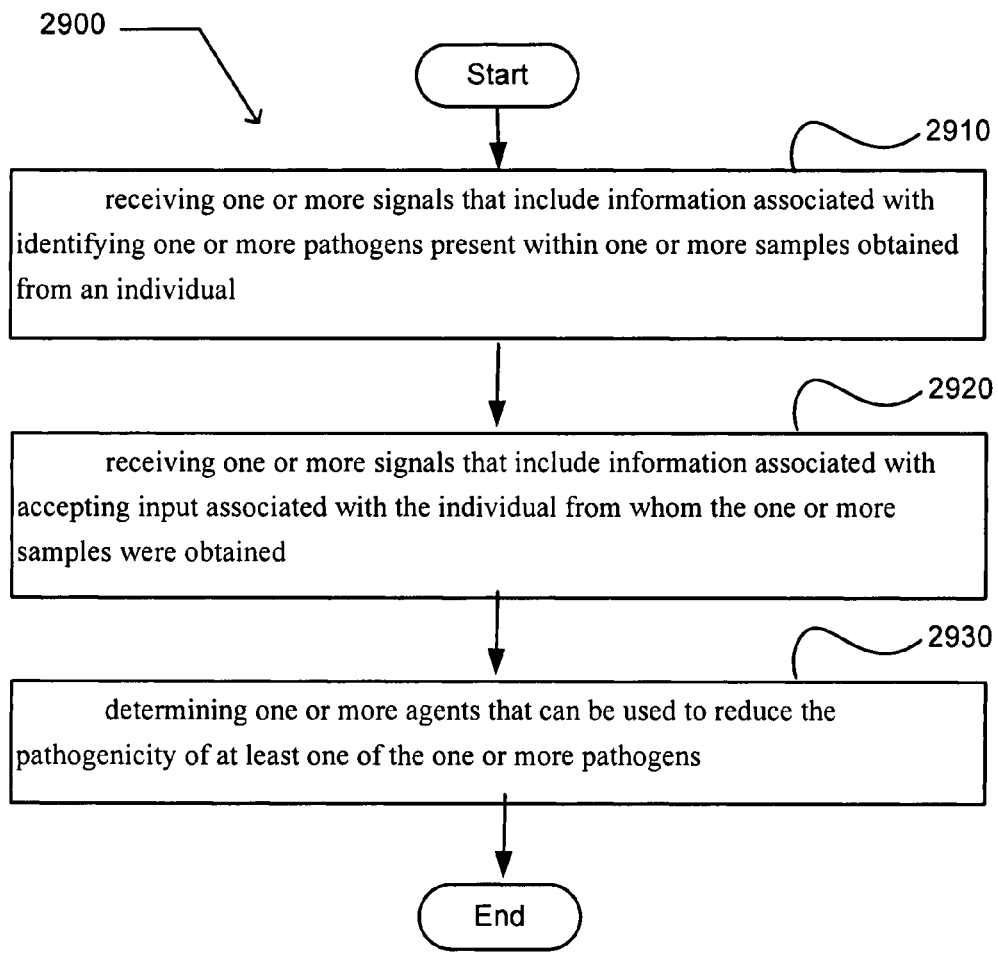

FIG. 29 illustrates an operational flow 2900 representing examples of operations that are related to the performance of a method for identifying one or more pathogens 106 and determining one or more agents 142 that may be used to reduce the pathogenicity of at least one of the one or more pathogens 106. In FIG. 29 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 2900 includes a receiving operation 2910 involving receiving one or more signals that include information associated with identifying one or more pathogens present within one or more samples obtained from an individual. In some embodiments, one or more receiving units 136 may be used to receive one or more signals 126 that include information associated with identifying one or more pathogens 106 present within one or more samples 104 obtained from an individual 102.

After a start operation, the operational flow 2900 includes a receiving operation 2920 involving receiving one or more signals that include information associated with accepting input associated with the individual from whom the one or more samples were obtained. In some embodiments, one or more receiving units 136 may be used to receive one or more signals 126 that include information associated with accepting input 120 associated with an individual 102 from whom one or more samples 104 were obtained.

After a start operation, the operational flow 2900 includes a determining operation 2930 involving determining one or more agents that can be used to reduce the pathogenicity of at least one of the one or more pathogens. In some embodiments, one or more processing units 112 may be used to determine one or more agents 142 that can be used to reduce the pathogenicity of at least one of one or more pathogens 106.

Figure 30:

FIG. 30 illustrates alternative embodiments of the example operational flow 2900 of FIG. 29. FIG. 30 illustrates example embodiments where the receiving operation 2910 may include at least one additional operation. Additional operations may include an operation 3002, operation 3004, operation 3006, operation 3008, and/or operation 3010.

At operation 3002, the receiving operation 2910 may include receiving the one or more signals that include information associated with an identity of the at least one of the one or more pathogens. In some embodiments, one or more receiving units 136 may receive one or more signals 126 that include information associated with an identity of at least one of one or more pathogens 106. Such information may include information associated with a particular strain of one or more pathogens 106.

At operation 3004, the receiving operation 2910 may include receiving the one or more signals that include information associated with a concentration of the at least one of the one or more pathogens. In some embodiments, one or more receiving units 136 may receive one or more signals 126 that include information associated with a concentration of at least one of one or more pathogens 106. In some embodiments, such information may indicate the severity of a pathogen infection. In some embodiments, such information may be used to track treatment of an infection. For example, in some embodiments, one or more signals 126 may be received at times following the initiation of a treatment schedule. Accordingly, the effectiveness of a treatment scheme may be monitored.

At operation 3006, the receiving operation 2910 may include receiving one or more signals that include information associated with drug resistance of at least one of the one or more pathogens. In some embodiments, one or more receiving units 136 may receive one or more signals 126 that include information associated with drug resistance of at least one of one or more pathogens 106. For example, in some embodiments, one or more receiving units 136 may receive one or more signals 126 that include information associated with one or more pathogens 106 that are resistant to one or more antibiotics.

At operation 3008, the receiving operation 2910 may include receiving the one or more signals that include information associated with virulence of at least one of the one or more pathogens. In some embodiments, one or more receiving units 136 may receive one or more signals 126 that include information associated with virulence of at least one of the one or more pathogens 106. For example, some pathogenic strains of *E. coli* exhibit increased virulence relative to other strains of *E. coli*. Such virulent strains may be identified by the presence of virulence determinants. Examples of such virulence determinants include, but are not limited to, adhesions (e.g., CFAI/CFAII, type 1 fimbriae, P fimbriae, S fimbriae, Intimin), invasions (e.g., hemolysisn, siderophores and siderophore uptake systems, *Shigella*-like "invasins" for intracellular invasion and spread), toxins (e.g., LT toxin, ST toxin, Shiga-like toxin, cytotoxins, endotoxin LPS), antiphagocytic surface properties (e.g., capsules, K antigens, lipopolysaccharides), somatic antigens, flagellar antigens, and the like. Accordingly, one or more signals may include information related to numerous types of virulence indicators.

At operation 3010, the receiving operation 2910 may include receiving the one or more signals through use of a secure connection. In some embodiments, one or more receiving units 136 may receive one or more signals 126 through use of a secure connection. For example, in some embodiments, one or more signals may be received that are encrypted. In some embodiments, one or more signals may be received through use of a secure mode. For example, in some embodiments, one or more signals may only be received by a specified individual. In some embodiments, one or more signals may be received by a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be received in a manner that conforms with privacy regulations as set forth by law. For example, in some embodiments, one or more signals may be received in accordance with the Health Information Privacy and Protection Act. In some embodiments, receipt of one or more signals will cause a return receipt to be sent that confirms receipt of the one or more signals.

Figure 31:
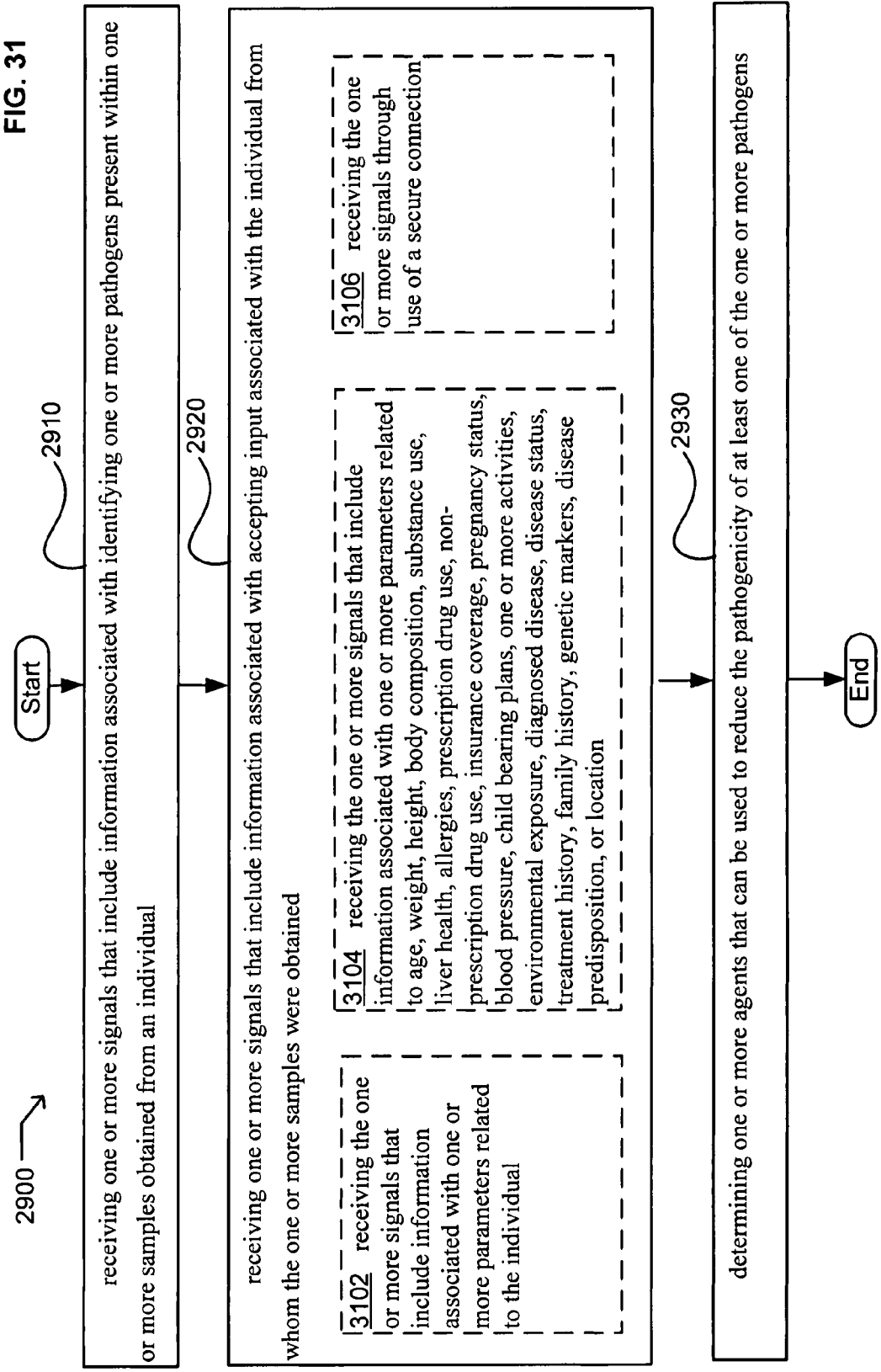

FIG. 31 illustrates alternative embodiments of the example operational flow 2900 of FIG. 29. FIG. 31 illustrates example embodiments where the receiving operation 2920 may include at least one additional operation. Additional operations may include an operation 3102, operation 3104, and/or operation 3106.

At operation 3102, the receiving operation 2920 may include receiving the one or more signals that include information associated with one or more parameters related to the individual. In some embodiments, one or more receiving units 136 may receive one or more signals 126 that include information associated with one or more parameters related to an individual 102. In some embodiments, the one or more parameters may be physical parameters. In some embodiments, the one or more parameters may be psychological parameters. In some embodiments, the one or more parameters may be financial parameters. In some embodiments, the one or more parameters may be health care provided related parameters (e.g., physician's name, insurance provider, HMO name, prescription plan, etc.).

At operation 3104, the receiving operation 2920 may include receiving the one or more signals that include information associated with one or more parameters related to age, weight, height, body composition, substance use, liver health, allergies, prescription drug use, non-prescription drug use, insurance coverage, pregnancy status, blood pressure, child bearing plans, one or more activities, environmental exposure, diagnosed disease, disease status, treatment history, family history, genetic markers, disease predisposition, or location. In some embodiments, one or more receiving units 136 may receive one or more signals 126 that include information associated with one or more parameters related to age, weight, height, body composition, substance use, liver health, allergies, prescription drug use, non-prescription drug use, insurance coverage, pregnancy status, blood pressure, child bearing plans, one or more activities, location, or substantially any combination thereof.

At operation 3106, the receiving operation 2920 may include receiving the one or more signals through use of a secure connection. In some embodiments, one or more receiving units 136 may receive one or more signals 126 through use of a secure connection. For example, in some embodiments, one or more signals may be received that are encrypted. In some embodiments, one or more signals may be received through use of a secure mode. For example, in some embodiments, one or more signals may only be received by a specified individual. In some embodiments, one or more signals may be received by a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be received in a manner that conforms with privacy regulations as set forth by law. For example, in some embodiments, one or more signals may be received in accordance with the Health Information Privacy and Protection Act. In some embodiments, receipt of one or more signals will cause a return receipt to be sent that confirms receipt of the one or more signals.

Figure 32:
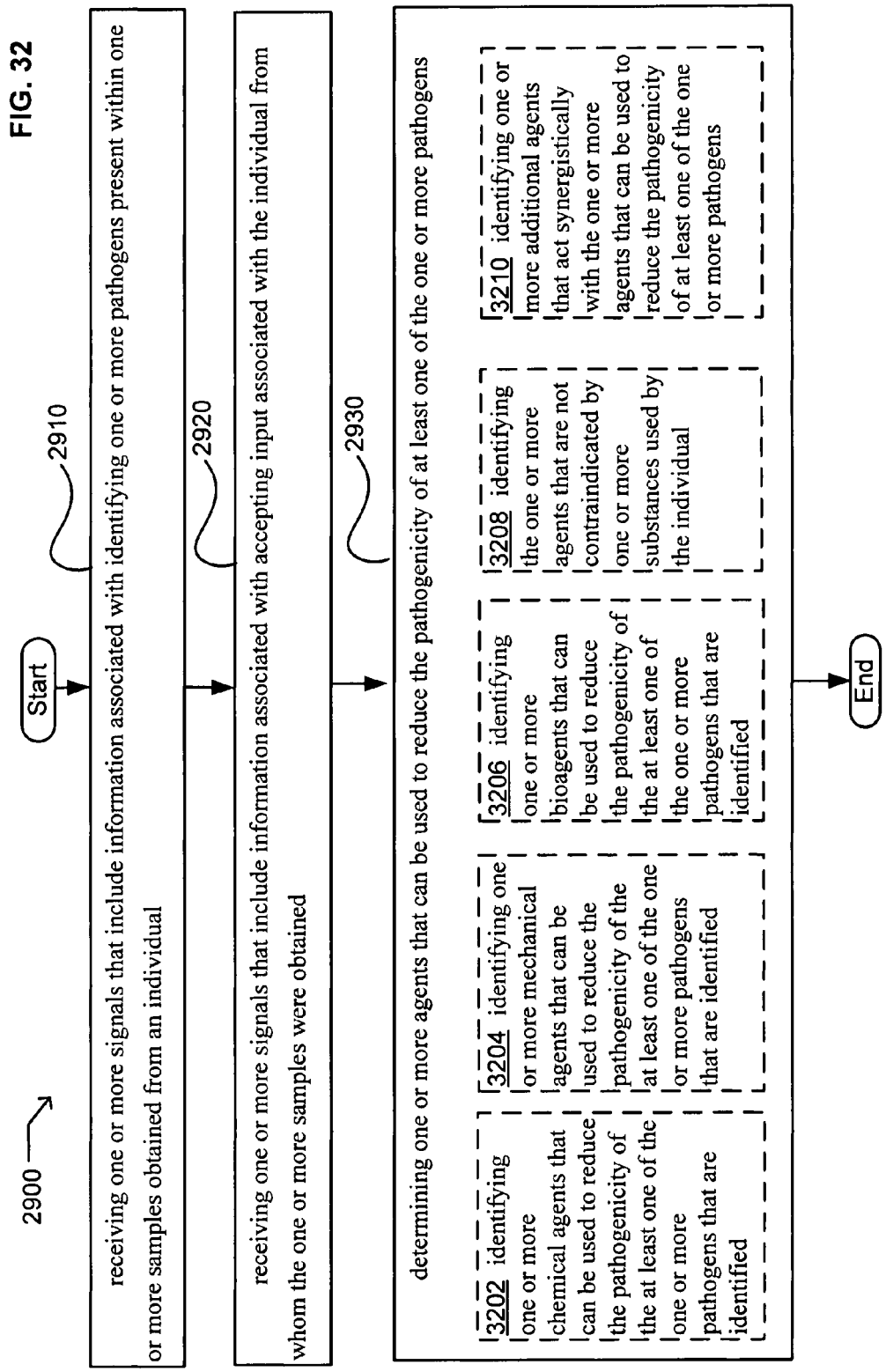

FIG. 32 illustrates alternative embodiments of the example operational flow 2900 of FIG. 29. FIG. 32 illustrates example embodiments where the receiving operation 2930 may include at least one additional operation. Additional operations may include an operation 3202, operation 3204, operation 3206, operation 3208, and/or operation 3210.

At operation 3202, the determining operation 2930 may include identifying the one or more chemical agents that can be used to reduce the pathogenicity of at least one of the one or more pathogens that are identified. In some embodiments, one or more processing units 112 may identify one or more chemical agents 142 that can be used to reduce the pathogenicity of at least one of one or more pathogens 106 that are identified. Numerous chemical agents 142 may be used to reduce the pathogenicity of one or more pathogens 106. Examples of such chemical agents 142 include, but are not limited to, antibiotics, ozone, peroxides, chlorinated compounds, acids, bases, alcohols, and the like (e.g., Merck Index, Thirteenth Edition, Merck & Co., Inc., Whitehouse Station, N.J. (2001) and Mosby's Drug Guide, An Imprint of Elsevier, St. Louis, Mo. (2004)). In some embodiments, such chemical agents 142 may be specific for one or more identified pathogens 106.

At operation 3204, the determining operation 2930 may include identifying the one or more mechanical agents that can be used to reduce the pathogenicity of at least one of the one or more pathogens that are identified. In some embodiments, one or more processing units 112 may identify one or more mechanical agents 142 that can be used to reduce the pathogenicity of at least one of one or more pathogens 106 that are identified. Examples of such mechanical agents 142 include, but are not limited to, ultraviolet light, irradiation, and the like. In some embodiments, such mechanical agents 142 may be specific for one or more identified pathogens 106.

At operation 3206, the determining operation 2930 may include identifying the one or more bioagents that can be used to reduce the pathogenicity of at least one of the one or more pathogens that are identified. In some embodiments, one or more processing units 112 may identify one or more bioagents that can be used to reduce the pathogenicity of at least one of the one or more pathogens that are identified. For example, in some embodiments, one or more processing units 112 may identify one or more bacteriophages that may be used to reduce the disease causing ability of a bacteria. In some embodiments, one or more processing units 112 may identify one or more invasive recombinant bacteria that may be used to deliver a gene product that may be used to reduce the disease causing ability of one or more pathogens. For example, in some embodiments, such recombinant bacteria may be engineered to produce an antibiotic. In some embodiments, one or more processing units 112 may identify one or more inactivated pathogens (e.g., viruses, bacteria, fungi) that may be used to induce an immune response against one or more pathogens.

At operation 3208, the determining operation 2930 may include identifying the one or more agents that are not contraindicated by one or more substances used by the individual. In some embodiments, one or more processing units 112 may identify one or more agents 142 that are not contraindicated by one or more substances used by an individual 102. For example, in some embodiments, an individual 102 may use one or more prescription medications. In such embodiments, one or more processing units 112 may identify one or more agents 142 that do not contraindicate the one or more prescription medications. In some embodiments, an individual 102 may use one or more substances such as tobacco or alcohol that may contraindicate an agent 142. Accordingly, one or more processing units 112 may identify one or more agents 142 that are not affected by one or more substances used by an individual 102 and/or that do not affect one or more substances used by an individual 102. Accordingly, one or more processing units 112 may identify one or more agents 142 with regard to numerous types of substances used by an individual 102.

At operation 3210, the determining operation 2930 may include identifying the one or more additional agents that act synergistically with the one or more agents that can be used to reduce the pathogenicity of at least one of the one or more pathogens. In some embodiments, one or more processing units 112 may identify one or more additional agents 142 that act synergistically with the one or more agents 142 that can be used to reduce the pathogenicity of at least one of the one or more pathogens. In some embodiments, one or more processing units 112 may identify one or more additional agents 142 that increase the effectiveness of one or more antibiotics. For example, in some embodiments, one or more processing units 112 may identify one or more antibacterial adjuvants (e.g., beta-lactamase inhibitors) that may act synergistically with one or more antibiotics. In some embodiments, one or more processing units 112 may identify one or more agents 142 that up regulate an immune response against a pathogen that may act synergistically with one or more other agents 142. In some embodiments, one or more processing units 112 may identify one or more agents 142 that down regulate an immune response against a pathogen that may act synergistically with one or more other agents 142.

Figure 33:
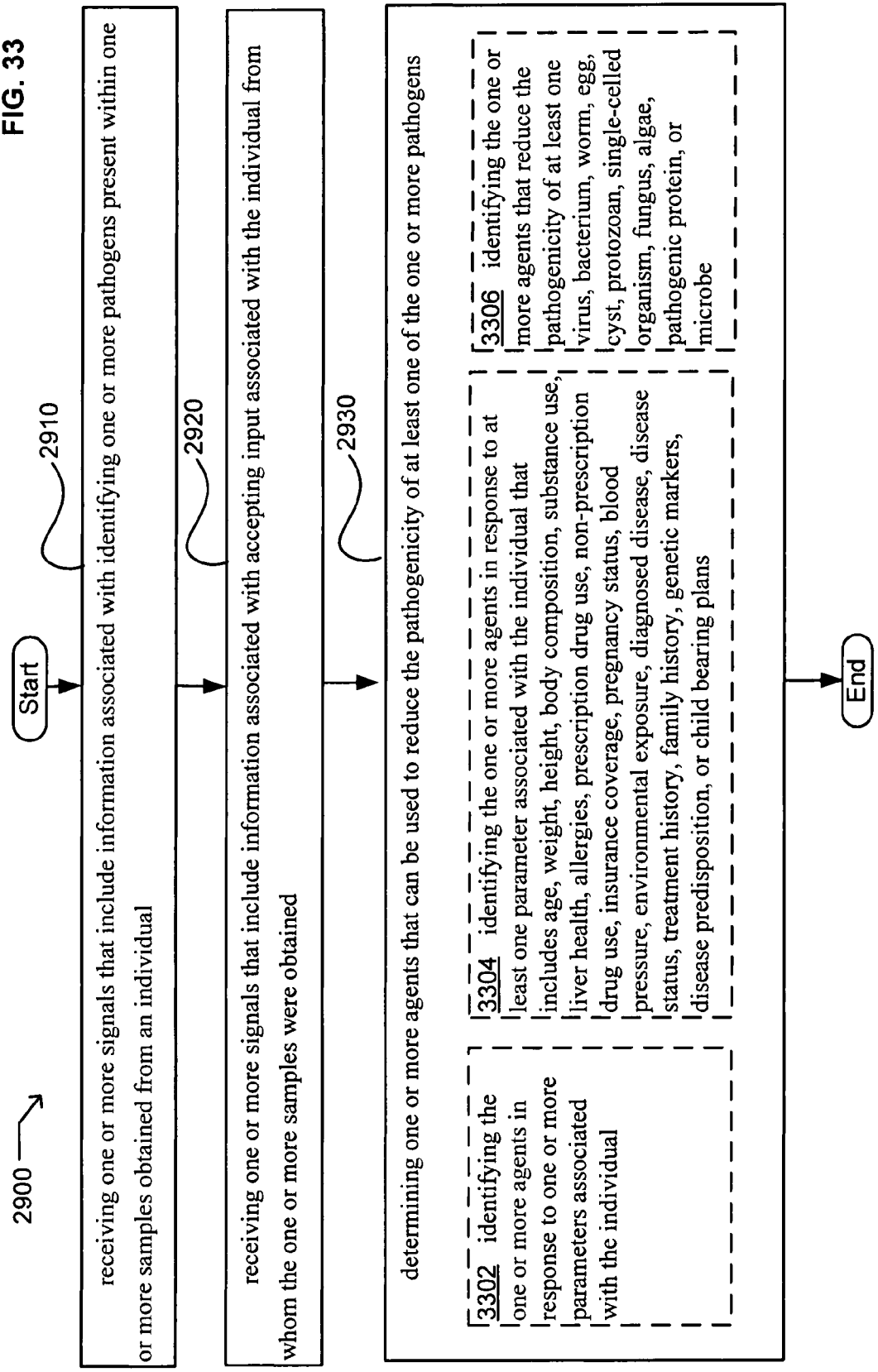

FIG. 33 illustrates alternative embodiments of the example operational flow 2900 of FIG. 29. FIG. 33 illustrates example embodiments where the receiving operation 2930 may include at least one additional operation. Additional operations may include an operation 3302, operation 3304, and/or operation 3306.

At operation 3302, the determining operation 2930 may include identifying the one or more agents in response to one or more parameters associated with the individual. In some embodiments, one or more processing units 112 may identify one or more agents 142 in response to one or more parameters associated with the individual 102. Accordingly, in some embodiments, one or more agents 142 may be identified for application to a specific individual 102. Such embodiments provide for personalized selection and dosing of agents 142 that may be used to treat pathogen infection. Numerous parameters associated with an individual 102 may be considered. Examples of such parameters include, but are not limited to, size, weight, allergies, body composition, substance use, and the like.

At operation 3304, the determining operation 2930 may include identifying the one or more agent in response to at least one parameter associated with the individual that includes age, weight, height, body composition, substance use, liver health, allergies, prescription drug use, non-prescription drug use, insurance coverage, pregnancy status, blood pressure, environmental exposure, diagnosed disease, disease status, treatment history, family history, genetic markers, disease predisposition, or child bearing plans. In some embodiments, one or more processing units 112 may identify one or more agents 142 in response to at least one parameter associated with the individual 102 that includes age, weight, height, body composition, substance use, liver health, allergies, prescription drug use, non-prescription drug use, insurance coverage, pregnancy status, blood pressure, child bearing plans, or substantially any combination thereof.

At operation 3306, the determining operation 2930 may include identifying the one or more agents that reduce the pathogenicity of at least one virus, bacterium, worm, egg, cyst, protozoan, single-celled organism, fungus, algae, pathogenic protein, or microbe. In some embodiments, one or more processing units 112 may identify one or more agents 142 that reduce the pathogenicity of at least one virus, bacterium, worm, egg, cyst, protozoan, single-celled organism, fungus, algae, pathogenic protein, or microbe. Numerous agents 142 are known that will reduce the pathogenicity of one or more pathogens 106 (The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, 58th Edition, Thompson, PDR, Montvale, N.J. 2004).

Figure 34:
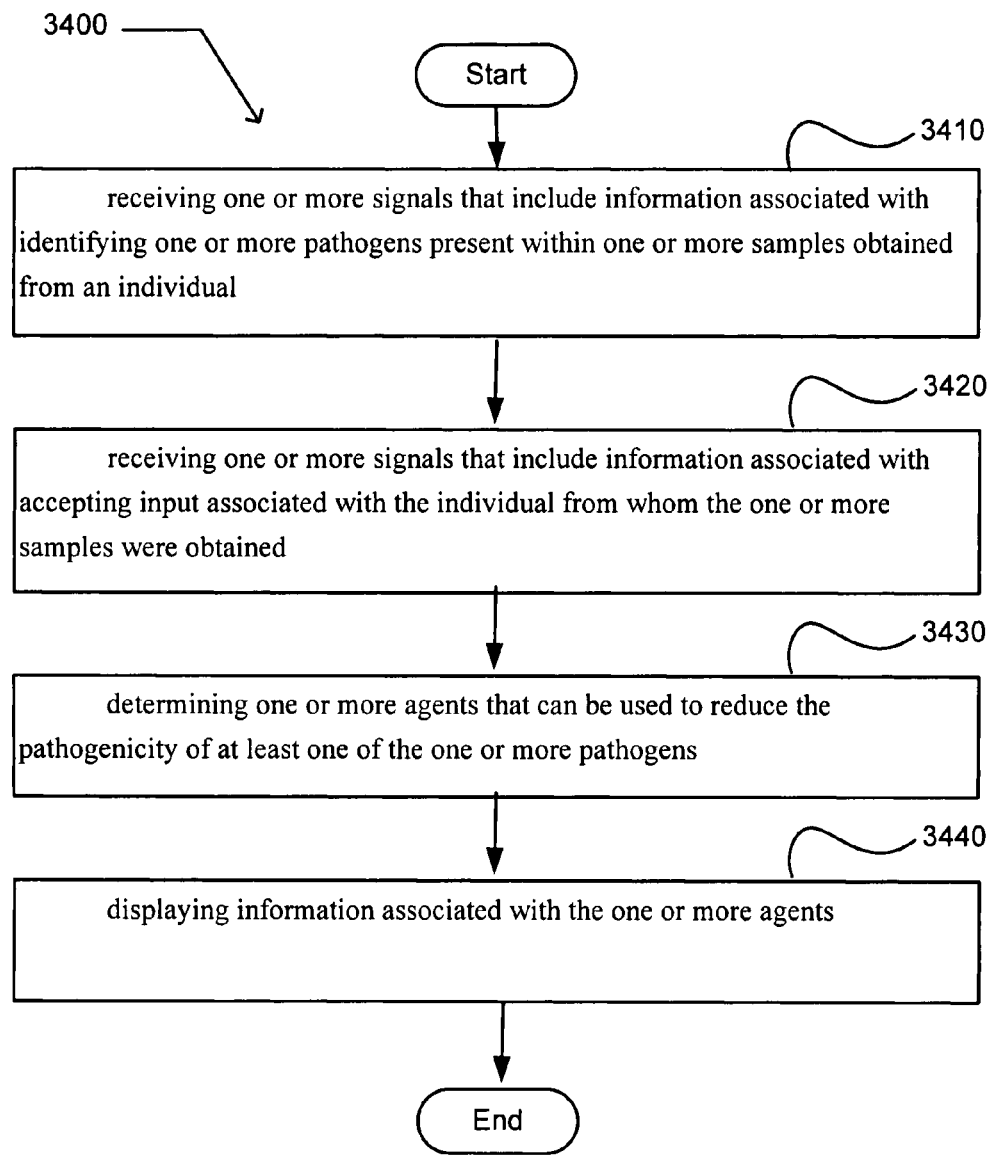

FIG. 34 illustrates operational flow 3400 that includes operations 3410, 3420, and 3430, that correspond to operations 2910, 2920, and 2930 as illustrated in FIG. 29, with an optionally included displaying operation 3440 and represents examples of operations that are related to the performance of a method for identifying one or more pathogens 106 and determining one or more agents 142 that may be used to reduce the pathogenicity of at least one of the one or more pathogens 106. In FIG. 34 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 3400 optionally includes a displaying operation 3440 involving displaying information associated with the one or more agents. In some embodiments, one or more display units 114 may be used to display information associated with one or more agents 142. Numerous types of display units 114 may be used to display information. Examples of such display units 114 include, but are not limited to, liquid crystal displays, light emitting diode displays, audio displays, Braille displays, graphical displays, and the like. Numerous types of information may be displayed. Examples of such types of information include, but are not limited to, the identity of one or more agents 142, the dosage of one or more agents 142, contraindications associated with the one or more agents 142, administration method to be used with one or more agents 142, administration schedule associated with one or more agents 142, and the like.

Figure 35:
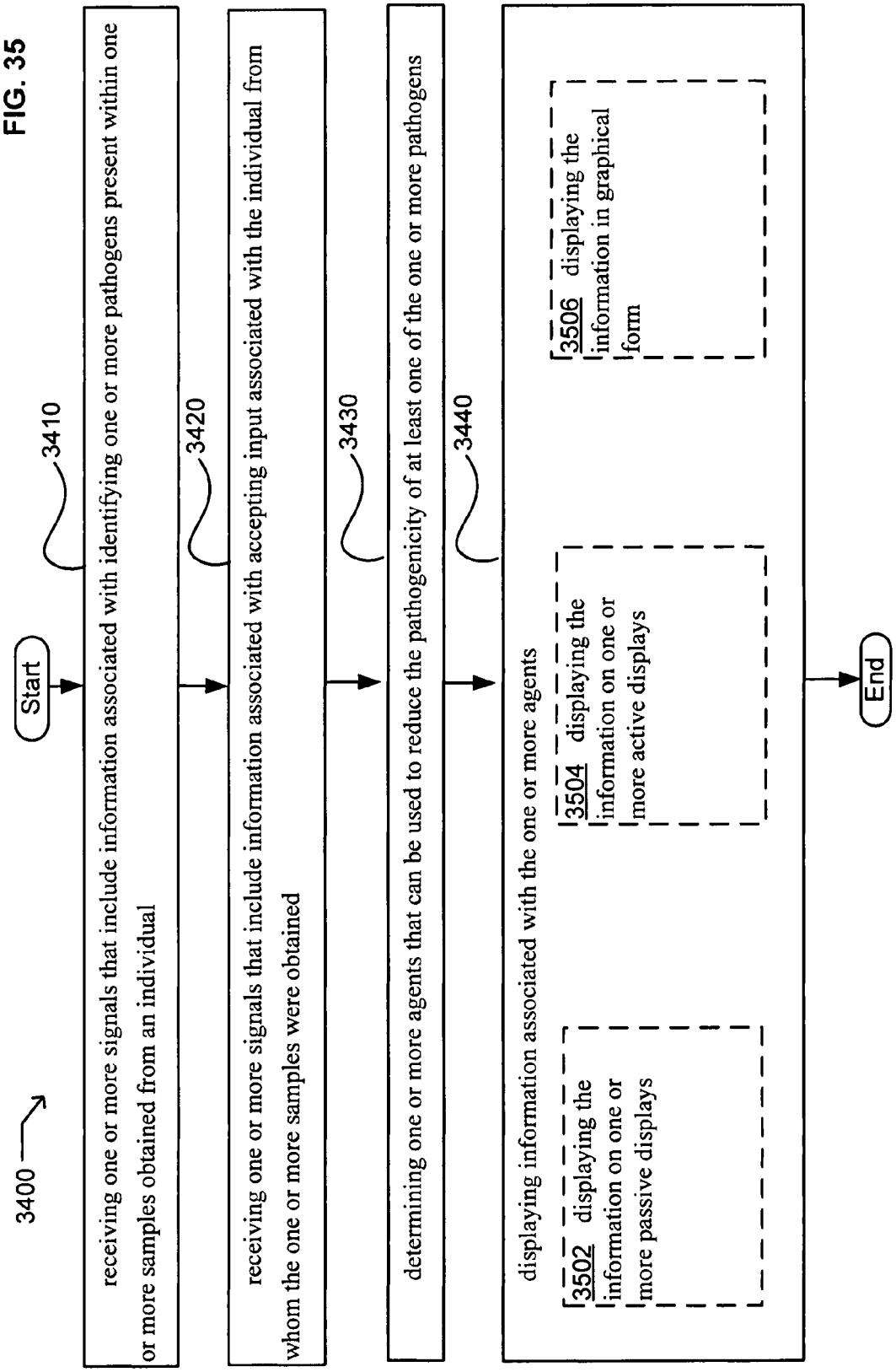

FIG. 35 illustrates alternative embodiments of the example operational flow 3400 of FIG. 34. FIG. 35 illustrates example embodiments where the displaying operation 3440 may include at least one additional operation. Additional operations may include an operation 3502, operation 3504, and/or operation 3506.

At operation 3502, the displaying operation 3440 may include displaying the information on one or more passive displays. In some embodiments, one or more display units 114 may display information on one or more passive displays. In some embodiments, one or more display units 114 may include one or more liquid crystal displays (LCD). Methods to construct passive displays have been described (e.g., U.S. Pat. Nos. 4,807,967; 4,729,636; 4,436,378; 4,257,041; herein incorporated by reference).

At operation 3504, the displaying operation 3440 may include displaying the information on one or more active displays. In some embodiments, one or more display units 114 may display information on one or more active displays. Numerous active display units 114 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), and wide ultra extended graphics array (WUXGA).

At operation 3506, the displaying operation 3440 may include displaying the information in graphical form. In some embodiments, one or more display units 114 may display information in graphical form. Numerous types of graphical formats may be used. Examples of such graphical formats include, but are not limited to, use of shapes, use of colors, use of symbols (e.g., smiley face, frowny face, thumbs up sign, thumbs down sign, histograms, bar graphs, pie charts, and the like).

Figure 36:
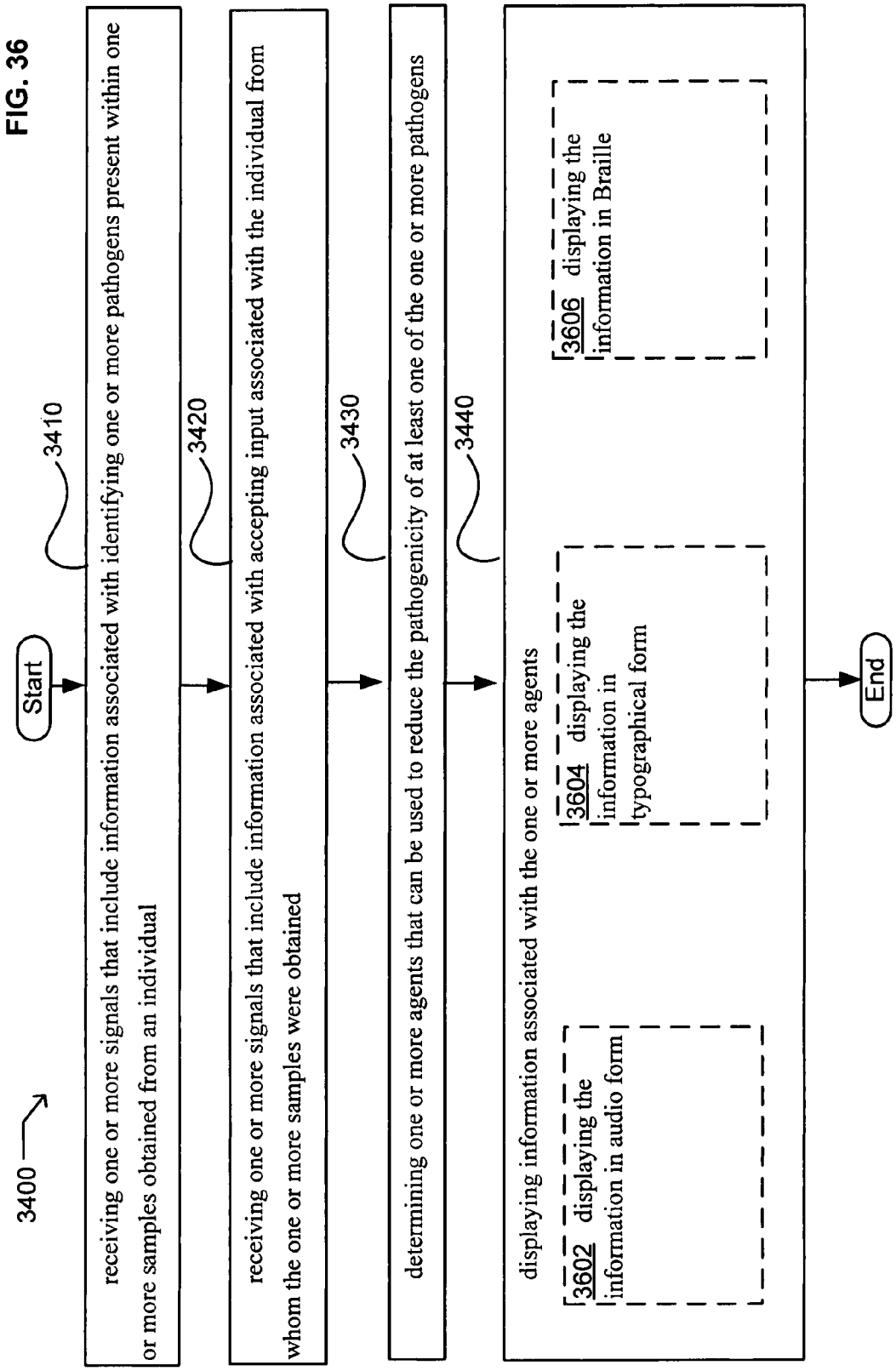
FIG. 36 illustrates alternate embodiments of the example operational flow of FIG. 34.

FIG. 36 illustrates alternative embodiments of the example operational flow 3400 of FIG. 34. FIG. 36 illustrates example embodiments where the displaying operation 3440 may include at least one additional operation. Additional operations may include an operation 3602, operation 3604, and/or operation 3606.

At operation 3602, the displaying operation 3440 may include displaying the information in audio form. In some embodiments, one or more display units 114 may display information in audio form. In some embodiments, one or more display units 114 may display information in voice format. For example, in some embodiments, a human voice may indicate the identity of one or more agents 142 that may be used to reduce the pathogenicity of one or more pathogens 106. Numerous types of information may be presented in audio format.

At operation 3604, the displaying operation 3440 may include displaying the information in typographical form. In some embodiments, one or more display units 114 may display information in typographical form. Information may be presented in numerous languages (e.g., Italian, Spanish, English, Japanese). In some embodiments, the typographical form may include numbers.

At operation 3606, the displaying operation 3440 may include displaying the information in Braille. In some embodiments, one or more display units 114 may display information in Braille. Accordingly, in some embodiments, one or more display units 114 may include a pad on which messages in Braille may be displayed. In some embodiments, such pads may be constructed of an elastomeric material that is positioned relative to a series of movable rods such that the rods may be positioned to create messages in Braille. In some embodiments, one or more display units 114 may print information in Braille.

Figure 37:
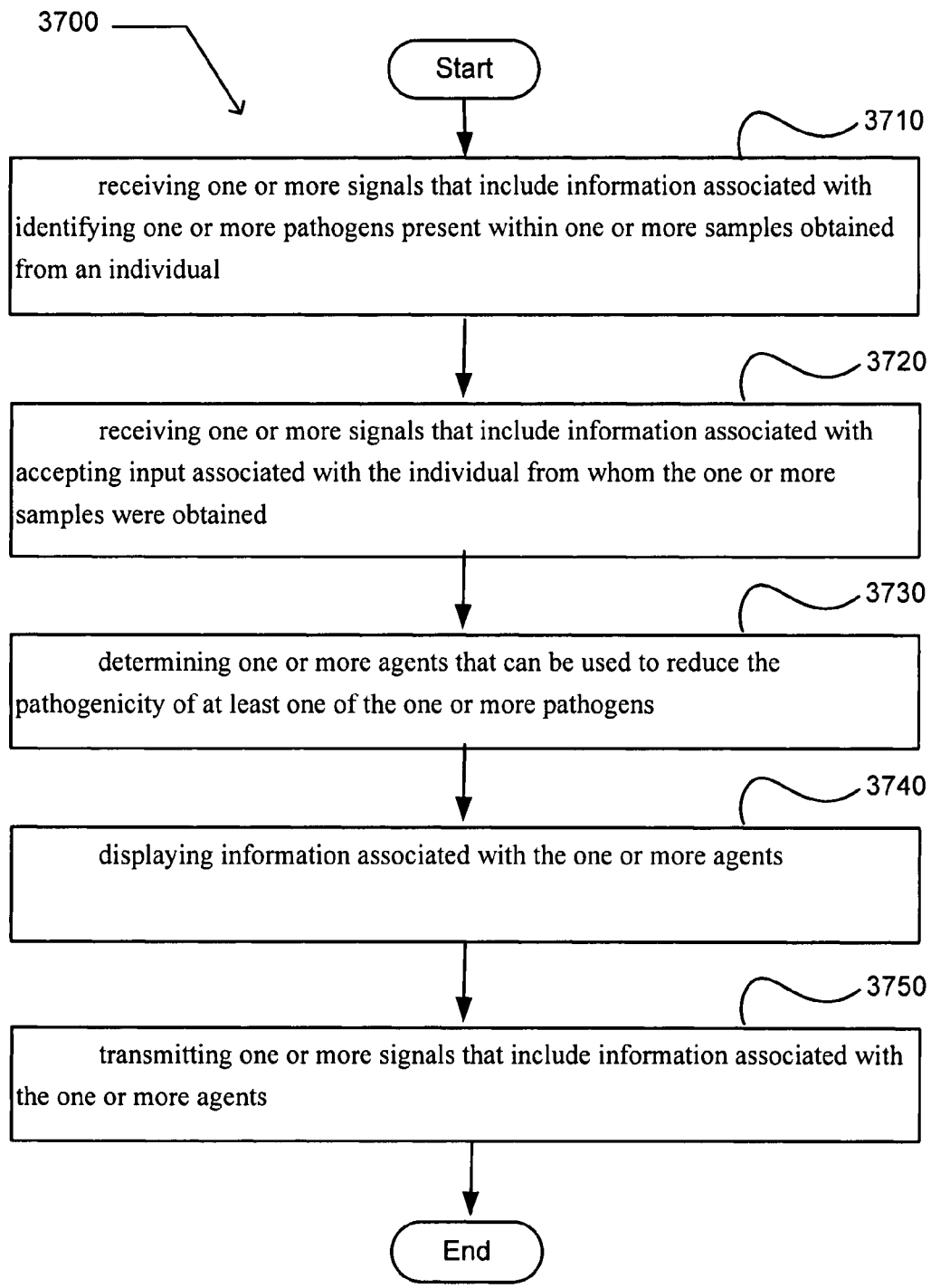
FIG. 37 illustrates an operational flow representing example operations related to methods and systems responsive to the detection of pathogens.

FIG. 37 illustrates operational flow 3700 that includes operations 3710, 3720, 3730, and 3740, that correspond to operations 3410, 3420, 3430, and 3440 as illustrated in FIG. 34, with an optionally included transmitting operation 3750 and represents examples of operations that are related to the performance of a method for identifying one or more pathogens 106 and determining one or more agents 142 that may be used to reduce the pathogenicity of at least one of the one or more pathogens 106. In FIG. 37 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 3700 optionally includes a transmitting operation 3750 involving transmitting the one or more signals that include information associated with the one or more agents. In some embodiments, one or more transmitting units 116 may transmit one or more signals 126 that include information associated with one or more agents 142. The one or more transmitting units 116 may transmit signals 126 through use of numerous technologies. For example, such signals 126 may be transmitted through use of the internet, radio waves, optical cables, cellular telephone connections, telephone connections, satellite telephone connections, and the like. The one or more signals 126 may be transmitted to, and received by, numerous types of receivers. For example, one or more signals 126 may be received by pharmacies, hospitals, pharmaceutical companies, health care providers, nutraceutical companies, and the like.

FIG. 38 illustrates alternative embodiments of the example operational flow 3700 of FIG. 37. FIG. 38 illustrates example embodiments where the transmitting operation 3750 may include at least one additional operation. Additional operations may include an operation 3802, operation 3804, operation 3806, operation 3808, operation 3810, and/or operation 3812.

At operation 3802, the transmitting operation 3750 may include transmitting the one or more signals that include information associated with the identity of one or more agents. In some embodiments, one or more transmitting units 116 may transmit one or more signals 126 that include information associated with the identity of one or more agents 142. For example, in some embodiments, one or more transmitting units 116 may transmit one or more signals 126 that include information associated with the brand name, the generic name, the chemical name, the structure, identifiers associated with an agent 142, or substantially any combination thereof.

At operation 3804, the transmitting operation 3750 may include transmitting the one or more signals that include information associated with an individual. In some embodiments, one or more transmitting units 116 may transmit one or more signals 126 that include information associated with an individual 102. One or more signals 126 that include numerous types of information associated with an individual 102 may be transmitted. Examples of such information include, but are not limited to, height, weight, age, substances used by an individual 102 (e.g., alcohol, tobacco, prescription medication, non-prescription medication, illicit drugs, etc.), body composition, allergies, physical characteristics (e.g., blood pressure, heart rate, intraocular pressure, etc.), activities, and the like.

At operation 3806, the transmitting operation 3750 may include transmitting the one or more signals through use of a secure connection. In some embodiments, one or more transmitting units 116 may transmit one or more signals 126 through use of a secure connection. For example, in some embodiments, one or more signals may be encrypted. In some embodiments, one or more signals may be sent through use of a secure mode of transmission. For example, in some embodiments, one or more signals may be transmitted to a specified individual. In some embodiments, one or more signals may be transmitted to a specified group. In some embodiments, one or more signals may include code that is specific for an individual. In some embodiments, such code may include anonymous code that is specific for an individual. Accordingly, information included within one or more signals may be protected against being accessed by others who are not the intended recipient. In some embodiments, one or more signals may include information that includes statements regarding non-disclosure of information included within the one or more signals (e.g., statements against copying information, statements against unauthorized dissemination of information, statements about unauthorized opening of an information packet by an unintended recipient, and the like). In some embodiments, one or more signals may be sent in a manner that conforms with privacy regulations as set forth by law. For example, in some embodiments, one or more signals may be transmitted in accordance with the Health Information Privacy and Protection Act. In some embodiments, one or more signals may be sent with information that includes a request for a return receipt.

At operation 3808, the transmitting operation 3750 may include transmitting the one or more signals that include information associated with the one or more pathogens. In some embodiments, one or more transmitting units 116 may transmit one or more signals 126 that include information associated with the one or more pathogens 106. The one or more signals 126 may include numerous types of information associated with one or more pathogens 106. Examples of such information include the identity of a pathogen 106, the concentration of a pathogen 106, drug resistance characteristics of a pathogen 106, and the like.

At operation 3810, the transmitting operation 3750 may include transmitting the one or more signals that include information associated with one or more locations of the one or more pathogens. In some embodiments, one or more transmitting units 116 may transmit one or more signals 126 that include information associated with one or more locations of the one or more pathogens 106. For example, in some embodiments, one or more transmitting units 116 may transmit one or more signals 126 that include information associated with where an individual 102 is physically experiencing a pathogen infection (e.g., eye infection, nasal infection, gastrointestinal tract infection, etc). In some embodiments, one or more transmitting units 116 may transmit one or more signals 126 that include information associated with the geographical location of the pathogen 106. For example, one or more signals 126 may include information that indicates where the pathogen 106 and/or individual 102 who is infected with the pathogen 106 is located (e.g., United States, Canada, Europe, Asia, Middle East, etc.). In some embodiments, the one or more signals 126 may include global positioning system (GPS) coordinates.

At operation 3812, the transmitting operation 3750 may include transmitting the one or more signals that include information associated with one or more locations of the individual. In some embodiments, one or more transmitting units 116 may transmit one or more signals 126 that include information associated with one or more locations of the individual 102. In some embodiments, one or more transmitting units 116 may transmit one or more signals 126 that include information associated with the geographical location of an individual 102. For example, one or more signals 126 may include information that indicates where an individual 102 is located (e.g., United States, Canada, Europe, Asia, Middle East, etc.). In some embodiments, the one or more signals 126 may include global positioning system (GPS) coordinates.

FIG. 39 illustrates operational flow 3900 that includes operations 3910, 3920, 3930, 3940, and 3950 that correspond to operations 3710, 3720, 3730, 3740, and 3750 as illustrated in FIG. 37 with an optionally included packaging operation 3960 and represents examples of operations that are related to the performance of a method for identifying one or more pathogens 106 and determining one or more agents 142 that may be used to reduce the pathogenicity of at least one of the one or more pathogens 106. In FIG. 39 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 3900 optionally includes a packaging operation 3960 involving packaging the one or more agents. In some embodiments, one or more packaging units 138 may package one or more agents 142. In some embodiments, one or more packaging units 138 may be used to package one or more agents 142 in packaging material. In some embodiments, one or more packaging units 138 may package one or more agents 142 for administration to an individual 102. For example, in some embodiments, one or more packaging units 138 may package individual dosages of one or more agents 142 for a specific individual 102. Accordingly, in such embodiments, a packaging unit 138 may be used for individualized agent 142 packaging.

FIG. 40 illustrates alternative embodiments of the example operational flow 3900 of FIG. 39. FIG. 40 illustrates example embodiments where the packaging operation 3960 may include at least one additional operation. Additional operations may include an operation 4002, operation 4004, and/or operation 4006.

At operation 4002, the packaging operation 3960 may include formulating the one or more agents into unit dosage form. In some embodiments, one or more packaging units 138 may formulate one or more agents 142 into unit dosage form. In some embodiments, a unit dosage form may include one or more amounts of one or more agents 142, such as pharmaceutical agents 142, that are suitable as unitary dosages for an individual 102 with each unit containing a predetermined quantity of at least one agent 142 calculated to produce a desired effect, such as a therapeutic effect, in association with one or more suitable pharmaceutical carriers. Such unit dosage forms may be packaged in numerous configurations that include, but are not limited to, tablets, capsules, ampoules, and other administration forms known in the art and described herein. In some embodiments, two or more unit dosage forms of one or more agents 142 may be packaged into an administration form. For example, in some embodiments, two unit dosage forms may be wrapped into an administration form through use of a continuous wrapper such that they are released at different times following administration to an individual 102. In such an example, two unit dosage forms are included within one administration form.

At operation 4004, the packaging operation 3960 may include packaging two or more of the agents into a single administration form. In some embodiments, one or more packaging units 138 may package two or more agents 142 into a single administration form. For example, in some embodiments, two agents 142 may be wrapped into a single administration form through use of a continuous wrapper such that they are released at different times following administration to an individual 102. In some examples, two unit dosage forms may be included within one administration form.

At operation 4006, the packaging operation 3960 may include formulating the one or more agents into an administration form in response to input associated with the individual from whom the one or more samples were obtained. In some embodiments, one or more packaging units 138 may formulate one or more agents 142 into an administration form in response to input 120 associated with an individual 102 from whom one or more samples 104 were obtained. For example, in some embodiments, an individual 102 may work at night where an agent 142 may interfere with the individual's function. Accordingly, one or more agents 142 may be formulated to be released during the day when the individual 102 is not working. In some embodiments, one or more agents 142 may be formulated for oral administration according to a preference of an individual 102. Accordingly, one or more agents 142 may be formulated in numerous ways in response to input 120 associated with an individual 102.

Figure 41:
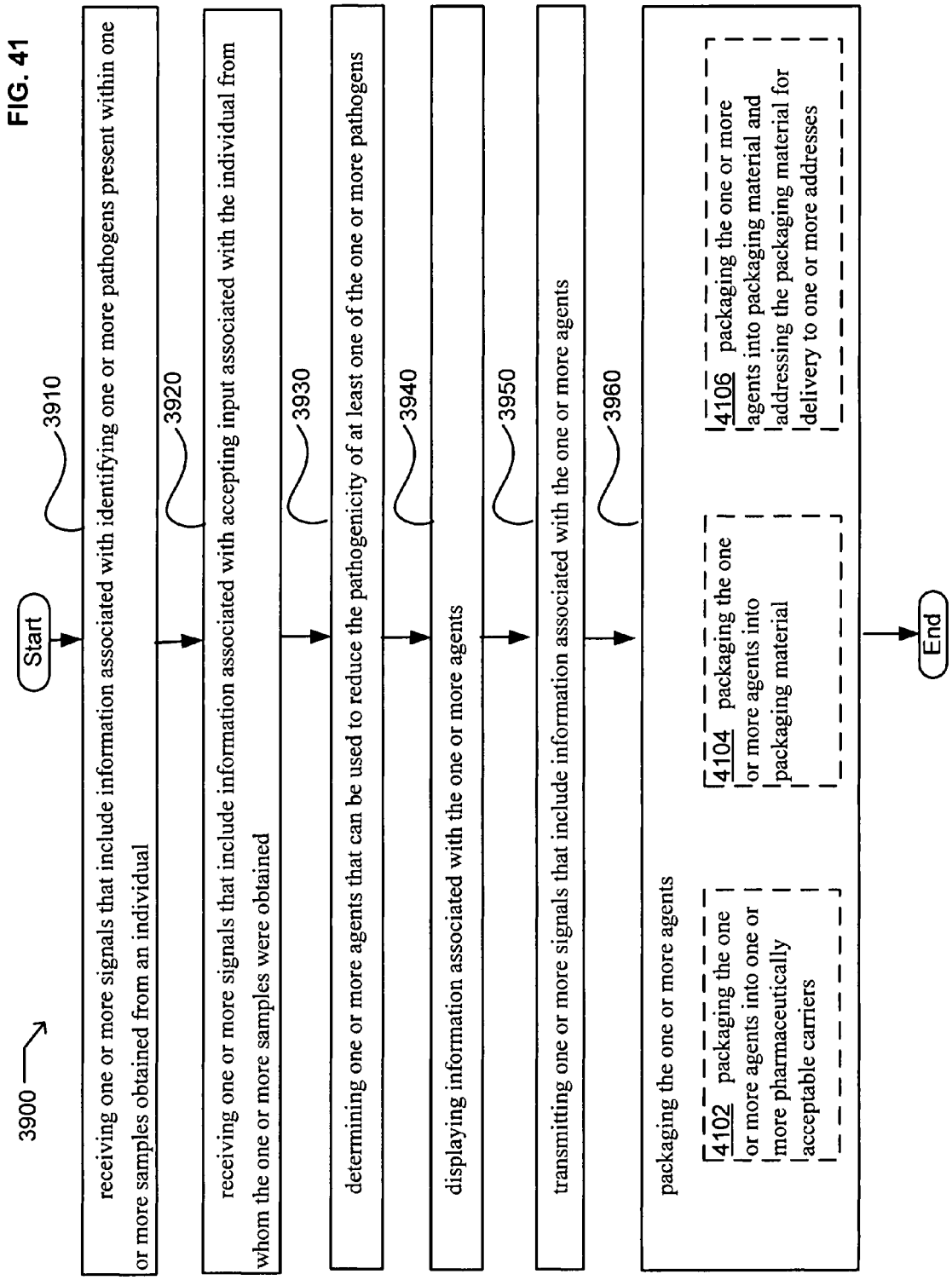
FIG. 41 illustrates alternate embodiments of the example operational flow of FIG. 39.

FIG. 41 illustrates alternative embodiments of the example operational flow 3900 of FIG. 39. FIG. 41 illustrates example embodiments where the packaging operation 3960 may include at least one additional operation. Additional operations may include an operation 4102, operation 4104, and/or operation 4106.

At operation 4102, the packaging operation 3960 may include packaging the one or more agents into one or more pharmaceutically acceptable carriers. In some embodiments, one or more packaging units 138 may package one or more agents 142 with one or more pharmaceutically acceptable carriers. In some embodiments, one or more agents 142 (e.g., pharmaceuticals) may be packaged with one or more solid or gel phase carriers or excipients. Examples of such carriers or excipients include, but are not limited to, croscarmellose sodium, povidone, microcrystalline cellulose, calcium carbonate, calcium phosphate, various sugars, starches, cellulose derivatives, gelatin, pregelatinized starch, polymers such as polyethylene glycols, lactose, lactose monohydrate, sucrose, talc, gelatin, agar, pectin, acacia, magnesium stearate, stearic acid and substantially any combination thereof. If a solid carrier is used, the one or more agents 142 may be tableted, placed in a hard gelatin capsule in powder or pellet form, packaged in the form of a troche or lozenge, and the like.

In some embodiments, one or more agents 142 may be packaged with a liquid carrier or excipient. Examples of such liquid carriers include syrup, peanut oil, olive oil, water, physiologically compatible buffers (i.e., Hanks solution and Ringers solution), physiological saline buffer, and the like. If a liquid carrier is used, the administration form may be in the form of a syrup, emulsion, drop, soft gelatin capsule, sterile injectable solution, suspension in an ampoule or vial, non-aqueous liquid suspension, and the like.

One or more agents 142 may be packaged in stable water-soluble administration forms. For example, in some embodiments, a pharmaceutically acceptable salt of one or more agents 142 may be dissolved in an aqueous solution of an organic or inorganic acid, such as 0.3M solution of succinic acid or citric acid. If a soluble salt form is not available, an agent 142 may be dissolved in a suitable cosolvent or combination of cosolvents. Examples of suitable cosolvents include, but are not limited to, alcohol, propylene glycol, polyethylene glycol 300, polysorbate 80, glycerin and the like in concentrations ranging from 0-60% of the total volume. In some embodiments, one or more agents 142 may be dissolved in DMSO and diluted with water. The administration form may also be in the form of a solution of a salt form of one or more agents 142 in an appropriate aqueous vehicle such as water or isotonic saline or dextrose solution.

In some embodiments, agents 142 that are hydrophobic may be packaged through use of a cosolvent system comprising benzyl alcohol, a nonpolar surfactant, a water-miscible organic polymer, and an aqueous phase. The cosolvent system may be the VPD co-solvent system. VPD is a solution of 3 percent weight/volume benzyl alcohol, 8 percent weight/volume of the nonpolar surfactant polysorbate 80, and 65 percent weight/volume polyethylene glycol 300, made up to volume in absolute ethanol. The VPD co-solvent system (VPD:5W) consists of VPD diluted 1:1 with a 5 percent dextrose in water solution. This co-solvent system dissolves hydrophobic agents 142, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol (i.e., polyvinyl pyrrolidone; and other sugars or polysaccharides may substitute for dextrose). Many other delivery systems may be used to administer hydrophobic agents 142 as well. For example, liposomes and emulsions are well known examples of delivery vehicles or carriers for hydrophobic drugs. Certain organic solvents such as dimethylsulfoxide also may be employed, although usually at the cost of greater toxicity.

Some agents 142 may be packaged as salts with pharmaceutically compatible counter ions. Pharmaceutically compatible salts may be formed with many acids, including hydrochloric, sulfuric, acetic, lactic, tartaric, malic, succinic, etc. Salts of agents 142 tend to be more soluble in aqueous or other protonic solvents than are the corresponding free-base forms.

Numerous carriers and excipients are known and are commercially available (i.e., The Merck Index, 13th Edition, An Encyclopedia of Chemicals, Drugs, and Biologicals, Merck & Co. Inc., Whitehouse Station, N.J. 2001; Mosby's Drug Guide, Mosby, Inc., St. Louis, Mo. 2004; Remington: The Science and Practice of Pharmacy, 20th Edition, Lippincott Williams & Wilkins, Philadelphia, Pa. 2000; Physicians' Desk Reference, 58th Edition, Thompson, PDR, Montvale, N.J. 2004; U.S. Pat. Nos. 6,773,721; 7,053,107; 7,049,312 and Published U.S. Patent Application No. 20040224916; herein incorporated by reference).

In addition, in some embodiments, one or more agents 142 may be packaged with pharmaceutically acceptable poloxamers, humectants, binders, disintegrants, fillers, diluents, lubricants, glidants, flow enhancers, compression aids, coloring agents, sweeteners, preservatives, suspending agents, dispersing agents, film formers, coatings, flavoring agents, printing inks, or substantially any combination thereof.

At operation 4104, the packaging operation 3960 may include packaging the one or more agents into packaging material. In some embodiments, one or more packaging units 138 may package one or more agents 142 with packaging material. One or more agents 142 (e.g., pharmaceuticals) may be packaged in numerous types of packaging material. Examples of packaging material include, but are not limited to, containers, boxes, ampoules, vials, syringes, and the like. In some embodiments, packaging material may include advertising. In some embodiments, packaging material may include instructions for administration. Such instructions may include time for administration, route of administration, the name of the individual 102 to whom the one or more agents 142 are to be administered, the identity of the one or more agents 142, the dosage of the one or more agents 142, appropriate buffers for suspension of the one or more agents 142, the source of the one or more agents 142, the name of a physician or physicians who prescribed the one or more agents 142, the date when the one or more agents 142 were prescribed, the date when the one or more agents 142 were packaged, the date when the one or more agents 142 were manufactured, the expiration date of the one or more agents 142, and the like.

At operation 4106, the packaging operation 3960 may include packaging the one or more agents into packaging material and addressing the packaging material for delivery to one or more addresses. In some embodiments, one or more packaging units 138 may package one or more agents 142 with packaging material and address the packaging material for delivery to one or more addresses. For example, in some embodiments, one or more packaging units 138 may package one or more agents 142 in one or more dispensing containers (e.g., a box, ampoule, vial, syringe, etc.), and then package the one or more dispensing containers in packaging material (e.g., boxes, crates, envelopes, pouches, etc.) that is addressed for delivery to one or more addresses. In some embodiments, one or more packaging units 138 may package one or more prepackaged agents 142 in one or more shipping containers (e.g., boxes, crates, envelopes, pouches, etc.) and addressing the one or more shipping containers for delivery to one or more addresses. Numerous addresses could be used. Examples of such addresses include, but are not limited to, addresses to hospitals, military field stations, pharmacies, individuals, health care facilities, and the like.

FIG. 42 illustrates operational flow 4200 that includes operations 4210, 4220, 4230, 4240, 4250, and 4260 that correspond to operations 3910, 3920, 3930, 3940, 3950, and 3960 as illustrated in FIG. 39 with an optionally included shipping operation 4270 and represents examples of operations that are related to the performance of a method for identifying one or more pathogens 106 and determining one or more agents 142 that may be used to reduce the pathogenicity of at least one of the one or more pathogens 106. In FIG. 42 and in following figures that include various examples of operations used during performance of the method, discussion and explanation may be provided with respect to any one or combination of the above-described examples of FIGS. 1-1C, and/or with respect to other examples and contexts. However, it should be understood that the operations may be executed in a number of other environments and contexts, and/or modified versions of FIGS. 1-1C. Also, although the various operations are presented in the sequence(s) illustrated, it should be understood that the various operations may be performed in other orders than those which are illustrated, or may be performed concurrently.

After a start operation, the operational flow 4200 optionally includes a shipping operation 4270 involving shipping one or more packages that include the one or more agents. In some embodiments, one or more shipping units 140 may ship one or more agents 142. In some embodiments, a shipping unit 140 may include logic that selects one or more routes that may be used to deliver one or more packages that include one or more agents 142. For example, in some embodiments, a shipping unit 140 may select a shipping route through the Southern United States in the winter time to avoid shipping delays due to snowfall. Accordingly, one or more shipping units 140 may select from numerous routes to ship one or more packages. In some embodiments, a shipping unit 140 may select a service to ship a package. Examples of such shipping services include, but are not limited to, United States Postal Service, United Postal Service, Federal Express, and the like.

FIG. 43 illustrates alternative embodiments of the example operational flow 4200 of FIG. 42. FIG. 43 illustrates example embodiments where the shipping operation 4270 may include at least one additional operation. Additional operations may include an operation 4302, and/or operation 4304.

At operation 4302, the shipping operation 4270 may include shipping the one or more packages through use of one or more common carriers. In some embodiments, one or more shipping units 140 may be used to ship one or more packages through use of one or more common carriers. In some embodiments, one or more shipping units 140 may include logic that selects one or more common carriers for shipping one or more packages. Examples of common carriers include, but are not limited to, airline shipping services, ground shipping services, nautical shipping services, and the like.

At operation 4304, the shipping operation 4270 may include shipping the one or more packages to the individual from whom the one or more samples were obtained. In some embodiments, one or more shipping units 140 may be used to ship one or more packages to an individual 102 from whom one or more samples 104 were obtained.

FIG. 44 illustrates alternative embodiments of the example operational flow 4200 of FIG. 42. FIG. 44 illustrates example embodiments where the shipping operation 4270 may include at least one additional operation. Additional operations may include an operation 4402, and/or operation 4404.

At operation 4402, the shipping operation 4270 may include shipping the one or more packages to one or more treatment facilities. In some embodiments, one or more shipping units 140 may be used to ship one or more packages to one or more treatment facilities. Examples of treatment facilities include, but are not limited to, hospitals, clinics, military field hospitals, ship infirmaries, and the like.

At operation 4404, the shipping operation 4270 may include shipping the one or more packages to one or more pharmacies. In some embodiments, one or more shipping units 140 may be used to ship one or more packages to one or more pharmacies.

Figure 45:
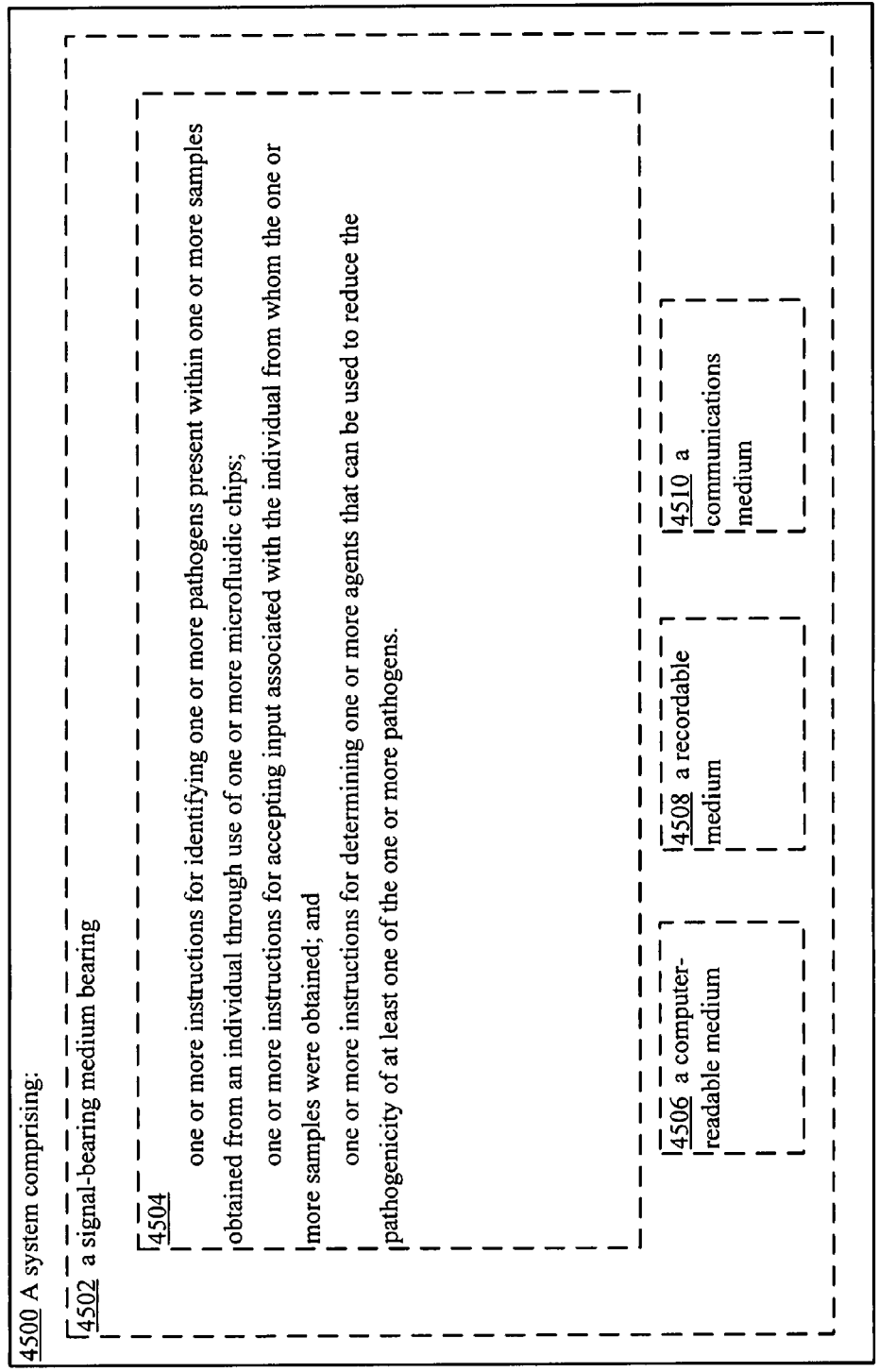
FIG. 45 illustrates an example system 4500 in which embodiments may be implemented.

FIG. 45 illustrates a partial view of a system 4500 that includes a computer program 4504 for executing a computer process on a computing device. An embodiment of the system 4500 is provided using a signal-bearing medium 4502 bearing one or more instructions for identifying one or more pathogens 106 present within one or more samples 104 obtained from an individual 102 through use of one or more microfluidic chips; one or more instructions for accepting input 120 associated with the individual 102 from whom the one or more samples 104 were obtained; and one or more instructions for determining one or more agents 142 that can be used to reduce the pathogenicity of at least one of the one or more pathogens 106. The one or more instructions may be, for example, computer executable and/or logic-implemented instructions. In some embodiments, the signal-bearing medium 4502 may include a computer-readable medium 4506. In some embodiments, the signal-bearing medium 4502 may include a recordable medium 4508. In some embodiments, the signal-bearing medium 4502 may include a communications medium 4510.

FIG. 45A illustrates a partial view of a system 4500 that includes a computer program 4504 for executing a computer process on a computing device. An embodiment of the system 4500 is provided using a signal-bearing medium 4502 bearing one or more instructions for identifying one or more pathogens 106 present within one or more samples 104 obtained from an individual 102 through use of one or more microfluidic chips; one or more instructions for accepting input 120 associated with the individual 102 from whom the one or more samples 104 were obtained; one or more instructions for determining one or more agents 142 that can be used to reduce the pathogenicity of at least one of the one or more pathogens; and one or more instructions for displaying information associated with the one or more agents 142. The one or more instructions may be, for example, computer executable and/or logic-implemented instructions. In some embodiments, the signal-bearing medium 4502 may include a computer-readable medium 4506. In some embodiments, the signal-bearing medium 4502 may include a recordable medium 4508. In some embodiments, the signal-bearing medium 4502 may include a communications medium 4510.

Figure 45B:
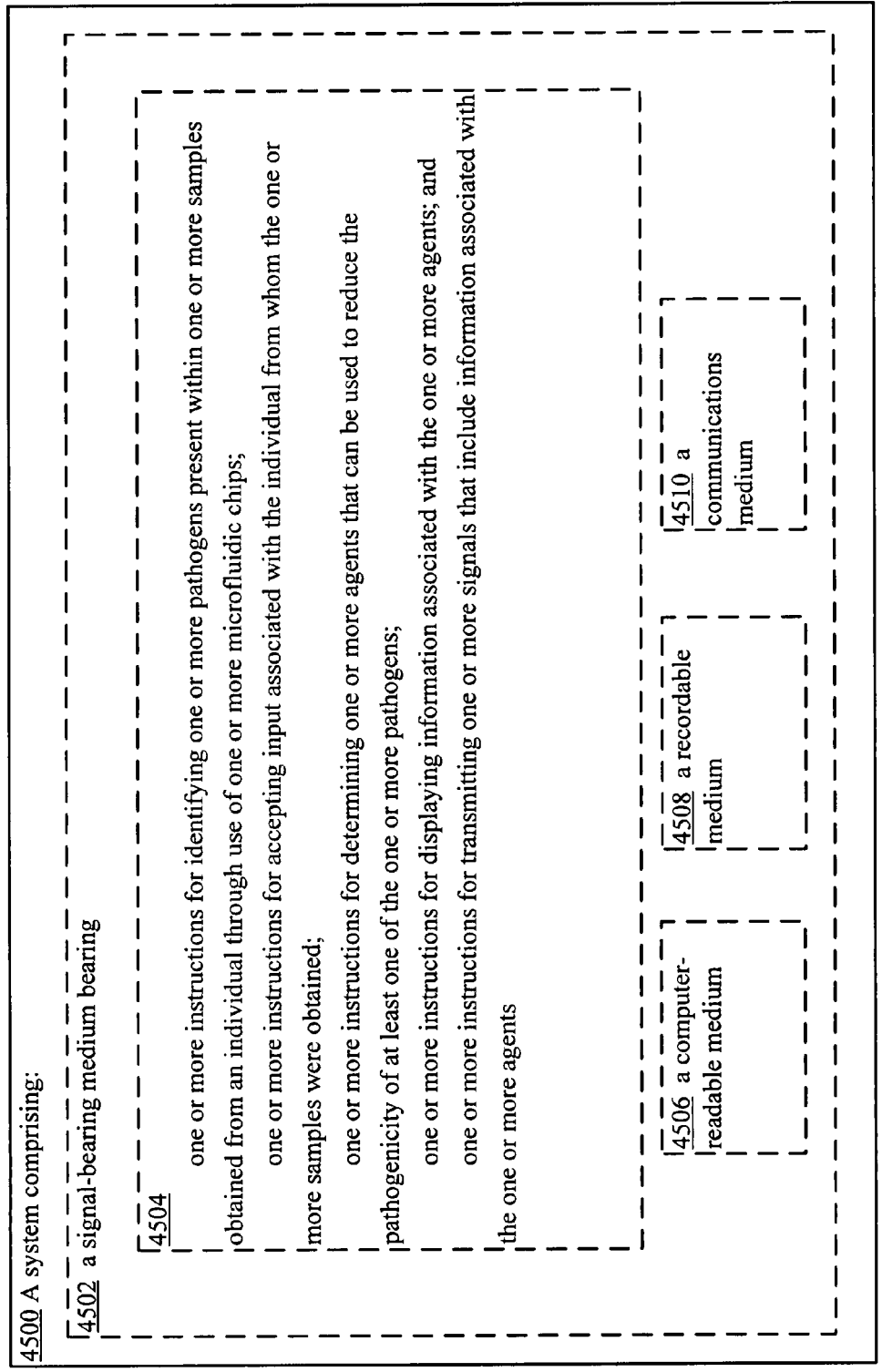
FIG. 45B illustrates an example system 4500 in which embodiments may be implemented.

FIG. 45B illustrates a partial view of a system 4500 that includes a computer program 4504 for executing a computer process on a computing device. An embodiment of the system 4500 is provided using a signal-bearing medium 4502 bearing one or more instructions for identifying one or more pathogens 106 present within one or more samples 104 obtained from an individual 102 through use of one or more microfluidic chips; one or more instructions for accepting input 120 associated with the individual 102 from whom the one or more samples 104 were obtained; one or more instructions for determining one or more agents 142 that can be used to reduce the pathogenicity of at least one of the one or more pathogens; one or more instructions for displaying information associated with the one or more agents; and one or more instructions for transmitting one or more signals 126 that include information associated with the one or more agents 142. The one or more instructions may be, for example, computer executable and/or logic-implemented instructions. In some embodiments, the signal-bearing medium 4502 may include a computer-readable medium 4506. In some embodiments, the signal-bearing medium 4502 may include a recordable medium 4508. In some embodiments, the signal-bearing medium 4502 may include a communications medium 4510.

Figure 46:
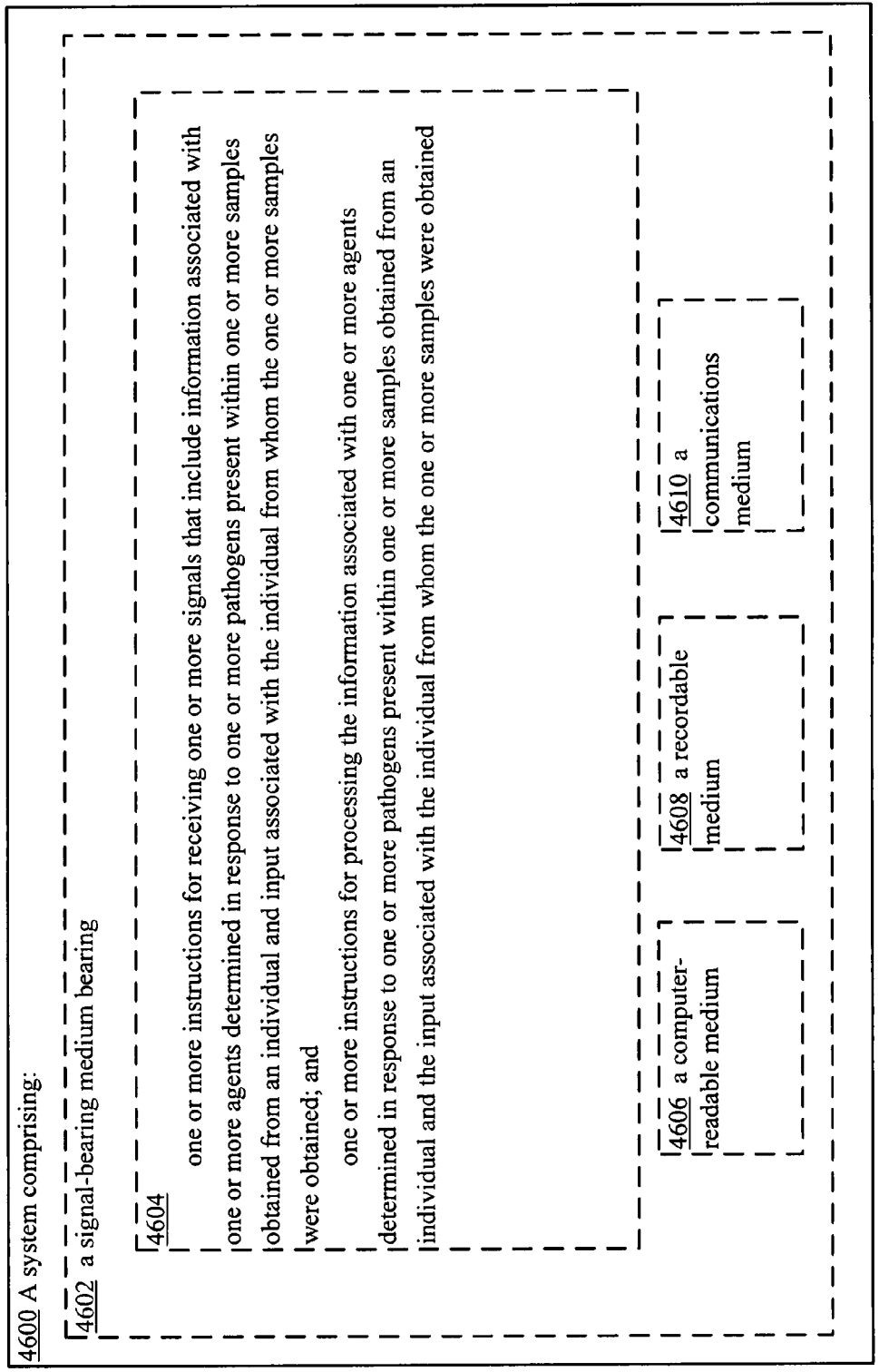
FIG. 46 illustrates an example system 4600 in which embodiments may be implemented.

FIG. 46 illustrates a partial view of a system 4600 that includes a computer program 4604 for executing a computer process on a computing device. An embodiment of the system 4600 is provided using a signal-bearing medium 4602 bearing one or more instructions for receiving one or more signals 126 that include information associated with one or more agents 142 determined in response to one or more pathogens 106 present within one or more samples 104 obtained from an individual 102 and input 120 associated with the individual 102 from whom the one or more samples 104 were obtained; and one or more instructions for processing the information associated with one or more agents 142 determined in response to one or more pathogens 106 present within one or more samples 104 obtained from an individual 102 and the input 120 associated with the individual 102 from whom the one or more samples 104 were obtained. The one or more instructions may be, for example, computer executable and/or logic-implemented instructions. In some embodiments, the signal-bearing medium 4602 may include a computer-readable medium 4606. In some embodiments, the signal-bearing medium 4602 may include a recordable medium 4608. In some embodiments, the signal-bearing medium 4602 may include a communications medium 4610.

Figure 46A:
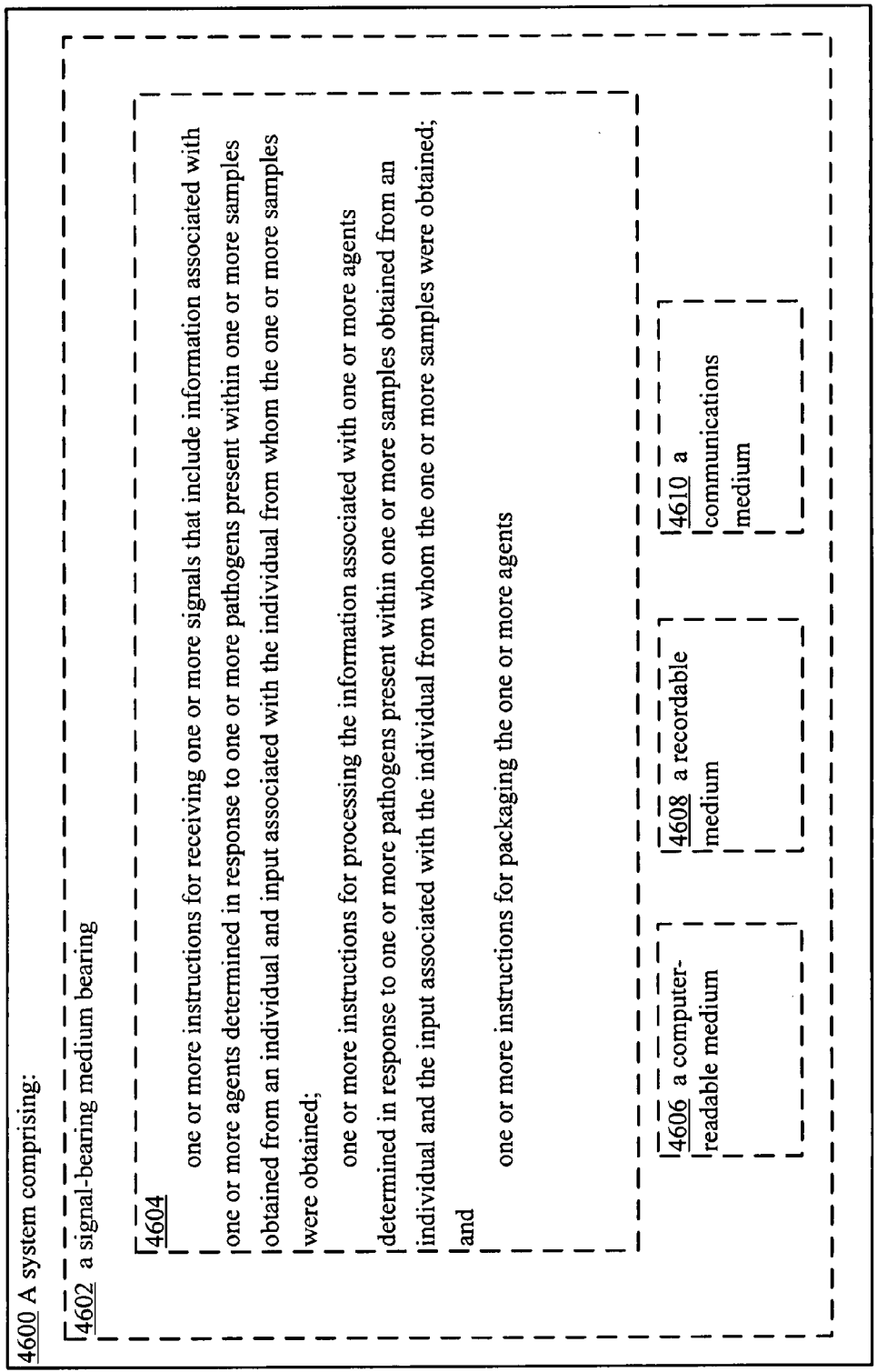
FIG. 46A illustrates an example system 4600 in which embodiments may be implemented.

FIG. 46A illustrates a partial view of a system 4600 that includes a computer program 4604 for executing a computer process on a computing device. An embodiment of the system 4600 is provided using a signal-bearing medium 4602 bearing one or more instructions for receiving one or more signals 126 that include information associated with one or more agents 142 determined in response to one or more pathogens 106 present within one or more samples 104 obtained from an individual 102 and input 120 associated with the individual 102 from whom the one or more samples 104 were obtained; one or more instructions for processing the information associated with one or more agents 142 determined in response to one or more pathogens 106 present within one or more samples 104 obtained from an individual 102 and the input 120 associated with the individual 102 from whom the one or more samples 104 were obtained; and one or more instructions for packaging the one or more agents 142. The one or more instructions may be, for example, computer executable and/or logic-implemented instructions. In some embodiments, the signal-bearing medium 4602 may include a computer-readable medium 4606. In some embodiments, the signal-bearing medium 4602 may include a recordable medium 4608. In some embodiments, the signal-bearing medium 4602 may include a communications medium 4610.

Figure 46B:
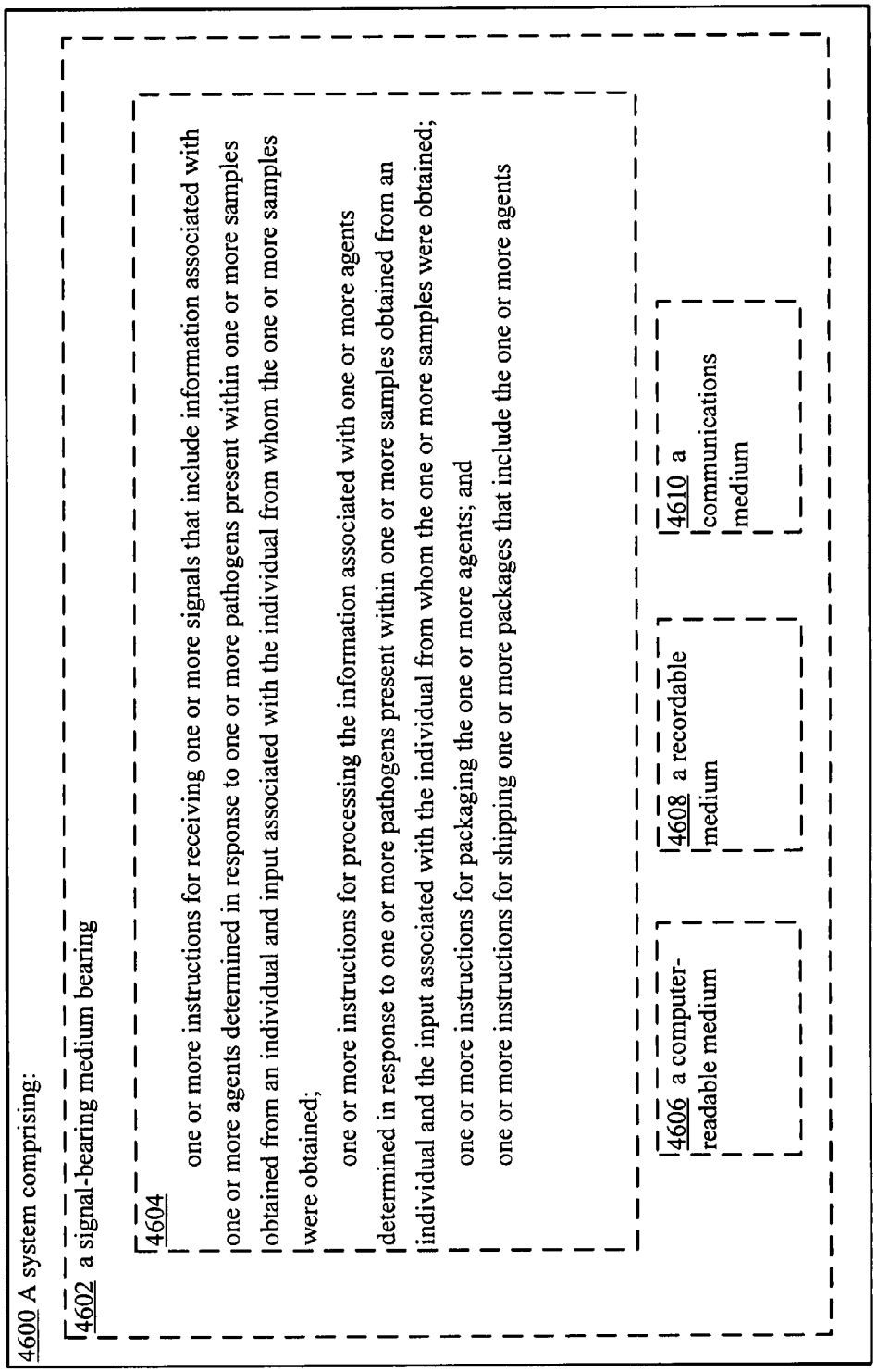
FIG. 46B illustrates an example system 4600 in which embodiments may be implemented.

FIG. 46B illustrates a partial view of a system 4600 that includes a computer program 4604 for executing a computer process on a computing device. An embodiment of the system 4600 is provided using a signal-bearing medium 4602 bearing one or more instructions for receiving one or more signals 126 that include information associated with one or more agents 142 determined in response to one or more pathogens 106 present within one or more samples 104 obtained from an individual 102 and input 120 associated with the individual 102 from whom the one or more samples 104 were obtained; one or more instructions for processing the information associated with one or more agents 142 determined in response to one or more pathogens 106 present within one or more samples 104 obtained from an individual 102 and the input 120 associated with the individual 102 from whom the one or more samples 104 were obtained; one or more instructions for packaging the one or more agents; and one or more instructions for shipping one or more packages that include the one or more agents 142. The one or more instructions may be, for example, computer executable and/or logic-implemented instructions. In some embodiments, the signal-bearing medium 4602 may include a computer-readable medium 4606. In some embodiments, the signal-bearing medium 4602 may include a recordable medium 4608. In some embodiments, the signal-bearing medium 4602 may include a communications medium 4610.

Figure 47:
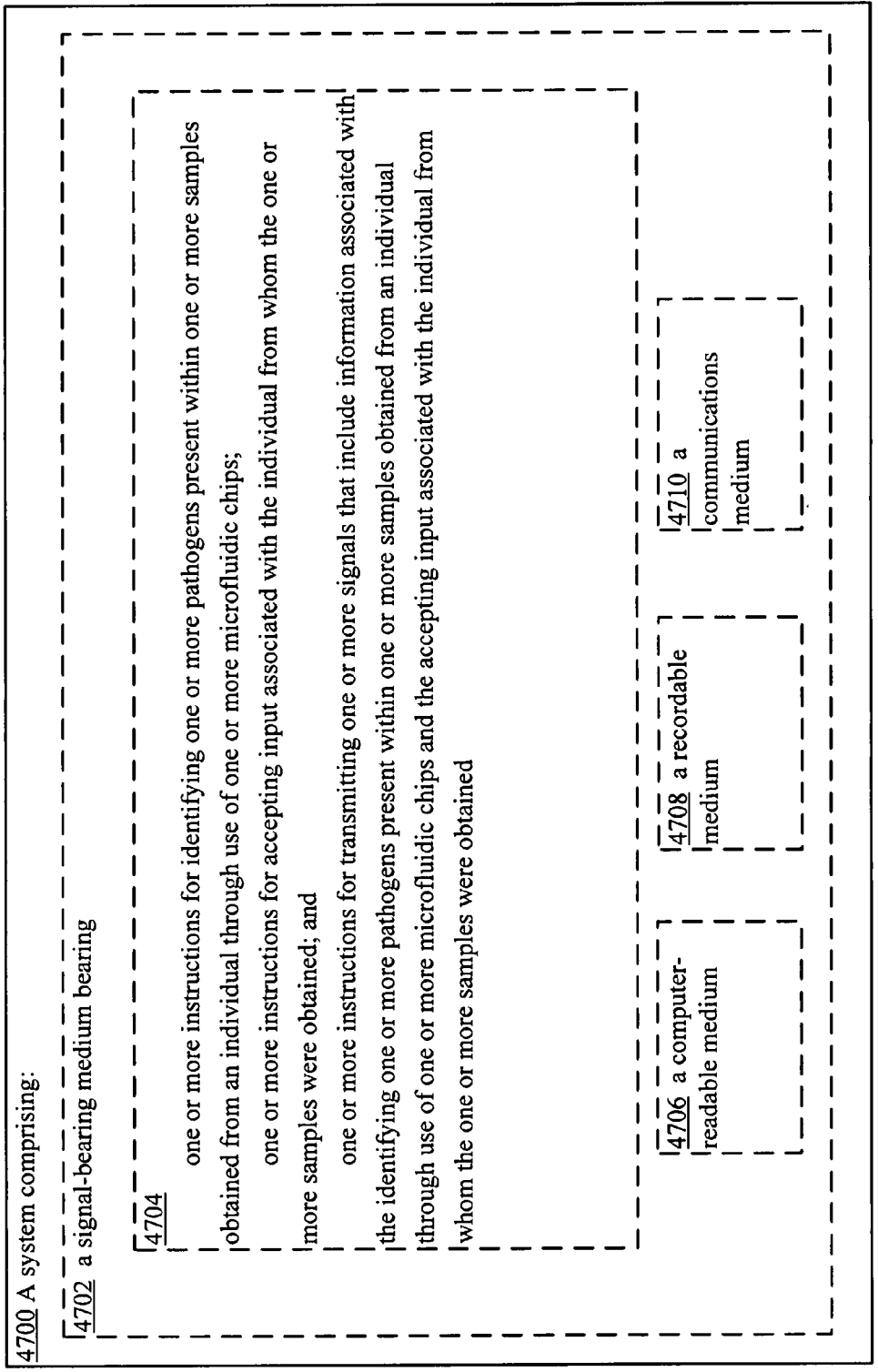
FIG. 47 illustrates an example system 4700 in which embodiments may be implemented.

FIG. 47 illustrates a partial view of a system 4700 that includes a computer program 4704 for executing a computer process on a computing device. An embodiment of the system 4700 is provided using a signal-bearing medium 4702 bearing one or more instructions for identifying one or more pathogens 106 present within one or more samples 104 obtained from an individual 102 through use of one or more microfluidic chips; one or more instructions for accepting input 120 associated with the individual 102 from whom the one or more samples 104 were obtained; and one or more instructions for transmitting one or more signals 126 that include information associated with the identifying one or more pathogens 106 present within one or more samples 104 obtained from an individual 102 through use of one or more microfluidic chips 108 and the accepting input 120 associated with the individual 102 from whom the one or more samples 104 were obtained. The one or more instructions may be, for example, computer executable and/or logic-implemented instructions. In some embodiments, the signal-bearing medium 4702 may include a computer-readable medium 4706. In some embodiments, the signal-bearing medium 4702 may include a recordable medium 4708. In some embodiments, the signal-bearing medium 4702 may include a communications medium 4710.

Figure 47A:
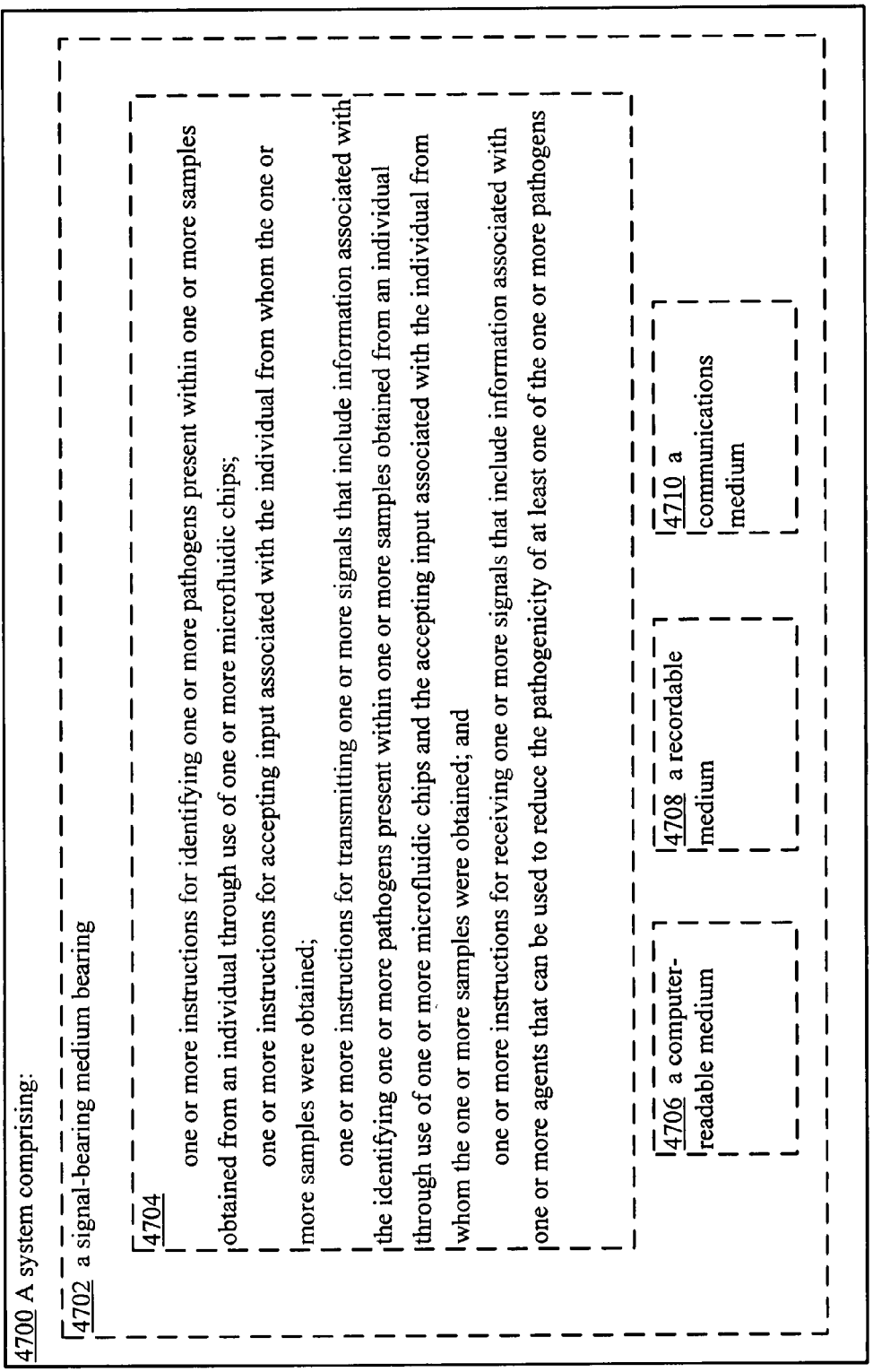
FIG. 47A illustrates an example system 4700 in which embodiments may be implemented.

FIG. 47A illustrates a partial view of a system 4700 that includes a computer program 4704 for executing a computer process on a computing device. An embodiment of the system 4700 is provided using a signal-bearing medium 4702 bearing one or more instructions for identifying one or more pathogens 106 present within one or more samples 104 obtained from an individual 102 through use of one or more microfluidic chips; one or more instructions for accepting input 120 associated with the individual 102 from whom the one or more samples 104 were obtained; one or more instructions for transmitting one or more signals 126 that include information associated with the identifying one or more pathogens 106 present within one or more samples 104 obtained from an individual 102 through use of one or more microfluidic chips 108 and the accepting input 120 associated with the individual 102 from whom the one or more samples 104 were obtained; and one or more instructions for receiving one or more signals 126 that include information associated with one or more agents 142 that can be used to reduce the pathogenicity of at least one of the one or more pathogens 106. The one or more instructions may be, for example, computer executable and/or logic-implemented instructions. In some embodiments, the signal-bearing medium 4702 may include a computer-readable medium 4706. In some embodiments, the signal-bearing medium 4702 may include a recordable medium 4708. In some embodiments, the signal-bearing medium 4702 may include a communications medium 4710.

Figure 47B:
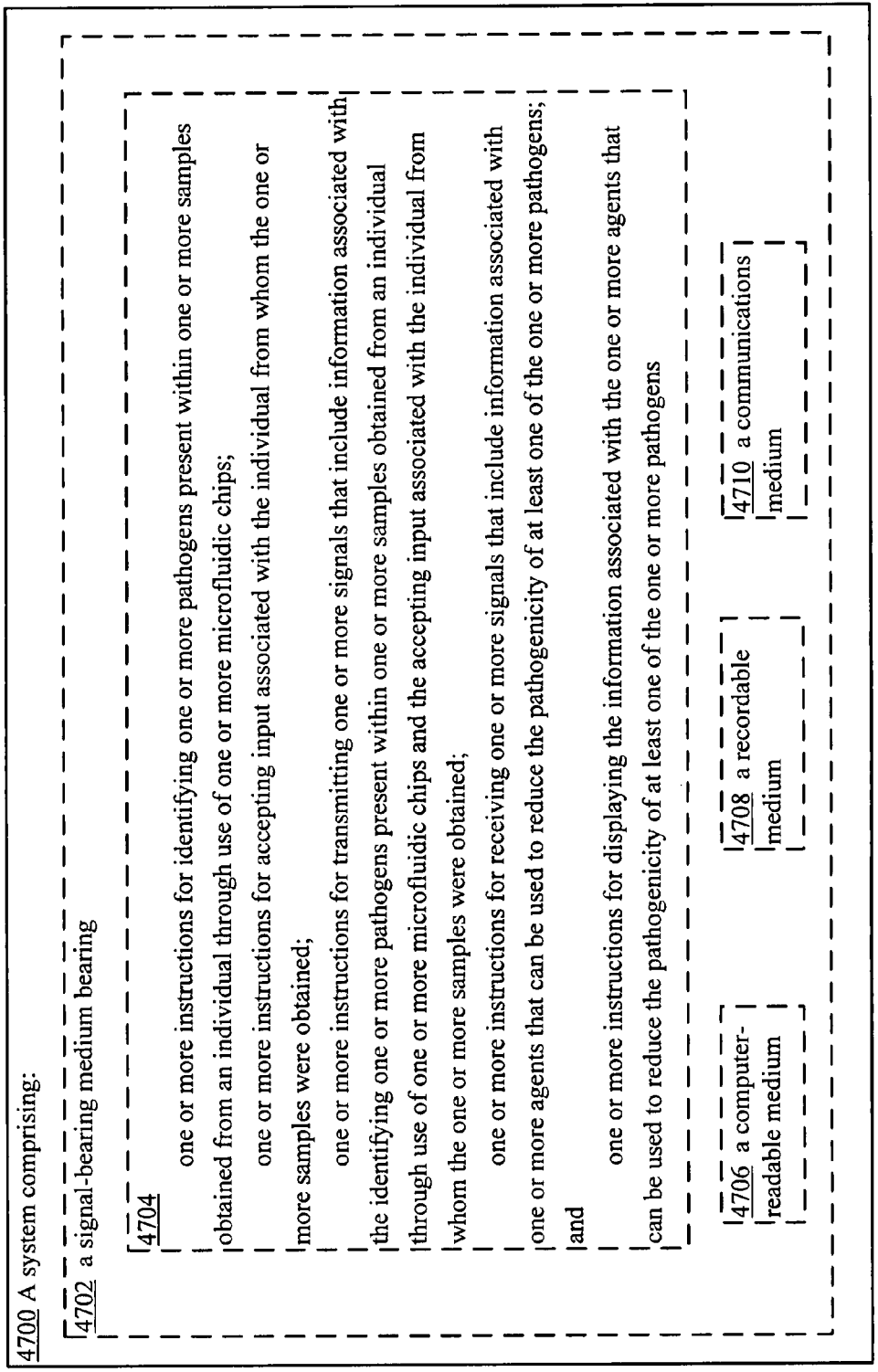
FIG. 47B illustrates an example system 4700 in which embodiments may be implemented.

FIG. 47B illustrates a partial view of a system 4700 that includes a computer program 4704 for executing a computer process on a computing device. An embodiment of the system 4700 is provided using a signal-bearing medium 4702 bearing one or more instructions for identifying one or more pathogens 106 present within one or more samples 104 obtained from an individual 102 through use of one or more microfluidic chips; one or more instructions for accepting input 120 associated with the individual 102 from whom the one or more samples 104 were obtained; one or more instructions for transmitting one or more signals 126 that include information associated with the identifying one or more pathogens 106 present within one or more samples 104 obtained from an individual 102 through use of one or more microfluidic chips 108 and the accepting input 120 associated with the individual 102 from whom the one or more samples 104 were obtained; one or more instructions for receiving one or more signals 126 that include information associated with one or more agents 142 that can be used to reduce the pathogenicity of at least one of the one or more pathogens; and one or more instructions for displaying the information associated with the one or more agents 142 that can be used to reduce the pathogenicity of at least one of the one or more pathogens 106. The one or more instructions may be, for example, computer executable and/or logic-implemented instructions. In some embodiments, the signal-bearing medium 4702 may include a computer-readable medium 4706. In some embodiments, the signal-bearing medium 4702 may include a recordable medium 4708. In some embodiments, the signal-bearing medium 4702 may include a communications medium 4710.

Figure 48:
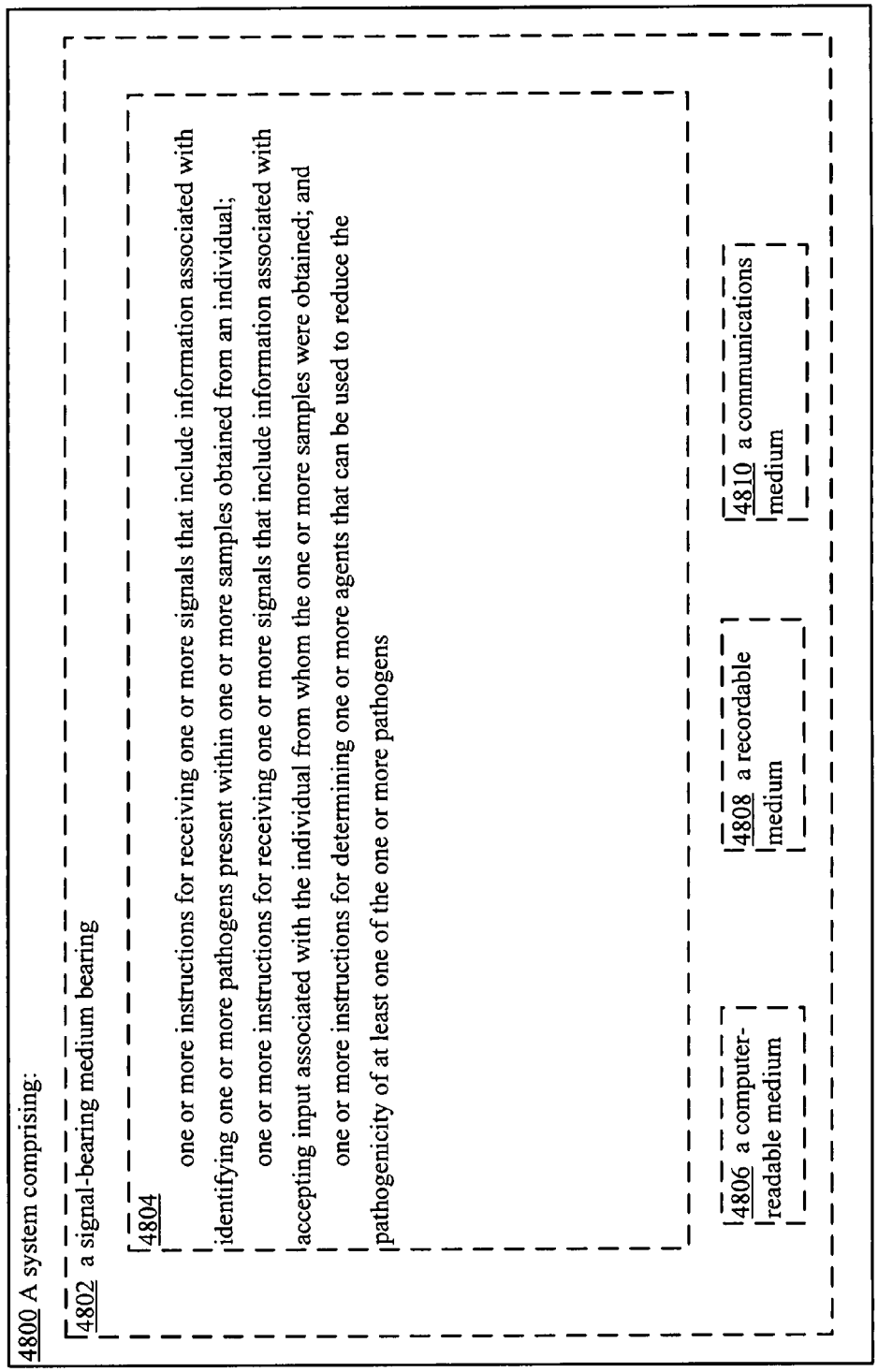
FIG. 48 illustrates an example system 4800 in which embodiments may be implemented.

FIG. 48 illustrates a partial view of a system 4800 that includes a computer program 4804 for executing a computer process on a computing device. An embodiment of the system 4800 is provided using a signal-bearing medium 4802 bearing one or more instructions for receiving one or more signals 126 that include information associated with identifying one or more pathogens 106 present within one or more samples 104 obtained from an individual; one or more instructions for receiving one or more signals 126 that include information associated with accepting input 120 associated with the individual 102 from whom the one or more samples 104 were obtained; and one or more instructions for determining one or more agents 142 that can be used to reduce the pathogenicity of at least one of the one or more pathogens 106. The one or more instructions may be, for example, computer executable and/or logic-implemented instructions. In some embodiments, the signal-bearing medium 4802 may include a computer-readable medium 4806. In some embodiments, the signal-bearing medium 4802 may include a recordable medium 4808. In some embodiments, the signal-bearing medium 4802 may include a communications medium 4810.

Figure 48A:
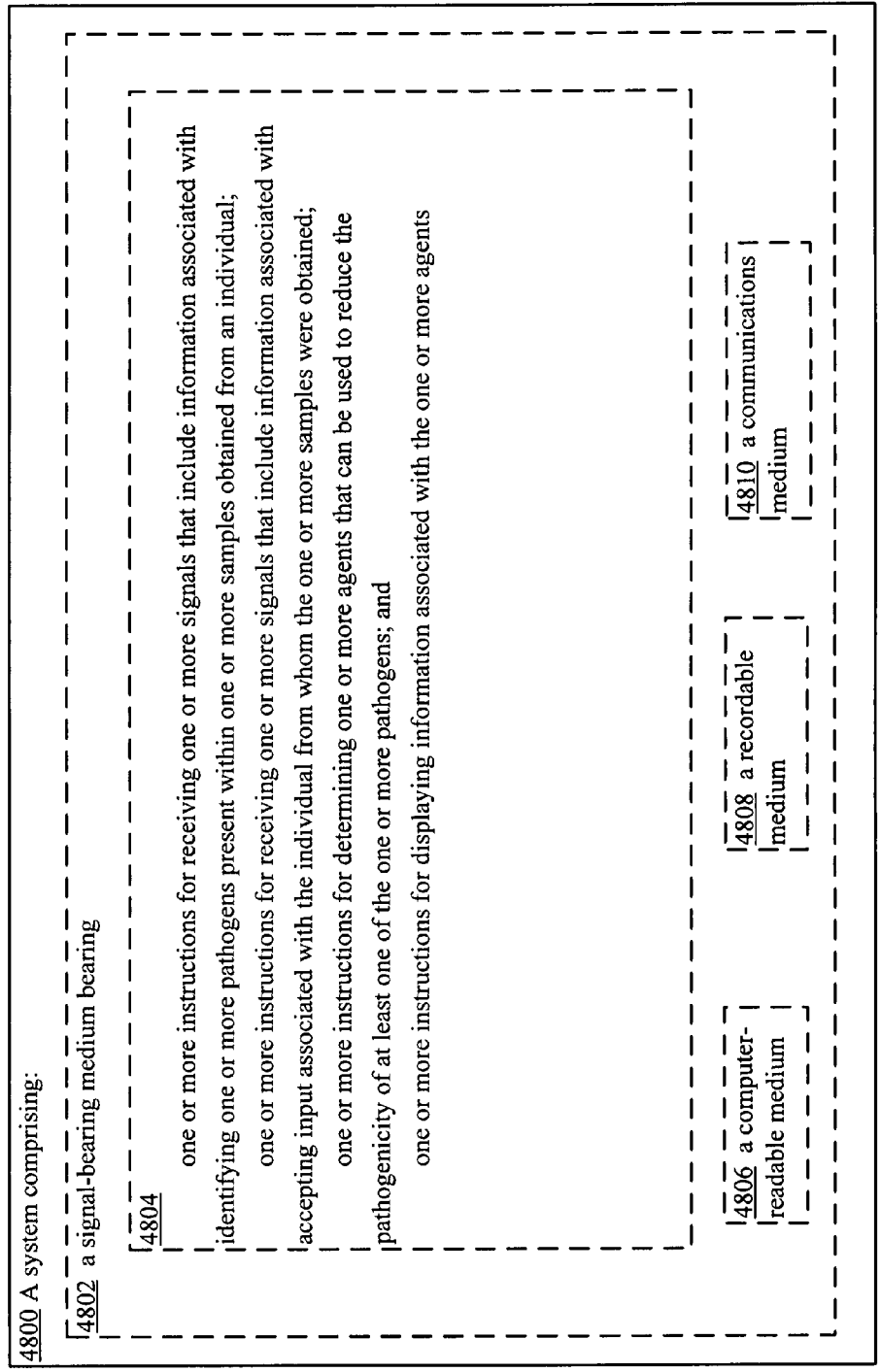
FIG. 48A illustrates an example system 4800 in which embodiments may be implemented.

FIG. 48A illustrates a partial view of a system 4800 that includes a computer program 4804 for executing a computer process on a computing device. An embodiment of the system 4800 is provided using a signal-bearing medium 4802 bearing one or more instructions for receiving one or more signals 126 that include information associated with identifying one or more pathogens 106 present within one or more samples 104 obtained from an individual; one or more instructions for receiving one or more signals 126 that include information associated with accepting input 120 associated with the individual 102 from whom the one or more samples 104 were obtained; one or more instructions for determining one or more agents 142 that can be used to reduce the pathogenicity of at least one of the one or more pathogens; and one or more instructions for displaying information associated with the one or more agents 142. The one or more instructions may be, for example, computer executable and/or logic-implemented instructions. In some embodiments, the signal-bearing medium 4802 may include a computer-readable medium 4806. In some embodiments, the signal-bearing medium 4802 may include a recordable medium 4808. In some embodiments, the signal-bearing medium 4802 may include a communications medium 4810.

Figure 48B:
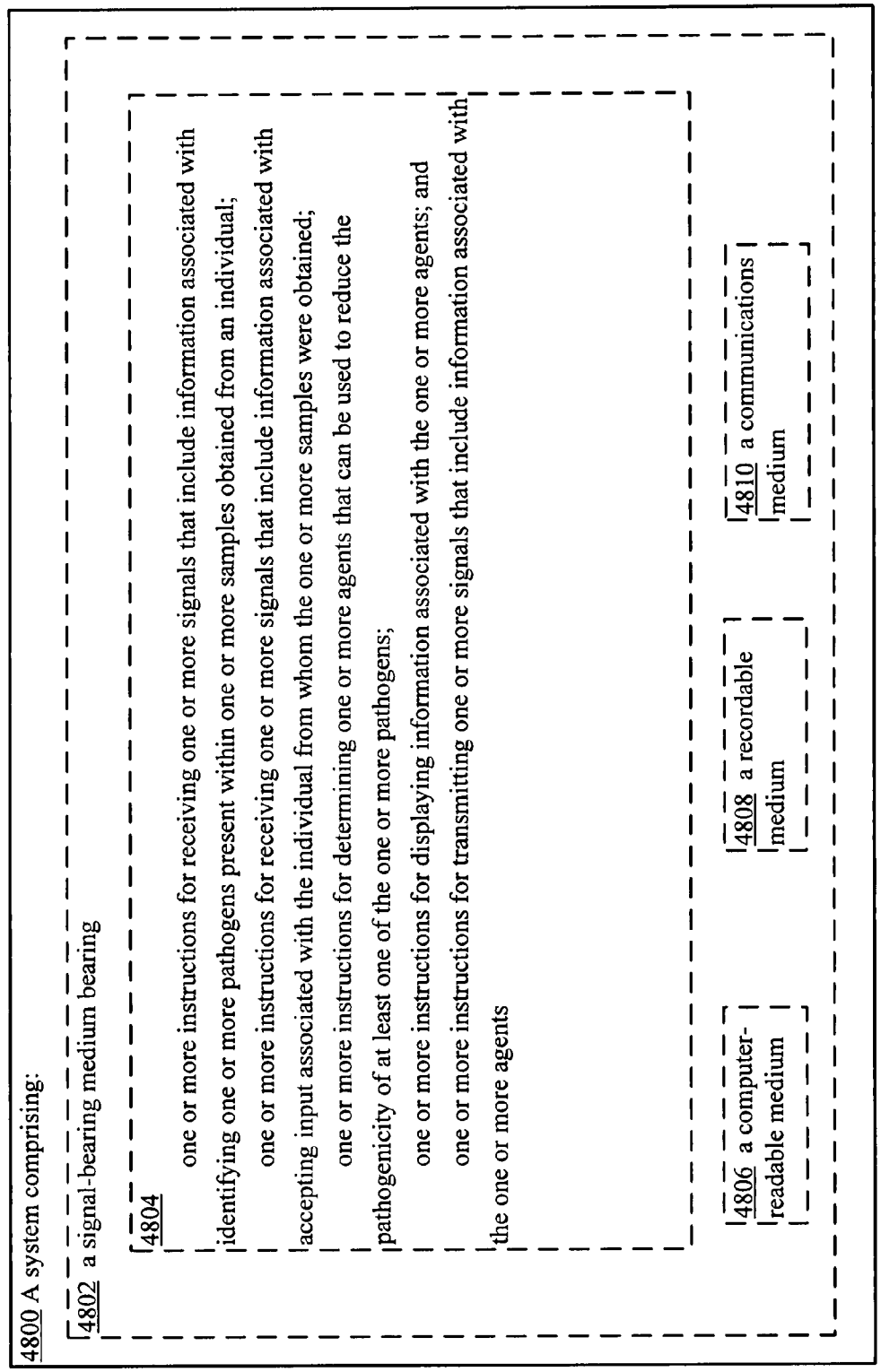
FIG. 48B illustrates an example system 4800 in which embodiments may be implemented.

FIG. 48B illustrates a partial view of a system 4800 that includes a computer program 4804 for executing a computer process on a computing device. An embodiment of the system 4800 is provided using a signal-bearing medium 4802 bearing one or more instructions for receiving one or more signals 126 that include information associated with identifying one or more pathogens 106 present within one or more samples 104 obtained from an individual; one or more instructions for receiving one or more signals 126 that include information associated with accepting input 120 associated with the individual 102 from whom the one or more samples 104 were obtained; one or more instructions for determining one or more agents 142 that can be used to reduce the pathogenicity of at least one of the one or more pathogens; one or more instructions for displaying information associated with the one or more agents; and one or more instructions for transmitting one or more signals 126 that include information associated with the one or more agents 142. The one or more instructions may be, for example, computer executable and/or logic-implemented instructions. In some embodiments, the signal-bearing medium 4802 may include a computer-readable medium 4806. In some embodiments, the signal-bearing medium 4802 may include a recordable medium 4808. In some embodiments, the signal-bearing medium 4802 may include a communications medium 4810.

Figure 48C:
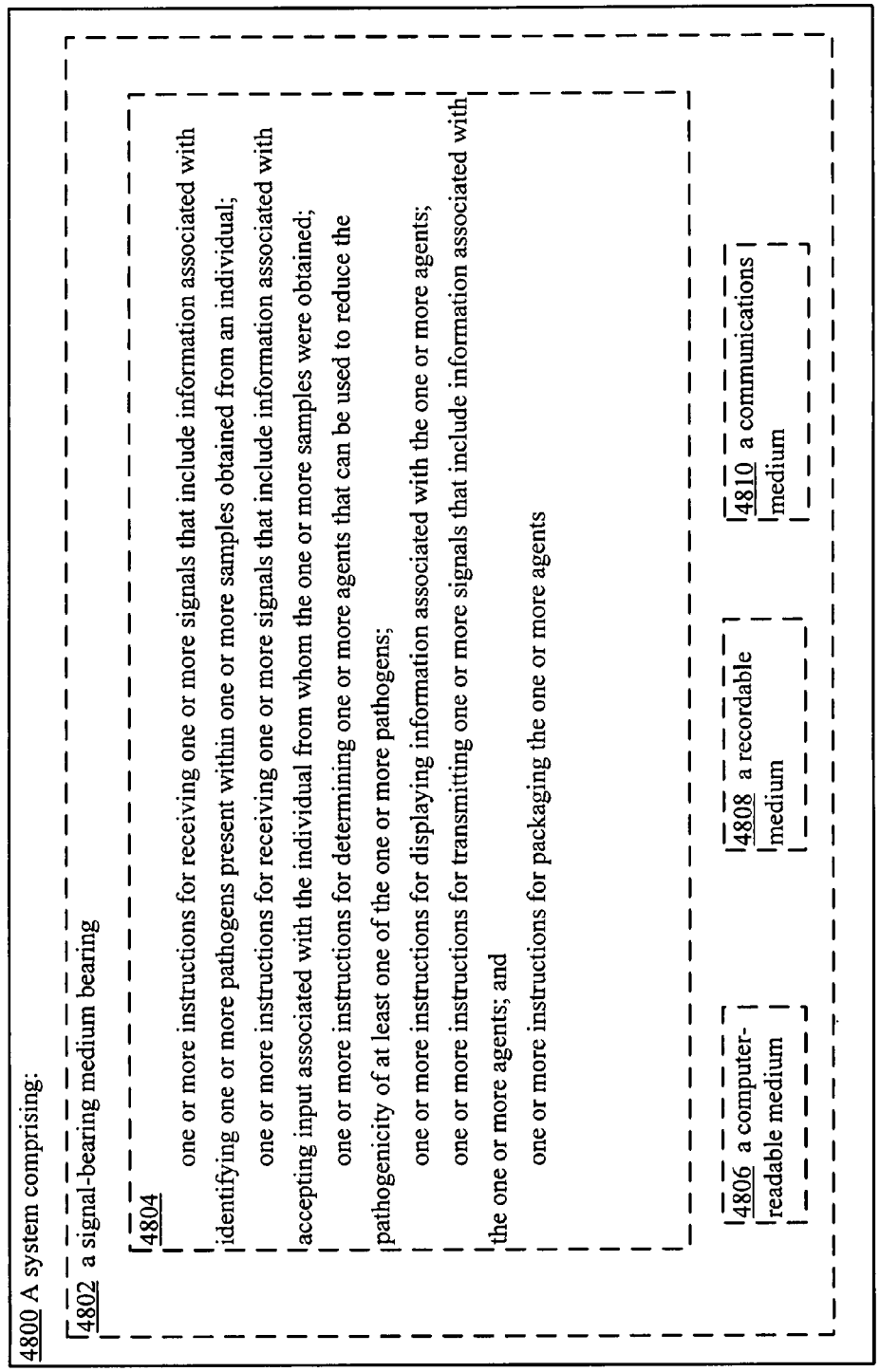
FIG. 48C illustrates an example system 4800 in which embodiments may be implemented.

FIG. 48C illustrates a partial view of a system 4800 that includes a computer program 4804 for executing a computer process on a computing device. An embodiment of the system 4800 is provided using a signal-bearing medium 4802 bearing one or more instructions for receiving one or more signals 126 that include information associated with identifying one or more pathogens 106 present within one or more samples 104 obtained from an individual; one or more instructions for receiving one or more signals 126 that include information associated with accepting input 120 associated with the individual 102 from whom the one or more samples 104 were obtained; one or more instructions for determining one or more agents 142 that can be used to reduce the pathogenicity of at least one of the one or more pathogens; one or more instructions for displaying information associated with the one or more agents; one or more instructions for transmitting one or more signals 126 that include information associated with the one or more agents; and one or more instructions for packaging the one or more agents 142. The one or more instructions may be, for example, computer executable and/or logic-implemented instructions. In some embodiments, the signal-bearing medium 4802 may include a computer-readable medium 4806. In some embodiments, the signal-bearing medium 4802 may include a recordable medium 4808. In some embodiments, the signal-bearing medium 4802 may include a communications medium 4810.

Figure 48D:
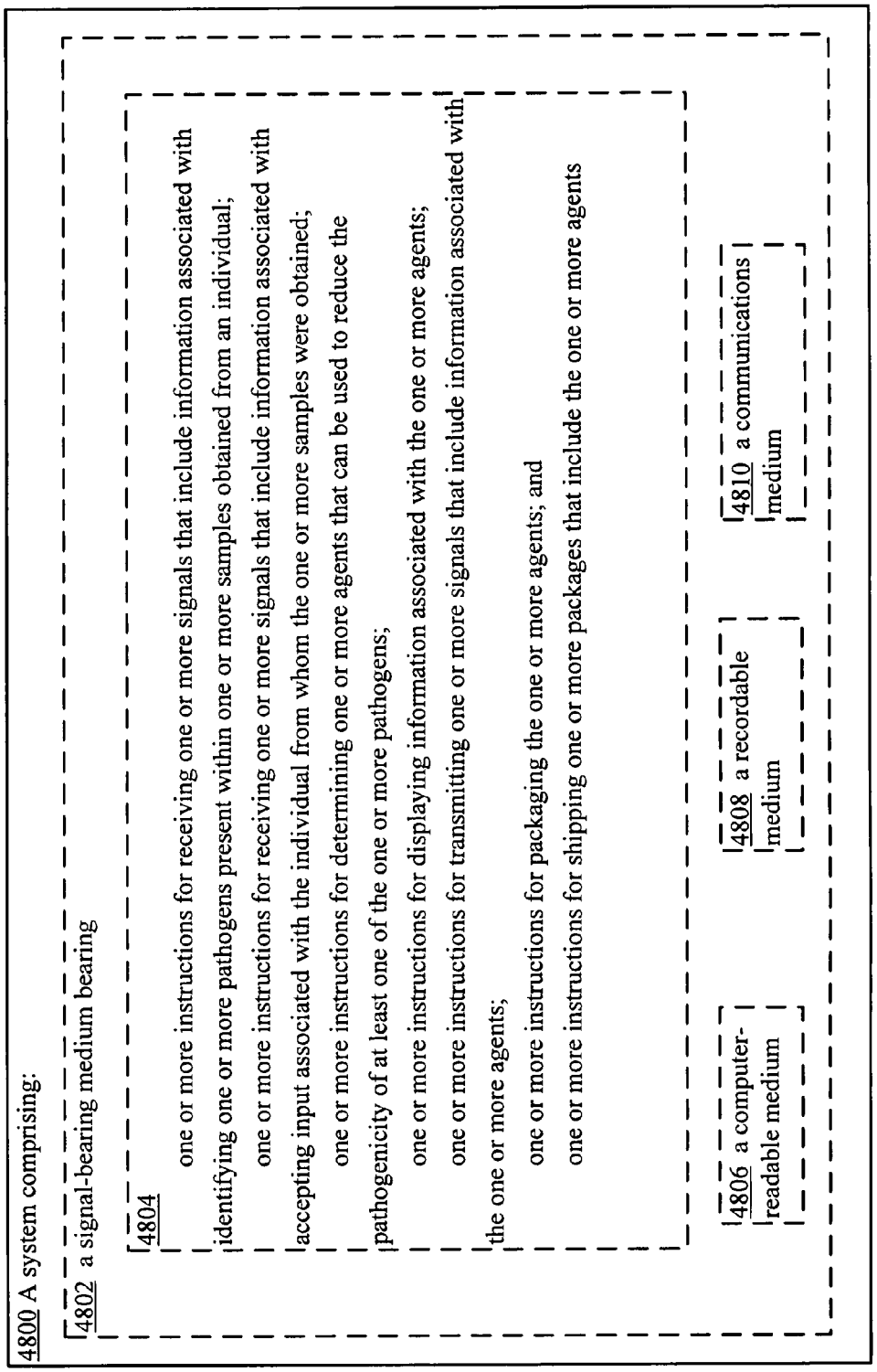
FIG. 48D illustrates an example system 4800 in which embodiments may be implemented.

FIG. 48D illustrates a partial view of a system 4800 that includes a computer program 4804 for executing a computer process on a computing device. An embodiment of the system 4800 is provided using a signal-bearing medium 4802 bearing one or more instructions for receiving one or more signals 126 that include information associated with identifying one or more pathogens 106 present within one or more samples 104 obtained from an individual; one or more instructions for receiving one or more signals 126 that include information associated with accepting input 120 associated with the individual 102 from whom the one or more samples 104 were obtained; one or more instructions for determining one or more agents 142 that can be used to reduce the pathogenicity of at least one of the one or more pathogens; one or more instructions for displaying information associated with the one or more agents; one or more instructions for transmitting one or more signals 126 that include information associated with the one or more agents; one or more instructions for packaging the one or more agents; and one or more instructions for shipping one or more packages that include the one or more agents 142. The one or more instructions may be, for example, computer executable and/or logic-implemented instructions. In some embodiments, the signal-bearing medium 4802 may include a computer-readable medium 4806. In some embodiments, the signal-bearing medium 4802 may include a recordable medium 4808. In some embodiments, the signal-bearing medium 4802 may include a communications medium 4810.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although user 170 is shown/described herein as a single illustrated figure, those skilled in the art will appreciate that a user 124 may be representative of a human user 124, a robotic user 124 (e.g., computational entity), and/or substantially any combination thereof (e.g., a user 124 may be assisted by one or more robotic). In addition, a user 124 as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A method comprising:
   receiving data identifying one or more pathogens present within one or more samples obtained from an individual through use of one or more microfluidic chips;
   receiving input associated with the individual from whom the one or more samples were obtained, the input including at least one of: one or more physical characteristics, medical history information, one or more activities, and/or substance usage information associated with the individual; and
   processing, using one or more processing devices, the input associated with the individual and the data identifying the one or more pathogens by at least determining versus time one or more values associated with the one or more pathogens and one or more values associated with agent usage by the one or more individuals; determining whether at least one relationship exists between the agent usage and the one or more pathogens; and determining based at least in part upon at least one determined relationship one or more agents or agent dosages.

2. The method of claim 1, wherein the receiving data identifying one or more pathogens present within one or more samples obtained from an individual through use of one or more microfluidic chips comprises:
   receiving data identifying one or more pathogens from one or more analysis units operably associated with one or more microfluidic chips.

3. The method of claim 1, further comprising:
   transmitting one or more signals that include information associated with the data identifying one or more pathogens.

4. The method of claim 1, further comprising:
   receiving one or more signals that include information associated with the one or more agents.

5. The method of claim 4, wherein the receiving one or more signals that include information associated with the one or more agents comprises:
   receiving one or more signals that include information associated with contraindicators of the one or more agents.

6. The method of claim 4, wherein the receiving one or more signals that include information associated with the one or more agents comprises:
   receiving one or more signals that include information associated with side-effects of the one or more agents.

7. The method of claim 4, further comprising:
   displaying the information associated with the one or more agents.

8. The method of claim 7, wherein the displaying the information associated with the one or more agents comprises:
   displaying the information in Braille.

9. A system comprising:
   a non-transitory signal-bearing medium bearing:
   one or more instructions for receiving data identifying one or more pathogens present within one or more samples obtained from an individual through use of one or more microfluidic chips;
   one or more instructions for receiving input associated with the individual from whom the one or more samples were obtained, the input including at least one of: one or more physical characteristics, medical history information, one or more activities, and/or substance usage information associated with the individual; and
   one or more instructions for processing the input associated with the individual and the data identifying the one or more pathogens by at least determining versus time one or more values associated with the one or more pathogens and one or more values associated with agent usage by the one or more individuals; determining whether at least one relationship exists between the agent usage and the one or more pathogens; and determining based at least in part upon at least one determined relationship one or more agents or agent dosages.

10. The system of claim 9, further comprising:
    one or more instructions for receiving one or more signals that include information associated with the one or more agents.

11. The system of claim 10, further comprising:
    one or more instructions for displaying the information associated with the one or more agents.

12. A system comprising:
    circuitry for receiving data identifying one or more pathogens present within one or more samples obtained from an individual through use of one or more microfluidic chips;
    circuitry for receiving input associated with the individual from whom the one or more samples were obtained, the input including at least one of: one or more physical characteristics, medical history information, one or more activities, and/or substance usage information associated with the individual; and
    circuitry for processing the input associated with the individual and the data identifying the one or more pathogens by at least determining versus time one or more values associated with the one or more pathogens and one or more values associated with agent usage by the one or more individuals; determining whether at least one relationship exists between the agent usage and the one or more pathogens; and determining based at least in part upon at least one determined relationship one or more agents or agent dosages.

13. The system of claim 12, wherein the circuitry for receiving data identifying one or more pathogens present within one or more samples obtained from an individual through use of one or more microfluidic chips comprises:
    circuitry for receiving data identifying one or more pathogens from one or more analysis units operably associated with one or more microfluidic chips.

14. The system of claim 12, further comprising:
    circuitry for transmitting one or more signals that include information associated with the data identifying one or more pathogens.

15. The system of claim 12, further comprising:
    circuitry for receiving one or more signals that include information associated with the one or more agents.

16. The system of claim 15, further comprising:
    circuitry for displaying the information associated with the one or more agents.

17. The system of claim 16, wherein the circuitry for displaying the information associated with the one or more comprises:
    circuitry for displaying the information in audio form.
18. The system of claim 16, wherein the circuitry for displaying the information associated with the one or more agents comprises:
    circuitry for displaying the information in Braille.
19. The method of claim 1, wherein the receiving input associated with the individual from whom the one or more samples were obtained comprises:
    receiving input associated with the individual via a user interface of a handheld portable device operably couplable with the one or more microfluidic chips.
20. The method of claim 1, further comprising:
    determining one or more personalized release rates of the one or more agents using the input associated with the individual.
21. The method of claim 1, further comprising:
    transmitting one or more signals that include at least one order for the one or more agents.
22. The method of claim 1, further comprising:
    transmitting one or more signals that include at least one order for two or more agents in single administration form.
23. The method of claim 1, further comprising:
    determining treatment effectiveness by receiving data associated with the one or more pathogens following consumption of the one or more agents.
24. The method of claim 7, wherein the displaying the information associated with the one or more agents comprises:
    displaying the information in audio form.
25. The method of claim 1, wherein the processing, using one or more processing devices, the input associated with the individual and the data identifying the one or more pathogens by at least determining versus time one or more values associated with the one or more pathogens and one or more values associated with agent usage by the one or more individuals; determining whether at least one relationship exists between the agent usage and the one or more pathogens; and determining based at least in part upon at least one determined relationship one or more agents or agent dosages comprises:
    processing, using one or more processing devices, the input associated with the individual and the data identifying the one or more pathogens by at least determining versus time one or more values associated with the one or more pathogens, at least one value of which is determined from the input associated with the individual, and one or more values associated with agent usage by the one or more individuals; determining whether at least one relationship exists between the agent usage and the one or more pathogens; and determining based at least in part upon at least one determined relationship one or more agents or agent dosages.
26. The method of claim 1, further comprising:
    transmitting one or more signals that include information associated with the one or more agents or agent dosages.
27. The system of claim 12, further comprising:
    circuitry for transmitting one or more signals that include at least one order for the one or more agents.
28. The system of claim 12, further comprising:
    circuitry for determining treatment effectiveness by receiving data associated with the one or more pathogens following consumption of the one or more agents.
29. The system of claim 12, wherein the circuitry for processing the input associated with the individual and the data identifying the one or more pathogens by at least determining versus time one or more values associated with the one or more pathogens and one or more values associated with agent usage by the one or more individuals; determining whether at least one relationship exists between the agent usage and the one or more pathogens; and determining based at least in part upon at least one determined relationship one or more agents or agent dosages comprises:
    circuitry for processing the input associated with the individual and the data identifying the one or more pathogens by at least determining versus time one or more values associated with the one or more pathogens, at least one value of which is determined from the input associated with the individual, and one or more values associated with agent usage by the one or more individuals; determining whether at least one relationship exists between the agent usage and the one or more pathogens; and determining based at least in part upon at least one determined relationship one or more agents or agent dosages.
30. The system of claim 12, further comprising:
    circuitry for transmitting one or more signals that include information associated with the one or more agents or agent dosages.

* * * * *

UNITED STATES PATENT AND TRADEMARK OFFICE
CERTIFICATE OF CORRECTION

| | | |
|---|---|---|
| PATENT NO. | : 8,068,991 B2 | Page 1 of 1 |
| APPLICATION NO. | : 11/900660 | |
| DATED | : November 29, 2011 | |
| INVENTOR(S) | : Jung et al. | |

It is certified that error appears in the above-identified patent and that said Letters Patent is hereby corrected as shown below:

In Col. 97, line 2, claim 17 "displaying the information associated with the one or more comprises" should read --displaying the information associated with the one or more agents comprises--

Signed and Sealed this
Third Day of April, 2012

David J. Kappos
*Director of the United States Patent and Trademark Office*